US008026368B2

(12) United States Patent
Miyaji et al.

(10) Patent No.: US 8,026,368 B2
(45) Date of Patent: Sep. 27, 2011

(54) HYDRAZIDE COMPOUNDS AND THROMBOPOIETIN RECEPTOR ACTIVATORS

(75) Inventors: Katsuaki Miyaji, Funabashi (JP);
Yukihiro Shigeta, Funabashi (JP);
Satoshi Nakano, Funabashi (JP);
Hirofumi Ota, Funabashi (JP); Norihisa Ishiwata, Minamisaitama-gun (JP)

(73) Assignee: Nissan Chemical Industries, Ltd., Tokyo (JP)

( * ) Notice: Subject to any disclaimer, the term of this patent is extended or adjusted under 35 U.S.C. 154(b) by 365 days.

(21) Appl. No.: 12/092,834

(22) PCT Filed: Nov. 7, 2006

(86) PCT No.: PCT/JP2006/322193
§ 371 (c)(1),
(2), (4) Date: May 7, 2008

(87) PCT Pub. No.: WO2007/052808
PCT Pub. Date: May 10, 2007

(65) Prior Publication Data
US 2009/0253751 A1    Oct. 8, 2009

(30) Foreign Application Priority Data
Nov. 7, 2005  (JP) .................................. 2005-322114

(51) Int. Cl.
*C07D 401/00*   (2006.01)
*A61K 31/44*    (2006.01)
(52) U.S. Cl. ..................................... 546/276.1; 514/341
(58) Field of Classification Search ............... 546/276.1; 514/341
See application file for complete search history.

(56) References Cited

FOREIGN PATENT DOCUMENTS

| JP | 10 72492 | 3/1998 |
|---|---|---|
| JP | 11 1477 | 1/1999 |
| JP | 11 152276 | 6/1999 |
| JP | 2001 97948 | 4/2001 |
| JP | 2003 238565 | 8/2003 |
| WO | 96 40189 | 12/1996 |
| WO | 96 40750 | 12/1996 |
| WO | 98 25965 | 6/1998 |
| WO | 99 11262 | 3/1999 |
| WO | 00 35446 | 6/2000 |
| WO | 00 66112 | 11/2000 |
| WO | 01 07423 | 2/2001 |
| WO | 01 17349 | 3/2001 |
| WO | 01 21180 | 3/2001 |
| WO | 01 34585 | 5/2001 |
| WO | 01 39773 | 6/2001 |
| WO | 01 53267 | 7/2001 |
| WO | 01 89457 | 11/2001 |
| WO | 02 49413 | 6/2002 |
| WO | 02 059099 | 8/2002 |
| WO | 02 059100 | 8/2002 |
| WO | 02 062775 | 8/2002 |
| WO | 02 085343 | 10/2002 |
| WO | 03 062233 | 7/2003 |
| WO | 2004 033433 | 4/2004 |
| WO | 2004 108683 | 12/2004 |
| WO | 2006 062247 | 6/2006 |
| WO | 2006 062249 | 6/2006 |
| WO | 2006 064957 | 6/2006 |

OTHER PUBLICATIONS

West, Anthony R., Solid State Chemistry and its Applications, Wiley, New York, 1988, pp. 358 & 365.*
Tavora de Albuquerque Silva, Mini-Reviews in Med. Chem., 2005, vol. 5, pp. 893-914.*
U.S. Appl. No. 12/492,435, filed Jun. 26, 2009, Owada, et al.
U.S. Appl. No. 12/303,436, filed Dec. 4, 2008, Miyaji, et al.
Nakamura, Takanori et al., "Thrombopoietin-yo Kassei o Yusuru Shinki Teibunshi Kagobutsu (NIP-004) no Sosei", Rinsho Ketsueki, vol. 46, No. 8, p. 728, (2005).
Nakamura, Takanori et al., "A novel nonpeptidyl human c-Mpl activator stimulates human megakaryopoiesis and thrombopoiesis", Blood, vol. 107, No. 11, p. 4300-4307, (2006).
Cardier, Jose E. et al., "Effects of Megakaryocyte Growth and Development Factor (Thrombopoietin) on Liver Endothelial Cells in Vitro", Microvascular Research, vol. 58, pp. 108-113, (1999).
Brizzi, Maria Felice et al., "Thrombopoietin Stimulates Endothelial Cell Motility and Neoangiogenesis by a Platelet-Activating Factor-Dependent Mechanism", Circ Res., vol. 84. p. 785-796, (1999).
"Journal of the American Society of Hematology, Blood", vol. 98, p. 71a-72a, (2001).

* cited by examiner

*Primary Examiner* — Janet Andres
*Assistant Examiner* — Heidi Reese
(74) *Attorney, Agent, or Firm* — Oblon, Spivak, McClelland, Maier & Neustadt, L.L.P.

(57) ABSTRACT

Compounds effective for preventing, treatment or improving diseases against which activation of the thrombopoietin receptor is effective are provided.
A compound represented by the formula (I) (wherein $R^1$, $R^2$, $R^3$, $L^1$, $L^2$, X and Y are defined in the description), a tautomer, prodrug or pharmaceutically acceptable salt of the compound or a solvate thereof.

(I)

38 Claims, No Drawings

HYDRAZIDE COMPOUNDS AND THROMBOPOIETIN RECEPTOR ACTIVATORS

TECHNICAL FIELD

The present invention relates to preventive, therapeutic and improving agents having affinity for and agonistic action on the thrombopoietin receptor for diseases against which activation of the thrombopoietin receptor is effective. Specifically, it relates to pharmaceutical compositions comprising compounds which increase platelets through stimulation of differentiation and proliferation of hematopoietic stem cells, megakaryocytic progenitor cells and megakaryocytes or compounds for therapeutic angiogenesis or with anti-arteriosclerosis action that stimulate differentiation and proliferation of vascular endothelial cells and endothelial progenitor cells.

BACKGROUND ART

Thrombopoietin is a cytokine consisting of 332 amino acids that increases platelet production by stimulating differentiation and proliferation of hematopoietic stem cells, megakaryocytic progenitor cells and megakaryocytes mediated by its receptor and therefore is promising as a drug for hematological disorders. Recent reports that it stimulates differentiation and proliferation of vascular endothelial cells and endothelial progenitor cells have raised expectations of therapeutic angiogenesis, anti-arteriosclerosis and prevention of cardiovascular events (for example, non-patent document 1, non-patent document 2 and non-patent document 3).

Biologically active substances which have been known so far to regulate platelet production through the thrombopoietin receptor include, in addition to thrombopoietin itself, low molecular weight peptides having affinity for the thrombopoietin receptor (for example, patent document 1, patent document 2, patent document 3 and patent document 4).

As a result of search for nonpeptidic low molecular weight compounds that increase platelet production mediated by the thrombopoietin receptor, low molecular weight compounds having affinity for the thrombopoietin receptor have been reported (for example, patent document 5 to patent document 26).

1) Applications filed by Hokuriku Seiyaku Co., Ltd. relating to 1,4-benzodiazepine derivatives (patent documents 5 and 6)
2) International Laid-open Patent Applications filed by Shionogi & Co., Ltd. (patent documents 7-10)
3) International Laid-open Patent Applications filed by SmithKline Beecham Corp (patent documents 11-19)
4) Japanese Laid-open Patent Application filed by Torii Pharmaceutical Co., Ltd. (patent document 20)
5) International Laid-open Patent Application filed by Roche Diagnostics GMBH (patent document 21)
6) International Laid-open Patent Applications filed by Yamanouchi Pharmaceutical Co., Ltd. (patent documents 22 and 23)
7) Japanese Laid-open Patent Application filed by Japan Tabacco Inc. (patent document 24)
8) Japanese Laid-open Patent Applications filed by Nissan Chemical Industries, Ltd. (patent documents 25 and 26)
Patent document 1 JP-A-10-72492
Patent document 2 WO96/40750
Patent document 3 WO96/40189
Patent document 4 WO98/25965
Patent document 5 JP-A-11-1477
Patent document 6 JP-A-11-152276
Patent document 7 WO01/07423
Patent document 8 WO01/53267
Patent document 9 WO02/059099
Patent document 10 WO02/059100
Patent document 11 WO00/35446
Patent document 12 WO00/66112
Patent document 13 WO01/34585
Patent document 14 WO01/17349
Patent document 15 WO01/39773
Patent document 16 WO01/21180
Patent document 17 WO01/89457
Patent document 18 WO02/49413
Patent document 19 WO02/085343
Patent document 20 JP-A-2001-97948
Patent document 21 WO99/11262
Patent document 22 WO02/062775
Patent document 23 WO03/062233
Patent document 24 JP-A-2003-238565
Patent document 25 WO04/033433
Patent document 26 WO04/108683
Non-patent document 1 Microvasc. Res., 1999: 58, P. 108-113
Non-patent document 2 Circ. Res., 1999: 84, p. 785-796
Non-patent document 3 Blood 2001:98, p. 71a-72a

DISCLOSURE OF THE INVENTION

Problems that the Invention is to Solve

Thrombopoietin and low molecular weight peptides having affinity for the thrombopoietin receptor are likely to be easily degraded in the gastrointestinal tract and are usually difficult to orally administer. As to thrombopoietin itself, the appearance of anti-thrombopoietin antibodies have been reported.

Besides, though it is probably possible to orally administer nonpeptidic low molecular weight compounds, no practical drugs have been put on the market.

Therefore, orally administrable low molecular weight compounds having excellent affinity for and agonistic action on the thrombopoietin receptor as preventive, therapeutic and improving agents for diseases against which activation of the thrombopoietin receptor is effective have been demanded. Specifically, low molecular weight compounds which can serve as platelet increasing agents or increasing agents for other blood cells by stimulating differentiation and proliferation of hematopoietic stem cells, megakaryocytic progenitor cells and megakaryocytes or low molecular weight compounds which can be used for therapeutic angiogenesis or as preventive and therapeutic agents for arteriosclerosis by stimulating endothelial cells and endothelial progenitor cells have been demanded.

Means of Solving the Problems

The present inventors conducted extensive research to find low molecular weight compounds having affinity for and agonistic action on the thrombopoietin receptor, and as a result, found that the compounds of the present invention have high affinity and agonistic action which enable them to show potent platelet increasing action by stimulating differentiation and proliferation of megakaryocytic progenitor cells and megakaryocytes. The present invention was accomplished on the basis of this discovery.

Namely, the present invention relates to:
1. A compound represented by the formula (I):

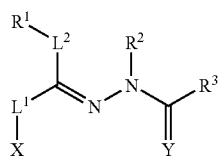

[wherein each of $R^1$ and $R^2$ is independently a hydrogen atom, a formyl group, a $C_{1-10}$ alkyl group, a $C_{2-6}$ alkenyl group, a $C_{2-6}$ alkynyl group, a $C_{1-10}$ alkoxy group, a $C_{1-10}$ alkylcarbonyl group (the $C_{1-10}$ alkyl group, the $C_{2-6}$ alkenyl group, the $C_{2-6}$ alkynyl group, the $C_{1-10}$ alkoxyl group and the $C_{1-10}$ alkylcarbonyl group may optionally be substituted with one or more substituents independently represented by $—V^1$ (wherein $V^1$ is a carboxyl group, a carbamoyl group, a sulfamoyl group, a phosphono group, a sulfo group, a teterazole group, a formyl group, a nitro group, a cyano group, a halogen atom, a $C_{1-3}$ alkyl group, a $C_{1-3}$ alkoxy group (the $C_{1-3}$ alkyl group and the $C_{1-3}$ alkoxy group are substituted with at least one halogen atom), a thiol group, a protected thiol group, a hydroxyl group, a protected hydroxyl group, an amino group, a protected amino group, a $C_{1-10}$ thioalkyl group, a $C_{1-10}$ alkoxy group, a $C_{1-10}$ alkylcarbonyl group, a $C_{1-10}$ alkylcarbonyloxy group, a $C_{1-10}$ alkoxycarbonyl group, a $C_{1-10}$ alkylcarbonylamino group, a $C_{1-10}$ alkylaminocarbonyl group, a $C_{1-10}$ alkylsulfonyl group, a $C_{1-10}$ alkylsulfonylamino group, a $C_{1-10}$ alkylaminosulfonyl group, a mono- or di-$C_{1-10}$ alkylamino group, a $C_{2-14}$ aryl group, a $C_{2-14}$ aryloxy group or a $C_{2-9}$ heterocyclyl group (the thioalkyl group, the $C_{1-10}$ alkoxy group, the $C_{1-10}$ alkylcarbonyl group, the $C_{1-10}$ alkylcarbonyloxy group, the $C_{1-10}$ alkoxycarbonyl group, the $C_{1-10}$ alkylcarbonylamino group, the $C_{1-10}$ alkylaminocarbonyl group, the $C_{1-10}$ alkylsulfonyl group, the $C_{1-10}$ alkylsulfonylamino group, the $C_{1-10}$ alkylaminosulfonyl group, the mono- or di-$C_{1-10}$ alkylamino group, the $C_{2-14}$ aryl group, the $C_{2-14}$ aryloxy group and the $C_{2-9}$ heterocyclyl group may be substituted with one or more substituents selected from the group consisting of: $C_{1-10}$ alkyl groups, $C_{2-6}$ alkenyl groups, $C_{2-6}$ alkynyl groups, carboxyl groups, carbamoyl groups, sulfamoyl groups, phosphono groups, sulfo groups, tetrazole groups, formyl groups, nitro groups, cyano groups, halogen atoms, $C_{1-3}$ alkyl groups, $C_{1-3}$ alkoxy groups (the $C_{1-3}$ alkyl groups and $C_{1-3}$ alkoxy groups are substituted with at least one halogen atom), thiol groups, protected thiol groups, hydroxyl groups, protected hydroxyl groups, amino groups, protected amino groups, $C_{1-10}$ thioalkyl groups, $C_{1-10}$ alkoxy groups, $C_{1-10}$ alkylcarbonyl groups, $C_{1-10}$ alkylcarbonyloxy groups, $C_{1-10}$ alkoxycarbonyl groups, $C_{1-10}$ alkylcarbonylamino groups, $C_{1-10}$ alkylaminocarbonyl groups, $C_{1-10}$ alkylsulfonyl groups, $C_{1-10}$ alkylsulfonylamino groups, $C_{1-10}$ alkylaminosulfonyl groups, mono- or di-$C_{1-10}$ alkylamino groups, $C_{2-14}$ aryl groups, $C_{2-14}$ aryloxy groups and $C_{2-9}$ heterocyclyl groups (the $C_{2-14}$ aryl groups, the $C_{2-14}$ aryloxy groups and the $C_{2-9}$ heterocyclyl groups may be substituted with one or more $C_{1-6}$ alkyl groups, one or more $C_{1-6}$ alkoxy groups (the $C_{1-6}$ alkyl groups and the $C_{1-6}$ alkoxy groups may be substituted with one or more halogen atoms) or one or more halogen atoms)))), a $C_{2-14}$ aryl group (the $C_{2-14}$ aryl group may optionally be substituted with one or more substituents independently represented by $—V^2$ (wherein $V^2$ is a $C_{1-10}$ alkyl group, a $C_{2-6}$ alkenyl group, a $C_{2-6}$ alkynyl group (the $C_{1-10}$ alkyl group, the $C_{2-6}$ alkenyl group and the $C_{2-6}$ alkynyl group may be substituted with one or more halogen atoms) or $—V^3$ (wherein $V^3$ is the same as $V^1$, and $V^1$ is the same as defined above))) or a $C_{2-9}$ heterocyclyl group (the $C_{2-9}$ heterocyclyl group may optionally be substituted with one or more substituents independently represented by $—V^4$ (wherein $V^4$ is the same as $V^2$, and $V^2$ is the same as defined above)), $R^3$ is a $C_{2-14}$ aryl group (the $C_{2-14}$ aryl group is optionally substituted with one or more substituents independently represented by $—V^5$ (wherein $V^5$ is a hydrogen atom, a hydroxyl group, a protected hydroxyl group, an amino group, a protected amino group, a thiol group, a protected thiol group, a nitro group, a cyano group, a halogen atom, a carboxyl group, a carbamoyl group, a sulfamoyl group, a sulfo group, a formyl group, a $C_{1-10}$ alkyl group, a $C_{2-6}$ alkenyl group, a $C_{2-6}$ alkynyl group, a $C_{1-10}$ alkylcarbonyloxy group, a $C_{1-10}$ alkoxycarbonyl group, a $C_{1-10}$ alkoxy group, a $C_{1-10}$ alkylcarbonyl group, a $C_{1-10}$ alkylcarbonylamino group, a mono- or di-$C_{1-10}$ alkylamino group, a $C_{1-10}$ alkylaminosulfonyl group, a $C_{1-10}$ alkylaminocarbonyl group, a $C_{1-10}$ alkylsulfonylamino group, a $C_{1-10}$ thioalkyl group (the $C_{1-10}$ alkyl group, the $C_{2-6}$ alkenyl group, the $C_{2-6}$ alkynyl group, the $C_{1-10}$ alkylcarbonyloxy group, the $C_{1-10}$ alkoxycarbonyl group, the $C_{1-10}$ alkoxy group, the $C_{1-10}$ alkylcarbonyl group, the $C_{1-10}$ alkylcarbonylamino group, the mono- or di-$C_{1-10}$ alkylamino group, the $C_{1-10}$ alkylaminosulfonyl group, the $C_{1-10}$ alkylaminocarbonyl group, the $C_{1-10}$ alkylsulfonylamino group and the $C_{1-10}$ thioalkyl group may optionally be substituted with one or more substituents selected from the group consisting of: carboxyl groups, carbamoyl groups, sulfamoyl groups, sulfo groups, nitro groups, cyano groups, halogen atoms, $C_{1-10}$ alkoxy groups, $C_{1-10}$ alkylcarbonyl groups, $C_{1-10}$ alkylcarbonyloxy groups, $C_{1-10}$ alkoxycarbonyl groups, $C_{1-10}$ alkylcarbonylamino groups, amino groups, protected amino groups, mono- or di-$C_{1-10}$ alkylamino groups, hydroxyl groups, protected hydroxyl groups, $C_{2-14}$ aryl groups and $C_{2-14}$ aryloxy groups (the $C_{2-14}$ aryl groups and the $C_{2-14}$ aryloxy groups may be substituted with one or more $C_{1-6}$ alkyl groups (the $C_{1-6}$ alkyl groups may be substituted with one or more halogen atoms)) or one or more halogen atoms)), a $C_{2-14}$ aryl group or a $C_{2-14}$ aryloxy group (the $C_{2-14}$ aryl group and the $C_{2-14}$ aryloxy group may optionally be substituted with one or more substituents selected from the group consisting of: $C_{1-10}$ alkyl groups (the $C_{1-10}$ alkyl groups may be substituted with one or more halogen atoms), $C_{2-6}$ alkenyl groups, $C_{2-6}$ alkynyl groups, carboxyl groups, nitro groups, cyano groups, halogen atoms, $C_{1-10}$ alkoxy groups, $C_{1-10}$ alkylcarbonyl groups, $C_{1-10}$ alkylcarbonyloxy groups, $C_{1-10}$ alkoxycarbonyl groups, $C_{1-10}$ alkylcarbonylamino groups, amino groups, protected amino groups, mono- or di-$C_{1-10}$ alkylamino groups, hydroxyl groups, protected hydroxyl groups, $C_{2-14}$ aryl groups and $C_{2-14}$ aryloxy groups)) and with one or more substituents independently represented by $—W^1(CW^2W^3)_{p1}W^4$ (wherein $W^1$ is $(CR^4R^5)_{q1}$ (wherein each of $R^4$ and $R^5$ is independently a hydrogen atom or a $C_{1-6}$ alkyl group (the $C_{1-6}$ alkyl group may be substituted with one or more halogen atoms), $q_1$ is 0, 1, 2, or 3), an oxygen atom, a sulfur atom or $NR^6$ (wherein $R^6$ is a hydrogen atom, a $C_{1-6}$ alkyl group, a formyl group or a $C_{1-6}$ alkylcarbonyl group), each of $W^2$ and $W^3$ is independently a hydrogen atom or a $C_{1-3}$ alkyl group (the $C_{1-3}$ alkyl group may be substituted with one or more halogen atoms), p1 is 0, 1, 2 or 3, and $W^4$ is $SO_2R^7$, $SOR^7$ or $COR^7$ (wherein $R^7$ is $NR^8R^9$ (wherein each of $R^8$ and $R^9$ is independently a hydrogen atom, a hydroxyl group, a formyl group, a $C_{1-10}$ alkyl group, a $C_{2-6}$ alkenyl group, a $C_{2-6}$ alkynyl group, a $C_{1-10}$ alkoxy group, a $C_{1-10}$ alkylcarbonyloxy group, a $C_{1-10}$ alkoxycarbonyl group, a $C_{1-10}$ alkylcarbonyl group (the $C_{1-10}$ alkyl group, the $C_{2-6}$ alkenyl group, the $C_{2-6}$ alkynyl group, the $C_{1-10}$ alkoxy group, the $C_{1-10}$ alkylcarbonyloxy group, the $C_{1-10}$ alkoxycarbonyl group and the $C_{1-10}$ alkylcarbonyl group may optionally be substituted with one or more substituents selected from the group consisting of: carboxyl groups, nitro groups, cyano groups, halogen atoms, $C_{1-10}$ alkoxy groups, $C_{1-10}$ alkylcarbonyl groups, $C_{1-10}$ alkylcarbonyloxy groups, $C_{1-10}$ alkoxycarbonyl groups, $C_{1-10}$ alkylcarbonylamino groups, amino groups, protected amino groups, mono- or di-$C_{1-10}$ alkylamino groups, hydroxyl groups, protected hydroxyl groups, $C_{2-14}$ aryl groups and $C_{2-14}$ aryloxy groups (the $C_{2-14}$ aryl groups and the $C_{2-14}$ aryloxy groups may optionally be substituted with one or more substituents selected from the group consisting of $C_{1-10}$ alkyl groups, $C_{1-10}$ alkoxy groups (the $C_{1-10}$ alkyl groups and the $C_{1-10}$ alkoxy groups may be substituted with one or more halogen atoms), $C_{2-6}$ alkenyl groups, $C_{2-6}$ alkynyl groups, carboxyl groups, carbamoyl groups, sulfo groups, sulfamoyl groups, tetrazole groups, nitro groups, cyano groups, halogen atoms, $C_{1-10}$ alkylcarbonyl groups, $C_{1-10}$ alkylcarbonyloxy groups, $C_{1-10}$ alkoxycarbonyl groups, $C_{1-10}$ alkylcarbonylamino groups, amino groups, protected amino groups, mono- or di-$C_{1-10}$ alkylamino groups, hydroxyl groups, protected hydroxyl groups, $C_{2-14}$ aryl groups and $C_{2-14}$ aryloxy groups)) or a $C_{2-14}$ aryl group (the $C_{2-14}$ aryl group may optionally be substituted with one or more substituents selected from the group consisting of: $C_{1-10}$ alkyl groups (the $C_{1-10}$ alkyl groups may be substituted with one or more halogen atoms), $C_{2-6}$ alkenyl groups, $C_{2-6}$ alkynyl groups, carboxyl groups, nitro groups, cyano groups, halogen atoms, $C_{1-10}$ alkoxy groups, $C_{1-10}$ alkylcarbonyl groups, $C_{1-10}$ alkylcarbonyloxy groups, $C_{1-10}$ alkoxycarbonyl groups, $C_{1-10}$ alkylcarbonylamino groups, amino groups, protected amino groups, mono- or di-$C_{1-10}$ alkylamino groups, hydroxyl groups, protected hydroxyl groups, $C_{2-14}$ aryl groups and $C_{2-14}$ aryloxy groups), or $R^8$ and $R^9$ mean together with each other, —$(CH_2)_{m1}$—E—$(CH_2)_{m2}$— (wherein E is an oxygen atom, a sulfur atom, $CR^{10}R^{11}$ (wherein each of $R^{10}$ and $R^{11}$ is independently a hydrogen atom, a $C_{1-10}$ alkyl group, a $C_{2-14}$ aryl group, a $C_{1-10}$ alkoxy group, a $C_{2-14}$ aryloxy group, a hydroxyl group or a protected hydroxyl group) or $NR^{12}$ (wherein $R^{12}$ is a hydrogen atom, a hydroxyl group, a formyl group, a $C_{1-10}$ alkyl group, a $C_{2-6}$ alkenyl group, a $C_{2-6}$ alkynyl group, a $C_{1-10}$ alkoxy group, a $C_{1-10}$ alkylcarbonyloxy group, a $C_{1-10}$ alkoxycarbonyl group, a $C_{1-10}$ alkylcarbonyl group (the $C_{1-10}$ alkyl group, the $C_{2-6}$ alkenyl group, the $C_{2-6}$ alkynyl group, the $C_{1-10}$ alkoxy group, the $C_{1-10}$ alkylcarbonyloxy group, the $C_{1-10}$ alkoxycarbonyl group and the $C_{1-10}$ alkylcarbonyl group may optionally be substituted with one or more substituents selected from the group consisting of: carboxyl groups, nitro groups, cyano groups, halogen atoms, $C_{1-10}$ alkoxy groups, $C_{1-10}$ alkylcarbonyl groups, $C_{1-10}$ alkylcarbonyloxy groups, $C_{1-10}$ alkoxycarbonyl groups, $C_{1-10}$ alkylcarbonylamino groups, amino groups, protected amino groups, mono- or di-$C_{1-10}$ alkylamino groups, hydroxyl groups, protected hydroxyl groups, $C_{2-14}$ aryl groups and $C_{2-14}$ aryloxy groups (the $C_{2-14}$ aryl groups and the $C_{2-14}$ aryloxy groups may be substituted with one or more $C_{1-6}$ alkyl groups (the $C_{1-6}$ alkyl groups may be substituted with one or more halogen atoms) or one or more halogen atoms)) or a $C_{2-14}$ aryl group (the $C_{2-14}$ aryl group may optionally be substituted with one or more substituents selected from the group consisting of: $C_{1-10}$ alkyl groups (the $C_{1-10}$ alkyl groups may be substituted with one or more halogen atoms), $C_{2-6}$ alkenyl groups, $C_{2-6}$ alkynyl groups, carboxyl groups, nitro groups, cyano groups, halogen atoms, $C_{1-10}$ alkoxy groups, $C_{1-10}$ alkylcarbonyl groups, $C_{1-10}$ alkylcarbonyloxy groups, $C_{1-10}$ alkoxycarbonyl groups, $C_{1-10}$ alkylcarbonylamino groups, amino groups, protected amino groups, mono- or di-$C_{1-10}$ alkylamino groups, hydroxyl groups, protected hydroxyl groups, $C_{2-14}$ aryl groups and $C_{2-14}$ aryloxy groups)), and each of m1 and m2 is independently an integer of from 0 to 5 provided that m1+m2 is 2, 3, 4 or 5))))), or a $C_{2-14}$ aryl group (the $C_{2-14}$ aryl group is optionally substituted with one or more substituents independently represented by —$V^5$ (wherein $V^5$ is the same as defined above) and with one or more substituents independently represented by —$W^5(CW^6W^7)_{p2}W^8$ (wherein $W^5$ is $(CR^{13}R^{14})_{q2}$ (wherein each of $R^{13}$ and $R^{14}$ is independently a hydrogen atom, a hydroxyl group, an amino group, a $C_{1-6}$ alkyl group or a $C_{1-6}$ alkoxy group (the $C_{1-6}$ alkyl group and the $C_{1-6}$ alkoxy group may be substituted with one or more halogen atoms), and q2 is 0, 1, 2 or 3), an oxygen atom, a sulfur atom or $NR^{15}$ (wherein $R^{15}$ is a hydrogen atom, a $C_{1-6}$ alkyl group, a formyl group or a $C_{1-6}$ alkylcarbonyl group), each of $W^6$ and $W^7$ is independently a hydrogen atom or a $C_{1-3}$ alkyl group (the $C_{1-3}$ alkyl group may be substituted with one or more halogen atoms), p2 is 0, 1, 2 or 3, and $W^8$ is $SO_2R^{16}$, $SOR^{16}$ or $COR^{16}$ (wherein $R^{16}$ is $NR^{17}R^{18}$ (wherein $R^{17}$ is a hydrogen atom, a hydroxyl group, a formyl group, a $C_{1-10}$ alkyl group, a $C_{2-6}$ alkenyl group, a $C_{2-6}$ alkynyl group, a $C_{1-10}$ alkylcarbonyloxy group, a $C_{1-10}$ alkoxycarbonyl group, a $C_{1-10}$ alkylcarbonyl group (the $C_{1-10}$ alkyl group, the $C_{2-6}$ alkenyl group, the $C_{2-6}$ alkynyl group, the $C_{1-10}$ alkylcarbonyloxy group, the $C_{1-10}$ alkoxycarbonyl group and the $C_{1-10}$ alkylcarbonyl group may optionally be substituted with one or more substituents selected from the group consisting of: carboxyl groups, nitro groups, cyano groups, halogen atoms, $C_{1-10}$ alkoxy groups, $C_{1-10}$ alkylcarbonyl groups, $C_{1-10}$ alkylcarbonyloxy groups, $C_{1-10}$ alkoxycarbonyl groups, $C_{1-10}$ alkylcarbonylamino groups, amino groups, protected amino groups, mono- or di-$C_{1-10}$ alkylamino groups, hydroxyl groups, protected hydroxyl groups, $C_{2-14}$ aryl groups and $C_{2-14}$ aryloxy groups (the $C_{2-14}$ aryl groups and the $C_{2-14}$ aryloxy groups may optionally be substituted with one or more substituents selected from the group consisting of: $C_{1-10}$ alkyl groups, $C_{1-10}$ alkoxy groups, (the $C_{1-10}$ alkyl groups and the $C_{1-10}$ alkoxy groups may be substituted with one or more halogen atoms), $C_{2-6}$ alkenyl groups, $C_{2-6}$ alkynyl groups, carboxyl groups, carbamoyl groups, sulfo groups, sulfamoyl groups, tetrazole groups, nitro groups, cyano groups, halogen atoms, $C_{1-10}$ alkylcarbonyl groups, $C_{1-10}$ alkylcrabonyloxy groups, $C_{1-10}$ alkoxycarbonyl groups, $C_{1-10}$ alkylcarbonylamino groups, amino groups, protected amino groups, mono- or di-$C_{1-10}$ alkylamino groups, hydroxyl groups, protected hydroxyl groups, $C_{2-14}$ aryl groups and $C_{2-14}$ aryloxy groups)), a $C_{2-14}$ aryl group or a $C_{2-14}$ aryloxy group (the $C_{2-14}$ aryl group and the $C_{2-14}$ aryloxy group may optionally be substituted with one or more substituents selected from the group consisting of: $C_{1-10}$ alkyl groups (the $C_{1-10}$ alkyl groups may be substituted with one or more halogen atoms), $C_{2-6}$ alkenyl groups, $C_{2-6}$ alkynyl groups, carboxyl groups, nitro groups, cyano groups, halogen atoms, $C_{1-10}$ alkoxy groups, $C_{1-10}$ alkylcarbonyl groups, $C_{1-10}$ alkylcarbonyloxy groups, $C_{1-10}$ alkoxycarbonyl groups, $C_{1-10}$ alkylcarbonylamino groups, amino groups, protected amino groups, mono- or di-$C_{1-10}$ alkylamino groups, hydroxyl groups, protected hydroxyl groups, $C_{2-14}$ aryl groups and $C_{2-14}$ aryloxy groups), and $R^{18}$ is an amino group, a mono- or di-$C_{1-10}$ alkylamino group, a $C_{1-10}$ alkylcarbonylamino group, a $C_{1-10}$ alkylaminocarbonyl group, a $C_{2-9}$ heterocyclyl group (the mono- or di-$C_{1-10}$ alkylamino group, the $C_{1-10}$ alkylcarbonylamino group, the $C_{1-10}$ alkylaminocarbonyl group and the $C_{2-9}$ heterocyclyl group may be substituted with one or more substituents selected from the group consisting of: hydrogen atoms, carboxyl groups, carbamoyl groups, sulfamoyl groups, sulfo groups, nitro groups, cyano groups, halogen atoms, hydroxyl groups, formyl groups, $C_{1-10}$ alkyl groups, $C_{2-6}$ alkenyl groups, $C_{2-6}$ alkynyl groups, $C_{1-10}$ alkylcarbonyloxy groups, $C_{1-10}$ alkoxycarbonyl groups, $C_{1-10}$ alkylcarbonyl groups (the $C_{1-10}$ alkyl groups, the $C_{2-6}$ alkenyl groups, the $C_{2-6}$ alkynyl groups, the $C_{1-10}$ alkylcarbonyloxy groups, the $C_{1-10}$ alkoxycarbonyl groups and the $C_{1-10}$ alkylcarbonyl groups may optionally be substituted with one or more substituents selected from the group consisting of: carboxyl groups, nitro groups, cyano groups, halogen atoms, $C_{1-10}$ alkoxy groups, $C_{1-10}$ alkylcarbonyl groups, $C_{1-10}$ alkylcarbonyloxy groups, $C_{1-10}$ alkoxycarbonyl groups, $C_{1-10}$ alkylcarbonylamino groups, amino groups, protected amino groups, mono- or di-$C_{1-10}$ alkylamino groups, hydroxyl groups, protected hydroxyl groups, $C_{2-14}$ aryl groups and $C_{2-14}$ aryloxy groups (the $C_{2-14}$ aryl groups and the $C_{2-14}$ aryloxy groups may be substituted with one or more $C_{1-6}$ alkyl groups (the $C_{1-6}$ alkyl groups may be substituted with one or more halogen atoms) or one or more halogen atoms)), $C_{2-14}$ aryl groups and $C_{2-14}$ aryloxy groups (the $C_{2-14}$ aryl groups and the $C_{2-14}$ aryloxy groups may optionally be substituted with one or more substituents selected from the group consisting of: $C_{1-10}$ alkyl groups (the $C_{1-10}$ alkyl groups may be substituted with one or more halogen atoms), $C_{2-6}$ alkenyl groups, $C_{2-6}$ alkynyl groups, carboxyl groups, nitro groups, cyano groups, halogen atoms, $C_{1-10}$ alkoxy groups, $C_{1-10}$ alkylcarbonyl groups, $C_{1-10}$ alkylcarbonyloxy groups, $C_{1-10}$ alkoxycarbonyl groups, $C_{1-10}$ alkylcarbonylamino groups, amino groups, protected amino groups, mono- or di-$C_{1-10}$ alkylamino groups, hydroxyl groups, protected hydroxyl groups, $C_{2-14}$ aryl groups and $C_{2-14}$ aryloxy groups)), a $C_{1-10}$ alkyl group, a $C_{2-6}$ alkenyl group, a $C_{2-6}$ alkynyl group, a $C_{1-10}$ alkylcarbonyloxy group, a $C_{1-10}$ alkoxycarbonyl group, a $C_{1-10}$ alkylcarbonyl group (the $C_{1-10}$ alkyl group, the $C_{2-6}$ alkenyl group, the $C_{2-6}$ alkynyl group, the $C_{1-10}$ alkylcarbonyloxy group, the $C_{1-10}$ alkoxycarbonyl group and the $C_{1-10}$ alkylcarbonyl group are optionally substituted with one or more substituents selected from the group consisting of: hydrogen atoms, carboxyl groups, carbamoyl groups, sulfamoyl groups, sulfo groups, nitro groups, cyano groups, halogen atoms, hydroxyl groups, formyl groups, $C_{1-10}$ alkyl groups, $C_{2-6}$ alkenyl groups, $C_{2-6}$ alkynyl groups, $C_{1-10}$ alkylcarbonyloxy groups, $C_{1-10}$ alkoxycarbonyl groups, $C_{1-10}$ alkylcarbonyl groups (the $C_{1-10}$ alkyl groups, the $C_{2-6}$ alkenyl groups, the $C_{2-6}$ alkynyl groups, the $C_{1-10}$ alkylcarbonyloxy groups, the $C_{1-10}$ alkoxycarbonyl groups and the $C_{1-10}$ alkylcarbonyl groups may optionally be substituted with one or more substituents selected from the group consisting of: carboxyl groups, nitro groups, cyano groups, halogen atoms, $C_{1-10}$ alkoxy groups, $C_{1-10}$ alkylcarbonyl groups, $C_{1-10}$ alkylcarbonyloxy groups, $C_{1-10}$ alkoxycarbonyl groups, $C_{1-10}$ alkylcarbonylamino groups, amino groups, protected amino groups, mono- or di-$C_{1-10}$ alkylamino groups, hydroxyl groups, protected hydroxyl groups, $C_{2-14}$ aryl groups and $C_{2-14}$ aryloxy groups (the $C_{2-14}$ aryl groups and the $C_{2-14}$ aryloxy groups may be substituted with one or more $C_{1-6}$ alkyl groups (the $C_{1-6}$ alkyl groups may be substituted with one or more halogen atoms) or one or more halogen atoms)), $C_{2-14}$ aryl groups and $C_{2-14}$ aryloxy groups (the $C_{2-14}$ aryl groups and the $C_{2-14}$ aryloxy groups may optionally be substituted with one or more substituents selected from the group consisting of: $C_{1-10}$ alkyl groups (the $C_{1-10}$ alkyl groups may be substituted with one or more halogen atoms), $C_{2-6}$ alkenyl groups, $C_{2-6}$ alkynyl groups, carboxyl groups, nitro groups, cyano groups, halogen atoms, $C_{1-10}$ alkoxy groups, $C_{1-10}$ alkylcarbonyl groups, $C_{1-10}$ alkylcarbonyloxy groups, $C_{1-10}$ alkoxycarbonyl groups, $C_{1-10}$ alkylcarbonylamino groups, amino groups, protected amino groups, mono- or di-$C_{1-10}$ alkylamino groups, hydroxyl groups, protected hydroxyl groups, $C_{2-14}$ aryl groups and $C_{2-14}$ aryloxy groups) and with one or more substituents selected from the group consisting of: carboxyl groups, carbamoyl groups, sulfo groups, sulfamoyl groups and $C_{2-9}$ heterocyclyl groups (the $C_{2-9}$ heterocyclyl groups may optionally be substituted with one or more substituents selected from the group consisting of: hydrogen atoms, hydroxyl groups, protected hydroxyl groups, formyl groups, $C_{1-10}$ alkyl groups, $C_{2-6}$ alkenyl groups, $C_{2-6}$ alkynyl groups, $C_{1-10}$ alkylcarbonyloxy groups, $C_{1-10}$ alkoxycarbonyl groups, $C_{1-10}$ alkylcarbonyl groups, $C_{2-9}$ heterocyclyl groups (the $C_{1-10}$ alkyl groups, the $C_{2-6}$ alkenyl groups, the $C_{2-6}$ alkynyl groups, the $C_{1-10}$ alkylcarbonyloxy groups, the $C_{1-10}$ alkoxycarbonyl groups, the $C_{1-10}$ alkylcarbonyl groups and the $C_{2-9}$ heterocyclyl groups may optionally be substituted with one or more substituents selected from the group consisting of: hydrogen atoms, carboxyl groups, carbamoyl groups, sulfamoyl groups, sulfo groups, nitro groups, cyano groups, halogen atoms, $C_{1-10}$ alkoxy groups, $C_{1-10}$ alkylcarbonyl groups, $C_{1-10}$ alkylcarbonyloxy groups, $C_{1-10}$ alkoxycarbonyl groups, $C_{1-10}$ alkylcarbonylamino groups, amino groups, protected amino groups, mono- or di-$C_{1-10}$ alkylamino groups, hydroxyl groups, protected hydroxyl groups, $C_{2-14}$ aryl groups and $C_{2-14}$ aryloxy groups (the $C_{2-14}$ aryl groups and the $C_{2-14}$ aryloxy groups may be substituted with one or more $C_{1-6}$ alkyl groups (the $C_{1-6}$ alkyl groups may be substituted with one or more halogen atoms) or one or more halogen atoms)), $C_{2-14}$ aryl groups and $C_{2-14}$ aryloxy groups (the $C_{2-14}$ aryl groups and the $C_{2-14}$ aryloxy groups may optionally be substituted with one or more substituents selected from the group consisting of: $C_{1-10}$ alkyl groups (the $C_{1-10}$ alkyl groups may be substituted with one or more halogen atoms), $C_{2-6}$ alkenyl groups, $C_{2-6}$ alkynyl groups, carboxyl groups, nitro groups, cyano groups, halogen atoms, $C_{1-10}$ alkoxy groups, $C_{1-10}$ alkylcarbonyl groups, $C_{1-10}$ alkylcarbonyloxy groups, $C_{1-10}$ alkoxycarbonyl groups, $C_{1-10}$ alkylcarbonylamino groups, amino groups, protected amino groups, mono- or di-$C_{1-10}$ alkylamino groups, hydroxyl groups, protected hydroxyl groups, $C_{2-14}$ aryl groups and $C_{2-14}$ aryloxy groups))), or $R^{17}$ and $R^{18}$ mean, together with each other, —$(CH_2)_{m3}$—G—$(CH_2)_{m4}$— (wherein G is $CR^{19}R^{20}$ (wherein $R^{19}$ is a hydrogen atom, a $C_{1-10}$ alkyl group, a $C_{2-14}$ aryl group, a $C_{1-10}$ alkoxy group, a $C_{2-14}$ aryloxy group (the $C_{1-10}$ alkyl group, the $C_{2-14}$ aryl group, the $C_{1-10}$ alkoxy group and the $C_{2-14}$ aryloxy group may optionally be substituted with one or more substituents selected from the group consisting of: carboxyl groups, nitro groups, cyano groups, halogen atoms, $C_{1-10}$ alkoxy groups, $C_{1-10}$ alkylcarbonyl groups, $C_{1-10}$ alkylcarbonyloxy groups, $C_{1-10}$ alkoxycarbonyl groups, $C_{1-10}$ alkylcarbonylamino groups, amino groups, mono- or di-$C_{1-10}$ alkylamino groups, $C_{2-14}$ aryl groups and $C_{2-14}$ aryloxy groups (the $C_{2-14}$ aryl groups and the $C_{2-14}$ aryloxy groups may be substituted with one or more $C_{1-6}$ alkyl groups (the $C_{1-6}$ alkyl groups may be substituted with one or more halogen atoms) or one or more halogen atoms)), a hydroxyl group or a protected hydroxyl group, and $R^{20}$ is an amino group, a mono- or di-$C_{1-10}$ alkylamino group, a $C_{1-10}$ alkylcarbonylamino group, a $C_{1-10}$ alkylaminocarbonyl group or a $C_{2-9}$ heterocyclyl group (the mono- or di-$C_{1-10}$ alkylamino group, the $C_{1-10}$ alkylcarbonylamino group, the $C_{1-10}$ alkylaminocarbonyl group and the $C_{2-9}$ heterocyclyl group may be substituted with one or more substituents selected from the group consisting of: hydrogen atoms, carboxyl groups, carbamoyl groups, sulfamoyl groups, sulfo groups, nitro groups, cyano groups, halogen atoms, amino groups, hydroxyl groups, formyl groups, $C_{1-10}$ alkyl groups, $C_{2-6}$ alkenyl groups, $C_{2-6}$ alkynyl groups, $C_{1-10}$ alkylcarbonyloxy groups, $C_{1-10}$ alkoxycarbonyl groups, $C_{1-10}$ alkylcarbonyl groups (the $C_{1-10}$ alkyl groups, the $C_{2-6}$ alkenyl groups, the $C_{2-6}$ alkynyl groups, the $C_{1-10}$ alkylcarbonyloxy groups, the $C_{1-10}$ alkoxycarbonyl groups and the $C_{1-10}$ alkylcarbonyl groups may optionally be substituted with one or more substituents selected from the group consisting of: carboxyl groups, nitro groups, cyano groups, halogen atoms, $C_{1-10}$ alkoxy groups, $C_{1-10}$ alkylcarbonyl groups, $C_{1-10}$ alkylcarbonyloxy groups, $C_{1-10}$ alkoxycarbonyl groups, $C_{1-10}$ alkylcarbonylamino groups, amino groups, protected amino groups, mono- or di-$C_{1-10}$ alkylamino groups, hydroxyl groups, protected hydroxyl groups, $C_{2-14}$ aryl groups and $C_{2-14}$ aryloxy groups (the $C_{2-14}$ aryl groups and the $C_{2-14}$ aryloxy groups may be substituted with one or more $C_{1-6}$ alkyl groups (the $C_{1-6}$ alkyl groups may be substituted with one or more halogen atoms) or one or more halogen atoms)), $C_{2-14}$ aryl groups and $C_{2-14}$ aryloxy groups (the $C_{2-14}$ aryl groups and the $C_{2-14}$ aryloxy groups may optionally be substituted with one or more substituents selected from the group consisting of: $C_{1-10}$ alkyl groups (the $C_{1-10}$ alkyl groups may be substituted with one or more halogen atoms), $C_{2-6}$ alkenyl groups, $C_{2-6}$ alkynyl groups, carboxyl groups, nitro groups, cyano groups, halogen atoms, $C_{1-10}$ alkoxy groups, $C_{1-10}$ alkylcarbonyl groups, $C_{1-10}$ alkylcarbonyloxy groups, $C_{1-10}$ alkoxycarbonyl groups, $C_{1-10}$ alkylcarbonylamino groups, amino groups, protected amino groups, mono- or di-$C_{1-10}$ alkylamino groups, hydroxyl groups, protected hydroxyl groups, $C_{2-14}$ aryl groups and $C_{2-14}$ aryloxy groups))) or $NR^{21}$ (wherein $R^{21}$ is an amino group, a mono- or di-$C_{1-10}$ alkylamino group, a $C_{1-10}$ alkylcarbonylamino group, a $C_{1-10}$ alkylaminocarbonyl group or a $C_{2-9}$ heterocyclyl group (the mono- or di-$C_{1-10}$ alkylamino group, the $C_{1-10}$ alkylcarbonylamino group, the $C_{1-10}$ alkylaminocarbonyl group and the $C_{2-9}$ heterocyclyl group may be substituted with one or more substituents selected from the group consisting of: hydrogen atoms, carboxyl groups, carbamoyl groups, sulfamoyl groups, sulfo groups, nitro groups, cyano groups, halogen atoms, amino groups, hydroxyl groups, formyl groups, $C_{1-10}$ alkyl groups, $C_{2-6}$ alkenyl groups, $C_{2-6}$ alkynyl groups, $C_{1-10}$ alkylcarbonyloxy groups, $C_{1-10}$ alkoxycarbonyl groups, $C_{1-10}$ alkylcarbonyl groups (the $C_{1-10}$ alkyl groups, the $C_{2-6}$ alkenyl groups, the $C_{2-6}$ alkynyl groups, the $C_{1-10}$ alkylcarbonyloxy groups, the $C_{1-10}$ alkoxycarbonyl groups and the $C_{1-10}$ alkylcarbonyl groups may optionally be substituted with one or more substituents selected from the group consisting of: carboxyl groups, nitro groups, cyano groups, halogen atoms, $C_{1-10}$ alkoxy groups, $C_{1-10}$ alkylcarbonyl groups, $C_{1-10}$ alkylcarbonyloxy groups, $C_{1-10}$ alkoxycarbonyl groups, $C_{1-10}$ alkylcarbonylamino groups, amino groups, protected amino groups, mono- or di-$C_{1-10}$ alkylamino groups, hydroxyl groups, protected hydroxyl groups, $C_{2-14}$ aryl groups and $C_{2-14}$ aryloxy groups (the $C_{2-14}$ aryl groups and the $C_{2-14}$ aryloxy groups may be substituted with one or more $C_{1-6}$ alkyl groups (the $C_{1-6}$ alkyl groups may be substituted with one or more halogen atoms) or one or more halogen atoms)), $C_{2-14}$ aryl groups and $C_{2-14}$ aryloxy groups (the $C_{2-14}$ aryl groups and the $C_{2-14}$ aryloxy groups may optionally be substituted with one or more substituents selected from the group consisting of: $C_{1-10}$ alkyl groups (the $C_{1-10}$ alkyl groups may be substituted with one or more halogen atoms), $C_{2-6}$ alkenyl groups, $C_{2-6}$ alkynyl groups, carboxyl groups, nitro groups, cyano groups, halogen atoms, $C_{1-10}$ alkoxy groups, $C_{1-10}$ alkylcarbonyl groups, $C_{1-10}$ alkylcarbonyloxy groups, $C_{1-10}$ alkoxycarbonyl groups, $C_{1-10}$ alkylcarbonylamino groups, amino groups, protected amino groups, mono- or di-$C_{1-10}$ alkylamino groups, hydroxyl groups, protected hydroxyl groups, $C_{2-14}$ aryl groups and $C_{2-14}$ aryloxy groups))), and each of m3 and m4 is independently an integer of from 0 to 5, provided that m3+m4 is 2, 3, 4 or 5), or $NR^{17}R^{18}$, as a whole, means a nitrogen-containing $C_{2-9}$ cyclyl group (the nitrogen-containing $C_{2-9}$ cyclyl group may optionally be substituted with one or more hydrogen atoms and is substituted with two or three substituents independently selected from the group consisting of: hydroxyl groups, amino groups, protected amino groups, thiol groups, protected thiol groups, nitro groups, cyano groups, halogen atoms, carboxyl groups, carbamoyl groups, sulfamoyl groups, formyl groups, $C_{1-10}$ alkyl groups, $C_{2-6}$ alkenyl groups, $C_{2-6}$ alkynyl groups, $C_{1-10}$ alkoxy groups, $C_{1-10}$ alkylcarbonyloxy groups, $C_{1-10}$ alkoxycarbonyl groups, $C_{1-10}$ alkylcarbonyl groups, $C_{1-10}$ alkylcarbonylamino groups, mono- or di-$C_{1-10}$ alkylamino groups, $C_{1-10}$ alkylsulfonylamino groups, $C_{1-10}$ thioalkyl groups, $C_{2-9}$ heterocyclyl groups (the $C_{1-10}$ alkyl groups, the $C_{2-6}$ alkenyl groups, the $C_{2-6}$ alkynyl groups, the $C_{1-10}$ alkoxy groups, the $C_{1-10}$ alkylcarbonyloxy groups, the $C_{1-10}$ alkoxycarbonyl groups, the $C_{1-10}$ alkylcarbonyl groups, the $C_{1-10}$ alkylcarbonylamino groups, the mono- or di-$C_{1-10}$ alkylamino groups, the $C_{1-10}$ alkylsulfonylamino groups, the $C_{1-10}$ thioalkyl groups and the $C_{2-9}$ heterocyclyl groups may optionally be substituted with one or more substituents selected from the group consisting of: hydrogen atoms, carboxyl groups, carbamoyl groups, sulfamoyl groups, sulfo groups, nitro groups, cyano groups, halogen atoms, $C_{1-10}$ alkoxy groups, $C_{1-10}$ alkylcarbonyl groups, $C_{1-10}$ alkylcarbonyloxy groups, $C_{1-10}$ alkoxycarbonyl groups, $C_{1-10}$ alkylcarbonylamino groups, amino groups, protected amino groups, mono- or di-$C_{1-10}$ alkylamino groups, hydroxyl groups, protected hydroxyl groups, $C_{2-14}$ aryl groups and $C_{2-14}$ aryloxy groups)))))), $L^1$ means the formula (II):

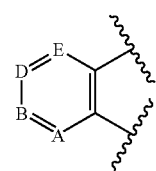

(II)

(the substituent represented by the formula (II) may be fused with a $C_{2-14}$ aryl group, a $C_{3-7}$ carbocyclyl group or a $C_{2-9}$ heterocyclyl group (the $C_{2-14}$ aryl group, the $C_{3-7}$ carbocyclyl group and the $C_{2-9}$ heterocyclyl group may optionally be substituted with one or more substituents independently represented by —$V^6$ (wherein $V^6$ is the same as $V^2$, and $V^2$ is the same as defined above)) at any two positions, and each of A, B, D and E is independently $CR^{22}$ (wherein $R^{22}$ is a hydrogen atom, a carboxyl group, a carbamoyl group, a sulfamoyl group, a thiol group, a phosphono group, a sulfo group, a teterazole group, a formyl group, a nitro group, a cyano group, a halogen atom, a $C_{1-3}$ alkyl group, a $C_{1-3}$ alkoxy group (the $C_{1-3}$ alkyl group and the $C_{1-3}$ alkoxy group are substituted with at least one halogen atom), a $C_{1-10}$ alkoxy group, a $C_{1-10}$ alkylcarbonyl group, a $C_{1-10}$ alkylcarbonyloxy group, a $C_{1-10}$ alkoxycarbonyl group, a $C_{1-10}$ alkylcarbonylamino group, a $C_{1-10}$ alkylaminocarbonyl group, a $C_{1-10}$ alkylsulfonyl group, a $C_{1-10}$ alkylsulfonylamino group, a $C_{1-10}$ alkylaminosulfonyl group, an amino group, a protected amino group, a mono- or di-$C_{1-10}$ alkylamino group, a hydroxyl group, a protected hydroxyl group, a $C_{1-10}$ alkyl group, a $C_{2-6}$ alkenyl group, a $C_{2-6}$ alkynyl group (the $C_{1-10}$ alkoxy group, the $C_{1-10}$ alkylcarbonyl group, the $C_{1-10}$ alkylcarbonyloxy group, the $C_{1-10}$ alkoxycarbonyl group, the $C_{1-10}$ alkylcarbonylamino group, the $C_{1-10}$ alkylaminocarbonyl group, the $C_{1-10}$ alkylsulfonyl group, the $C_{1-10}$ alkylsulfonylamino group, the $C_{1-10}$ alkylaminosulfonyl group, the amino group, the protected amino group, the mono- or di-$C_{1-10}$ alkylamino group, the hydroxyl group, the protected hydroxyl group, the $C_{1-10}$ alkyl group, the $C_{2-6}$ alkenyl group and the $C_{2-6}$ alkynyl group may optionally be substituted with one or more substituents represented by —$V^7$ (wherein $V^7$ is the same as $V^1$, and $V^1$ is the same as defined above)), a $C_{2-14}$ aryl group, a $C_{2-14}$ aryloxy group or a $C_{2-9}$ heterocyclyl group (the $C_{2-14}$ aryl group, the $C_{2-14}$ aryloxy group and the $C_{2-9}$ heterocyclyl group may be substituted with one or more substituents independently represented by —$V^8$ (wherein $V^8$ is the same as $V^2$, and $V^2$ is the same as defined above))) or a nitrogen atom, or A=B or D=E, as a whole, means an oxygen atom, a sulfur atom or $NR^{23}$ (wherein $R^{23}$ is the same as $R^{22}$, and $R^{22}$ is the same as defined above)), $L^2$ is a single bond, $CR^{24}C^{25}$ (wherein each of $R^{24}$ and $R^{25}$ is independently a hydrogen atom, a $C_{1-3}$ alkyl group (the $C_{1-3}$ alkyl group may optionally be substituted with one or more halogen atoms) or a halogen atom), an oxygen atom, a sulfur atom or $NR^{26}$ (wherein $R^{26}$ is a hydrogen atom, a formyl group or a $C_{1-3}$ alkyl group (the $C_{1-3}$ alkyl group may optionally be substituted with one or more halogen atoms)), X is $OR^{27}$, $SR^{27}$ (wherein $R^{27}$ is a hydrogen atom, a $C_{1-10}$ alkyl group, a $C_{2-6}$ alkenyl group, a $C_{2-6}$ alkynyl group or a $C_{1-10}$ alkylcarbonyl group (the $C_{1-10}$ alkyl group, the $C_{2-6}$ alkenyl group, the $C_{2-6}$ alkynyl group and the $C_{1-10}$ alkylcarbonyl group may optionally be substituted with one or more substituents independently represented by —$V^9$ (wherein $V^9$ is the same as $V^1$, and $V^1$ is the same as defined above))), $NR^{28}N^{29}$ (wherein each of $R^{28}$ and $N^{29}$ is independently a hydrogen atom, a formyl group, a $C_{1-10}$ alkyl group, a $C_{2-6}$ alkenyl group, a $C_{2-6}$ alkynyl group, a $C_{1-10}$ alkoxy group, a $C_{1-10}$ alkylcarbonyl group (the $C_{1-10}$ alkyl group, the $C_{2-6}$ alkenyl group, the $C_{2-6}$ alkynyl group, the $C_{1-10}$ alkoxy group and the $C_{1-10}$ alkylcarbonyl group may optionally be substituted with one or more substituents independently represented by —$V^{10}$ (wherein $V^{10}$ is the same as $V^1$, and $V^1$ is the same as defined above)), a $C_{2-14}$ aryl group or a $C_{2-9}$ heterocyclyl group (the $C_{2-14}$ aryl group and the $C_{2-9}$ heterocyclyl group may optionally be substituted with one or more substituents independently represented by —$V^{11}$ (wherein $V^{11}$ is the same as $V^2$, and $V^2$ is the same as defined above))), a $C_{2-9}$ heterocyclyl group (the $C_{2-9}$ heterocyclyl group may optionally be substituted with one or more substituents independently represented by —$V^{12}$ (wherein $V^{12}$ is the same as $V^1$, and $V^1$ is the same as defined above)), $COR^{30}$ or $SO_2R^{31}$ (wherein each of $R^{30}$ and $R^{31}$ is independently a hydrogen atom, a hydroxyl group, a protected hydroxyl group, am amino group, a protected amino group, a $C_{1-10}$ alkyl group, a $C_{2-6}$ alkenyl group, a $C_{2-6}$ alkynyl group, a $C_{1-3}$ alkyl group, a $C_{1-3}$ alkoxy group (the $C_{1-3}$ alkyl group and the $C_{1-3}$ alkoxy group are substituted with at least one halogen atom), a $C_{1-10}$ alkoxy group, a mono- or di-$C_{1-10}$ alkylamino group, a $C_{2-14}$ aryl group, a $C_{2-14}$ aryloxy group or a $C_{2-9}$ heterocyclyl group (the $C_{1-10}$ alkoxy group, the mono- or di-$C_{1-10}$ alkylamino group, the $C_{2-14}$ aryl group, the $C_{2-14}$ aryloxy group and the $C_{2-9}$ heterocyclyl group may optionally be substituted with one or more substituents independently represented by —$V^{13}$ (wherein $V^{13}$ is the same as $V^1$, and $V^1$ is the same as defined above))), and Y is an oxygen atom, a sulfur atom or $NR^{32}$ (wherein $R^{32}$ is a hydrogen atom, a formyl group, a hydroxyl group, a $C_{1-10}$ alkyl group, a $C_{2-6}$ alkenyl group, a $C_{2-6}$ alkynyl group, a $C_{1-10}$ alkoxy group, a $C_{1-10}$ alkylcarbonyl group, a $C_{1-10}$ alkylcarbonyloxy group, a $C_{1-10}$ alkoxycarbonyl group, a $C_{1-10}$ alkylcarbonylamino group, a $C_{1-10}$ alkylaminocaronyl group, a $C_{1-10}$ alkylsulfonyl group, a $C_{1-10}$ alkylsulfonylamino group, a $C_{1-10}$ alkylaminosulfonyl group, a mono- or di-$C_{1-10}$ alkylamino group, a $C_{2-14}$ aryl group, a $C_{2-14}$ aryloxy group or a $C_{2-9}$ heterocyclyl group (the $C_{1-10}$ alkyl group, the $C_{2-6}$ alkenyl group, the $C_{2-6}$ alkynyl group, the $C_{1-10}$ alkoxy group, the $C_{1-10}$ alkylcarbonyl group, the $C_{1-10}$ alkylcarbonyloxy group, the $C_{1-10}$ alkoxycarbonyl group, the $C_{1-10}$ alkylcarbonylamino group, the $C_{1-10}$ alkylaminocaronyl group, the $C_{1-10}$ alkylsulfonyl group, the $C_{1-10}$ alkylsulfonylamino group, the $C_{1-10}$ alkylaminosulfonyl group, the mono- or di-$C_{1-10}$ alkylamino group, the $C_{2-14}$ aryl group, the $C_{2-14}$ aryloxy group and the $C_{2-9}$ heterocyclyl group may optionally be substituted with one or more substituents independently represented by —$V^{14}$ (wherein $V^{14}$ is the same as $V^1$, and $V^1$ is the same as defined above)))], a tautomer, prodrug or pharmaceutically acceptable salt of the compound or a solvate thereof.

2. The compound according to 1 mentioned above, wherein $L^2$ is a single bond, $R^1$ is a hydrogen atom, a $C_{1-10}$ alkyl group, a $C_{1-10}$ alkoxy group, a $C_{1-3}$ alkyl group or a $C_{1-3}$ alkoxy group (the $C_{1-3}$ alkyl group and the $C_{1-3}$ alkoxy group are substituted with at least one halogen atom), $R^2$ is a hydrogen atom, X is OH, and Y is an oxygen atom, a tautomer, prodrug or pharmaceutically acceptable salt of the compound or a solvate thereof.

3. The compound according to 2 mentioned above, wherein $L^1$ means the formula (II):

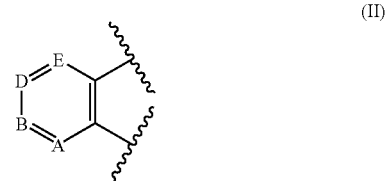

(II)

(wherein D is a nitrogen atom, E is $CR^{33}$ (wherein $R^{33}$ is the same as $R^{22}$, and $R^{22}$ is the same as defined above), and A=B, as a whole, means $NR^{34}$ (wherein $R^{34}$ is the same as $R^{23}$, and $R^{23}$ is the same as defined above)), a tautomer, prodrug or pharmaceutically acceptable salt of the compound or a solvate thereof.

4. The compound according to 2 mentioned above, wherein $L^1$ means the formula (II):

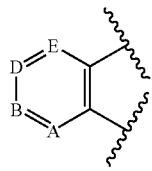

(II)

(wherein D is a nitrogen atom, E is $CR^{33}$ (wherein $R^{33}$ is a hydrogen atom, a $C_{1-3}$ alkyl group, a $C_{1-3}$ alkoxy group (the $C_{1-3}$ alkyl group and the $C_{1-3}$ alkoxy group are substituted with at least one halogen atom), a $C_{1-10}$ alkoxy group, a $C_{1-10}$ alkyl group, a $C_{2-6}$ alkenyl group or a $C_{2-6}$ alkynyl group), and A=B, as a whole, means $NR^{34}$ (wherein $R^{34}$ is a $C_{2-14}$ aryl group or a $C_{2-9}$ heterocyclyl group (the $C_{2-14}$ aryl group and the $C_{2-9}$ heterocyclyl group may optionally be substituted with one or more substituents selected from the group consisting of: $C_{1-10}$ alkyl groups, $C_{2-6}$ alkenyl groups, $C_{2-6}$ alkynyl groups (the $C_{1-10}$ alkyl groups, the $C_{2-6}$ alkenyl groups and the $C_{2-6}$ alkynyl groups may be substituted with one or more halogen atoms), nitro groups, cyano groups, halogen atoms, $C_{1-3}$ alkoxy groups (the $C_{1-3}$ alkoxy groups are substituted with at least one halogen atom), protected thiol groups, protected hydroxyl groups, protected amino groups, $C_{1-10}$ thioalkyl groups, $C_{1-10}$ alkoxy groups, $C_{1-10}$ alkylcarbonyl groups, $C_{1-10}$ alkylcarbonyloxy groups, $C_{1-10}$ alkoxycarbonyl groups, $C_{1-10}$ alkylcarbonylamino groups, $C_{1-10}$ alkylaminocarbonyl groups, $C_{1-10}$ alkylsulfonyl groups, $C_{1-10}$ alkylsulfonylamino groups, $C_{1-10}$ alkylaminosulfonyl groups, mono- or di-$C_{1-10}$ alkylamino groups, $C_{2-14}$ aryl groups, $C_{2-14}$ aryloxy groups and $C_{2-9}$ heterocyclyl groups (the $C_{2-14}$ aryl groups, the $C_{2-14}$ aryloxy groups and the $C_{2-9}$ heterocyclyl groups may be substituted with one or more substituents selected from the group consisting of: $C_{1-10}$ alkyl groups, $C_{2-6}$ alkenyl groups, $C_{2-6}$ alkynyl groups, nitro groups, cyano groups, halogen atoms, $C_{1-3}$ alkyl groups, $C_{1-3}$ alkoxy groups (the $C_{1-3}$ alkyl groups and the $C_{1-3}$ alkoxy groups are substituted with at least one halogen atom), protected thiol groups, protected hydroxyl groups, protected amino groups, $C_{1-10}$ thioalkyl groups, $C_{1-10}$ alkoxy groups, $C_{1-10}$ alkylcarbonyl groups, $C_{1-10}$ alkylcarbonyloxy groups, $C_{1-10}$ alkoxycarbonyl groups, $C_{1-10}$ alkylcarbonylamino groups, $C_{1-10}$ alkylaminocarbonyl groups, $C_{1-10}$ alkylsulfonyl groups, $C_{1-10}$ alkylsulfonylamino groups, $C_{1-10}$ alkylaminosulfonyl groups, mono- or di-$C_{1-10}$ alkylamino groups, $C_{2-14}$ aryl groups, $C_{2-14}$ aryloxy groups and $C_{2-9}$ heterocyclyl groups)))), a tautomer, prodrug or pharmaceutically acceptable salt of the compound or a solvate thereof.

5. The compound according to 2 mentioned above, wherein $L^1$ means the formula (II):

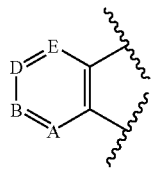

(II)

(wherein D is a nitrogen atom, E is $CR^{33}$ (wherein $R^{33}$ is a hydrogen atom, a $C_{1-3}$ alkyl group, a $C_{1-3}$ alkoxy group (the $C_{1-3}$ alkyl group and the $C_{1-3}$ alkoxy group are substituted with at least one halogen atom) or a $C_{1-10}$ alkyl group) and A=B, as a whole, means $NR^{34}$ (wherein $R^{34}$ is a $C_{2-14}$ aryl group or a $C_{2-9}$ heterocyclyl group (the $C_{2-14}$ aryl group and the $C_{2-9}$ heterocyclyl group may optionally be substituted with one or more substituents selected from the group consisting of: $C_{1-10}$ alkyl groups, $C_{2-6}$ alkenyl groups, $C_{2-6}$ alkynyl groups (the $C_{1-10}$ alkyl groups, the $C_{2-6}$ alkenyl groups and the $C_{2-6}$ alkynyl groups may be substituted with one or more halogen atoms), halogen atoms, $C_{1-3}$ alkoxy groups (the $C_{1-3}$ alkoxy groups are substituted with at least one halogen atom), $C_{1-10}$ thioalkyl groups, $C_{1-10}$ alkoxy groups, $C_{1-10}$ alkylcarbonyl groups, $C_{1-10}$ alkylcarbonyloxy groups, $C_{1-10}$ alkoxycarbonyl groups, $C_{1-10}$ alkylcarbonylamino groups, $C_{1-10}$ alkylaminocarbonyl groups, $C_{1-10}$ alkylsulfonyl groups, $C_{1-10}$ alkylsulfonylamino groups, $C_{1-10}$ alkylaminosulfonyl groups, mono- or di-$C_{1-10}$ alkylamino groups and $C_{2-14}$ aryl groups))), a tautomer, prodrug or pharmaceutically acceptable salt of the compound or a solvate thereof.

6. The compound according to 2 mentioned above, wherein $L^1$ means the formula (II):

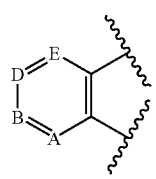

(II)

(wherein D is a nitrogen atom, E is $CR^{33}$ (wherein $R^{33}$ is a hydrogen atom, a $C_{1-3}$ alkyl group (the $C_{1-3}$ alkyl group is substituted with at least one halogen atom) or a $C_{1-10}$ alkyl group), and A=B, as a whole, means $NR^{34}$ (wherein $R^{34}$ is a $C_{2-14}$ aryl group or a $C_{2-9}$ heterocyclyl group (the $C_{2-14}$ aryl group and the $C_{2-9}$ heterocyclyl group may optionally be substituted with one or more substituents selected from the group consisting of: $C_{1-10}$ alkyl groups (the $C_{1-10}$ alkyl groups may be substituted with one or more halogen atoms), halogen atoms, $C_{1-10}$ alkoxy groups or $C_{1-3}$ alkoxy groups (the $C_{1-3}$ alkoxy groups are substituted with at least one halogen atom)))), a tautomer, prodrug or pharmaceutically acceptable salt of the compound or a solvate thereof.

7. The compound according to 2 mentioned above, wherein $L^1$ means the formula (II):

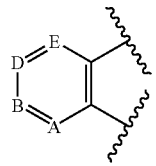

(II)

(wherein D is a nitrogen atom, E is $CR^{33}$ (wherein $R^3$ is a hydrogen atom, a $C_{1-3}$ alkyl group (the $C_{1-3}$ alkyl group is substituted with at least one halogen atom) or a $C_{1-10}$ alkyl group), and A=B, as a whole, means $NR^{34}$ (wherein $R^{34}$ is a $C_{2-14}$ aryl group (the $C_{2-14}$ aryl group may optionally be substituted with one or more substituents selected from the group consisting of: $C_{1-10}$ alkyl groups (the $C_{1-10}$ alkyl groups may be substituted with one or more halogen atoms), halogen atoms, $C_{1-10}$ alkoxy groups and $C_{1-3}$ alkoxy groups (the $C_{1-3}$ alkoxy groups are substituted with at least one halogen atom)))), a tautomer, prodrug or pharmaceutically acceptable salt of the compound or a solvate thereof.

8. The compound according to 2 mentioned above, wherein $L^1$ means the formula (II):

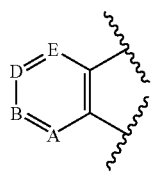

(II)

(wherein D is a nitrogen atom, E is $CR^{33}$ (wherein $R^{33}$ is a hydrogen atom, a $C_{1-3}$ alkyl group (the $C_{1-3}$ alkyl group is substituted with at least one halogen atom) or a $C_{1-10}$ alkyl group), and A=B, as a whole, means $NR^{34}$ (wherein $R^{34}$ is a phenyl group (the phenyl group may optionally be substituted with one or more substituents selected from the group consisting of: $C_{1-10}$ alkyl groups (the $C_{1-10}$ alkyl groups may be substituted with one or more halogen atoms), halogen atoms, $C_{1-10}$ alkoxy groups and $C_{1-3}$ alkoxy groups (the $C_{1-3}$ alkoxy groups are substituted with at least one halogen atom)))), a tautomer, prodrug or pharmaceutically acceptable salt of the compound or a solvate thereof.

9. The compound according to 2 mentioned above, wherein $L^1$ means the formula (II):

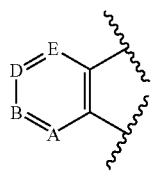

(II)

(wherein D is a nitrogen atom, E is $CR^{33}$ (wherein $R^{33}$ is a hydrogen atom, a $C_{1-3}$ alkyl group (the $C_{1-3}$ alkyl group is substituted with at least one halogen atom) or a $C_{1-3}$ alkyl group), and A=B, as a whole, means $NR^{34}$ (wherein $R^{34}$ is a phenyl group (the phenyl group may optionally be substituted with one or more substituents selected from the group consisting of: $C_{1-10}$ alkyl groups (the $C_{1-10}$ alkyl groups may be substituted with one or more halogen atoms), halogen atoms, $C_{1-10}$ alkoxy groups and $C_{1-3}$ alkoxy groups (the $C_{1-3}$ alkoxy groups are substituted with at least one halogen atom)))), a tautomer, prodrug or pharmaceutically acceptable salt of the compound or a solvate thereof.

10. The compound according to 2 mentioned above, wherein $L^1$ means the formula (II):

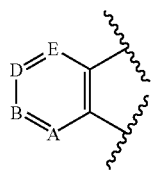

(II)

(wherein B is a nitrogen atom, D=E, as a whole, means $NR^{33}$ (wherein $R^{33}$ is a hydrogen atom, a $C_{1-3}$ alkyl group (the $C_{1-3}$ alkyl group is substituted with at least one halogen atom) or a $C_{1-3}$ alkyl group), and A is $CR^{34}$ (wherein $R^{34}$ is a phenyl group (the phenyl group may optionally be substituted with one or more substituents selected from the group consisting of: $C_{1-10}$ alkyl groups (the $C_{1-10}$ alkyl groups may be substituted with one or more halogen atoms), halogen atoms, $C_{1-10}$ alkoxy groups and $C_{1-3}$ alkoxy groups (the $C_{1-3}$ alkoxy groups are substituted with at least one halogen atom)))), a tautomer, prodrug or pharmaceutically acceptable salt of the compound or a solvate thereof.

11. The compound according to 2 mentioned above, wherein $L^1$ means the formula (II):

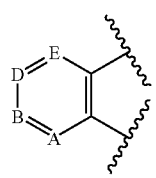

(II)

(wherein D=E, as a whole, means a sulfur atom, B is $CR^{35}$ (wherein $R^{35}$ is a hydrogen atom, a $C_{1-3}$ alkyl group (the $C_{1-3}$ alkyl group is substituted with at least one halogen atom) or a $C_{1-3}$ alkyl group), and A is $CR^{34}$ (wherein $R^{34}$ is a phenyl group (the phenyl group may optionally be substituted with one or more substituents selected from the group consisting of: $C_{1-10}$ alkyl groups (the $C_{1-10}$ alkyl groups may be substituted with one or more halogen atoms), halogen atoms, $C_{1-10}$ alkoxy groups and $C_{1-3}$ alkoxy groups (the $C_{1-3}$ alkoxy groups are substituted with at least one halogen atom)))), a tautomer, prodrug or pharmaceutically acceptable salt of the compound or a solvate thereof.

12. The compound according to 2 mentioned above, wherein $L^1$ means the formula (II):

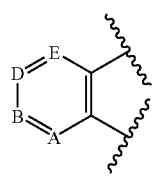

(II)

(wherein D=E, as a whole, means an oxygen atom, B is $CR^{35}$ (wherein $R^{35}$ is a hydrogen atom, a $C_{1-3}$ alkyl group (the $C_{1-3}$ alkyl group is substituted with at least one halogen atom) or a $C_{1-3}$ alkyl group), and A is $CR^{34}$ (wherein $R^{34}$ is a phenyl group (the phenyl group may optionally be substituted with one or more substituents selected from the group consisting of: $C_{1-10}$ alkyl groups (the $C_{1-10}$ alkyl groups may be substituted with one or more halogen atoms), halogen atoms, $C_{1-10}$ alkoxy groups and $C_{1-3}$ alkoxy groups (the $C_{1-3}$ alkoxy groups are substituted with at least one halogen atom)))), a tautomer, prodrug or pharmaceutically acceptable salt of the compound or a solvate thereof.

13. The compound according to 2 mentioned above, wherein $L^1$ means the formula (II):

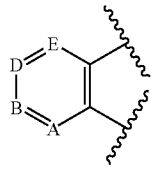

(II)

(wherein E is a nitrogen atom, D is $CR^{35}$ (wherein $R^{35}$ is a hydrogen atom, a $C_{1-3}$ alkyl group (the $C_{1-3}$ alkyl group is substituted with at least one halogen atom) or a $C_{1-3}$ alkyl group), and A=B, as a whole, means $NR^{34}$ (wherein $R^{34}$ is a phenyl group (the phenyl group may optionally be substituted with one or more substituents selected from the group consisting of: $C_{1-10}$ alkyl groups (the $C_{1-10}$ alkyl groups may be substituted with one or more halogen atoms), halogen atoms, $C_{1-10}$ alkoxy groups and $C_{1-3}$ alkoxy groups (the $C_{1-3}$ alkoxy groups are substituted with at least one halogen atom)))), a tautomer, prodrug or pharmaceutically acceptable salt of the compound or a solvate thereof.

14. The compound according to 2 mentioned above, wherein $L^1$ means the formula (II):

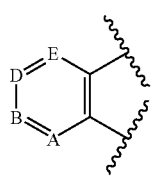

(II)

(wherein A=B, as a whole, means $NR^{34}$ (wherein $R^{34}$ is a phenyl group (the phenyl group may optionally be substituted with one or more substituents selected from the group consisting of: $C_{1-10}$ alkyl groups (the $C_{1-10}$ alkyl groups may be substituted with one or more halogen atoms), halogen atoms, $C_{1-10}$ alkoxy groups and $C_{1-3}$ alkoxy groups (the $C_{1-3}$ alkoxy groups are substituted with at least one halogen atom))), D is $CR^{35}$ (wherein $R^{35}$ is a hydrogen atom, a $C_{1-3}$ alkyl group (the $C_{1-3}$ alkyl group is substituted with at least one halogen atom) or a $C_{1-3}$ alkyl group), and E is $CR^{33}$ (wherein $R^{33}$ is a hydrogen atom, a $C_{1-3}$ alkyl group (the $C_{1-3}$ alkyl group is substituted with at least one halogen atom) or a $C_{1-3}$ alkyl group)), a tautomer, prodrug or pharmaceutically acceptable salt of the compound or a solvate thereof.

15. The compound according to 2 mentioned above, wherein $L^1$ means the formula (II):

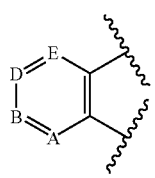

(II)

(wherein D=E, as a whole, means $NR^{33}$ (wherein $R^{33}$ is a hydrogen atom, a $C_{1-3}$ alkyl group (the $C_{1-3}$ alkyl group is substituted with at least one halogen atom) or a $C_{1-3}$ alkyl group), B is $CR^{35}$ (wherein $R^{35}$ is a hydrogen atom, a $C_{1-3}$ alkyl group (the $C_{1-3}$ alkyl group is substituted with at least one halogen atom) or a $C_{1-3}$ alkyl group), and A is $CR^{34}$ (wherein $R^{34}$ is a phenyl group (the phenyl group may be substituted with one or more substituents selected from the group consisting of: $C_{1-10}$ alkyl groups (the $C_{1-10}$ alkyl groups may be substituted with one or more halogen atoms), halogen atoms, $C_{1-10}$ alkoxy groups and $C_{1-3}$ alkoxy groups (the $C_{1-3}$ alkoxy groups are substituted with at least one halogen atom)))), a tautomer, prodrug or pharmaceutically acceptable salt of the compound or a solvate thereof.

16. The compound according to 2 mentioned above, wherein $L^1$ means the formula (II):

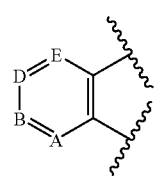

(II)

(wherein B is a nitrogen atom, D=E, as a whole, means an oxygen atom, and A is $CR^{34}$ (wherein $R^{34}$ is a phenyl group (the phenyl group may optionally be substituted with one or more substituents selected from the group consisting of: $C_{1-10}$ alkyl groups (the $C_{1-10}$ alkyl groups may be substituted with one or more halogen atoms), halogen atoms, $C_{1-10}$ alkoxy groups and $C_{1-3}$ alkoxy groups (the $C_{1-3}$ alkoxy groups are substituted with at least one halogen atom)))), a tautomer, prodrug or pharmaceutically acceptable salt of the compound or a solvate thereof.

17. The compound according to 2 mentioned above, wherein $L^1$ means the formula (II):

(II)

(wherein B is a nitrogen atom, D=E, as a whole, means a sulfur atom, and A is $CR^{34}$ (wherein $R^{34}$ is a phenyl group (the phenyl group may optionally be substituted with one or more substituents selected from the group consisting of: $C_{1-10}$ alkyl groups (the $C_{1-10}$ alkyl groups may be substituted with one or more halogen atoms), halogen atoms, $C_{1-10}$ alkoxy groups and $C_{1-3}$ alkoxy groups (the $C_{1-3}$ alkoxy groups are substituted with at least one halogen atom)))), a tautomer, prodrug or pharmaceutically acceptable salt of the compound or a solvate thereof.

18. The compound according to 2 mentioned above, wherein $L^1$ means the formula (II):

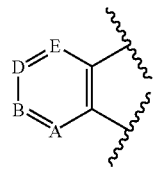

(wherein D and E are nitrogen atoms, and A=B, as a whole, means $NR^{34}$ (wherein $R^{34}$ is a phenyl group (the phenyl group may optionally be substituted with one or more substituents selected from the group consisting of: $C_{1-10}$ alkyl groups (the $C_{1-10}$ alkyl groups may be substituted with one or more halogen atoms), halogen atoms, $C_{1-10}$ alkoxy groups and $C_{1-3}$ alkoxy groups (the $C_{1-3}$ alkoxy groups are substituted with at least one halogen atom)))), a tautomer, prodrug or pharmaceutically acceptable salt of the compound or a solvate thereof.

19. The compound according to any one of 2 to 18 mentioned above, wherein $R^3$ is a thienyl group (the thienyl group is optionally substituted with one or more substituents independently represented by $—V^5$ (wherein $V^5$ is the same as defined above in 1) and with one or more substituents independently represented by $—W^1(CW^2W^3)_{p1}W^4$ (wherein $W^1$ is $(CR^4R^5)_{q1}$ (wherein each of $R^4$ and $R^5$ is independently a hydrogen atom or a $C_{1-6}$ alkyl group (the $C_{1-6}$ alkyl group may be substituted with one or more halogen atoms), and $q_1$ is 0, 1, 2 or 3), an oxygen atom, a sulfur atom or $NR^6$ (wherein $R^6$ is a hydrogen atom, a $C_{1-6}$ alkyl group, a formyl group or a $C_{1-6}$ alkylcarbonyl group), each of $W^2$ and $W^3$ is independently a hydrogen atom or a $C_{1-3}$ alkyl group (the $C_{1-3}$ alkyl group may be substituted with one or more halogen atoms), p1 is 0, 1, 2 or 3, and $W^4$ is $SO_2R^7$, $SOR^7$, $COR^7$ (wherein $R^7$ is $NR^8R^9$ (wherein each of $R^8$ and $R^9$ is independently a hydrogen atom, a hydroxyl group, a formyl group, a $C_{1-10}$ alkyl group, a $C_{2-6}$ alkenyl group, a $C_{2-6}$ alkynyl group, a $C_{1-10}$ alkoxy group, a $C_{1-10}$ alkylcarbonyloxy group, a $C_{1-10}$ alkoxycarbonyl group, a $C_{1-10}$ alkylcarbonyl group (the $C_{1-10}$ alkyl group, the $C_{2-6}$ alkenyl group, the $C_{2-6}$ alkynyl group, the $C_{1-10}$ alkoxy group, the $C_{1-10}$ alkylcarbonyloxy group, the $C_{1-10}$ alkoxycarbonyl group and the $C_{1-10}$ alkylcarbonyl group may optionally be substituted with one or more substituents selected from the group consisting of: carboxyl groups, nitro groups, cyano groups, halogen atoms, $C_{1-10}$ alkoxy groups, $C_{1-10}$ alkylcarbonyl groups, $C_{1-10}$ alkylcarbonyloxy groups, $C_{1-10}$ alkoxycarbonyl groups, $C_{1-10}$ alkylcarbonylamino groups, amino groups, protected amino groups, mono- or di-$C_{1-10}$ alkylamino groups, hydroxyl groups, protected hydroxyl groups, $C_{2-14}$ aryl groups or $C_{2-14}$ aryloxy groups (the $C_{2-14}$ aryl groups and the $C_{2-14}$ aryloxy groups may be substituted with one or more $C_{1-6}$ alkyl groups (the $C_{1-6}$ alkyl groups may be substituted with one or more halogen atoms) or one or more halogen atoms)) or a $C_{2-14}$ aryl group (the $C_{2-14}$ aryl group may optionally be substituted with one or more substituents selected from the group consisting of: $C_{1-10}$ alkyl groups (the $C_{1-10}$ alkyl groups may be substituted with one or more halogen atoms), $C_{2-6}$ alkenyl groups, $C_{2-6}$ alkynyl groups, carboxyl groups, nitro groups, cyano groups, halogen atoms, $C_{1-10}$ alkyoxy groups, $C_{1-10}$ alkylcarbonyl groups, $C_{1-10}$ alkylcarbonyloxy groups, $C_{1-10}$ alkoxycarbonyl groups, $C_{1-10}$ alkylcarbonylamino groups, amino groups, protected amino groups, mono- or di-$C_{1-10}$ alkylamino groups, hydroxyl groups, protected hydroxyl groups, $C_{2-14}$ aryl groups and $C_{2-14}$ aryloxy groups))))), a tautomer, prodrug or pharmaceutically acceptable salt of the compound or a solvate thereof.

20. The compound according to any one of 2 to 18 mentioned above, wherein $R^3$ is a thienyl group (the thienyl group is optionally substituted with one or more substituents independently represented by $—V^5$ (wherein $V^5$ is the same as defined above in 1) and with one or more substituents independently represented by $—W^1(CW^2W^3)_{p1}W^4$ (wherein $W^1$ is $(CR^4R^5)_{q1}$ (wherein each of $R^4$ and $R^5$ is independently a hydrogen atom or a $C_{1-6}$ alkyl group (the $C_{1-6}$ alkyl group may be substituted with one or more halogen atoms), and $q_1$ is 0, 1, 2 or 3), an oxygen atom, a sulfur atom or $NR^6$ (wherein $R^6$ is a hydrogen atom, a $C_{1-6}$ alkyl group, a formyl group or a $C_{1-6}$ alkylcarbonyl group), each of $W^2$ and $W^3$ is independently a hydrogen atom or a $C_{1-3}$ alkyl group (the $C_{1-3}$ alkyl group may be substituted with one or more halogen atoms), p1 is 0, 1, 2 or 3, and $W^4$ is $SO_2R^7$, $SOR^7$, $COR^7$ (wherein $R^7$ is $NR^8R^9$ (wherein $R^8$ and $R^9$ mean together with each other, $—(CH_2)_{m1}—E—(CH_2)_{m2}—$ (wherein E is an oxygen atom, a sulfur atom, $CR^{10}R^{11}$ (wherein each of $R^{10}$ and $R^{11}$ is independently a hydrogen atom, a $C_{1-10}$ alkyl group, a $C_{2-14}$ aryl group, a $C_{1-10}$ alkoxy group, a $C_{2-14}$ aryloxy group, a hydroxyl group or a protected hydroxyl group) or $NR^{12}$ (wherein $R^{12}$ is a hydrogen atom, a hydroxyl group, a formyl group, a $C_{1-10}$ alkyl group, a $C_{2-6}$ alkenyl group, a $C_{2-6}$ alkynyl group, a $C_{1-10}$ alkoxy group, a $C_{1-10}$ alkylcarbonyloxy group, a $C_{1-10}$ alkoxycarbonyl group, a $C_{1-10}$ alkylcarbonyl group (the $C_{1-10}$ alkyl group, the $C_{2-6}$ alkenyl group, the $C_{2-6}$ alkynyl group, the $C_{1-10}$ alkoxy group, the $C_{1-10}$ alkylcarbonyloxy group, the $C_{1-10}$ alkoxycarbonyl group and the $C_{1-10}$ alkylcarbonyl group may optionally be substituted with one or more substituents selected from the group consisting of: carboxyl groups, nitro groups, cyano groups, halogen atoms, $C_{1-10}$ alkoxy groups, $C_{1-10}$ alkylcarbonyl groups, $C_{1-10}$ alkylcarbonyloxy groups, $C_{1-10}$ alkoxycarbonyl groups, $C_{1-10}$ alkylcarbonylamino groups, amino groups, protected amino groups, mono- or di-$C_{1-10}$ alkylamino groups, hydroxyl groups, protected hydroxyl groups, $C_{2-14}$ aryl groups and $C_{2-14}$ aryloxy groups (the $C_{2-14}$ aryl groups and the $C_{2-14}$ aryloxy groups may be substituted with one or more $C_{1-6}$ alkyl groups (the $C_{1-6}$ alkyl groups may be substituted with one or more halogen atoms) or one or more halogen atoms)) or a $C_{2-14}$ aryl group (the $C_{2-14}$ aryl group may optionally be substituted with one or more substituents selected from the group consisting of: $C_{1-10}$ alkyl groups (the $C_{1-10}$ alkyl groups may be substituted with one or more halogen atoms), $C_{2-6}$ alkenyl groups, $C_{2-6}$ alkynyl groups, carboxyl groups, nitro groups, cyano groups, halogen atoms, $C_{1-10}$ alkoxy groups, $C_{1-10}$ alkylcarbonyl groups, $C_{1-10}$ alkylcarbonyloxy groups, $C_{1-10}$ alkoxycarbonyl groups, $C_{1-10}$ alkylcarbonylamino groups, amino groups, protected amino groups, mono- or di-$C_{1-10}$ alkylamino groups, hydroxyl groups, protected hydroxyl groups, $C_{2-14}$ aryl groups and $C_{2-14}$ aryloxy groups)), and each of m1 and m2 is independently an integer of from 0 to 5 provided that m1+m2 is 3, 4 or 5))))), a tautomer, prodrug or pharmaceutically acceptable salt of the compound or a solvate thereof.

21. The compound according to any one of 2 to 18 mentioned above, wherein $R^3$ is a thienyl group (the thienyl group is optionally substituted with one or more substituents independently represented by $—V^5$ (wherein $V^5$ is the same as defined above in 1) and with one or more substituents independently represented by $—W^5(CW^6W^7)_{p2}W^8$ (wherein $W^5$ is $(CR^{13}R^{14})_{q2}$ (wherein each of $R^{13}$ and $R^{14}$ is independently a hydrogen atom, a hydroxyl group, an amino group, a $C_{1-6}$ alkyl group or a $C_{1-6}$ alkoxy group (the $C_{1-6}$ alkyl group and the $C_{1-6}$ alkoxy group may be substituted with one or more halogen atoms), and q2 is 0, 1, 2 or 3), an oxygen atom, a sulfur atom or $NR^{15}$ (wherein $R^{15}$ is a hydrogen atom, a $C_{1-6}$ alkyl group, a formyl group or a $C_{1-6}$ alkylcarbonyl group), each of $W^6$ and $W^7$ is independently a hydrogen atom or a $C_{1-3}$ alkyl group (the $C_{1-3}$ alkyl group may be substituted with one or more halogen atoms), p2 is 0, 1, 2 or 3, and $W^8$ is $SO_2R^{16}$, $SOR^{16}$ or $COR^{16}$ (wherein $R^{16}$ is $NR^{17}R^{18}$ (wherein $R^{17}$ is a hydrogen atom, a hydroxyl group, a formyl group, a $C_{1-10}$ alkyl group, a $C_{2-6}$ alkenyl group, a $C_{2-6}$ alkynyl group, a $C_{1-10}$ alkylcarbonyloxy group, a $C_{1-10}$ alkoxycarbonyl group, a $C_{1-10}$ alkylcarbonyl group (the $C_{1-10}$ alkyl group, the $C_{2-6}$ alkenyl group, the $C_{2-6}$ alkynyl group, the $C_{1-10}$ alkylcarbonyloxy group, the $C_{1-10}$ alkoxycarbonyl group and the $C_{1-10}$ alkylcarbonyl group may optionally be substituted with one or more substituents selected from the group consisting of: carboxyl groups, nitro groups, cyano groups, halogen atoms, $C_{1-10}$ alkoxy groups, $C_{1-10}$ alkylcarbonyl groups, $C_{1-10}$ alkylcarbonyloxy groups, $C_{1-10}$ alkoxycarbonyl groups, $C_{1-10}$ alkylcarbonylamino groups, amino groups, protected amino groups, mono- or di-$C_{1-10}$ alkylamino groups, hydroxyl groups, protected hydroxyl groups, $C_{2-14}$ aryl groups and $C_{2-14}$ aryloxy groups (the $C_{2-14}$ aryl groups and the $C_{2-14}$ aryloxy groups may be substituted with one or more $C_{1-6}$ alkyl groups (the $C_{1-6}$ alkyl groups may be substituted with one or more halogen atoms) or one or more halogen atoms)), a $C_{2-14}$ aryl group or a $C_{2-14}$ aryloxy group (the $C_{2-14}$ aryl group and the $C_{2-14}$ aryloxy group may optionally be substituted with one or more substituents selected from the group consisting of: $C_{1-10}$ alkyl groups (the $C_{1-10}$ alkyl groups may be substituted with one or more halogen atoms), $C_{2-6}$ alkenyl groups, $C_{2-6}$ alkynyl groups, carboxyl groups, nitro groups, cyano groups, halogen atoms, $C_{1-10}$ alkoxy groups, $C_{1-10}$ alkylcarbonyl groups, $C_{1-10}$ alkylcarbonyloxy groups, $C_{1-10}$ alkoxycarbonyl groups, $C_{1-10}$ alkylcarbonylamino groups, amino groups, protected amino groups, mono- or di-$C_{1-10}$ alkylamino groups, hydroxyl groups, protected hydroxyl groups, $C_{2-14}$ aryl groups and $C_{2-14}$ aryloxy groups), and $R^{18}$ is an amino group, a mono- or di-$C_{1-10}$ alkylamino group, a $C_{1-10}$ alkylcarbonylamino group, a $C_{1-10}$ alkylaminocarbonyl group, a $C_{2-9}$ heterocyclyl group (the mono- or di-$C_{1-10}$ alkylamino group, the $C_{1-10}$ alkylcarbonylamino group, the $C_{1-10}$ alkylaminocarbonyl group and the $C_{2-9}$ heterocyclyl group may be substituted with one or more substituents selected from the group consisting of: hydrogen atoms, carboxyl groups, carbamoyl groups, sulfamoyl groups, sulfo groups, nitro groups, cyano groups, halogen atoms, hydroxyl groups, formyl groups, $C_{1-10}$ alkyl groups, $C_{2-6}$ alkenyl groups, $C_{2-6}$ alkynyl groups, $C_{1-10}$ alkylcarbonyloxy groups, $C_{1-10}$ alkoxycarbonyl groups, $C_{1-10}$ alkylcarbonyl groups (the $C_{1-10}$ alkyl groups, the $C_{2-6}$ alkenyl groups, the $C_{2-6}$ alkynyl groups, the $C_{1-10}$ alkylcarbonyloxy groups, the $C_{1-10}$ alkoxycarbonyl groups and the $C_{1-10}$ alkylcarbonyl groups may optionally be substituted with one or more substituents selected from the group consisting of: carboxyl groups, nitro groups, cyano groups, halogen atoms, $C_{1-10}$ alkoxy groups, $C_{1-10}$ alkylcarbonyl groups, $C_{1-10}$ alkylcarbonyloxy groups, $C_{1-10}$ alkoxycarbonyl groups, $C_{1-10}$ alkylcarbonylamino groups, amino groups, protected amino groups, mono- or di-$C_{1-10}$ alkylamino groups, hydroxyl groups, protected hydroxyl groups, $C_{2-14}$ aryl groups and $C_{2-14}$ aryloxy groups (the $C_{2-14}$ aryl groups and the $C_{2-14}$ aryloxy groups may be substituted with one or more $C_{1-6}$ alkyl groups (the $C_{1-6}$ alkyl groups may be substituted with one or more halogen atoms) or one or more halogen atoms)), $C_{2-14}$ aryl groups and $C_{2-14}$ aryloxy groups (the $C_{2-14}$ aryl groups and the $C_{2-14}$ aryloxy groups may optionally be substituted with one or more substituents selected from the group consisting of: $C_{1-10}$ alkyl groups (the $C_{1-10}$ alkyl groups may be substituted with one or more halogen atoms), $C_{2-6}$ alkenyl groups, $C_{2-6}$ alkynyl groups, carboxyl groups, nitro groups, cyano groups, halogen atoms, $C_{1-10}$ alkoxy groups, $C_{1-10}$ alkylcarbonyl groups, $C_{1-10}$ alkylcarbonyloxy groups, $C_{1-10}$ alkoxycarbonyl groups, $C_{1-10}$ alkylcarbonylamino groups, amino groups, protected amino groups, mono- or di-$C_{1-10}$ alkylamino groups, hydroxyl groups, protected hydroxyl groups, $C_{2-14}$ aryl groups and $C_{2-14}$ aryloxy groups)), a $C_{1-10}$ alkyl group, a $C_{2-6}$ alkenyl group, a $C_{2-6}$ alkynyl group, a $C_{1-10}$ alkylcarbonyloxy group, a $C_{1-10}$ alkoxycarbonyl group, a $C_{1-10}$ alkylcarbonyl group (the $C_{1-10}$ alkyl group, the $C_{2-6}$ alkenyl group, the $C_{2-6}$ alkynyl group, the $C_{1-10}$ alkylcarbonyloxy group, the $C_{1-10}$ alkoxycarbonyl group and the $C_{1-10}$ alkylcarbonyl group are optionally substituted with one or more substituents selected from the group consisting of: hydrogen atoms, carboxyl groups, carbamoyl groups, sulfamoyl groups, sulfo groups, nitro groups, cyano groups, halogen atoms, hydroxyl groups, formyl groups, $C_{1-10}$ alkyl groups, $C_{2-6}$ alkenyl groups, $C_{2-6}$ alkynyl groups, $C_{1-10}$ alkylcarbonyloxy groups, $C_{1-10}$ alkoxycarbonyl groups, $C_{1-10}$ alkylcarbonyl groups (the $C_{1-10}$ alkyl groups, the $C_{2-6}$ alkenyl groups, the $C_{2-6}$ alkynyl groups, the $C_{1-10}$ alkylcarbonyloxy groups, the $C_{1-10}$ alkoxycarbonyl groups and the $C_{1-10}$ alkylcarbonyl groups may optionally be substituted with one or more substituents selected from the group consisting of: carboxyl groups, nitro groups, cyano groups, halogen atoms, $C_{1-10}$ alkoxy groups, $C_{1-10}$ alkylcarbonyl groups, $C_{1-10}$ alkylcarbonyloxy groups, $C_{1-10}$ alkoxycarbonyl groups, $C_{1-10}$ alkylcarbonylamino groups, amino groups, protected amino groups, mono- or di-$C_{1-10}$ alkylamino groups, hydroxyl groups, protected hydroxyl groups, $C_{2-14}$ aryl groups and $C_{2-14}$ aryloxy groups (the $C_{2-14}$ aryl groups and the $C_{2-14}$ aryloxy groups may be substituted with one or more $C_{1-6}$ alkyl groups (the $C_{1-6}$ alkyl groups may be substituted with one or more halogen atoms) or one or more halogen atoms)), $C_{2-14}$ aryl groups and $C_{2-14}$ aryloxy groups (the $C_{2-14}$ aryl groups and the $C_{2-14}$ aryloxy groups may optionally be substituted with one or more substituents selected from the group consisting of: $C_{1-10}$ alkyl groups (the $C_{1-10}$ alkyl groups may be substituted with one or more halogen atoms), $C_{2-6}$ alkenyl groups, $C_{2-6}$ alkynyl groups, carboxyl groups, nitro groups, cyano groups, halogen atoms, $C_{1-10}$ alkoxy groups, $C_{1-10}$ alkylcarbonyl groups, $C_{1-10}$ alkylcarbonyloxy groups, $C_{1-10}$ alkoxycarbonyl groups, $C_{1-10}$ alkylcarbonylamino groups, amino groups, protected amino groups, mono- or di-$C_{1-10}$ alkylamino groups, hydroxyl groups, protected hydroxyl groups, $C_{2-14}$ aryl groups and $C_{2-14}$ aryloxy groups) and with one or more substituents selected from the group consisting of: carboxyl groups, carbamoyl groups, sulfo groups, sulfamoyl groups and $C_{2-9}$ heterocyclyl groups (the $C_{2-9}$ heterocyclyl groups may optionally be substituted with one or more substituents selected from the group consisting of: hydrogen atoms, hydroxyl groups, protected hydroxyl groups, formyl groups, $C_{1-10}$ alkyl groups, $C_{2-6}$ alkenyl groups, $C_{2-6}$ alkynyl groups, $C_{1-10}$ alkylcarbonyloxy groups, $C_{1-10}$ alkoxycarbonyl groups, $C_{1-10}$ alkylcarbonyl groups, $C_{2-9}$ heterocyclyl groups (the $C_{1-10}$ alkyl groups, the $C_{2-6}$ alkenyl groups, the $C_{2-6}$ alkynyl groups, the $C_{1-10}$ alkylcarbonyloxy groups, the $C_{1-10}$ alkoxycarbonyl groups, the $C_{1-10}$ alkylcarbonyl groups and the $C_{2-9}$ heterocyclyl groups may optionally be substituted with one or more substituents selected from the group consisting of: hydrogen atoms, carboxyl groups, carbamoyl groups, sulfamoyl groups, sulfo groups, nitro groups, cyano groups, halogen atoms, $C_{1-10}$ alkoxy groups, $C_{1-10}$ alkylcarbonyl groups, $C_{1-10}$ alkylcarbonyloxy groups, $C_{1-10}$ alkoxycarbonyl groups, $C_{1-10}$ alkylcarbonylamino groups, amino groups, protected amino groups, mono- or di-$C_{1-10}$ alkylamino groups, hydroxyl groups, protected hydroxyl groups, $C_{2-14}$ aryl groups and $C_{2-14}$ aryloxy groups (the $C_{2-14}$ aryl groups and the $C_{2-14}$ aryloxy groups may be substituted with one or more $C_{1-6}$ alkyl groups (the $C_{1-6}$ alkyl groups may be substituted with one or more halogen atoms)), $C_{2-14}$ aryl groups and $C_{2-14}$ aryloxy groups (the $C_{2-14}$ aryl groups and the $C_{2-14}$ aryloxy groups may optionally be substituted with one or more substituents selected from the group consisting of: $C_{1-10}$ alkyl groups (the $C_{1-10}$ alkyl groups may be substituted with one or more halogen atoms), $C_{2-6}$ alkenyl groups, $C_{2-6}$ alkynyl groups, carboxyl groups, nitro groups, cyano groups, halogen atoms, $C_{1-10}$ alkoxy groups, $C_{1-10}$ alkylcarbonyl groups, $C_{1-10}$ alkylcarbonyloxy groups, $C_{1-10}$ alkoxycarbonyl groups, $C_{1-10}$ alkylcarbonylamino groups, amino groups, protected amino groups, mono- or di-$C_{1-10}$ alkylamino groups, hydroxyl groups, protected hydroxyl groups, $C_{2-14}$ aryl groups and $C_{2-14}$ aryloxy groups)))))), a tautomer, prodrug or pharmaceutically acceptable salt of the compound or a solvate thereof.

22. The compound according to any one of 2 to 18 mentioned above, wherein $R^3$ is a thienyl group (the thienyl group is optionally substituted with one or more substituents independently represented by —$V^5$ (wherein $V^5$ is the same as defined above in 1) and with one or more substituents independently represented by —$W^5(CW^6W^7)_{p2}W^8$ (wherein $W^5$ is $(CR^{13}R^{14})_{q2}$ (wherein each of $R^{13}$ and $R^{14}$ is independently a hydrogen atom, a hydroxyl group, an amino group, a $C_{1-6}$ alkyl group or a $C_{1-6}$ alkoxy group (the $C_{1-6}$ alkyl group and the $C_{1-6}$ alkoxy group may be substituted with one or more halogen atoms), and q2 is 0, 1, 2 or 3), an oxygen atom, a sulfur atom or $NR^{15}$ (wherein $R^{15}$ is a hydrogen atom, a $C_{1-6}$ alkyl group, a formyl group or a $C_{1-6}$ alkylcarbonyl group), each of $W^6$ and $W^7$ is independently a hydrogen atom or a $C_{1-3}$ alkyl group (the $C_{1-3}$ alkyl group may be substituted with one or more halogen atoms), p2 is 0, 1, 2 or 3, and $W^8$ is $SO_2R^{16}$, $SOR^{16}$ or $COR^{16}$ (wherein $R^{16}$ is $NR^{17}R^{18}$ (wherein $R^{17}$ and $R^{18}$ mean, together with each other, —$(CH_2)_{m3}$—G—$(CH_2)_{m4}$— (wherein G is $CR^{19}R^{20}$ (wherein $R^{19}$ is a hydrogen atom, a $C_{1-10}$ alkyl group, a $C_{2-14}$ aryl group, a $C_{1-10}$ alkoxy group, a $C_{2-14}$ aryloxy group (the $C_{1-10}$ alkyl group, the $C_{2-14}$ aryl group, the $C_{1-10}$ alkoxy group and the $C_{2-14}$ aryloxy group may optionally be substituted with one or more substituents selected from the group consisting of: carboxyl groups, nitro groups, cyano groups, halogen atoms, $C_{1-10}$ alkoxy groups, $C_{1-10}$ alkylcarbonyl groups, $C_{1-10}$ alkylcarbonyloxy groups, $C_{1-10}$ alkoxycarbonyl groups, $C_{1-10}$ alkylcarbonylamino groups, amino groups, mono- or di-$C_{1-10}$ alkylamino groups, $C_{2-14}$ aryl groups and $C_{2-14}$ aryloxy groups (the $C_{2-14}$ aryl groups and the $C_{2-14}$ aryloxy groups may be substituted with one or more $C_{1-6}$ alkyl groups (the $C_{1-6}$ alkyl groups may be substituted with one or more halogen atoms) or one or more halogen atoms)), a hydroxyl group or a protected hydroxyl group, and $R^{20}$ is an amino group, a mono- or di-$C_{1-10}$ alkylamino group, a $C_{1-10}$ alkylcarbonylamino group, a $C_{1-10}$ alkylaminocarbonyl group or a $C_{2-9}$ heterocyclyl group (the mono- or di-$C_{1-10}$ alkylamino group, the $C_{1-10}$ alkylcarbonylamino group, the $C_{1-10}$ alkylaminocarbonyl group and the $C_{2-9}$ heterocyclyl group may optionally be substituted with one or more substituents selected from the group consisting of: hydrogen atoms, carboxyl groups, carbamoyl groups, sulfamoyl groups, sulfo groups, nitro groups, cyano groups, halogen atoms, amino groups, hydroxyl groups, formyl groups, $C_{1-10}$ alkyl groups, $C_{2-6}$ alkenyl groups, $C_{2-6}$ alkynyl groups, $C_{1-10}$ alkylcarbonyloxy groups, $C_{1-10}$ alkoxycarbonyl groups, $C_{1-10}$ alkylcarbonyl groups (the $C_{1-10}$ alkyl groups, the $C_{2-6}$ alkenyl groups, the $C_{2-6}$ alkynyl groups, the $C_{1-10}$ alkylcarbonyloxy groups, the $C_{1-10}$ alkoxycarbonyl groups and the $C_{1-10}$ alkylcarbonyl groups may optionally be substituted with one or more substituents selected from the group consisting of: carboxyl groups, nitro groups, cyano groups, halogen atoms, $C_{1-10}$ alkoxy groups, $C_{1-10}$ alkylcarbonyl groups, $C_{1-10}$ alkylcarbonyloxy groups, $C_{1-10}$ alkoxycarbonyl groups, $C_{1-10}$ alkylcarbonylamino groups, amino groups, protected amino groups, mono- or di-$C_{1-10}$ alkylamino groups, hydroxyl groups, protected hydroxyl groups, $C_{2-14}$ aryl groups and $C_{2-14}$ aryloxy groups (the $C_{2-14}$ aryl groups and the $C_{2-14}$ aryloxy groups may be substituted with one or more $C_{1-6}$ alkyl groups (the $C_{1-6}$ alkyl groups may be substituted with one or more halogen atoms) or one or more halogen atoms)), $C_{2-14}$ aryl groups and $C_{2-14}$ aryloxy groups (the $C_{2-14}$ aryl groups and the $C_{2-14}$ aryloxy groups may optionally be substituted with one or more substituents selected from the group consisting of: $C_{1-10}$ alkyl groups (the $C_{1-10}$ alkyl groups may be substituted with one or more halogen atoms), $C_{2-6}$ alkenyl groups, $C_{2-6}$ alkynyl groups, carboxyl groups, nitro groups, cyano groups, halogen atoms, $C_{1-10}$ alkoxy groups, $C_{1-10}$ alkylcarbonyl groups, $C_{1-10}$ alkylcarbonyloxy groups, $C_{1-10}$ alkoxycarbonyl groups, $C_{1-10}$ alkylcarbonylamino groups, amino groups, protected amino groups, mono- or di-$C_{1-10}$ alkylamino groups, hydroxyl groups, protected hydroxyl groups, $C_{2-14}$ aryl groups and $C_{2-14}$ aryloxy groups))) or $NR^{21}$ (wherein $R^{21}$ is an amino group, a mono- or di-$C_{1-10}$ alkylamino group, a $C_{1-10}$ alkylcarbonylamino group, a $C_{1-10}$ alkylaminocarbonyl group or a $C_{2-9}$ heterocyclyl group (the mono- or di-$C_{1-10}$ alkylamino group, the $C_{1-10}$ alkylcarbonylamino group, the $C_{1-10}$ alkylaminocarbonyl group and the $C_{2-9}$ heterocyclyl group may optionally be substituted with one or more substituents selected from the group consisting of: hydrogen atoms, carboxyl groups, carbamoyl groups, sulfamoyl groups, sulfo groups, nitro groups, cyano groups, halogen atoms, amino groups, hydroxyl groups, formyl groups, $C_{1-10}$ alkyl groups, $C_{2-6}$ alkenyl groups, $C_{2-6}$ alkynyl groups, $C_{1-10}$ alkylcarbonyloxy groups, $C_{1-10}$ alkoxycarbonyl groups, $C_{1-10}$ alkylcarbonyl groups (the $C_{1-10}$ alkyl groups, the $C_{2-6}$ alkenyl groups, the $C_{2-6}$ alkynyl groups, the $C_{1-10}$ alkylcarbonyloxy groups, the $C_{1-10}$ alkoxycarbonyl groups and the $C_{1-10}$ alkylcarbonyl groups may optionally be substituted with one or more substituents selected from the group consisting of: carboxyl groups, nitro groups, cyano groups, halogen atoms, $C_{1-10}$ alkoxy groups, $C_{1-10}$ alkylcarbonyl groups, $C_{1-10}$ alkylcarbonyloxy groups, $C_{1-10}$ alkoxycarbonyl groups, $C_{1-10}$ alkylcarbonylamino groups, amino groups, protected amino groups, mono- or di-$C_{1-10}$ alkylamino groups, hydroxyl groups, protected hydroxyl groups, $C_{2-14}$ aryl groups and $C_{2-14}$ aryloxy groups (the $C_{2-14}$ aryl groups and the $C_{2-14}$ aryloxy groups may be substituted with one or more $C_{1-6}$ alkyl groups (the $C_{1-6}$ alkyl groups may be substituted with one or more halogen atoms) or one or more halogen atoms)), $C_{2-14}$ aryl groups and $C_{2-14}$ aryloxy groups (the $C_{2-14}$ aryl groups and the $C_{2-14}$ aryloxy groups may optionally be substituted with one or more substituents selected from the group consisting of: $C_{1-10}$ alkyl groups (the $C_{1-10}$ alkyl groups may be substituted with one or more halogen atoms), $C_{2-6}$ alkenyl groups, $C_{2-6}$ alkynyl groups, carboxyl groups, nitro groups, cyano groups, halogen atoms, $C_{1-10}$ alkoxy groups, $C_{1-10}$ alkylcarbonyl groups, $C_{1-10}$ alkylcarbonyloxy groups, $C_{1-10}$ alkoxycarbonyl groups, $C_{1-10}$ alkylcarbonylamino groups, amino groups, protected amino groups, mono- or di-$C_{1-10}$ alkylamino groups, hydroxyl groups, protected hydroxyl groups, $C_{2-14}$ aryl groups and $C_{2-14}$ aryloxy groups))), and each of m3 and m4 is independently an integer of from 0 to 5, provided that m3+m4 is 3, 4 or 5))))), a tautomer, prodrug or pharmaceutically acceptable salt of the compound or a solvate thereof.

23. The compound according to any one of 2 to 18 mentioned above, wherein $R^3$ is a thienyl group (the thienyl group is optionally substituted with one or more substituents independently represented by $-V^5$ (wherein $V^5$ is the same as defined above in 1) and with one or more substituents independently represented by $-W^5(CW^6W^7)_{p2}W^8$ (wherein $W^5$ is $(CR^{13}R^{14})_{q2}$ (wherein each of $R^{13}$ and $R^{14}$ is independently a hydrogen atom, a hydroxyl group, an amino group, a $C_{1-6}$ alkyl group or a $C_{1-6}$ alkoxy group (the $C_{1-6}$ alkyl group and the $C_{1-6}$ alkoxy group may be substituted with one or more halogen atoms), and q2 is 0, 1, 2 or 3), an oxygen atom, a sulfur atom or $NR^{15}$ (wherein $R^{15}$ is a hydrogen atom, a $C_{1-6}$ alkyl group, a formyl group or a $C_{1-6}$ alkylcarbonyl group), each of $W^6$ and $W^7$ is independently a hydrogen atom or a $C_{1-3}$ alkyl group (the $C_{1-3}$ alkyl group may be substituted with one or more halogen atoms), p2 is 0, 1, 2 or 3, and $W^8$ is $SO_2R^{16}$, $SOR^{16}$ or $COR^{16}$ (wherein $R^{16}$ is $NR^{17}R^{18}$ (wherein $NR^{17}R^{18}$, as a whole, means a nitrogen-containing $C_{2-9}$ cyclyl group (the nitrogen-containing $C_{2-9}$ cyclyl group may optionally be substituted with one or more hydrogen atoms and is substituted with two or three substituents independently selected from the group consisting of: hydroxyl groups, amino groups, protected amino groups, thiol groups, protected thiol groups, nitro groups, cyano groups, halogen atoms, carboxyl groups, carbamoyl groups, sulfamoyl groups, formyl groups, $C_{1-10}$ alkyl groups, $C_{2-6}$ alkenyl groups, $C_{2-6}$ alkynyl groups, $C_{1-10}$ alkoxy groups, $C_{1-10}$ alkylcarbonyloxy groups, $C_{1-10}$ alkoxycarbonyl groups, $C_{1-10}$ alkylcarbonyl groups, $C_{1-10}$ alkylcarbonylamino groups, mono- or di-$C_{1-10}$ alkylamino groups, $C_{1-10}$ alkylsulfonylamino groups, $C_{1-10}$ thioalkyl groups, $C_{2-9}$ heterocyclyl groups (the $C_{1-10}$ alkyl groups, the $C_{2-6}$ alkenyl groups, the $C_{2-6}$ alkynyl groups, the $C_{1-10}$ alkoxy groups, the $C_{1-10}$ alkylcarbonyloxy groups, the $C_{1-10}$ alkoxycarbonyl groups, the $C_{1-10}$ alkylcarbonyl groups, the $C_{1-10}$ alkylcarbonylamino groups, the mono- or di-$C_{1-10}$ alkylamino groups, the $C_{1-10}$ alkylsulfonylamino groups, the $C_{1-10}$ thioalkyl groups and the $C_{2-9}$ heterocyclyl groups may optionally be substituted with one or more substituents selected from the group consisting of: hydrogen atoms, carboxyl groups, carbamoyl groups, sulfamoyl groups, sulfo groups, nitro groups, cyano groups, halogen atoms, $C_{1-10}$ alkoxy groups, $C_{1-10}$ alkylcarbonyl groups, $C_{1-10}$ alkylcarbonyloxy groups, $C_{1-10}$ alkoxycarbonyl groups, $C_{1-10}$ alkylcarbonylamino groups, amino groups, protected amino groups, mono- or di-$C_{1-10}$ alkylamino groups, hydroxyl groups, protected hydroxyl groups, $C_{2-14}$ aryl groups and $C_{2-14}$ aryloxy groups (the $C_{2-14}$ aryl groups and the $C_{2-14}$ aryloxy groups may be substituted with one or more $C_{1-6}$ alkyl groups (the $C_{1-6}$ alkyl groups may be substituted with one or more halogen atoms) or one or more halogen atoms)), $C_{2-14}$ aryl groups and $C_{2-14}$ aryloxy groups (the $C_{2-14}$ aryl groups and the $C_{2-14}$ aryloxy groups may optionally be substituted with one or more substituents selected from the group consisting of: $C_{1-10}$ alkyl groups (the $C_{1-10}$ alkyl groups may be substituted with one or more halogen atoms), $C_{2-6}$ alkenyl groups, $C_{2-6}$ alkynyl groups, carboxyl groups, nitro groups, cyano groups, halogen atoms, $C_{1-10}$ alkoxy groups, $C_{1-10}$ alkylcarbonyl groups, $C_{1-10}$ alkylcarbonyloxy groups, $C_{1-10}$ alkoxycarbonyl groups, $C_{1-10}$ alkylcarbonylamino groups, amino groups, protected amino groups, mono- or di-$C_{1-10}$ alkylamino groups, hydroxyl groups, protected hydroxyl groups, $C_{2-14}$ aryl groups and $C_{2-14}$ aryloxy groups)))))), a tautomer, prodrug or pharmaceutically acceptable salt of the compound or a solvate thereof.

24. The compound according to 19 mentioned above, wherein $W^4$ is $COR^7$ (wherein $R^7$ is the same as defined above in 19), a tautomer, prodrug or pharmaceutically acceptable salt of the compound or a solvate thereof.

25. The compound according to 20 mentioned above, wherein $W^4$ is $COR^7$ (wherein $R^7$ is the same as defined above in 20), a tautomer, prodrug or pharmaceutically acceptable salt of the compound or a solvate thereof.

26. The compound according to 21 mentioned above, wherein $W^8$ is $COR^{16}$ (wherein $R^{16}$ is the same as defined above in 21), a tautomer, prodrug or pharmaceutically acceptable salt of the compound or a solvate thereof.

27. The compound according to 22 mentioned above, wherein $W^8$ is $COR^{16}$ (wherein $R^{16}$ is the same as defined above in 22), a tautomer, prodrug or pharmaceutically acceptable salt of the compound or a solvate thereof.

28. The compound according to 23 mentioned above, wherein $W^8$ is $COR^{16}$ (wherein $R^{16}$ is the same as defined above in 23), a tautomer, prodrug or pharmaceutically acceptable salt of the compound or a solvate thereof.

29. The compound according to any one of 19, 20, 24 and 25 mentioned above, wherein p1 and q1 are 0, a tautomer, prodrug or pharmaceutically acceptable salt of the compound or a solvate thereof.

30. The compound according to any one of 21, 22, 23, 26, 27 and 28 mentioned above, wherein p2 and q2 are 0, a tautomer, prodrug or pharmaceutically acceptable salt of the compound or a solvate thereof.

31. The compound according to any one of 1 to 30 mentioned above, wherein $V^5$ is a hydrogen atom, a hydroxyl group, an amino group, a thiol group, a nitro group, a cyano group, a hydrogen atom, a carboxyl group, a carbamoyl group, a sulfamoyl group, a sulfo group, a formyl group, a $C_{1-10}$ alkyl group, a $C_{2-6}$ alkenyl group, a $C_{2-6}$ alkynyl group, a $C_{1-10}$ alkylcarbonyloxy group, a $C_{1-10}$ alkoxycarbonyl group, a $C_{1-10}$ alkoxy group, a $C_{1-10}$ alkylcarbonyl group, a $C_{1-10}$ alkylcarbonylamino group, a mono- or di-$C_{1-10}$ alkylamino group, a $C_{1-10}$ alkylaminosulfonyl group, a $C_{1-10}$ alkylaminocarbonyl group, a $C_{1-10}$ alkylsulfonylamino group or a $C_{1-10}$ thioalkyl group, a tautomer, prodrug or pharmaceutically acceptable salt of the compound or a solvate thereof.

32. The compound according to any one of 1 to 30 mentioned above, wherein $V^5$ is a hydrogen atom, a nitro group, a cyano group, a hydrogen atom, a carboxyl group, a carbamoyl group, a sulfamoyl group, a sulfo group, a formyl group, a $C_{1-10}$ alkoxycarbonyl group, a $C_{1-10}$ alkylaminosulfonyl group or a $C_{1-10}$ alkylaminocarbonyl group, a tautomer, prodrug or pharmaceutically acceptable salt of the compound or a solvate thereof.

33. The compound according to any one of 1 to 30 mentioned above, wherein $V^5$ is a hydrogen atom, a tautomer, prodrug or pharmaceutically acceptable salt of the compound or a solvate thereof.

34. The thrombopoietin receptor activator according to any one of 1 to 33 mentioned above.

35. A preventive, therapeutic or improving agent for diseases against which activation of the thrombopoietin receptor is effective, which contains the thrombopoietin receptor activator according to 34 mentioned above, a tautomer, prodrug or pharmaceutically acceptable salt of the activator or a solvate thereof, as an active ingredient.

36. A platelet increasing agent containing the thrombopoietin receptor activator according to 34 mentioned above, a tautomer, prodrug or pharmaceutically acceptable salt of the activator or a solvate thereof, as an active ingredient.

37. Medicament containing the compound according to any one of 1 to 33 mentioned above, a tautomer, prodrug or pharmaceutically acceptable salt of the compound or a solvate thereof, as an active ingredient.

Although patent documents 13, 18 and 26 disclose hydrazide compounds having platelet increasing effect, they do not specifically disclose the hydrazide compounds of the present invention. The hydrazide compounds of the present invention show as high megakaryocyte colony stimulating activity as unexpected from the disclosure in patent documents 13, 18 and 26 and are useful as medicines.

Effects of the Invention

The present invention provides pharmaceutical compositions containing compounds which can serve as platelet increasing agents or increasing agents for other blood cells by stimulating differentiation and proliferation of hematopoietic stem cells, megakaryocytic progenitor cells and megakaryocytes or compounds which can be used for therapeutic angiogenesis or show antiarteriosclerotic action by stimulating endothelial cells and endothelial progenitor cells.

BEST MODE FOR CARRYING OUT THE INVENTION

Now, the present invention will be described in detail.

In the present invention, "n" denotes normal, "i" denotes iso, "s" denotes secondary, "t" denotes tertiary, "c" denotes cyclo, "p" denotes para, "Ph" denotes phenyl, "Et" denotes ethyl, "Pr" denotes propyl, and "Bu" denotes butyl.

First, the terms in the respective substituents $R^1$ to $R^{35}$ will be explained.

As a halogen atom, a fluorine atom, a chlorine atom, a bromine atom or an iodine atom may be mentioned.

A $C_{1-3}$ alkyl group may be linear, branched or a $C_3$ cycloalkyl group, and methyl, ethyl, n-propyl, i-propyl and c-propyl and the like may be mentioned.

A $C_{1-6}$ alkyl group may be linear, branched or a $C_{3-6}$ cycloalkyl group, and in addition to those mentioned above, n-butyl, i-butyl, s-butyl, t-butyl, c-butyl, 1-methyl-c-propyl, 2-methyl-c-propyl, n-pentyl, 1-methyl-n-butyl, 2-methyl-n-butyl, 3-methyl-n-butyl, 1,1-dimethyl-n-propyl, 1,2-dimethyl-n-propyl, 2,2-dimethyl-n-propyl, 1-ethyl-n-propyl, c-pentyl, 1-methyl-c-butyl, 2-methyl-c-butyl, 3-methyl-c-butyl, 1,2-dimethyl-c-propyl, 2,3-dimethyl-c-propyl, 1-ethyl-c-propyl, 2-ethyl-c-propyl, n-hexyl, 1-methyl-n-pentyl, 2-methyl-n-pentyl, 3-methyl-n-pentyl, 4-methyl-n-pentyl, 1,1-dimethyl-n-butyl, 1,2-dimethyl-n-butyl, 1,3-dimethyl-n-butyl, 2,2-dimethyl-n-butyl, 2,3-dimethyl-n-butyl, 3,3-dimethyl-n-butyl, 1-ethyl-n-butyl, 2-ethyl-n-butyl, 1,1,2-trimethyl-n-propyl, 1,2,2-trimethyl-n-propyl, 1-ethyl-1-methyl-n-propyl, 1-ethyl-2-methyl-n-propyl, c-hexyl, 1-methyl-c-pentyl, 2-methyl-c-pentyl, 3-methyl-c-pentyl, 1-ethyl-c-butyl, 2-ethyl-c-butyl, 3-ethyl-c-butyl, 1,2-dimethyl-c-butyl, 1,3-dimethyl-c-butyl, 2,2-dimethyl-c-butyl, 2,3-dimethyl-c-butyl, 2,4-dimethyl-c-butyl, 3,3-dimethyl-c-butyl, 1-n-propyl-c-propyl, 2-n-propyl-c-propyl, 1-i-propyl-c-propyl, 2-i-propyl-c-propyl, 1,2,2-trimethyl-c-propyl, 1,2,3-trimethyl-c-propyl, 2,2,3-trimethyl-c-propyl, 1-ethyl-2-methyl-c-propyl, 2-ethyl-1-methyl-c-propyl, 2-ethyl-2-methyl-c-propyl, 2-ethyl-3-methyl-c-propyl and the like may be mentioned.

A $C_{1-10}$ alkyl group may be linear, branched or a $C_{3-10}$ cycloalkyl group, and in addition to those mentioned above, 1-methyl-1-ethyl-n-pentyl, 1-heptyl, 2-heptyl, 1-ethyl-1,2-dimethyl-n-propyl, 1-ethyl-2,2-dimethyl-n-propyl, 1-octyl, 3-octyl, 4-methyl-3-n-heptyl, 6-methyl-2-n-heptyl, 2-propyl-1-n-heptyl, 2,4,4-trimethyl-1-n-pentyl, 1-nonyl, 2-nonyl, 2,6-dimethyl-4-n-heptyl, 3-ethyl-2,2-dimethyl-3-n-pentyl, 3,5,5-trimethyl-1-n-hexyl, 1-decyl, 2-decyl, 4-decyl, 3,7-dimethyl-1-n-octyl, 3,7-dimethyl-3-n-octyl and the like may be mentioned.

As a $C_{2-6}$ alkynyl group, ethynyl, 1-propynyl, 2-propynyl, 1-butynyl, 2-butynyl, 3-butynyl, 1-methyl-2-propynyl, 1-pentynyl, 2-pentynyl, 3-pentynyl, 4-pentynyl, 1-methyl-2-butynyl, 1-methyl-3-butynyl, 2-methyl-3-butynyl, 3-methyl-1-butynyl, 1,1-dimethyl-2-propynyl, 1-hexynyl, 2-hexynyl, 3-hexynyl, 4-hexynyl, 5-hexynyl, 1-methyl-2-pentynyl, 1-methyl-3-pentynyl, 1-methyl-4-pentynyl, 2-methyl-3-pentynyl, 2-methyl-4-pentynyl, 3-methyl-1-pentynyl, 3-methyl-4-pentynyl, 4-methyl-1-pentynyl, 4-methyl-2-pentynyl, 1,1-dimethyl-2-butynyl, 1,1-dimethyl-3-butynyl, 1,2-dimethyl-3-butynyl, 2,2-dimethyl-3-butynyl, 3,3-dimethyl-1-butynyl, 1-ethyl-2-butynyl, 1-ethyl-3-butynyl, 1-n-propyl-2-propynyl, 2-ethyl-3-butynyl, 1-methyl-1-ethyl-2-propynyl, 1-i-propyl-2-propynyl and the like may be mentioned.

A $C_{2-6}$ alkenyl group may be linear, branched or a $C_{3-6}$ cycloalkenyl group, and ethenyl, 1-propenyl, 2-propenyl, 1-methyl-1-ethenyl, 1-butenyl, 2-butenyl, 3-butenyl, 2-methyl-1-propenyl, 2-methyl-2-propenyl, 1-ethylethenyl, 1-methyl-1-propenyl, 1-methyl-2-propenyl, 1-pentenyl, 2-pentenyl, 3-pentenyl, 4-pentenyl, 1-n-propylethenyl, 1-methyl-1-butenyl, 1-methyl-2-butenyl, 1-methyl-3-butenyl, 2-ethyl-2-propenyl, 2-methyl-1-butenyl, 2-methyl-2-butenyl, 2-methyl-3-butenyl, 3-methyl-1-butenyl, 3-methyl-2-butenyl, 3-methyl-3-butenyl, 1,1-dimethyl-2-propenyl, 1-i-propylethenyl, 1,2-dimethyl-1-propenyl, 1,2-dimethyl-2-propenyl, 1-c-pentenyl, 2-c-pentenyl, 3-c-pentenyl, 1-hexenyl, 2-hexenyl, 3-hexenyl, 4-hexenyl, 5-hexenyl, 1-methyl-1-pentenyl, 1-methyl-2-pentenyl, 1-methyl-3-pentenyl, 1-methyl-4-pentenyl, 1-n-butylethenyl, 2-methyl-1-pentenyl, 2-methyl-2-pentenyl, 2-methyl-3-pentenyl, 2-methyl-4-pentenyl, 2-n-propyl-2-propenyl, 3-methyl-1-pentenyl, 3-methyl-2-pentenyl, 3-methyl-3-pentenyl, 3-methyl-4-pentenyl, 3-ethyl-3-butenyl, 4-methyl-1-pentenyl, 4-methyl-2-pentenyl, 4-methyl-3-pentenyl, 4-methyl-4-pentenyl, 1,1-dimethyl-2-butenyl, 1,1-dimethyl-3-butenyl, 1,2-dimethyl-1-butenyl, 1,2-dimethyl-2-butenyl, 1,2-dimethyl-3-butenyl, 1-methyl-2-ethyl-2-propenyl, 1-s-butylethenyl, 1,3-dimethyl-1-butenyl, 1,3-dimethyl-2-butenyl, 1,3-dimethyl-3-butenyl, 1-i-butylethenyl, 2,2-dimethyl-3-butenyl, 2,3-dimethyl-1-butenyl, 2,3-dimethyl-2-butenyl, 2,3-dimethyl-3-butenyl, 2-i-propyl-2-propenyl, 3,3-dimethyl-1-butenyl, 1-ethyl-1-butenyl, 1-ethyl-2-butenyl, 1-ethyl-3-butenyl, 1-n-propyl-1-propenyl, 1-n-propyl-2-propenyl, 2-ethyl-1-butenyl, 2-ethyl-2-butenyl, 2-ethyl-3-butenyl, 1,1,2-trimethyl-2-propenyl, 1-t-butylethenyl, 1-methyl-1-ethyl-2-propenyl, 1-ethyl-2-methyl-1-propenyl, 1-ethyl-2-methyl-2-propenyl, 1-i-propyl-1-propenyl, 1-i-propyl-2-propenyl, 1-methyl-2-c-pentenyl, 1-methyl-3-c-pentenyl, 2-methyl-1-c-pentenyl, 2-methyl-2-c-pentenyl, 2-methyl-3-c-pentenyl, 2-methyl-4-c-pentenyl, 2-methyl-5-c-pentenyl, 2-methylene-c-pentyl, 3-methyl-1-c-pentenyl, 3-methyl-2-c-pentenyl, 3-methyl-3-c-pentenyl, 3-methyl-4-c-pentenyl, 3-methyl-5-c-pentenyl, 3-methylene-c-pentyl, 1-c-hexenyl, 2-c-hexenyl, 3-c-hexenyl and the like may be mentioned.

A $C_{1-6}$ alkylcarbonyl group may linear, branched or a $C_{3-6}$ cycloalkylcarbonyl group, and be methylcarbonyl, ethylcarbonyl, n-propylcarbonyl, i-propylcarbonyl, c-propylcarbonyl, n-butylcarbonyl, i-butylcarbonyl, s-butylcarbonyl, t-butylcarbonyl, c-butylcarbonyl, 1-methyl-c-propylcarbonyl, 2-methyl-c-propylcarbonyl, n-pentylcarbonyl, 1-methyl-n-butylcarbonyl, 2-methyl-n-butylcarbonyl, 3-methyl-n-butylcarbonyl, 1,1-dimethyl-n-propylcarbonyl, 1,2-dimethyl-n-propylcarbonyl, 2,2-dimethyl-n-propylcarbonyl, 1-ethyl-n-propylcarbonyl, c-pentylcarbonyl, 1-methyl-c- butylcarbonyl, 2-methyl-c-butylcarbonyl, 3-methyl-c-butylcarbonyl, 1,2-dimethyl-c-propylcarbonyl, 2,3-dimethyl-c-propylcarbonyl, 1-ethyl-c-propylcarbonyl, 2-ethyl-c-propylcarbonyl, n-hexylcarbonyl, 1-methyl-n-pentylcarbonyl, 2-methyl-n-pentylcarbonyl, 3-methyl-n-pentylcarbonyl, 4-methyl-n-pentylcarbonyl, 1,1-dimethyl-n-butylcarbonyl, 1,2-dimethyl-n-butylcarbonyl, 1,3-dimethyl-n-butylcarbonyl, 2,2-dimethyl-n-butylcarbonyl, 2,3-dimethyl-n-butylcarbonyl, 3,3-dimethyl-n-butylcarbonyl, 1-ethyl-n-butylcarbonyl, 2-ethyl-n-butylcarbonyl, 1,1,2-trimethyl-n-propylcarbonyl, 1,2,2-trimethyl-n-propylcarbonyl, 1-ethyl-1-methyl-n-propylcarbonyl, 1-ethyl-2-methyl-n-propylcarbonyl, c-hexylcarbonyl, 1-methyl-c-pentylcarbonyl, 2-methyl-c-pentylcarbonyl, 3-methyl-c-pentylcarbonyl, 1-ethyl-c-butylcarbonyl, 2-ethyl-c-butylcarbonyl, 3-ethyl-c-butylcarbonyl, 1,2-dimethyl-c-butylcarbonyl, 1,3-dimethyl-c-butylcarbonyl, 2,2-dimethyl-c-butylcarbonyl, 2,3-dimethyl-c-butylcarbonyl, 2,4-dimethyl-c-butylcarbonyl, 3,3-dimethyl-c-butylcarbonyl, 1-n-propyl-c-propylcarbonyl, 2-n-propyl-c-propylcarbonyl, 1-i-propyl-c-propylcarbonyl, 2-i-propyl-c-propylcarbonyl, 1,2,2-trimethyl-c-propylcarbonyl, 1,2,3-trimethyl-c-propylcarbonyl, 2,2,3-trimethyl-c-propylcarbonyl, 1-ethyl-2-methyl-c-propylcarbonyl, 2-ethyl-1-methyl-c-propylcarbonyl, 2-ethyl-2-methyl-c-propylcarbonyl, 2-ethyl-3-methyl-c-propylcarbonyl or the like may be mentioned.

A $C_{1-10}$ alkylcarbonyl may be linear, branched or a $C_{3-10}$ cycloalkylcarbonyl group, and in addition to those mentioned above, 1-methyl-1-ethyl-n-pentylcarbonyl, 1-heptylcarbonyl, 2-heptylcarbonyl, 1-ethyl-1,2-dimethyl-n-propylcarbonyl, 1-ethyl-2,2-dimethyl-n-propylcarbonyl, 1-octylcarbonyl, 3-octylcarbonyl, 4-methyl-3-n-heptylcarbonyl, 6-methyl-2-n-heptylcarbonyl, 2-propyl-1-n-heptylcarbonyl, 2,4,4-trimethyl-1-n-pentylcarbonyl, 1-nonylcarbonyl, 2-nonylcarbonyl, 2,6-dimethyl-4-n-heptylcarbonyl, 3-ethyl-2,2-dimethyl-3-n-pentylcarbonyl, 3,5,5-trimethyl-1-n-hexylcarbonyl, 1-decylcarbonyl, 2-decylcarbonyl, 4-decylcarbonyl, 3,7-dimethyl-1-n-octylcarbonyl, 3,7-dimethyl-3-n-octylcarbonyl or the like may be mentioned.

A $C_{1-3}$ alkoxy group may be linear, branched or a $C_3$ cycloalkoxy group, and methoxy, ethoxy, n-propoxy, i-propoxy, c-propoxy or the like may be mentioned.

A $C_{1-6}$ alkoxy group may be linear, branched or a $C_{3-6}$ cycloalkoxy group, and in addition to those mentioned above, n-butoxy, i-butoxy, s-butoxy, t-butoxy, c-butoxy, 1-methyl-c-propoxy, 2-methyl-c-propoxy, n-pentyloxy, 1-methyl-n-butoxy, 2-methyl-n-butoxy, 3-methyl-n-butoxy, 1,1-dimethyl-n-propoxy, 1,2-dimethyl-n-propoxy, 2,2-dimethyl-n-propoxy, 1-ethyl-n-propoxy, c-pentyloxy, 1-methyl-c-butoxy, 2-methyl-c-butoxy, 3-methyl-c-butoxy, 1,2-dimethyl-c-propoxy, 2,3-dimethyl-c-propoxy, 1-ethyl-c-propoxy, 2-ethyl-c-propoxy, n-hexyloxy, 1-methyl-n-pentyloxy, 2-methyl-n-pentyloxy, 3-methyl-n-pentyloxy, 4-methyl-n-pentyloxy, 1,1-dimethyl-n-butoxy, 1,2-dimethyl-n-butoxy, 1,3-dimethyl-n-butoxy, 2,2-dimethyl-n-butoxy, 2,3-dimethyl-n-butoxy, 3,3-dimethyl-n-butoxy, 1-ethyl-n-butoxy, 2-ethyl-n-butoxy, 1,1,2-trimethyl-n-propoxy, 1,2,2-trimethyl-n-propoxy, 1-ethyl-1-methyl-n-propoxy, 1-ethyl-2-methyl-n-propoxy, c-hexyloxy, 1-methyl-c-pentyloxy, 2-methyl-c-pentyloxy, 3-methyl-c-pentyloxy, 1-ethyl-c-butoxy, 2-ethyl-c-butoxy, 3-ethyl-c-butoxy, 1,2-dimethyl-c-butoxy, 1,3-dimethyl-c-butoxy, 2,2-dimethyl-c-butoxy, 2,3-dimethyl-c-butoxy, 2,4-dimethyl-c-butoxy, 3,3-dimethyl-c-butoxy, 1-n-propyl-c-propoxy, 2-n-propyl-c-propoxy, 1-i-propyl-c-propoxy, 2-i-propyl-c-propoxy, 1,2,2-trimethyl-c-propoxy, 1,2,3-trimethyl-c-propoxy, 2,2,3-trimethyl-c-propoxy, 1-ethyl-2-methyl-c-propoxy, 2-ethyl-1-methyl-c-propoxy, 2-ethyl-2-methyl-c-propoxy, 2-ethyl-3-methyl-c-propoxy or the like may be mentioned.

A $C_{1-10}$ alkoxy group may be linear, branched or a $C_{3-10}$ cycloalkoxy group, and in addition to those mentioned above, 1-methyl-1-ethyl-n-pentyloxy, 1-heptyloxy, 2-heptyloxy, 1-ethyl-1,2-dimethyl-n-propyloxy, 1-ethyl-2,2-dimethyl-n-propyloxy, 1-octyloxy, 3-octyloxy, 4-methyl-3-n-heptyloxy, 6-methyl-2-n-heptyloxy, 2-propyl-1-n-heptyloxy, 2,4,4-trimethyl-1-n-pentyloxy, 1-nonyloxy, 2-nonyloxy, 2,6-dimethyl-4-n-heptyloxy, 3-ethyl-2,2-dimethyl-3-n-pentyloxy, 3,5,5-trimethyl-1-n-hexyloxy, 1-decyloxy, 2-decyloxy, 4-decyloxy, 3,7-dimethyl-1-n-octyloxy, 3,7-dimethyl-3-n-octyloxy or the like may be mentioned.

A $C_{1-10}$ thioalkyl group may linear, branched or a $C_{3-10}$ cyclothioalkyl group, and be methylthio, ethylthio, n-propylthio, i-propylthio, c-propylthio, n-butylthio, i-butylthio, s-butylthio, t-butylthio, c-butylthio, 1-methyl-c-propylthio, 2-methyl-c-propylthio, n-pentylthio, 1-methyl-n-butylthio, 2-methyl-n-butylthio, 3-methyl-n-butylthio, 1,1-dimethyl-n-propylthio, 1,2-dimethyl-n-propylthio, 2,2-dimethyl-n-propylthio, 1-ethyl-n-propylthio, c-pentylthio, 1-methyl-c-butylthio, 2-methyl-c-butylthio, 3-methyl-c-butylthio, 1,2-dimethyl-c-propylthio, 2,3-dimethyl-c-propylthio, 1-ethyl-c-propylthio, 2-ethyl-c-propylthio, n-hexylthio, 1-methyl-n-pentylthio, 2-methyl-n-pentylthio, 3-methyl-n-pentylthio, 4-methyl-n-pentylthio, 1,1-dimethyl-n-butylthio, 1,2-dimethyl-n-butylthio, 1,3-dimethyl-n-butylthio, 2,2-dimethyl-n-butylthio, 2,3-dimethyl-n-butylthio, 3,3-dimethyl-n-butylthio, 1-ethyl-n-butylthio, 2-ethyl-n-butylthio, 1,1,2-trimethyl-n-propylthio, 1,2,2-trimethyl-n-propylthio, 1-ethyl-1-methyl-n-propylthio, 1-ethyl-2-methyl-n-propylthio, c-hexylthio, 1-methyl-c-pentylthio, 2-methyl-c-pentylthio, 3-methyl-c-pentylthio, 1-ethyl-c-butylthio, 2-ethyl-c-butylthio, 3-ethyl-c-butylthio, 1,2-dimethyl-c-butylthio, 1,3-dimethyl-c-butylthio, 2,2-dimethyl-c-butylthio, 2,3-dimethyl-c-butylthio, 2,4-dimethyl-c-butylthio, 3,3-dimethyl-c-butylthio, 1-n-propyl-c-propylthio, 2-n-propyl-c-propylthio, 1-i-propyl-c-propylthio, 2-i-propyl-c-propylthio, 1,2,2-trimethyl-c-propylthio, 1,2,3-trimethyl-c-propylthio, 2,2,3-trimethyl-c-propylthio, 1-ethyl-2-methyl-c-propylthio, 2-ethyl-1-methyl-c-propylthio, 2-ethyl-2-methyl-c-propylthio, 2-ethyl-3-methyl-c-propylthio, 1-methyl-1-ethyl-n-pentylthio, 1-heptylthio, 2-heptylthio, 1-ethyl-1,2-dimethyl-n-propylthio, 1-ethyl-2,2-dimethyl-n-propylthio, 1-octylthio, 3-octylthio, 4-methyl-3-n-heptylthio, 6-methyl-2-n-heptylthio, 2-propyl-1-n-heptylthio, 2,4,4-trimethyl-1-n-pentylthio, 1-nonylthio, 2-nonylthio, 2,6-dimethyl-4-n-heptylthio, 3-ethyl-2,2-dimethyl-3-n-pentylthio, 3,5,5-trimethyl-1-n-hexylthio, 1-decylthio, 2-decylthio, 4-decylthio, 3,7-dimethyl-1-n-octylthio, 3,7-dimethyl-3-n-octylthio or the like may be mentioned.

A $C_{1-6}$ alkylsulfonylamino group may be linear, branched or a $C_{3-6}$ cycloalkylsulfonylamino group, and methylsulfonylamino, ethylsulfonylamino, n-propylsulfonylamino, i-propylsulfonylamino, c-propylsulfonylamino, n-butylsulfonylamino, i-butylsulfonylamino, s-butylsulfonylamino, t-butylsulfonylamino, c-butylsulfonylamino, 1-methyl-c-propylsulfonylamino, 2-methyl-c-propylsulfonylamino, n-pentylsulfonylamino, 1-methyl-n-butylsulfonylamino, 2-methyl-n-butylsulfonylamino, 3-methyl-n-butylsulfonylamino, 1,1-dimethyl-n-propylsulfonylamino, 1,2-dimethyl-n-propylsulfonylamino, 2,2-dimethyl-n-propylsulfonylamino, 1-ethyl-n-propylsulfonylamino, c-pentylsulfonylamino, 1-methyl-c-butylsulfonylamino, 2-methyl-c-butylsulfonylamino, 3-methyl-c-butylsulfonylamino, 1,2-dimethyl-c-propylsulfonylamino, 2,3-dimethyl-c-propylsulfonylamino, 1-ethyl-c-propylsulfonylamino, 2-ethyl-c-propylsulfonylamino, n-hexylsulfonylamino, 1-methyl-n-pentylsulfonylamino, 2-methyl-n-pentylsulfonylamino, 3-methyl-n-pentylsulfonylamino, 4-methyl-n-pentylsulfonylamino, 1,1-dimethyl-n-butylsulfonylamino, 1,2-dimethyl-n-butylsulfonylamino, 1,3-dimethyl-n-butylsulfonylamino, 2,2-dimethyl-n-butylsulfonylamino, 2,3-dimethyl-n-butylsulfonylamino, 3,3-dimethyl-n-butylsulfonylamino, 1-ethyl-n-butylsulfonylamino, 2-ethyl-n-butylsulfonylamino, 1,1,2-trimethyl-n-propylsulfonylamino, 1,2,2-trimethyl-n-propylsulfonylamino, 1-ethyl-1-methyl-n-propylsulfonylamino, 1-ethyl-2-methyl-n-propylsulfonylamino, c-hexylsulfonylamino, 1-methyl-c-pentylsulfonylamino, 2-methyl-c-pentylsulfonylamino, 3-methyl-c-pentylsulfonylamino, 1-ethyl-c-butylsulfonylamino, 2-ethyl-c-butylsulfonylamino, 3-ethyl-c-butylsulfonylamino, 1,2-dimethyl-c-butylsulfonylamino, 1,3-dimethyl-c-butylsulfonylamino, 2,2-dimethyl-c-butylsulfonylamino, 2,3-dimethyl-c-butylsulfonylamino, 2,4-dimethyl-c-butylsulfonylamino, 3,3-dimethyl-c-butylsulfonylamino, 1-n-propyl-c-propylsulfonylamino, 2-n-propyl-c-propylsulfonylamino, 1-i-propyl-c-propylsulfonylamino, 2-i-propyl-c-propylsulfonylamino, 1,2,2-trimethyl-c-propylsulfonylamino, 1,2,3-trimethyl-c-propylsulfonylamino, 2,2,3-trimethyl-c-propylsulfonylamino, 1-ethyl-2-methyl-c-propylsulfonylamino, 2-ethyl-1-methyl-c-propylsulfonylamino, 2-ethyl-2-methyl-c-propylsulfonylamino, 2-ethyl-3-methyl-c-propylsulfonylamino or the like may be mentioned.

A $C_{1-10}$ alkylsulfonylamino group may be linear, branched or a $C_{3-10}$ cycloalkylsulfonylamino group, and in addition to those mentioned above, 1-methyl-1-ethyl-n-pentylsulfonylamino, 1-heptylsulfonylamino, 2-heptylsulfonylamino, 1-ethyl-1,2-dimethyl-n-propylsulfonylamino, 1-ethyl-2,2-dimethyl-n-propylsulfonylamino, 1-octylsulfonylamino, 3-octylsulfonylamino, 4-methyl-3-n-heptylsulfonylamino, 6-methyl-2-n-heptylsulfonylamino, 2-propyl-1-n-n-heptylsulfonylamino, 2,4,4-trimethyl-1-n-pentylsulfonylamino, 1-nonylsulfonylamino, 2-nonylsulfonylamino, 2,6-dimethyl-4-n-heptylsulfonylamino, 3-ethyl-2,2-dimethyl-3-n-pentylsulfonylamino, 3,5,5-trimethyl-1-n-hexylsulfonylamino, 1-decylsulfonylamino, 2-decylsulfonylamino, 4-decylsulfonylamino, 3,7-dimethyl-1-n-octylsulfonylamino, 3,7-dimethyl-3-n-octylsulfonylamino, c-heptylsulfonylamino, c-octylsulfonylamino, 1-methyl-c-hexylsulfonylamino, 2-methyl-c-hexylsulfonylamino, 3-methyl-c-hexylsulfonylamino, 1,2-dimethyl-c-hexylsulfonylamino, 1-ethyl-c-hexylsulfonylamino, 1-methyl-c-pentylsulfonylamino, 2-methyl-c-pentylsulfonylamino, 3-methyl-c-pentylsulfonylamino or the like may be mentioned.

A $C_{1-6}$ alkoxycarbonyl group may be linear, branched or a $C_{3-6}$ cycloalkoxycarbonyl group, and methoxycarbonyl, ethoxycarbonyl, n-propoxycarbonyl, i-propoxycarbonyl, c-propoxyl carbonyl, n-butoxycarbonyl, i-butoxycarbonyl, s-butoxycarbonyl, t-butoxycarbonyl, c-butoxycarbonyl, 1-methyl-c-propoxycarbonyl, 2-methyl-c-propoxycarbonyl, n-pentyloxycarbonyl, 1-methyl-n-butoxycarbonyl, 2-methyl-n-butoxycarbonyl, 3-methyl-n-butoxycarbonyl, 1,1-dimethyl-n-propoxycarbonyl, 1,2-dimethyl-n-propoxycarbonyl, 2,2-dimethyl-n-propoxycarbonyl, 1-ethyl-n-propoxycarbonyl, c-pentyloxycarbonyl, 1-methyl-c-butoxycarbonyl, 2-methyl-c-butoxycarbonyl, 3-methyl-c-butoxycarbonyl, 1,2-dimethyl-c-propoxycarbonyl, 2,3-dimethyl-c-propoxycarbonyl, 1-ethyl-c-propoxycarbonyl, 2-ethyl-c-propoxycarbonyl, n-hexyloxycarbonyl, 1-methyl-n-pentyloxycarbonyl, 2-methyl-n-pentyloxycarbonyl, 3-methyl-n-pentyloxycarbonyl, 4-methyl-n-pentyloxycarbonyl, 1,1-dimethyl-n-butoxycarbonyl, 1,2-dimethyl-n-butoxycarbonyl, 1,3-dimethyl-n-butoxycarbonyl, 2,2-dimethyl-n-butoxycarbonyl, 2,3-dimethyl-n-butoxycarbonyl, 3,3-dimethyl-n-butoxycarbonyl, 1-ethyl-n-butoxycarbonyl, 2-ethyl-n-butoxycarbonyl, 1,1,2-trimethyl-n-propoxycarbonyl, 1,2,2-trimethyl-n-propoxycarbonyl, 1-ethyl-1-methyl-n-propoxycarbonyl, 1-ethyl-2-methyl-n-propoxycarbonyl, c-hexyloxycarbonyl, 1-methyl-c-pentyloxycarbonyl, 2-methyl-c-pentyloxycarbonyl, 3-methyl-c-pentyloxycarbonyl, 1-ethyl-c-butoxycarbonyl, 2-ethyl-c-butoxycarbonyl, 3-ethyl-c-butoxycarbonyl, 1,2-dimethyl-c-butoxycarbonyl, 1,3-dimethyl-c-butoxycarbonyl, 2,2-dimethyl-c-butoxycarbonyl, 2,3-dimethyl-c-butoxycarbonyl, 2,4-dimethyl-c-butoxycarbonyl, 3,3-dimethyl-c-butoxycarbonyl, 1-n-propyl-c-propoxycarbonyl, 2-n-propyl-c-propoxycarbonyl, 1-i-propyl-c-propoxycarbonyl, 2-i-propyl-c-propoxycarbonyl, 1,2,2-trimethyl-c-propoxycarbonyl, 1,2,3-trimethyl-c-propoxycarbonyl, 2,2,3-trimethyl-c-propoxycarbonyl, 1-ethyl-2-methyl-c-propoxycarbonyl, 2-ethyl-1-methyl-c-propoxycarbonyl, 2-ethyl-2-methyl-c-propoxycarbonyl, 2-ethyl-3-methyl-c-propoxycarbonyl or the like may be mentioned.

A $C_{1-10}$ alkoxycarbonyl group may be linear, branched or a $C_{3-10}$ cycloalkoxycarbonyl group, and in addition to those mentioned above, 1-methyl-1-ethyl-n-pentyloxycarbonyl, 1-heptyloxycarbonyl, 2-heptyloxycarbonyl, 1-ethyl-1,2-dimethyl-n-propyloxycarbonyl, 1-ethyl-2,2-dimethyl-n-propyloxycarbonyl, 1-octyloxycarbonyl, 3-octyloxycarbonyl, 4-methyl-3-n-heptyloxycarbonyl, 6-methyl-2-n-heptyloxycarbonyl, 2-propyl-1-n-heptyloxycarbonyl, 2,4,4-trimethyl-1-n-pentyloxycarbonyl, 1-nonyloxycarbonyl, 2-nonyloxycarbonyl, 2,6-dimethyl-4-n-heptyloxycarbonyl, 3-ethyl-2,2-dimethyl-3-n-pentyloxycarbonyl, 3,5,5-trimethyl-1-n-hexyloxycarbonyl, 1-decyloxycarbonyl, 2-decyloxycarbonyl, 4-decyloxycarbonyl, 3,7-dimethyl-1-n-octyloxycarbonyl, 3,7-dimethyl-3-n-octyloxycarbonyl or the like may be mentioned.

A $C_{1-10}$ alkylcarbonyloxy group may be linear, branched or a $C_{3-10}$ cycloalkylcarbonyloxy group, and methylcarbonyloxy, ethylcarbonyloxy, n-propylcarbonyloxy, i-propylcarbonyloxy, c-propylcarbonyloxy, n-butylcarbonyloxy, i-butylcarbonyloxy, s-butylcarbonyloxy, t-butylcarbonyloxy, c-butylcarbonyloxy, 1-methyl-c-propylcarbonyloxy, 2-methyl-c-propylcarbonyloxy, n-pentylcarbonyloxy, 1-methyl-n-butylcarbonyloxy, 2-methyl-n-butylcarbonyloxy, 3-methyl-n-butylcarbonyloxy, 1,1-dimethyl-n-propylcarbonyloxy, 1,2-dimethyl-n-propylcarbonyloxy, 2,2-dimethyl-n-propylcarbonyloxy, 1-ethyl-n-propylcarbonyloxy, c-pentylcarbonyloxy, 1-methyl-c-butylcarbonyloxy, 2-methyl-c-butylcarbonyloxy, 3-methyl-c-butylcarbonyloxy, 1,2-dimethyl-c-propylcarbonyloxy, 2,3-dimethyl-c-propylcarbonyloxy, 1-ethyl-c-propylcarbonyloxy, 2-ethyl-c-propylcarbonyloxy, n-hexylcarbonyloxy, 1-methyl-n-pentylcarbonyloxy, 2-methyl-n-pentylcarbonyloxy, 3-methyl-n-pentylcarbonyloxy, 4-methyl-n-pentylcarbonyloxy, 1,1-dimethyl-n-butylcarbonyloxy, 1,2-dimethyl-n-butylcarbonyloxy, 1,3-dimethyl-n-butylcarbonyloxy, 2,2-dimethyl-n-butylcarbonyloxy, 2,3-dimethyl-n-butylcarbonyloxy, 3,3-dimethyl-n-butylcarbonyloxy, 1-ethyl-n-butylcarbonyloxy, 2-ethyl-n-butylcarbonyloxy, 1,1,2-trimethyl-n-propylcarbonyloxy, 1,2,2-trimethyl-n-propylcarbonyloxy, 1-ethyl-1-methyl-n-propylcarbonyloxy, 1-ethyl-2-methyl-n-propylcarbonyloxy, c-hexylcarbonyloxy, 1-methyl-c-pentylcarbonyloxy, 2-methyl-c-pentylcarbonyloxy, 3-methyl-c-pentylcarbonyloxy, 1-ethyl-c-butylcarbonyloxy, 2-ethyl-c-butylcarbonyloxy, 3-ethyl-c-butylcarbonyloxy, 1,2-dimethyl-c-butylcarbonyloxy, 1,3-dimethyl-c-butylcarbonyloxy, 2,2-dimethyl-c-butylcarbonylxoy, 2,3-dimethyl-c-butylcarbonyloxy, 2,4-dimethyl-c-butylcarbonyloxy, 3,3-dimethyl-c-butylcarbonyloxy, 1-n-propyl-c-propylcarbonyloxy, 2-n-propyl-c-propylcarbonyloxy, 1-i-propyl-c-propycarbonyloxy, 2-i-propyl-c-propylcarbonyloxy, 1,2,3-trimethyl-c-propylcarbonyloxy, 1,2,3-trimethyl-c-propylcarbonyloxy, 2,2,3-trimethyl-c-propylcarbonyloxy, 1-ethyl-2-methyl-c-propylcarbonyloxy, 2-ethyl-1-methyl-c-propylcarbonyloxy, 2-ethyl-2-methyl-c-propylcarbonyloxy, 2-ethyl-3-methyl-c-propylcarbonyloxy, 1-methyl-1-ethyl-n-pentylcarbonyloxy, 1-heptylcarbonyloxy, 2-heptylcarbonyloxy, 1-ethyl-1,2-dimethyl-n-propylcarbonyloxy, 1-ethyl-2,2-dimethyl-n-propylcarbonyloxy, 1-octylcarbonyloxy, 3-octylcarbonyloxy, 4-methyl-3-n-heptylcarbonyloxy, 6-methyl-2-n-heptylcarbonyloxy, 2-propyl-1-n-heptylcarbonyloxy, 2,4,4-trimethyl-1-n-pentylcarbonyloxy, 1-nonylcarbonyloxy, 2-nonylcarbonyloxy, 2,6-dimethyl-4-n-heptylcarbonyloxy, 3-ethyl-2,2-dimethyl-3-n-pentylcarbonyloxy, 3,5,5-trimethyl-1-n-hexylcarbonyloxy, 1-decylcarbonyloxy, 2-decylcarbonyloxy, 4-decylcarbonyloxy, 3,7-dimethyl-1-n-octylcarbonyloxy, 3,7-dimethyl-3-n-octylcarbonyloxy or the like may be mentioned.

A $C_{1-10}$ alkylcarbonylamino group may be linear, branched or a $C_{3-10}$ cycloalkylcarbonylamino group, and methylcarbonylamino, ethylcarbonylamino, n-propylcarbonylamino, i-propylcarbonylamino, c-propylcarbonylamino, n-butylcarbonylamino, i-butylcarbonylamino, s-butylcarbonylamino, t-butylcarbonylamino, c-butylcarbonylamino, 1-methyl-c-propylcarbonylamino, 2-methyl-c-propylcarbonylamino, n-pentylcarbonylamino, 1-methyl-n-butylcarbonylamino, 2-methyl-n-butylcarbonylamino, 3-methyl-n-butylcarbonylamino, 1,1-dimethyl-n-propylcarbonylamino, 1,2-dimethyl-n-propylcarbonylamino, 2,2-dimethyl-n-propylcarbonylamino, 1-ethyl-n-propylcarbonylamino, c-pentylcarbonylamino, 1-methyl-c-butylcarbonylamino, 2-methyl-c-butylcarbonylamino, 3-methyl-c-butylcarbonylamino, 1,2-dimethyl-c-propylcarbonylamino, 2,3-dimethyl-c-propylcarbonylamino, 1-ethyl-c-propylcarbonylamino, 2-ethyl-c-propylcarbonylamino, n-hexylcarbonylamino, 1-methyl-n-pentylcarbonylamino, 2-methyl-n-pentylcarbonylamino, 3-methyl-n-pentylcarbonylamino, 4-methyl-n-pentylcarbonylamino, 1,1-dimethyl-n-butylcarbonylamino, 1,2-dimethyl-n-butylcarbonylamino, 1,3-dimethyl-n-butylcarbonylamino, 2,2-dimethyl-n-butylcarbonylamino, 2,3-dimethyl-n-butylcarbonylamino, 3,3-dimethyl-n-butylcarbonylamino, 1-ethyl-n-butylcarbonylamino, 2-ethyl-n-butylcarbonylamino, 1,1,2-trimethyl-n-propylcarbonylamino, 1,2,2-trimethyl-n-propylcarbonylamino, 1-ethyl-1-methyl-n-propylcarbonylamino, 1-ethyl-2-methyl-n-propylcarbonylamino, c-hexylcarbonylamino, 1-methyl-c-pentylcarbonylamino, 2-methyl-c-pentylcarbonylamino, 3-methyl-c-pentylcarbonylamino, 1-ethyl-c-butylcarbonylamino, 2-ethyl-c-butylcarbonylamino, 3-ethyl-c-butylcarbonylamino, 1,2-dimethyl-c-butylcarbonylamino, 1,3-dimethyl-c-butylcarbonylamino, 2,2-dimethyl-c-butylcarbonylamino, 2,3-dimethyl-c-butylcarbonylamino, 2,4-dimethyl-c-butylcarbonylamino, 3,3-dimethyl-c-butylcarbonylamino, 1-n-propyl-c-propylcarbonylamino, 2-n-propyl-c-propylcarbonylamino, 1-i-propyl-c-propylcarbonylamino, 2-i-propyl-c-propylcarbonylamino, 1,2,2-trimethyl-c-propyl-carbonylamino, 1,2,3-trimethyl-c-propylcarbonylamino, 2,2,3-trimethyl-c-propylcarbonylamino, 1-ethyl-2-methyl-c-propylcarbonylamino, 2-ethyl-1-methyl-c-propylcarbonylamino, 2-ethyl-2-methyl-c-propylcarbonylamino, 2-ethyl-3-methyl-c-propylcarbonylamino, 1-methyl-1-ethyl-n-pentylcarbonylamino, 1-heptylcarbonylamino, 2-heptylcarbonylamino, 1-ethyl-1,2-dimethyl-n-propylcarbonylamino, 1-ethyl-2,2-dimethyl-n-propylcarbonylamino, 1-octylcarbonylamino, 3-octylcarbonylamino, 4-methyl-3-n-heptylcarbonylamino, 6-methyl-2-n-heptylcarbonylamino, 2-propyl-1-n-heptylcarbonylamino, 2,4,4-trimethyl-1-n-pentylcarbonylamino, 1-nonylcarbonylamino, 2-nonylcarbonylamino, 2,6-dimethyl-4-n-heptylcarbonylamino, 3-ethyl-2,2-dimethyl-3-n-pentylcarbonylamino, 3,5,5-trimethyl-1-n-hexylcarbonylamino, 1-decylcarbonylamino, 2-decylcarbonylamino, 4-decylcarbonylamino, 3,7-dimethyl-1-n-octylcarbonylamino, 3,7-dimethyl-3-n-octylcarbonylamino or the like may be mentioned.

A $C_{1-10}$ monoalkylamino group may be linear, branched or a $C_{3-10}$ cycloalkylamino group, and methylamino, ethylamino, n-propylamino, i-propylamino, c-propylamino, n-butylamino, i-butylamino, s-butylamino, t-butylamino, c-butylamino, 1-methyl-c-propylamino, 2-methyl-c-propylamino, n-pentylamino, 1-methyl-n-butylamino, 2-methyl-n-butylamino, 3-methyl-n-butylamino, 1,1-dimethyl-n-propylamino, 1,2-dimethyl-n-propylamino, 2,2-dimethyl-n-propylamino, 1-ethyl-n-propylamino, c-pentylamino, 1-methyl-c-butylamino, 2-methyl-c-butylamino, 3-methyl-c-butylamino, 1,2-dimethyl-c-propylamino, 2,3-dimethyl-c-propylamino, 1-ethyl-c-propylamino, 2-ethyl-c-propylamino, n-hexylamino, 1-methyl-n-pentylamino, 2-methyl-n-pentylamino, 3-methyl-n-pentylamino, 4-methyl-n-pentylamino, 1,1-dimethyl-n-butylamino, 1,2-dimethyl-n-butylamino, 1,3-dimethyl-n-butylamino, 2,2-dimethyl-n-butylamino, 2,3-dimethyl-n-butylamino, 3,3-dimethyl-n-butylamino, 1-ethyl-n-butylamino, 2-ethyl-n-butylamino, 1,1,2-trimethyl-n-propylamino, 1,2,2-trimethyl-n-propylamino, 1-ethyl-1-methyl-n-propylamino, 1-ethyl-2-methyl-n-propylamino, c-hexylamino, 1-methyl-c-pentylamino, 2-methyl-c-pentylamino, 3-methyl-c-pentylamino, 1-ethyl-c-butylamino, 2-ethyl-c-butylamino, 3-ethyl-c-butylamino, 1,2-dimethyl-c-butylamino, 1,3-dimethyl-c-butylamino, 2,2-dimethyl-c-butylamino, 2,3-dimethyl-c-butylamino, 2,4-dimethyl-c-butylamino, 3,3-dimethyl-c-butylamino, 1-n-propyl-c-propylamino, 2-n-propyl-c-propylamino, 1-i-propyl-c-propylamino, 2-i-propyl-c-propylamino, 1,2,2-trimethyl-c-propylamino, 1,2,3-trimethyl-c-propylamino, 2,2,3-trimethyl-c-propylamino, 1-ethyl-2-methyl-c-propylamino, 2-ethyl-1-methyl-c-propylamino, 2-ethyl-2-methyl-c-propylamino, 2-ethyl-3-methyl-c-propylamino, 1-methyl-1-ethyl-n-pentylamino, 1-heptylamino, 2-heptylamino, 1-ethyl-1,2-dimethyl-n-propylamino, 1-ethyl-2,2-dimethyl-n-propylamino, 1-octylamino, 3-octylamino, 4-methyl-3-n-heptylamino, 6-methyl-2-n-heptylamino, 2-propyl-1-n-heptylamino, 2,4,4-trimethyl-1-n-pentylamino, 1-nonylamino, 2-nonylamino, 2,6-dimethyl-4-n-heptylamino, 3-ethyl-2,2-dimethyl-3-n-pentylamino, 3,5,5-trimethyl-1-n-hexylamino, 1-decylamino, 2-decylamino, 4-decylamino, 3,7-dimethyl-1-n-octylamino, 3,7-dimethyl-3-n-octylamino or the like may be mentioned.

A $C_{1-10}$ dialkylamino group may be symmetric or asymmetric. A symmetric $C_{1-10}$ dialkylamino group may be linear, branched or a $C_{3-10}$ cycloalkylamino group, and dimethylamino, diethylamino, di-n-propylamino, di-i-propylamino, di-c-propylamino, di-n-butylamino, di-i-butylamino, di-s-butylamino, di-t-butylamino, di-c-butylamino, di-(1-methyl-c-propyl)amino, di-(2-methyl-c-propyl)amino, di-n-pentylamino, di-(1-methyl-n-butyl)amino, di-(2-methyl-n-butyl)amino, di-(3-methyl-n-butyl)amino, di-(1,1-dimethyl-n-propyl)amino, di-(1,2-dimethyl-n-propyl)amino, di-(2,2-dimethyl-n-propyl)amino, di-(1-ethyl-n-propyl)amino, di-c-pentylamino, di-(1-methyl-c-butyl)amino, di-(2-methyl-c- butyl)amino, di-(3-methyl-c-butyl)amino, di-(1,2-dimethyl-c-propyl)amino, di-(2,3-dimethyl-c-propyl)amino, di-(1-ethyl-c-propyl)amino, di-(2-ethyl-c-propyl)amino, di-n-hexylamino, di-(1-methyl-n-pentyl)amino, di-(2-methyl-n-pentyl)amino, di-(3-methyl-n-pentyl)amino, di-(4-methyl-n-pentyl)amino, di-(1,1-dimethyl-n-butyl)amino, di-(1,2-dimethyl-n-butyl)amino, di-(1,3-dimethyl-n-butyl)amino, di-(2,2-dimethyl-n-butyl)amino, di-(2,3-dimethyl-n-butyl)amino, di-(3,3-dimethyl-n-butyl)amino, di-(1-ethyl-n-butyl)amino, di-(2-ethyl-n-butyl)amino, di-(1,1,2-trimethyl-n-propyl)amino, di-(1,2,2-trimethyl-n-propyl)amino, di-(1-ethyl-1-methyl-n-propyl)amino, di-(1-ethyl-2-methyl-n-propyl)amino, di-c-hexylamino, di-(1-methyl-c-pentyl)amino, di-(2-methyl-c-pentyl)amino, di-(3-methyl-c-pentyl)amino, di-(1-ethyl-c-butyl)amino, di-(2-ethyl-c-butyl)amino, di-(3-ethyl-c-butyl)amino, di-(1,2-dimethyl-c-butyl)amino, di-(1,3-dimethyl-c-butyl)amino, di-(2,2-dimethyl-c-butyl)amino, di-(2,3-dimethyl-c-butyl)amino, di-(2,4-dimethyl-c-butyl)amino, di-(3,3-dimethyl-c-butyl)amino, di-(1-n-propyl-c-propyl)amino, di-(2-n-propyl-c-propyl)amino, di-(1-i-propyl-c-propyl)amino, di-(2-i-propyl-c-propyl)amino, di-(1,2,2-trimethyl-c-propyl)amino, di-(1,2,3-trimethyl-c-propyl)amino, di-(2,2,3-trimethyl-c-propyl)amino, di-(1-ethyl-2-methyl-c-propyl)amino, di-(2-ethyl-1-methyl-c-propyl)amino, di-(2-ethyl-2-methyl-c-propyl)amino, di-(2-ethyl-3-methyl-c-propyl)amino, di-(1-methyl-1-ethyl-n-pentyl)amino, di-(1-heptyl)amino, di-(2-heptyl)amino, di-(1-ethyl-1,2-dimethyl-n-propyl)amino, di-(1-ethyl-2,2-dimethyl-n-propyl)amino, di-(1-octyl)amino, di-(3-octyl)amino, di-(4-methyl-3-n-heptyl)amino, di-(6-methyl-2-n-heptyl)amino, di-(2-propyl-1-n-heptyl)amino, di-(2,4,4-trimethyl-1-n-pentyl)amino, di-(1-nonyl)amino, di-(2-nonyl)amino, di-(2,6-dimethyl-4-n-heptyl)amino, di-(3-ethyl-2,2-dimethyl-3-n-pentyl)amino, di-(3,5,5-trimethyl-1-n-hexyl)amino, di-(1-decyl)amino, di-(2-decyl)amino, di-(4-decyl)amino, di-(3,7-dimethyl-1-n-octyl)amino, di-(3,7-dimethyl-3-n-octyl)amino or the like may be mentioned.

An asymmetric $C_{1-10}$ dialkylamino group may be linear, branched or a $C_{3-10}$ cycloalkylamino group, and (methyl, ethyl)amino, (methyl, n-propyl)amino, (methyl, i-propyl)amino, (methyl, c-propyl)amino, (methyl, n-butyl)amino, (methyl, i-butyl)amino, (methyl, s-butyl)amino, (methyl, t-butyl)amino, (methyl, n-pentyl)amino, (methyl, c-pentyl)amino, (methyl, n-hexyl)amino, (methyl, c-hexyl)amino, (ethyl, n-propyl)amino, (ethyl, i-propyl)amino, (ethyl, c-propyl)amino, (ethyl, n-butyl)amino, (ethyl, i-butyl)amino, (ethyl, s-butyl)amino, (ethyl, t-butyl)amino, (ethyl, n-pentyl)amino, (ethyl, c-pentyl)amino, (ethyl, n-hexyl)amino, (ethyl, c-hexyl)amino, (n-propyl, i-propyl)amino, (n-propyl, c-propyl)amino, (n-propyl, n-butyl)amino, (n-propyl, i-butyl)amino, (n-propyl, s-butyl)amino, (n-propyl, t-butyl)amino, (n-propyl, n-pentyl)amino, (n-propyl, c-pentyl)amino, (n-propyl, n-hexyl)amino, (n-propyl, c-hexyl)amino, (i-propyl, c-propyl)amino, (i-propyl, n-butyl)amino, (i-propyl, i-butyl)amino, (i-propyl, s-butyl)amino, (i-propyl, t-butyl)amino, (i-propyl, n-pentyl)amino, (i-propyl, c-pentyl)amino, (i-propyl, n-hexyl)amino, (i-propyl, c-hexyl)amino, (c-propyl, n-butyl)amino, (c-propyl, i-butyl)amino, (c-propyl, s-butyl)amino, (c-propyl, t-butyl)amino, (c-propyl, n-pentyl)amino, (c-propyl, c-pentyl)amino, (c-propyl, n-hexyl)amino, (c-propyl, c-hexyl)amino, (n-butyl, i-butyl)amino, (n-butyl, s-butyl)amino, (n-butyl, t-butyl)amino, (n-butyl, n-pentyl)amino, (n-butyl, c-pentyl)amino, (n-butyl, n-hexyl)amino, (n-butyl, c-hexyl)amino, (i-butyl, s-butyl)amino, (i-butyl, t-butyl)amino, (i-butyl, n-pentyl)amino, (i-butyl, c-pentyl)amino, (i-butyl, n-hexyl)amino, (i-butyl, c-hexyl)amino, (s-butyl, t-butyl)amino, (s-butyl, n-pentyl)amino, (s-butyl, c-pentyl)amino, (s-butyl, n-hexyl)amino, (s-butyl, c-hexyl)amino, (t-butyl, n-pentyl)amino, (t-butyl, c-pentyl)amino, (t-butyl, n-hexyl)amino, (t-butyl, c-hexyl)amino, (n-pentyl, c-pentyl)amino, (n-pentyl, n-hexyl)amino, (n-pentyl, c-hexyl)amino, (c-pentyl, n-hexyl)amino, (c-pentyl, c-hexyl)amino, (n-hexyl, c-hexyl)amino, (methyl, n-heptyl)amino, (methyl, n-octyl)amino, (methyl, n-nonanyl)amino, (methyl, n-decyl)amino, (methyl, n-heptyl)amino, (ethyl, n-octyl)amino, (ethyl, n-nonanyl)amino, (ethyl, n-decyl)amino or the like may be mentioned.

A $C_{1-10}$ alkylaminocarbonyl group may be a $C_{1-10}$ monoalkylaminocarbonyl group or a $C_{1-10}$ dialkylaminocarbonyl group.

A $C_{1-10}$ monoalkylaminocarbonyl group may be linear, branched or a $C_{3-10}$ cycloalkylaminocarbonyl group, and methylaminocarbonyl, ethylaminocarbonyl, n-propylaminocarbonyl, i-propylaminocarbonyl, c-propylaminocarbonyl, n-butylaminocarbonyl, i-butylaminocarbonyl, s-butylaminocarbonyl, t-butylaminocarbonyl, c-butylaminocarbonyl, 1-methyl-c-propylaminocarbonyl, 2-methyl-c-propylaminocarbonyl, n-pentylaminocarbonyl, 1-methyl-n-butylaminocarbonyl, 2-methyl-n-butylaminocarbonyl, 3-methyl-n-butylaminocarbonyl, 1,1-dimethyl-n-propylaminocarbonyl, 1,2-dimethyl-n-propylaminocarbonyl, 2,2-dimethyl-n-propylaminocarbonyl, 1-ethyl-n-propylaminocarbonyl, c-pentylaminocarbonyl, 1-methyl-c-butylaminocarbonyl, 2-methyl-c-butylaminocarbonyl, 3-methyl-c-butylaminocarbonyl, 1,2-dimethyl-c-propylaminocarbonyl, 2,3-dimethyl-c-propylaminocarbonyl, 1-ethyl-c-propylaminocarbonyl, 2-ethyl-c-propylaminocarbonyl, n-hexylaminocarbonyl, 1-methyl-n-pentylaminocarbonyl, 2-methyl-n-pentylaminocarbonyl, 3-methyl-n-pentylaminocarbonyl, 4-methyl-n-pentylaminocarbonyl, 1,1-dimethyl-n-butylaminocarbonyl, 1,2-dimethyl-n-butylaminocarbonyl, 1,3-dimethyl-n-butylaminocarbonyl, 2,2-dimethyl-n-butylaminocarbonyl, 2,3-dimethyl-n-butylaminocarbonyl, 3,3-dimethyl-n-butylaminocarbonyl, 1-ethyl-n-butylaminocarbonyl, 2-ethyl-n-butylaminocarbonyl, 1,1,2-trimethyl-n-propylaminocarbonyl, 1,2,2-trimethyl-n-propylaminocarbonyl, 1-ethyl-1-methyl-n-propylaminocarbonyl, 1-ethyl-2-methyl-n-propylaminocarbonyl, c-hexylaminocarbonyl, 1-methyl-c-pentylaminocarbonyl, 2-methyl-c-pentylaminocarbonyl, 3-methyl-c-pentylaminocarbonyl, 1-ethyl-c-butylaminocarbonyl, 2-ethyl-c-butylaminocarbonyl, 3-ethyl-c-butylaminocarbonyl, 1,2-dimethyl-c-butylaminocarbonyl, 1,3-dimethyl-c-butylaminocarbonyl, 2,2-dimethyl-c-butylaminocarbonyl, 2,3-dimethyl-c-butylaminocarbonyl, 2,4-dimethyl-c-butylaminocarbonyl, 3,3-dimethyl-c-butylaminocarbonyl, 1-n-propyl-c-propylaminocarbonyl, 2-n-propyl-c-propylaminocarbonyl, 1-i-propyl-c-propylaminocarbonyl, 2-i-propyl-c-propylaminocarbonyl, 1,2,2-trimethyl-c-propylaminocarbonyl, 1,2,3-trimethyl-c-propylaminocarbonyl, 2,2,3-trimethyl-c-propylaminocarbonyl, 1-ethyl-2-methyl-c-propylaminocarbonyl, 2-ethyl-1-methyl-c-propylaminocarbonyl, 2-ethyl-2-methyl-c-propylaminocarbonyl, 2-ethyl-3-methyl-c-propylaminocarbonyl, 1-methyl-1-ethyl-n-pentylaminocarbonyl, 1-heptylaminocarbonyl, 2-heptylaminocarbonyl, 1-ethyl-1,2-dimethyl-n-propylaminocarbonyl, 1-ethyl-2,2-dimethyl-n-propylaminocarbonyl, 1-octylaminocarbonyl, 3-octylaminocarbonyl, 4-methyl-3-n-heptylaminocarbonyl, 6-methyl-2-n-heptylaminocarbonyl, 2-propyl-1-n-heptylaminocarbonyl, 2,4,4-trimethyl-1-n-pentylaminocarbonyl, 1-nonylaminocarbonyl, 2-nonylaminocarbonyl, 2,6-dimethyl-4-n-heptylaminocarbonyl, 3-ethyl-2,2-dimethyl-3-n-pentylaminocarbonyl, 3,5,5-trimethyl-1-n-hexylaminocarbonyl, 1-decylaminocarbonyl, 2-decylaminocarbonyl, 4-decylaminocarbonyl, 3,7- dimethyl-1-n-octylaminocarbonyl, 3,7-dimethyl-3-n-octylaminocarbonyl or the like may be mentioned.

A $C_{1-10}$ dialkylaminocarbonyl group may be symmetric or asymmetric. A symmetric $C_{1-10}$ dialkylaminocarbonyl group may be linear, branched or a $C_{3-10}$ cycloalkylaminocarbonyl group, and dimethylaminocarbonyl, diethylaminocarbonyl, di-n-propylaminocarbonyl, di-i-propylaminocarbonyl, di-c-propylaminocarbonyl, di-n-butylaminocarbonyl, di-i-butylaminocarbonyl, di-s-butylaminocarbonyl, di-t-butylaminocarbonyl, di-c-butylaminocarbonyl, di-(1-methyl-c-propyl)aminocarbonyl, di-(2-methyl-c-propyl)aminocarbonyl, di-n-pentylaminocarbonyl, di-(1-methyl-n-butyl)aminocarbonyl, di-(2-methyl-n-butyl)aminocarbonyl, di-(3-methyl-n-butyl)aminocarbonyl, di-(1,1-dimethyl-n-propyl)aminocarbonyl, di-(1,2-dimethyl-n-propyl)aminocarbonyl, di-(2,2-dimethyl-n-propyl)aminocarbonyl, di-(1-ethyl-n-propyl)aminocarbonyl, di-c-pentylaminocarbonyl, di-(1-methyl-c-butyl)aminocarbonyl, di-(2-methyl-c-butyl)aminocarbonyl, di-(3-methyl-c-butyl)aminocarbonyl, di-(1,2-dimethyl-c-propyl)aminocarbonyl, di-(2,3-dimethyl-c-propyl)aminocarbonyl, di-(1-ethyl-c-propyl)aminocarbonyl, di-(2-ethyl-c-propyl)aminocarbonyl, di-n-hexylaminocarbonyl, di-(1-methyl-n-pentyl)aminocarbonyl, di-(2-methyl-n-pentyl)aminocarbonyl, di-(3-methyl-n-pentyl)aminocarbonyl, di-(4-methyl-n-pentyl)aminocarbonyl, di-(1,1-dimethyl-n-butyl)aminocarbonyl, di-(1,2-dimethyl-n-butyl)aminocarbonyl, di-(1,3-dimethyl-n-butyl)aminocarbonyl, di-(2,2-dimethyl-n-butyl)aminocarbonyl, di-(2,3-dimethyl-n-butyl)aminocarbonyl, di-(3,3-dimethyl-n-butyl)aminocarbonyl, di-(1-ethyl-n-butyl)aminocarbonyl, di-(2-ethyl-n-butyl)aminocarbonyl, di-(1,1,2-trimethyl-n-propyl)aminocarbonyl, di-(1,2,2-trimethyl-n-propyl)aminocarbonyl, di-(1-ethyl-1-methyl-n-propyl)aminocarbonyl, di-(1-ethyl-2-methyl-n-propyl)aminocarbonyl, di-c-hexylaminocarbonyl, di-(1-methyl-c-pentyl)aminocarbonyl, di-(2-methyl-c-pentyl)aminocarbonyl, di-(3-methyl-c-pentyl)aminocarbonyl, di-(1-ethyl-c-butyl)aminocarbonyl, di-(2-ethyl-c-butyl)aminocarbonyl, di-(3-ethyl-c-butyl)aminocarbonyl, di-(1,2-dimethyl-c-butyl)aminocarbonyl, di-(1,3-dimethyl-c-butyl)aminocarbonyl, di-(2,2-dimethyl-c-butyl)aminocarbonyl, di-(2,3-dimethyl-c-butyl)aminocarbonyl, di-(2,4-dimethyl-c-butyl)aminocarbonyl, di-(3,3-dimethyl-c-butyl)aminocarbonyl, di-(1-n-propyl-c-propyl)aminocarbonyl, di-(2-n-propyl-c-propyl)aminocarbonyl, di-(1-i-propyl-c-propyl)aminocarbonyl, di-(2-i-propyl-c-propyl)aminocarbonyl, di-(1,2,2-trimethyl-c-propyl)aminocarbonyl, di-(1,2,3-trimethyl-c-propyl)aminocarbonyl, di-(2,2,3-trimethyl-c-propyl)aminocarbonyl, di-(1-ethyl-2-methyl-c-propyl)aminocarbonyl, di-(2-ethyl-1-methyl-c-propyl)aminocarbonyl, di-(2-ethyl-2-methyl-c-propyl)aminocarbonyl, di-(2-ethyl-3-methyl-c-propyl)aminocarbonyl, di-(1-methyl-1-ethyl-n-pentyl)aminocarbonyl, di-(1-heptyl)aminocarbonyl, di-(2-heptyl)aminocarbonyl, di-(1-ethyl-1,2-dimethyl-n-propyl)aminocarbonyl, di-(1-ethyl-2,2-dimethyl-n-propyl)aminocarbonyl, di-(1-octyl)aminocarbonyl, di-(3-octyl)aminocarbonyl, di-(4-methyl-3-n-heptyl)aminocarbonyl, di-(6-methyl-2-n-heptyl)aminocarbonyl, di-(2-propyl-1-n-heptyl)aminocarbonyl, di-(2,4,4-trimethyl-1-n-pentyl)aminocarbonyl, di-(1-nonyl)aminocarbonyl, di-(2-nonyl)aminocarbonyl, di-(2,6-dimethyl-4-n-heptyl)aminocarbonyl, di-(3-ethyl-2,2-dimethyl-3-n-pentyl)aminocarbonyl, di-(3,5,5-trimethyl-1-n-hexyl)aminocarbonyl, di-(1-decyl)aminocarbonyl, di-(2-decyl)aminocarbonyl, di-(4-decyl)aminocarbonyl, di-(3,7-dimethyl-1-n-octyl)aminocarbonyl, di-(3,7-dimethyl-3-n-octyl)aminocarbonyl or the like may be mentioned.

A $C_{1-10}$ dialkylaminocarbonyl group may be an asymmetric $C_{1-10}$ dialkylaminocarbonyl group or a symmetric $C_{1-10}$ dialkylaminocarbonyl group.

An asymmetric $C_{1-10}$ dialkylaminocarbonyl group may be linear, branched or a $C_{3-10}$ cycloalkylaminocarbonyl group, and (methyl, ethyl)aminocarbonyl, (methyl, n-propyl)aminocarbonyl, (methyl, i-propyl)aminocarbonyl, (methyl, c-propyl)aminocarbonyl, (methyl, n-butyl)aminocarbonyl, (methyl, i-butyl)aminocarbonyl, (methyl, s-butyl)aminocarbonyl, (methyl, t-butyl)aminocarbonyl, (methyl, n-pentyl)aminocarbonyl, (methyl, c-pentyl)aminocarbonyl, (methyl, n-hexyl)aminocarbonyl, (methyl, c-hexyl)aminocarbonyl, (ethyl, n-propyl)aminocarbonyl, (ethyl, i-propyl)aminocarbonyl, (ethyl, c-propyl)aminocarbonyl, (ethyl, n-butyl)aminocarbonyl, (ethyl, i-butyl)aminocarbonyl, (ethyl, s-butyl)aminocarbonyl, (ethyl, t-butyl)aminocarbonyl, (ethyl, n-pentyl)aminocarbonyl, (ethyl, c-pentyl)aminocarbonyl, (ethyl, n-hexyl)aminocarbonyl, (ethyl, c-hexyl)aminocarbonyl, (n-propyl, i-propyl)aminocarbonyl, (n-propyl, c-propyl)aminocarbonyl, (n-propyl, n-butyl)aminocarbonyl, (n-propyl, i-butyl)aminocarbonyl, (n-propyl, s-butyl)aminocarbonyl, (n-propyl, t-butyl)aminocarbonyl, (n-propyl, n-pentyl)aminocarbonyl, (n-propyl, c-pentyl)aminocarbonyl, (n-propyl, n-hexyl)aminocarbonyl, (n-propyl, c-hexyl)aminocarbonyl, (i-propyl, c-propyl)aminocarbonyl, (i-propyl, n-butyl)aminocarbonyl, (i-propyl, i-butyl)aminocarbonyl, (i-propyl, s-butyl)aminocarbonyl, (i-propyl, t-butyl)aminocarbonyl, (i-propyl, n-pentyl)aminocarbonyl, (i-propyl, c-pentyl)aminocarbonyl, (i-propyl, n-hexyl)aminocarbonyl, (i-propyl, c-hexyl)aminocarbonyl, (c-propyl, n-butyl)aminocarbonyl, (c-propyl, i-butyl)aminocarbonyl, (c-propyl, s-butyl)aminocarbonyl, (c-propyl, t-butyl)aminocarbonyl, (c-propyl, n-pentyl)aminocarbonyl, (c-propyl, c-pentyl)aminocarbonyl, (c-propyl, n-hexyl)aminocarbonyl, (c-propyl, c-hexyl)aminocarbonyl, (n-butyl, i-butyl)aminocarbonyl, (n-butyl, s-butyl)aminocarbonyl, (n-butyl, t-butyl)aminocarbonyl, (n-butyl, n-pentyl)aminocarbonyl, (n-butyl, c-pentyl)aminocarbonyl, (n-butyl, n-hexyl)aminocarbonyl, (n-butyl, c-hexyl)aminocarbonyl, (i-butyl, s-butyl)aminocarbonyl, (i-butyl, t-butyl)aminocarbonyl, (i-butyl, n-pentyl)aminocarbonyl, (i-butyl, c-pentyl)aminocarbonyl, (i-butyl, n-hexyl)aminocarbonyl, (i-butyl, c-hexyl)aminocarbonyl, (s-butyl, t-butyl)aminocarbonyl, (s-butyl, n-pentyl)aminocarbonyl, (s-butyl, c-pentyl)aminocarbonyl, (s-butyl, n-hexyl)aminocarbonyl, (s-butyl, c-hexyl)aminocarbonyl, (t-butyl, n-pentyl)aminocarbonyl, (t-butyl, c-pentyl)aminocarbonyl, (t-butyl, n-hexyl)aminocarbonyl, (t-butyl, c-hexyl)aminocarbonyl, (n-pentyl, c-pentyl)aminocarbonyl, (n-pentyl, n-hexyl)aminocarbonyl, (n-pentyl, c-hexyl)aminocarbonyl, (c-pentyl, n-hexyl)aminocarbonyl, (c-pentyl, c-hexyl)aminocarbonyl, (n-hexyl, c-hexyl)aminocarbonyl, (methyl, n-heptyl)aminocarbonyl, (methyl, n-octyl)aminocarbonyl, (methyl, n-nonanyl)aminocarbonyl, (methyl, n-decyl)aminocarbonyl, (methyl, n-heptyl)aminocarbonyl, (ethyl, n-octyl)aminocarbonyl, (ethyl, n-nonanyl)aminocarbonyl, (ethyl, n-decyl)aminocarbonyl or the like may be mentioned.

A $C_{1-6}$ alkylaminosulfonyl group may be linear, branched or a $C_{3-6}$ cycloalkylaminosulfonyl group, and methylaminosulfonyl, ethylaminosulfonyl, n-propylaminosulfonyl, i-propylaminosulfonyl, c-propylaminosulfonyl, n-butylaminosulfonyl, i-butylaminosulfonyl, s-butylaminosulfonyl, t-butylaminosulfonyl, c-butylaminosulfonyl, 1-methyl-c-propylaminosulfonyl, 2-methyl-c-propylaminosulfonyl, n-pentylaminosulfonyl, 1-methyl-n-butylaminosulfonyl, 2-methyl-n-butylaminosulfonyl, 3-methyl-n-butylaminosulfonyl, 1,1-dimethyl-n-propylaminosulfonyl, 1,2-dimethyln-propylaminosulfonyl, 2,2-dimethyln-propylaminosulfonyl, 1-ethyl-n-propylaminosulfonyl, c-pentylaminosulfonyl, 1-methyl-c-butylaminosulfonyl, 2-methyl-c-butylaminosulfonyl, 3-methyl-c-butylaminosulfonyl, 1,2-dimethyl-c-propylaminosulfonyl, 2,3-dimethyl-c-propylaminosulfonyl, 1-ethyl-c-propylaminosulfonyl, 2-ethyl-c-propylaminosulfonyl, n-hexylaminosulfonyl, 1-methyl-n-pentylaminosulfonyl, 2-methyl-n-pentylaminosulfonyl, 3-methyl-n-pentylaminosulfonyl, 4-methyl-n-pentylaminosulfonyl, 1,1-dimethyl-n-butylaminosulfonyl, 1,2-dimethyl-n-butylaminosulfonyl, 1,3-dimethyl-n-butylaminosulfonyl, 2,2-dimethyl-n-butylaminosulfonyl, 2,3-dimethyl-n-butylaminosulfonyl, 3,3-dimethyl-n-butylaminosulfonyl, 1-ethyl-n-butylaminosulfonyl, 2-ethyl-n-butylaminosulfonyl, 1,1,2-trimethyl-n-propylaminosulfonyl, 1,2,2-trimethyl-n-propylaminosulfonyl, 1-ethyl-1-methyl-n-propylaminosulfonyl, 1-ethyl-2-methyl-n-propylaminosulfonyl, c-hexylaminosulfonyl, 1-methyl-c-pentylaminosulfonyl, 2-methyl-c-pentylaminosulfonyl, 3-methyl-c-pentylaminosulfonyl, 1-ethyl-c-butylaminosulfonyl, 2-ethyl-c-butylaminosulfonyl, 3-ethyl-c-butylaminosulfonyl, 1,2-dimethyl-c-butylaminosulfonyl, 1,3-dimethyl-c-butylaminosulfonyl, 2,2-dimethyl-c-butylaminosulfonyl, 2,3-dimethyl-c-butylaminosulfonyl, 2,4-dimethyl-c-butylaminosulfonyl, 3,3-dimethyl-c-butylaminosulfonyl, 1-n-propyl-c-propylaminosulfonyl, 2-n-propyl-c-propylaminosulfonyl, 1-i-propyl-c-propylaminosulfonyl, 2-i-propyl-c-propylaminosulfonyl, 1,2,2-trimethyl-c-propylaminosulfonyl, 1,2,3-trimethyl-c-propylaminosulfonyl, 2,2,3-trimethyl-c-propylaminosulfonyl, 1-ethyl-2-methyl-c-propylaminosulfonyl, 2-ethyl-1-methyl-c-propylaminosulfonyl, 2-ethyl-2-methyl-c-propylaminosulfonyl, 2-ethyl-3-methyl-c-propylaminosulfonyl or the like may be mentioned.

A $C_{1-10}$ alkylaminosulfonyl group may be linear, branched or a $C_{3-10}$ cycloalkylsulfonylamino group, and in addition to those mentioned above, 1-methyl-1-ethyl-n-pentylaminosulfonyl, 1-heptylaminosulfonyl, 2-heptylaminosulfonyl, 1-ethyl-1,2-dimethyl-n-propylaminosulfonyl, 1-ethyl-2,2-dimethyl-n-propylaminosulfonyl, 1-octylaminosulfonyl, 3-octylaminosulfonyl, 4-methyl-3-n-heptylaminosulfonyl, 6-methyl-2-n-heptylaminosulfonyl, 2-propyl-1-n-heptylaminosulfonyl, 2,4,4-trimethyl-1-n-pentylaminosulfonyl, 1-nonylaminosulfonyl, 2-nonylaminosulfonyl, 2,6-dimethyl-4-n-heptylaminosulfonyl, 3-ethyl-2,2-dimethyl-3-n-pentylaminosulfonyl, 3,5,5-trimethyl-1-n-hexylaminosulfonyl, 1-decylaminosulfonyl, 2-decylaminosulfonyl, 4-decylaminosulfonyl, 3,7-dimethyl-1-n-octylaminosulfonyl, 3,7-dimethyl-3-n-octylaminosulfonyl, c-heptylaminosulfonyl, c-octylaminosulfonyl, 1-methyl-c-hexylaminosulfonyl, 2-methyl-c-hexylaminosulfonyl, 3-methyl-c-hexylaminosulfonyl, 1,2-dimethyl-c-hexylaminosulfonyl, 1-ethyl-c-hexylaminosulfonyl, 1-methyl-c-pentylaminosulfonyl, 2-methyl-c-pentylaminosulfonyl, 3-methyl-c-pentylaminosulfonyl or the like may be mentioned.

A $C_{1-6}$ alkylsulfonyl group may be linear, branched or a $C_{3-6}$ cycloalkylsulfonyl group, and methylsulfonyl, ethylsulfonyl, n-propylsulfonyl, i-propylsulfonyl, c-propylsulfonyl, n-butylsulfonyl, i-butylsulfonyl, s-butylsulfonyl, t-butylsulfonyl, c-butylsulfonyl, 1-methyl-c-propylsulfonyl, 2-methyl-c-propylsulfonyl, n-pentylsulfonyl, 1-methyl-n-butylsulfonyl, 2-methyl-n-butylsulfonyl, 3-methyl-n-butylsulfonyl, 1,1-dimethyl-n-propylsulfonyl, 1,2-dimethyl-n-propylsulfonyl, 2,2-dimethyl-n-propylsulfonyl, 1-ethyl-n-propylsulfonyl, c-pentylsulfonyl, 1-methyl-c-butylsulfonyl, 2-methyl-c-butylsulfonyl, 3-methyl-c-butylsulfonyl, 1,2-dimethyl-c-propylsulfonyl, 2,3-dimethyl-c-propylsulfonyl, 1-ethyl-c-propylsulfonyl, 2-ethyl-c-propylsulfonyl, n-hexylsulfonyl, 1-methyl-n-pentylsulfonyl, 2-methyl-n-pentylsulfonyl, 3-methyl-n-pentylsulfonyl, 4-methyl-n-pentylsulfonyl, 1,1-dimethyl-n-butylsulfonyl, 1,2-dimethyl-n-butylsulfonyl, 1,3-dimethyl-n-butylsulfonyl, 2,2-dimethyl-n-butylsulfonyl, 2,3-dimethyl-n-butylsulfonyl, 3,3-dimethyl-n-butylsulfonyl, 1-ethyl-n-butylsulfonyl, 2-ethyl-n-butylsulfonyl, 1,1,2-trimethyl-n-propylsulfonyl, 1,2,2-trimethyl-n-propylsulfonyl, 1-ethyl-1-methyl-n-propylsulfonyl, 1-ethyl-2-methyl-n-propylsulfonyl, c-hexylsulfonyl, 1-methyl-c-pentylsulfonyl, 2-methyl-c-pentylsulfonyl, 3-methyl-c-pentylsulfonyl, 1-ethyl-c-butylsulfonyl, 2-ethyl-c-butylsulfonyl, 3-ethyl-c-butylsulfonyl, 1,2-dimethyl-c-butylsulfonyl, 1,3-dimethyl-c-butylsulfonyl, 2,2-dimethyl-c-butylsulfonyl, 2,3-dimethyl-c-butylsulfonyl, 2,4-dimethyl-c-butylsulfonyl, 3,3-dimethyl-c-butylsulfonyl, 1-n-propyl-c-propylsulfonyl, 2-n-propyl-c-propylsulfonyl, 1-i-propyl-c-propylsulfonyl, 2-i-propyl-c-propylsulfonyl, 1,2,2-trimethyl-c-propylsulfonyl, 1,2,3-trimethyl-c-propylsulfonyl, 2,2,3-trimethyl-c-propylsulfonyl, 1-ethyl-2-methyl-c-propylsulfonyl, 2-ethyl-1-methyl-c-propylsulfonyl, 2-ethyl-2-methyl-c-propylsulfonyl, 2-ethyl-3-methyl-c-propylsulfonyl or the like may be mentioned.

A $C_{1-10}$ alkylsulfonyl group may be linear, branched or a $C_{3-10}$ cycloalkylsulfonyl group, and in addition to those mentioned above, 1-methyl-1-ethyl-n-pentylsulfonyl, 1-heptylsulfonyl, 2-heptylsulfonyl, 1-ethyl-1,2-dimethyl-n-propylsulfonyl, 1-ethyl-2,2-dimethyl-n-propylsulfonyl, 1-octylsulfonyl, 3-octylsulfonyl, 4-methyl-3-n-heptylsulfonyl, 6-methyl-2-n-heptylsulfonyl, 2-propyl-1-n-n-heptylsulfonyl, 2,4,4-trimethyl-1-n-pentylsulfonyl, 1-nonylsulfonyl, 2-nonylsulfonyl, 2,6-dimethyl-4-n-heptylsulfonyl, 3-ethyl-2,2-dimethyl-3-n-pentylsulfonyl, 3,5,5-trimethyl-1-n-hexylsulfonyl, 1-decylsulfonyl, 2-decylsulfonyl, 4-decylsulfonyl, 3,7-dimethyl-1-n-octylsulfonyl, 3,7-dimethyl-3-n-octylsulfonyl, c-heptylsulfonyl, c-octylsulfonyl, 1-methyl-c-hexylsulfonyl, 2-methyl-c-hexylsulfonyl, 3-methyl-c-hexylsulfonyl, 1,2-dimethyl-c-hexylsulfonyl, 1-ethyl-c-hexylsulfonyl, 1-methyl-c-pentylsulfonyl, 2-methyl-c-pentylsulfonyl, 3-methyl-c-pentylsulfonyl or the like may be mentioned.

A $C_{2-14}$ aryl group may be a $C_{6-14}$ aryl group containing no hetero atoms as ring constituting atoms or a $C_{2-9}$ aromatic heterocyclic group, and a $C_{2-9}$ aromatic heterocyclic group may be a 5 to 7-membered $C_{2-6}$ heteromonocyclic group or 8 to 10-membered $C_{5-9}$ fused heterobicyclic group containing from 1 to 3 oxygen atoms, nitrogen atoms or sulfur atoms singly or in combination.

As a $C_{6-14}$ aryl group containing no hetero atoms, a phenyl group, a 1-indenyl group, a 2-indenyl group, a 3-indenyl group, a 4-indenyl group, a 5-indenyl group, a 6-indenyl group, a 7-indenyl group, an α-naphthyl group, a β-naphthyl group, a 1-tetrahydronaphthyl group, a 2-tetrahydronaphthyl group, a 5-tetrahydronaphthyl group, a 6-tetrahydronaphthyl group, an o-biphenylyl group, a m-biphenylyl group, a p-biphenylyl group, a 1-anthryl group, a 2-anthryl group, a 9-anthryl group, a 1-phenanthryl group, a 2-phenanthryl group, a 3-phenanthryl group, a 4-phenanthryl group, a 9-phenanthryl group or the like may be mentioned.

A 5 to 7-membered $C_{2-6}$ heteromonocyclic group may be a 2-thienyl group, a 3-thienyl group, a 2-furyl group, a 3-furyl group, a 2-pyranyl group, a 3-pyranyl group, a 4-pyranyl group, a 1-pyrrolyl group, a 2-pyrrolyl group, a 3-pyrrolyl group, a 1-imidazolyl group, a 2-imidazolyl group, a 4-imidazolyl group, a 1-pyrazolyl group, a 3-pyrazolyl group, a 4-pyrazolyl group, a 2-thiazolyl group, a 4-thiazolyl group, a 5-thiazolyl group, a 3-isothiazolyl group, a 4-isothiazolyl group, a 5-isothiazolyl group, a 2-oxazolyl group, a 4-oxazolyl group, a 5-oxazolyl group, a 3-isoxazolyl group, a 4-isoxazolyl group, a 5-isoxazolyl group, a 2-pyridyl group, a 3-pyridyl group, a 4-pyridyl group, a 2-pyrazinyl group, a 2-pyrimidinyl group, a 4-pyrimidinyl group, a 5-pyrimidinyl group, a 3-pyridazinyl group, a 4-pyridazinyl group, a 2-1,3,4-oxadiazolyl group, a 2-1,3,4-thiadiazolyl group, a 3-1,2,4-oxadiazolyl group, a 5-1,2,4-oxadiazolyl group, a 3-1,2,4-thiadiazolyl group, a 5-1,2,4-thiadiazolyl group, a 3-1,2,5-oxadiazolyl group, a 3-1,2,5-thiadiazolyl group or the like.

A 8 to 10-membered $C_{5-9}$ fused heterocyclic group may be a 2-benzofuranyl group, a 3-benzofuranyl group, a 4-benzofuranyl group, a 5-benzofuranyl group, a 6-benzofuranyl group, a 7-benzofuranyl group, a 1-isobenzofuranyl group, a 4-isobenzofuranyl group, a 5-isobenzofuranyl group, a 2-benzothienyl group, a 3-benzothienyl group, a 4-benzothienyl group, a 5-benzothienyl group, a 6-benzothienyl group, a 7-benzothienyl group, a 1-isobenzothienyl group, a 4-isobenzothienyl group, a 5-isobenzothienyl group, a 2-chromenyl group, a 3-chromenyl group, a 4-chromenyl group, a 5-chromenyl group, a 6-chromenyl group, a 7-chromenyl group, a 8-chromenyl group, a 1-indolizinyl group, a 2-indolizinyl group, a 3-indolizinyl group, a 5-indolizinyl group, a 6-indolizinyl group, a 7-indolizinyl group, a 8-indolizinyl group, a 1-isoindolyl group, a 2-isoindolyl group, a 4-isoindolyl group, a 5-isoindolyl group, a 1-indolyl group, a 2-indolyl group, a 3-indolyl group, a 4-indolyl group, a 5-indolyl group, a 6-indolyl group, a 7-indolyl group, 1-indazolyl group, a 2-indazolyl group, a 3-indazolyl group, a 4-indazolyl group, a 5-indazolyl group, a 6-indazolyl group, a 7-indazolyl group, a 1-purinyl group, a 2-purinyl group, a 3-purinyl group, a 6-purinyl group, a 7-purinyl group, a 8-purinyl group, a 2-quinolyl group, a 3-quinolyl group, a 4-quinolyl group, a 5-quinolyl group, a 6-quinolyl group, a 7-quinolyl group, a 8-quinolyl group, a 1-isoquinolyl group, a 3-isoquinolyl group, a 4-isoquinolyl group, a 5-isoquinolyl group, a 6-isoquinolyl group, a 7-isoquinolyl group, a 8-isoquinolyl group, a 1-phthalazinyl group, a 5-phthalazinyl group, a 6-phthalazinyl group, a 1-2,7-naphthyridinyl group, a 3-2,7-naphthyridinyl group, a 4-2,7-naphthyridinyl group, a 1-2,6-naphthyridinyl group, a 3-2,6-naphthyridinyl group, a 4-2,6-naphthyridinyl group, a 2-1,8-naphthyridinyl group, a 3-1,8-naphthyridinyl group, a 4-1,8-naphthyridinyl group, a 2-1,7-naphthyridinyl group, a 3-1,7-naphthyridinyl group, a 4-1,7-naphthyridinyl group, a 5-1,7-naphthyridinyl group, a 6-1,7-naphthyridinyl group, a 8-1,7-naphthyridinyl group, 2-1,6-naphthyridinyl group, a 3-1,6-naphthyridinyl group, a 4-1,6-naphthyridinyl group, a 5-1,6-naphthyridinyl group, a 7-1,6-naphthyridinyl group, a 8-1,6-naphthyridinyl group, a 2-1,5-naphthyridinyl group, a 3-1,5-naphthyridinyl group, a 4-1,5-naphthyridinyl group, a 6-1,5-naphthyridinyl group, a 7-1,5-naphthyridinyl group, a 8-1,5-naphthyridinyl group, a 2-quinoxalinyl group, a 5-quinoxalinyl group, a 6-quinoxalinyl group, a 2-quinazolinyl group, a 4-quinazolinyl group, a 5-quinazolinyl group, a 6-quinazolinyl group, a 7-quinazolinyl group, a 8-quinazolinyl group, a 3-cinnolinyl group, a 4-cinnolinyl group, a 5-cinnolinyl group, a 6-cinnolinyl group, a 7-cinnolinyl group, a 8-cinnolinyl group, a 2-pterdinyl group, a 4-pterdinyl group, a 6-pterdinyl group, a 7-pterdinyl group or the like.

A $C_{2-14}$ aryloxy group may be a $C_{6-14}$ aryloxy group containing no hetero atoms as ring constituting atoms or a $C_{2-9}$ aromatic heterocyclyloxy group, and a $C_{2-9}$ aromatic heterocyclyloxy group may be a 5 to 7-membered $C_{2-6}$ monocyclic heterocyclyloxy group or 8 to 10-membered $C_{5-9}$ fused bicyclic heterocyclyloxy group containing from 1 to 3 oxygen atoms, nitrogen atoms or sulfur atoms singly or in combination.

As a $C_{6-14}$ aryloxy group containing no hetero atoms, a phenyloxy group, a 1-indenyloxy group, a 2-indenyloxy group, a 3-indenyloxy group, a 4-indenyloxy group, a 5-indenyloxy group, a 6-indenyloxy group, a 7-indenyloxy group, an α-naphthyloxy group, β-naphthyloxy group, a 1-tetrahydronaphthyloxy group, a 2-tetrahydronaphthyloxy group, a 5-tetrahydronaphthyloxy group, a 6-tetrahydronaphthyloxy group, an o-biphenylyloxy group, a m-biphenylyloxy group, a p-biphenylyloxy group, a 1-anthryloxy group, a 2-anthryloxy group, a 9-anthryloxy group, a 1-phenanthryloxy group, a 2-phenanthryloxy group, a 3-phenanthryloxy group, a 4-phenanthryloxy group, a 9-phenanthryloxy group or the like may be mentioned.

A 5 to 7-membered $C_{2-6}$ monocyclic heterocyclyloxy group may be a 2-thienyloxy group, a 3-thienyloxy group, 2-furyloxy group, a 3-furyloxy group, a 2-pyranyloxy group, a 3-pyranyloxy group, a 4-pyranyloxy group, a 1-pyrrolyloxy group, a 2-pyrrolyloxy group, a 3-pyrrolyloxy group, a 1-imidazolyloxy group, a 2-imidazolyloxy group, a 4-imidazolyloxy group, a 1-pyrazolyloxy group, a 3-pyrazolyloxy group, a 4-pyrazolyloxy group, a 2-thiazolyloxy group, a 4-thiazolyloxy group, a 5-thiazolyloxy group, a 3-isothiazolyloxy group, a 4-isothiazolyloxy group, a 5-isothiazolyloxy group, a 2-oxazolyloxy group, a 4-oxazolyloxy group, a 5-oxazolyloxy group, a 3-isoxazolyloxy group, a 4-isoxazolyloxy group, a 5-isoxazolyloxy group, a 2-pyridyloxy group, a 3-pyridyloxy group, a 4-pyridyloxy group, a 2-pyrazinyloxy group, a 2-pyrimidinyloxy group, a 4-pyrimidinyloxy group, a 5-pyrimidinyloxy group, a 3-pyridazinyloxy group, a 4-pyridazinyloxy group, a 2-1,3,4-oxadiazolyloxy group, a 2-1,3,4-thiadiazolyloxy group, a 3-1,2,4-oxadiazolyloxy group, a 5-1,2,4-oxadiazolyloxy group, a 3-1,2,4-thiadiazolyloxy group, a 5-1,2,4-thiadiazolyloxy group, a 3-1,2,5-oxadiazolyloxy group, a 3-1,2,5-thiadiazolyloxy group or the like.

A 8 to 10-membered $C_{5-9}$ fused bicyclic heterocyclyloxy group may be a 2-benzofuranyloxy group, a 3-benzofuranyloxy group, a 4-benzofuranyloxy group, a 5-benzofuranyloxy group, a 6-benzofuranyloxy group, a 7-benzofuranyloxy group, a 1-isobenzofuranyloxy group, a 4-isobenzofuranyloxy group, a 5-isobenzofuranyloxy group, a 2-benzothienyloxy group, a 3-benzothienyloxy group, a 4-benzothienyloxy group, a 5-benzothienyloxy group, a 6-benzothienyloxy group, a 7-benzothienyloxy group, a 1-isobenzothienyloxy group, a 4-isobenzothienyloxy group, a 5-isobenzothienyloxy group, a 2-chromenyloxy group, a 3-chromenyloxy group, a 4-chromenyloxy group, a 5-chromenyloxy group, a 6-chromenyloxy group, a 7-chromenyloxy group, a 8-chromenyloxy group, a 1-indolizinyloxy group, a 2-indolizinyloxy group, a 3-indolizinyloxy group, a 5-indolizinyloxy group, a 6-indolizinyloxy group, a 7-indolizinyloxy group, a 8-indolizinyloxy group, a 1-isoindolyloxy group, a 2-isoindolyloxy group, a 4-isoindolyloxy group, a 5-isoindolyloxy group, a 1-indolyloxy group, a 2-indolyloxy group, a 3-indolyloxy group, a 4-indolyloxy group, a 5-indolyloxy group, a 6-indolyloxy group, a 7-indolyloxy group, 1-indazolyloxy group, a 2-indazolyloxy group, a 3-indazolyloxy group, a 4-indazolyloxy group, a 5-indazolyloxy group, a 6-indazolyloxy group, a 7-indazolyloxy group, a 1-purinyloxy group, a 2-purinyloxy group, a 3-purinyloxy group, a 6-purinyloxy group, a 7-purinyloxy group, a 8-purinyloxy group, a 2-quinolyloxy group, a 3-quinolyloxy group, a 4-quinolyloxy group, a 5-quinolyloxy group, a 6-quinolyloxy group, a 7-quinolyloxy group, a 8-quinolyloxy group, a 1-isoquinolyloxy group, a 3-isoquinolyloxy group, a 4-isoquinolyloxy group, a 5-isoquinolyloxy group, a 6-isoquinolyloxy group, a 7-isoquinolyloxy group, a 8-isoquinolyloxy group, a 1-phthalazinyloxy group, a 5-phthalazinyloxy group, a 6-phthalazinyloxy group, a 1-2,7-naphthyridinyloxy group, a 3-2,7-naphthyridinyloxy group, a 4-2,7-naphthyridinyloxy group, a 1-2,6-naphthyridinyloxy group, a 3-2,6-naphthyridinyloxy group, a 4-2,6-naphthyridinyloxy group, a 2-1,8-naphthyridinyloxy group, a 3-1,8-naphthyridinyloxy group, a 4-1,8-naphthyridinyloxy group, a 2-1,7-naphthyridinyloxy group, a 3-1,7-naphthyridinyloxy group, a 4-1,7-naphthyridinyloxy group, a 5-1,7-naphthyridinyloxy group, a 6-1,7-naphthyridinyloxy group, a 8-1,7-naphthyridinyloxy group, 2-1,6-naphthyridinyloxy group, a 3-1,6-naphthyridinyloxy group, a 4-1,6-naphthyridinyloxy group, a 5-1,6-naphthyridinyloxy group, a 7-1,6-naphthyridinyloxy group, a 8-1,6-naphthyridinyloxy group, a 2-1,5-naphthyridinyloxy group, a 3-1,5-naphthyridinyloxy group, a 4-1,5-naphthyridinyloxy group, a 6-1,5-naphthyridinyloxy group, a 7-1,5-naphthyridinyloxy group, a 8-1,5-naphthyridinyloxy group, a 2-quinoxalinyloxy group, a 5-quinoxalinyloxy group, a 6-quinoxalinyloxy group, a 2-quinazolinyloxy group, a 4-quinazolinyloxy group, a 5-quinazolinyloxy group, a 6-quinazolinyloxy group, a 7-quinazolinyloxy group, a 8-quinazolinyloxy group, a 3-cinnolinyloxy group, a 4-cinnolinyloxy group, a 5-cinnolinyloxy group, a 6-cinnolinyloxy group, a 7-cinnolinyloxy group, a 8-cinnolinyloxy group, a 2-pterdinyloxy group, a 4-pterdinyloxy group, a 6-pterdinyloxy group, a 7-pterdinyloxy group or the like.

The protecting group in a protected hydroxyl group, a protected thiol group or a protected amino group may be a $C_{1-4}$ alkoxymethyl group (such as MOM: methoxymethyl, MEM: 2-methoxyethoxymethyl, ethoxymethyl, n-propoxymethyl, i-propoxymethyl, n-butoxymethyl, iBM: isobutyloxymethyl, BUM: t-butoxymethyl, POM: pivaloyloxymethyl, SEM: trimethylsilylethoxymethyl and the like, preferably a $C_{1-2}$ alkoxymethyl or the like), an aryloxymethyl (such as BOM: benzyloxymethyl, PMBM: p-methoxybenzyloxymethyl, p-AOM: p-anisyloxymethyl and the like, preferably benzyloxymethyl), a $C_{1-4}$ alkylaminomethyl group (such as dimethylaminomethyl), a substituted acetamidomethyl group (such as Acm: acetamidomethyl, Tacm: trimethylacetamidomethyl and the like), a substituted thiomethyl group (such as MTM: methylthiomethyl, PTM: phenylthiomethyl, Btm: benzylthiomethyl and the like), a carboxyl group, a $C_{1-7}$ acyl group (such as formyl, acetyl, fluoroacetyl, difluoroacetyl, trifluoroacetyl, chloroacetyl, dichloroacetyl, trichloroacetyl, propionyl, Pv: pivaloyl, tigloyl and the like), an arylcarbonyl group (such as benzoyl, benzoylformyl, benzoylpropionyl, phenylpropionyl and the like), a $C_{1-4}$ alkoxycarbonyl group (such as methoxycarbonyl, ethoxycarbonyl, n-propoxycarbonyl, i-propoxycarbonyl, n-butoxycarbonyl, i-butoxycarbonyl, BOC: t-butoxycarbonyl, AOC: t-amyloxycarbonyl, VOC: vinyloxycarbonyl, AOC: allyloxycarbonyl, Teoc: 2-(trimethylsilyl)ethoxycarbonyl, Troc: 2,2,2-trichloroethoxycarbonyl and the like, preferably BOC and the like), an aryloxycarbonyl group (such as Z: benzyloxycarbonyl, p-nitrobenzyloxycarbonyl, MOZ: p-methoxybenzyloxycarbonyl and the like), a $C_{1-4}$ alkylaminocarbonyl group (such as methylcarbamoyl, Ec: ethylcarbamoyl, n-propylcarbamoyl and the like), an arylaminocarbonyl group (such as phenylcarbamoyl and the like), a trialkylsilyl group (such as TMS: trimethylsilyl, TES: triethylsilyl, TIPS: triisopropylsilyl, DEIPS: diethylisopropylsilyl, DMIPS: dimethylisopropylsilyl, DTBMS: di-t-butylmethylsilyl, IPDMS: isopropyldimethylsilyl, TBDMS: t-butyldimethylsilyl, TDS: thexyldimethylsilyl and the like, preferably t-butyldimethylsilyl and the like), a trialkylarylsilyl group (such as DPMS: diphenylmethylsilyl, TBDPS: t-butyldiphenylsilyl, TBMPS: t-butyldimethoxyphenylsilyl, TPS: triphenylsilyl and the like), an alkylsulfonyl group, (such as Ms: methanesulfonyl, ethanesulfonyl and the like) or an arylsulfonyl group (such as benzenesulfonyl, Ts: p-toluenesulfonyl, p-chlorobenzenesulfonyl, MBS: p-methoxybenzenesulfonyl, m-nitrobenzenesulfonyl, iMds: 2,6-dimethoxy-4-methylbenzenesulfonyl, Mds: 2,6-dimethyl-4-methoxybenzenesulfonyl, Mtb: 2,4,6-trimethoxybenzenesulfonyl, Mte: 2,3,5,6-tetramethyl-4-methoxybenzenesulfonyl, Mtr: 2,3,6-trimethyl-4-methoxybenzenesulfonyl, Mts: 2,4,6-trimethylbenzenesulfonyl, Pme: pentamethylbenzenesulfonyl and the like).

A $C_{2-9}$ heterocyclyl group may be a heteromonocyclic or fused heterobicyclic group consisting of at least one atom optionally selected from nitrogen atoms, oxygen atoms and sulfur atoms and from 2 to 9 carbon atoms, and specifically mentioned are:

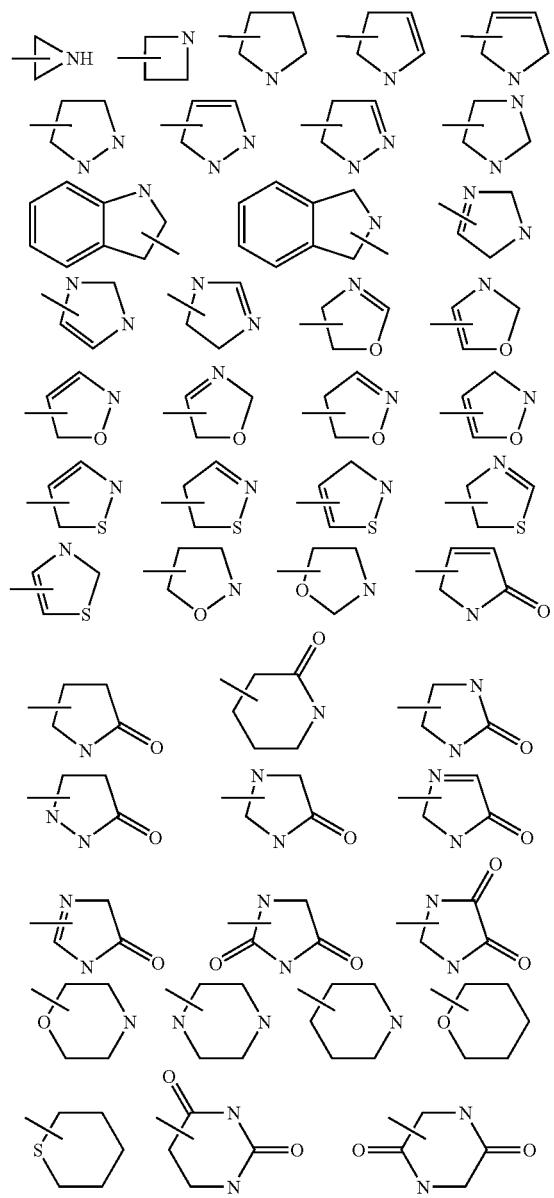

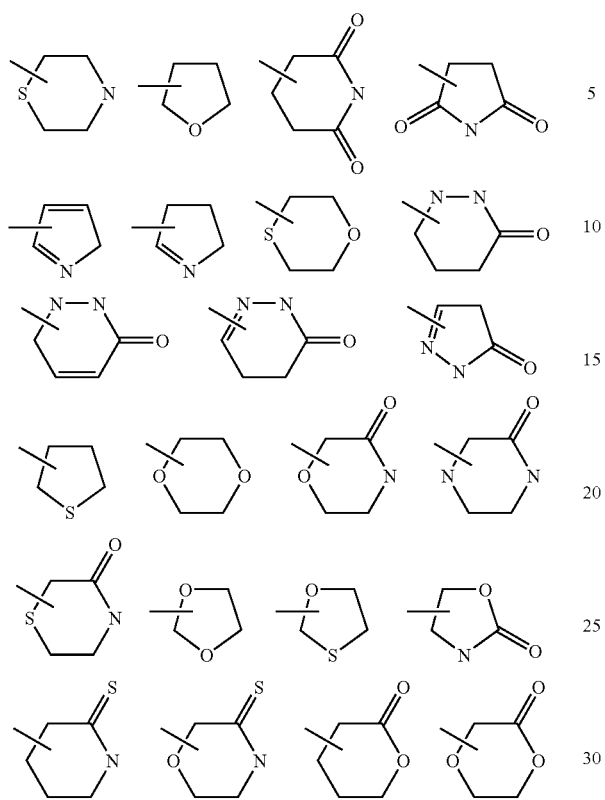

A nitrogen-containing $C_{2-9}$ heterocyclyl group may be, among those give above, a heteromonocyclic or fused heterobicyclic group which contains least one nitrogen atom, may contain at least one atom optionally selected from oxygen atoms and sulfur atoms and contains from 2 to 9 carbon atoms, and specifically mentioned are:

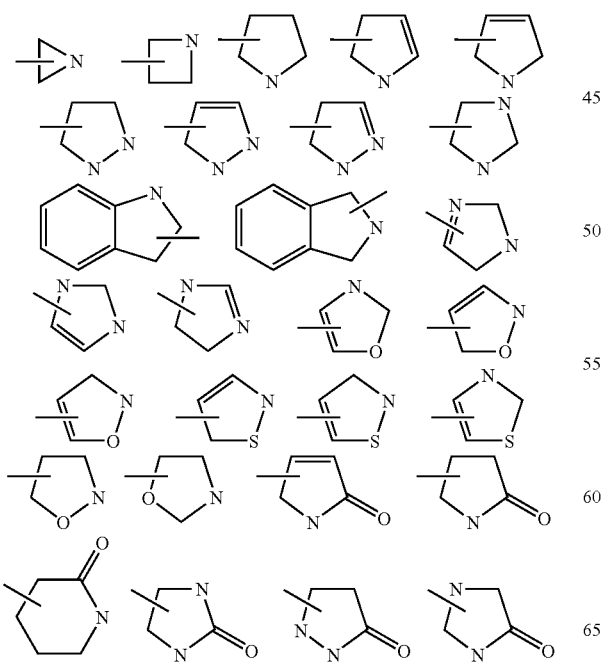

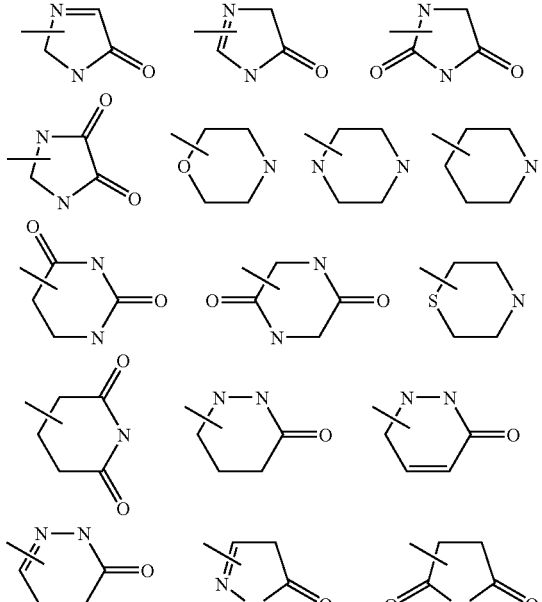

As a $C_{3-7}$ carbocyclyl group, specifically mentioned are:

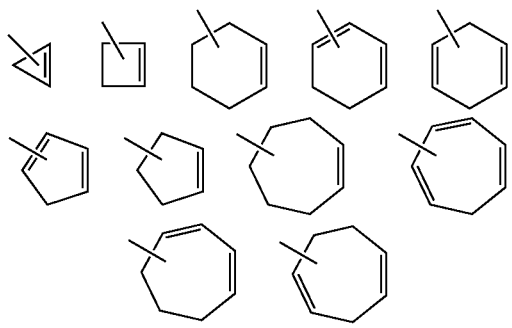

Preferred specific examples of $L^1$—X are the following structural formulae:

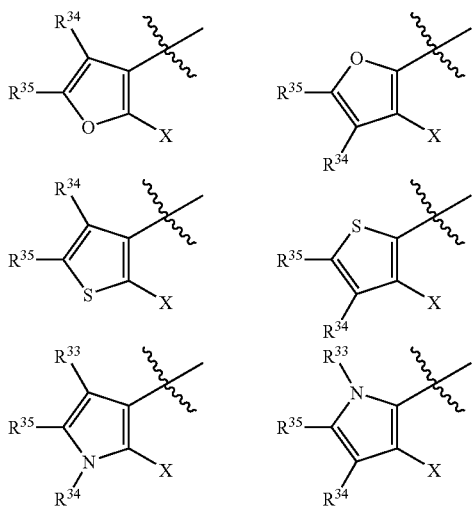

-continued

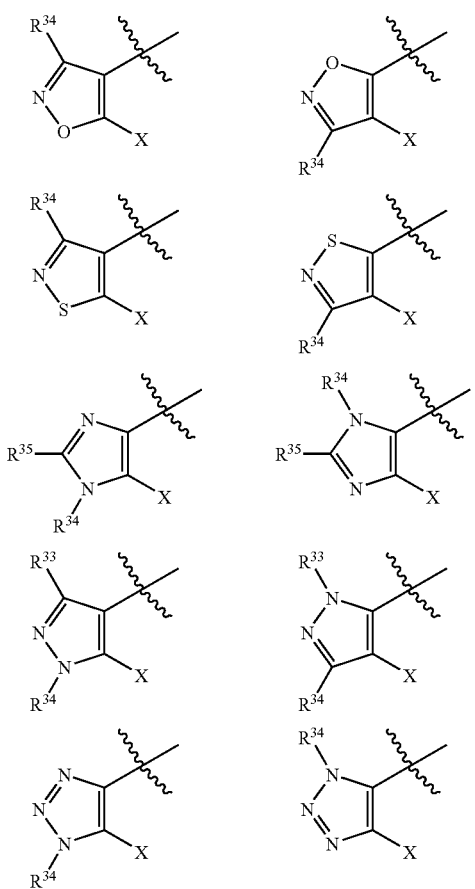

Particularly preferred are the following structural formulae:

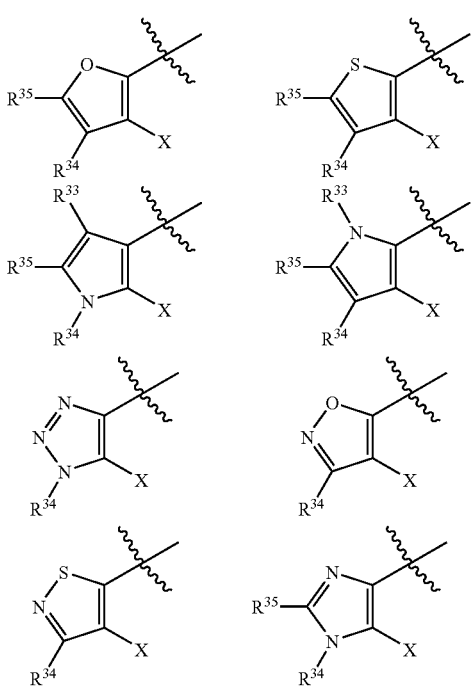

-continued

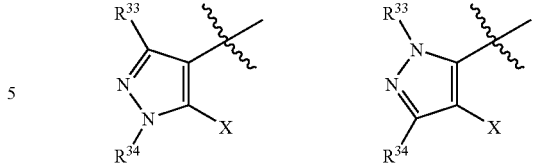

Preferred specific examples of $R^{33}$ and $R^{35}$ in the structural formulae are a hydrogen atom, a $C_{1-6}$ alkyl group (the $C_{1-6}$ alkyl group may be substituted with one or more halogen atoms) and a $C_{1-6}$ alkoxy group (the $C_{1-6}$ alkoxy group may be substituted with one or more halogen atoms).

Particularly preferred specific examples are a hydrogen atom, a $C_{1-3}$ alkyl group (the $C_{1-3}$ alkyl group may be substituted with one or more halogen atoms) and a $C_{1-3}$ alkoxy group (the $C_{1-3}$ alkoxy group may be substituted with one or more halogen atoms).

Preferred specific examples of $R^{34}$ are $C_{2-14}$ aryl groups optionally substituted with one or more of the following substituents.

Substituents: halogen atoms, $C_{1-6}$ alkyl groups (the $C_{1-6}$ alkyls group may be substituted with one or more halogen atoms) and $C_{1-6}$ alkoxy groups (the $C_{1-6}$ alkoxy groups may be substituted with one or more halogen atoms).

A particularly preferred specific example is a phenyl group optionally substituted with one or more of the following substituents.

Substituents: halogen atoms, $C_{1-6}$ alkyl groups (the $C_{1-6}$ alkyl groups may be substituted with one or more halogen atoms) and $C_{1-6}$ alkoxy groups (the $C_{1-6}$ alkoxy groups may be substituted with one or more halogen atoms).

Preferred specific examples of X are OH and SH, and a particularly preferred specific example is OH.

Preferred specific examples of Y are an oxygen atom, a sulfur atom and NH, and a particularly preferred specific example is an oxygen atom.

Preferred specific examples of $L^2$ are a single bond, an oxygen atom, a sulfur atom and NH, and a particularly is preferred specific example is a single bond.

Preferred specific examples of $R^1$ are a hydrogen atom and a $C_{1-10}$ alkyl group (the $C_{1-10}$ alkyl group may be substituted with one or more halogen atoms). Particularly preferred specific examples are a hydrogen atom and a $C_{1-3}$ alkyl group (the $C_{1-3}$ alkyl group may be substituted with one or more halogen atoms).

A preferred specific example of $R^2$ is a hydrogen atom.

A preferred specific example of $R^3$ is a $C_{2-14}$ aryl group substituted with one or more substituents selected from the following substituent set A and with one or more substituents selected from the following substituent set B.

Substituent set A: hydrogen atoms, nitro groups, halogen atoms, carboxyl groups, carbamoyl groups, sulfamoyl groups, sulfo groups, formyl groups, $C_{1-10}$ alkoxycarbonyl groups, $C_{1-10}$ alkylaminosulfonyl groups and $C_{1-10}$ alkylaminocarbonyl groups.

Substituent Set B:

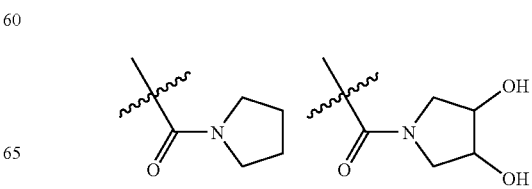

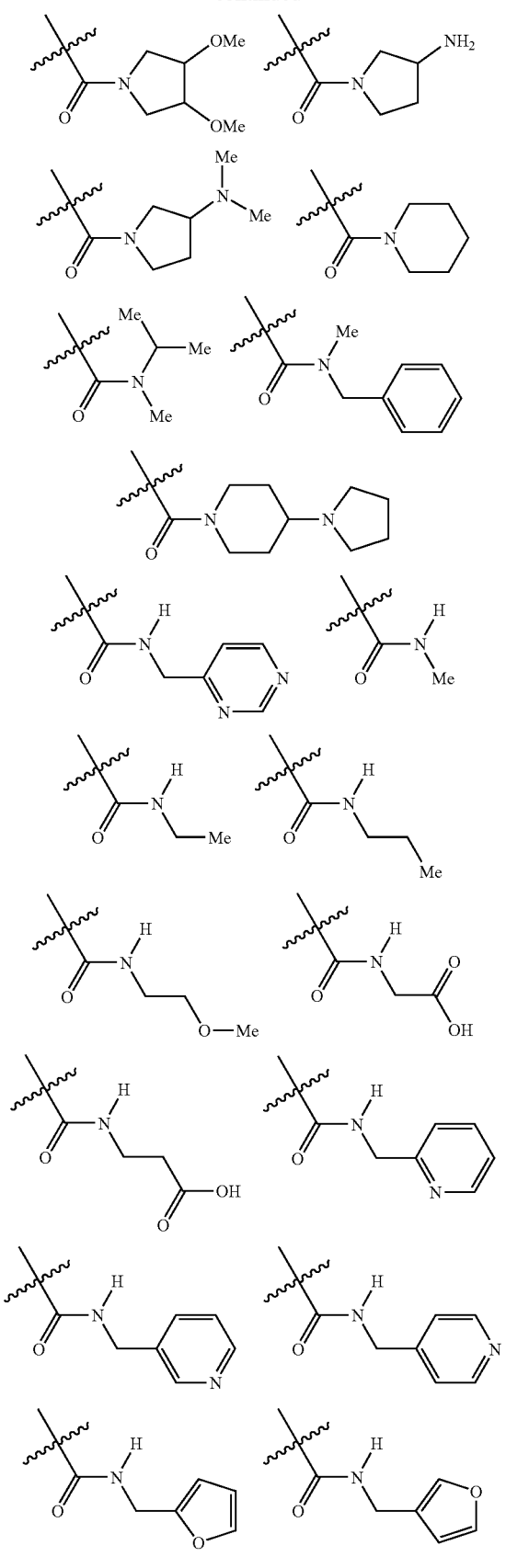
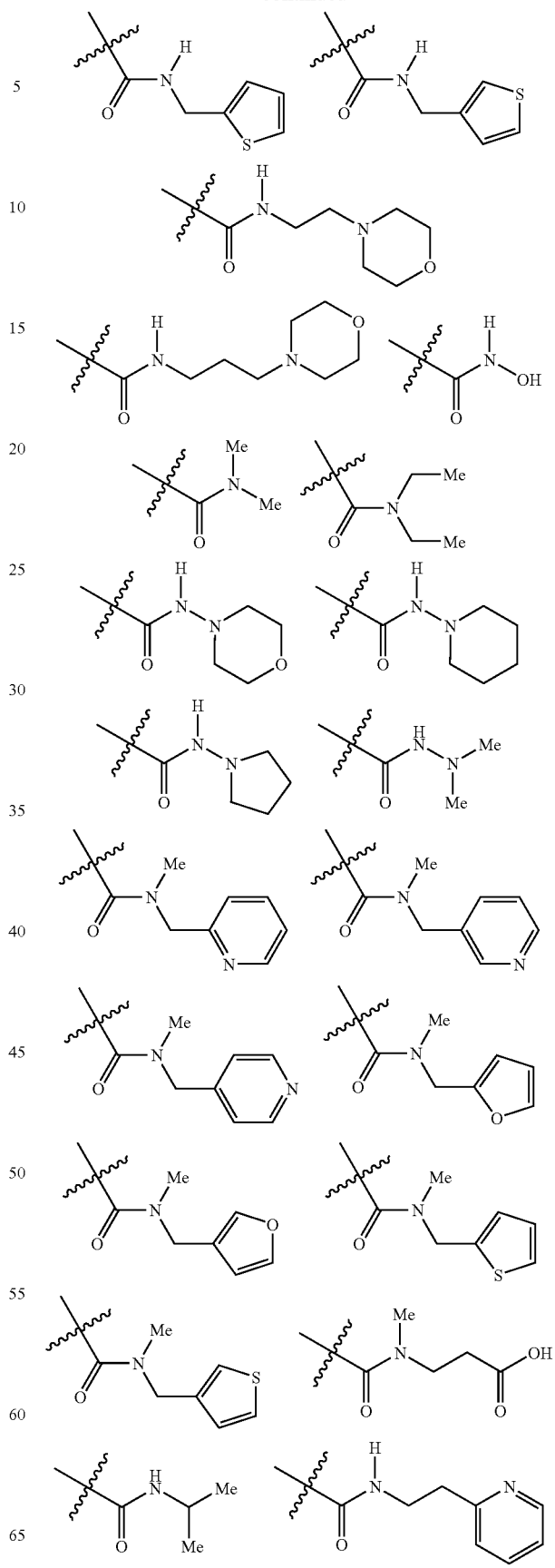

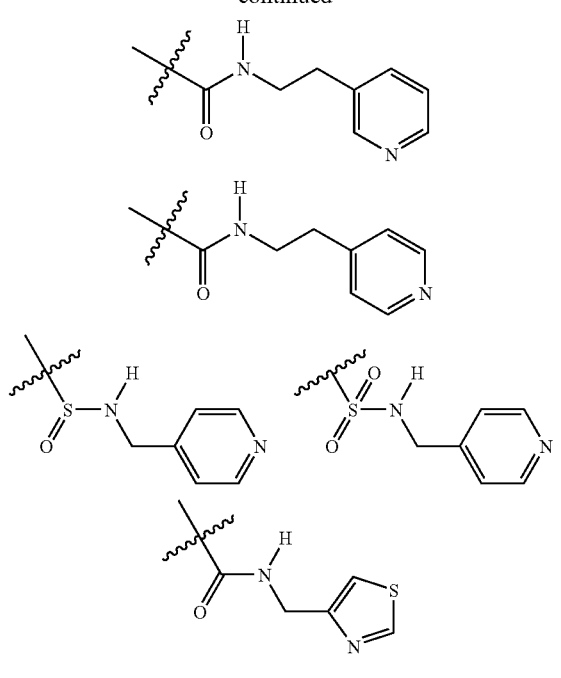
Particularly preferred specific examples are a phenyl group, a thienyl group, a furyl group and a pyridyl group which are substituted with one or more of the following substituents.
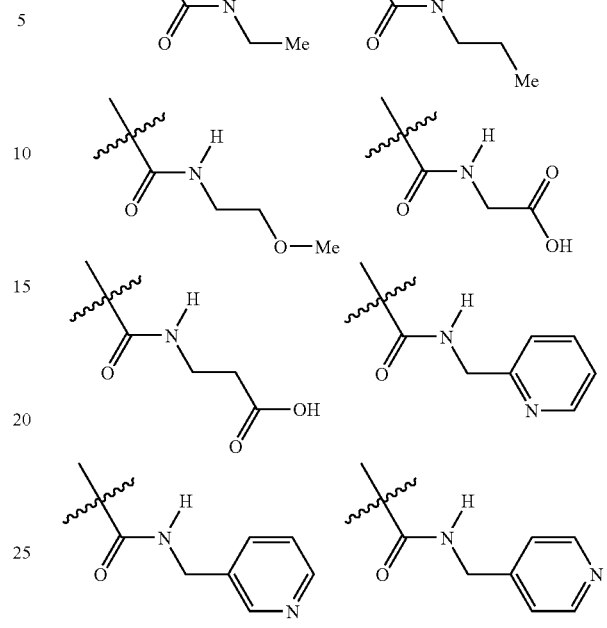
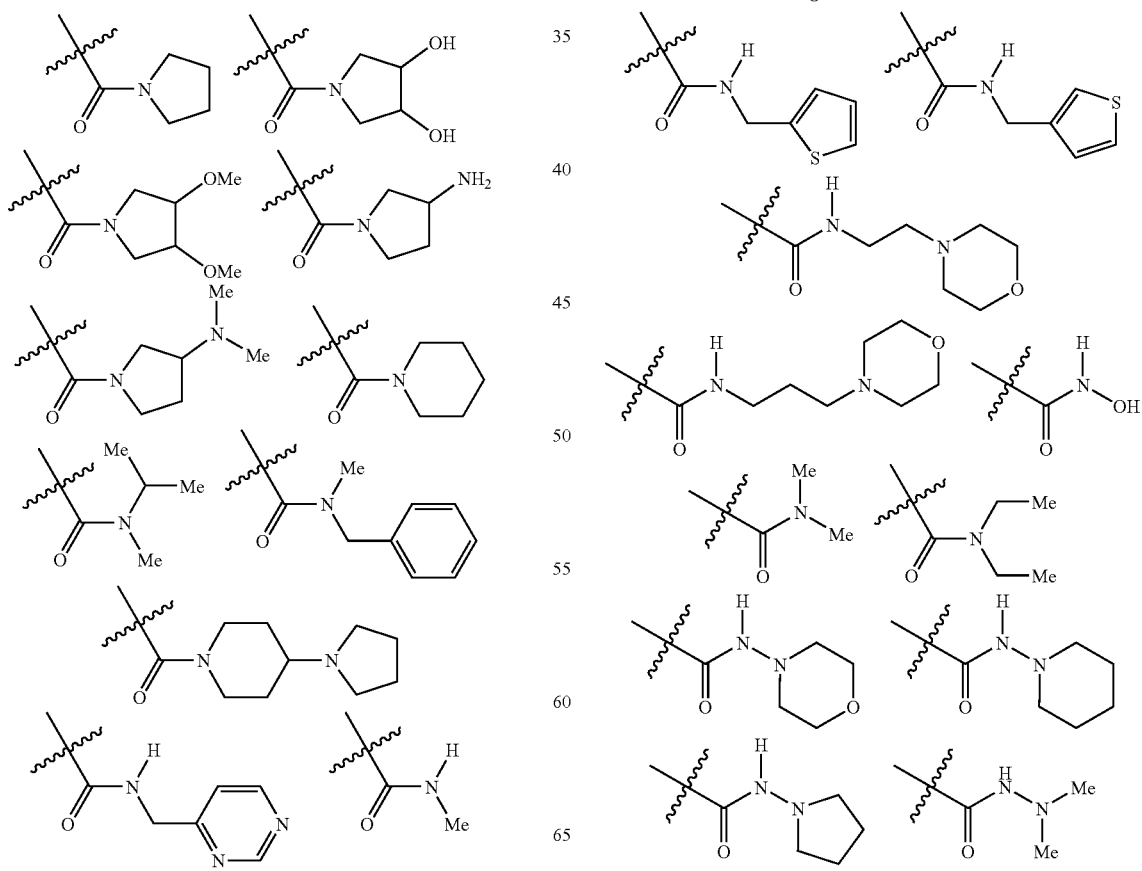

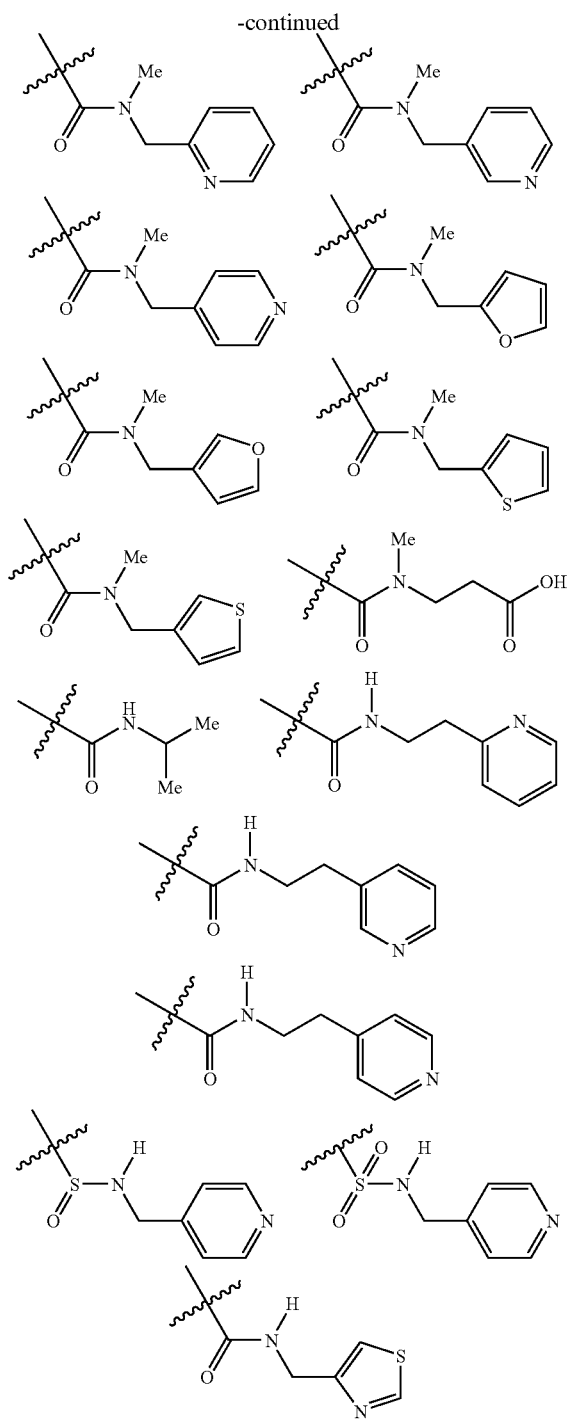

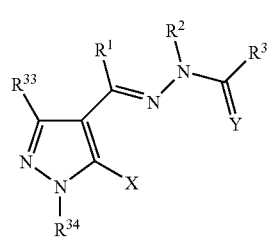

(III)

2) Compounds represented by the formula (IV), which are compounds represented by the formula (I) wherein $L^1$ is represented by the formula (II) wherein B is a nitrogen atom, D=E, as a whole, means $NR^{33}$, and A is $CR^{34}$, and $L^2$ is a single bond, tautomers, prodrugs or pharmaceutically acceptable salts of the compounds or solvates thereof.

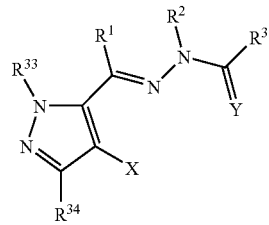

(IV)

3) The compounds according to 1) or 2), wherein $R^2$ is a hydrogen atom, tautomers, prodrugs or pharmaceutically acceptable salts of the compounds or solvates thereof.

4) The compounds according to 3), wherein Y is an oxygen atom, tautomers, prodrugs or pharmaceutically acceptable salts of the compounds or solvates thereof.

5) The compounds according to 4), wherein X is OH, tautomers, prodrugs or pharmaceutically acceptable salts of the compounds or solvates thereof.

6) The compounds according to 5), wherein $R^1$ is a hydrogen atom or a $C_{1-3}$ alkyl group (the $C_{1-3}$ alkyl group may be substituted with one or more halogen atoms), tautomers, prodrugs or pharmaceutically acceptable salts of the compounds or solvates thereof.

7) The compounds according to 6), wherein $R^{33}$ is a hydrogen atom or a $C_{1-3}$ alkyl group (the $C_{1-3}$ alkyl group may be substituted with one or more halogen atoms), tautomers, prodrugs or pharmaceutically acceptable salts of the compounds or solvates thereof.

8) The compound according to 7), wherein $R^{34}$ is a phenyl group optionally substituted with one or more of the following substituents, tautomers, prodrugs or pharmaceutically acceptable salts of the compounds or solvates thereof.
Substituents: t-butyl groups, methyl groups, methoxy groups, trifluoromethyl groups, trifluoromethoxy groups, chlorine atoms, bromine atoms and fluorine atoms.

9) The compounds according to 8), wherein $R^3$ is a $C_{2-14}$ aryl group substituted with one or more substituents selected from the following substituent set A and with one or more substituents selected from the following substituent set B, tautomers, prodrugs or pharmaceutically acceptable salts of the compounds or solvates thereof.
Substituent Set A:
Hydrogen atoms, nitro groups, halogen atoms, carboxyl groups, carbamoyl groups, sulfamoyl groups, sulfo groups, Favorable compounds as the thrombopoietin receptor activator, the preventive, therapeutic or improving agent for diseases against which activation of the thrombopoietin receptor is effective and the platelet increasing agent of the present invention are as follows.

1) Compound represented by the formula (III), which are compounds represented by the formula (I) wherein $L^1$ is represented by the formula (II) wherein A=B, as a whole, means $NR^{34}$, D is a nitrogen atom, and E is $CR^{33}$, and $L^2$ is a single bond, tautomers, prodrugs or pharmaceutically acceptable salts of the compounds or solvates thereof.

formyl groups, $C_{1-10}$ alkoxycarbonyl groups, $C_{1-10}$ alkylaminosulfonyl groups and $C_{1-10}$ alkylaminocarbonyl groups.
Substituent Set B:
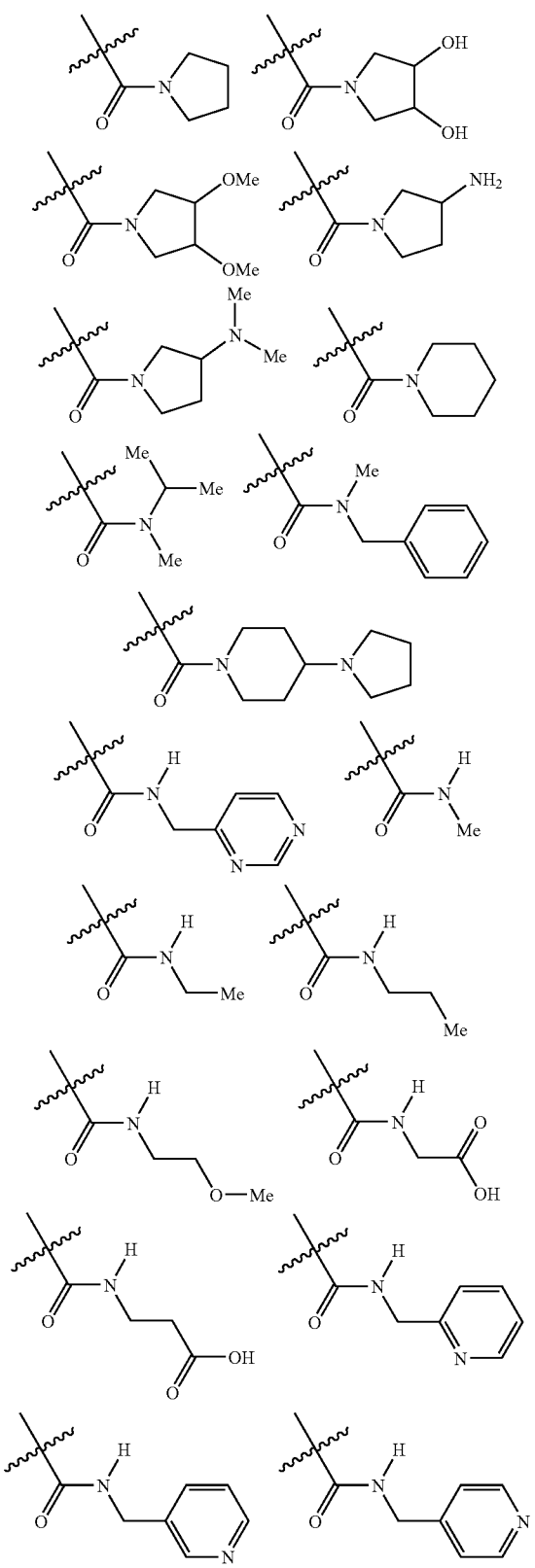
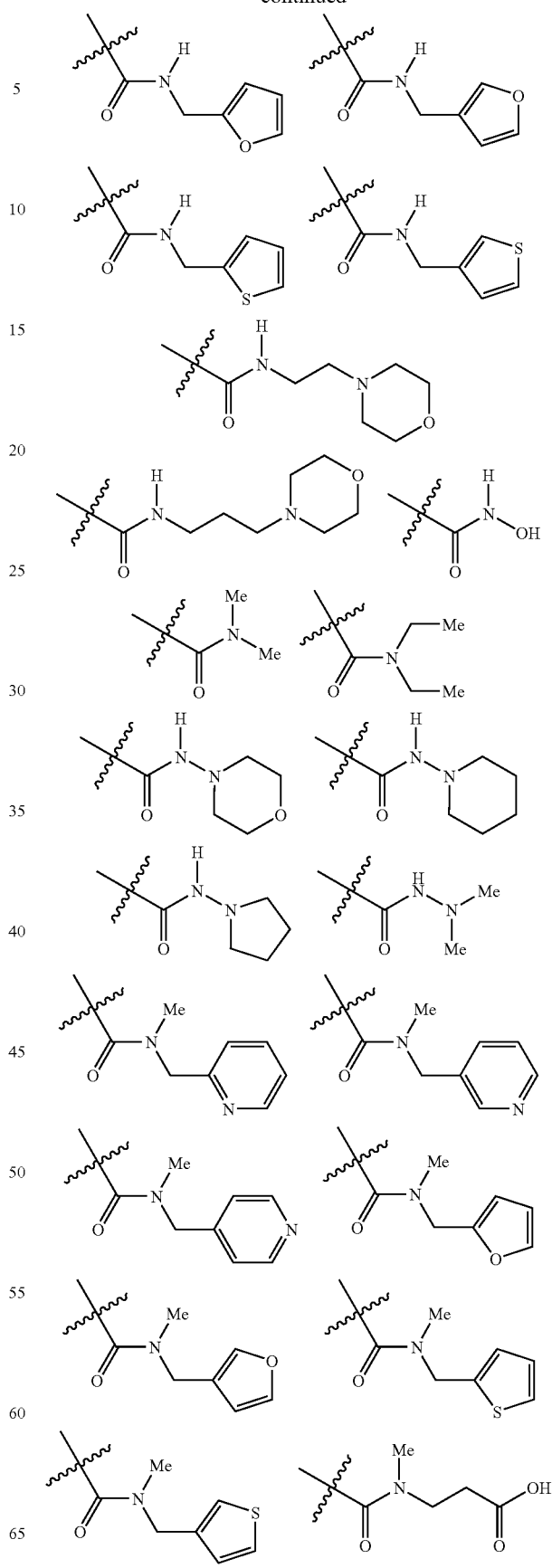

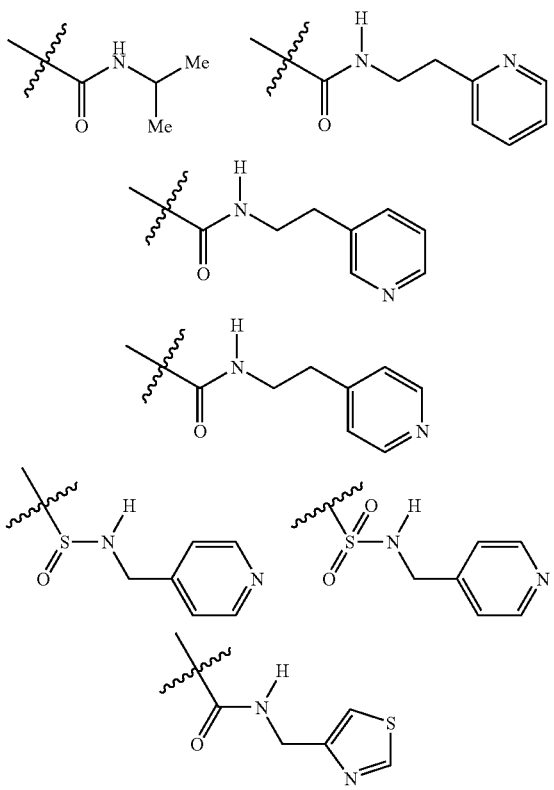

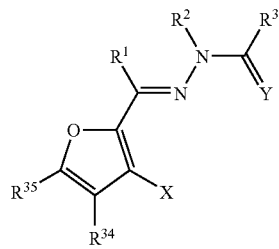

(VI)

14) Compounds represented by the formula (VII), which are compounds represented by the formula (I) wherein $L^1$ is represented by the formula (II) wherein A=B, as a whole, means $NR^{34}$, E is a nitrogen atom, and D is $CR^{35}$, and $L^2$ is a single bond, tautomers, prodrugs or pharmaceutically acceptable salts of the compounds or solvates thereof.

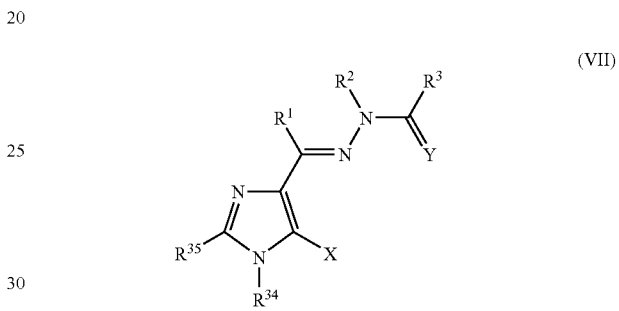

(VII)

10) The compounds according to 9), wherein the $C_{2-14}$ aryl group as $R^3$ is a phenyl group, a thienyl group, a furyl group or a pyridyl group, tautomers, prodrugs or pharmaceutically acceptable salts of the compounds or solvates thereof.

11) The compounds according to 9), wherein the $C_{2-14}$ aryl group as $R^3$ is a thienyl group, tautomers, prodrugs or pharmaceutically acceptable salts of the compounds or solvates thereof.

12) Compounds represented by the formula (V), which are compounds represented by the formula (I) wherein $L^1$ is represented by the formula (II) wherein D=E, as a whole, means a sulfur atom, B is $CR^{35}$, and A is $CR^{34}$, and $L^2$ is a single bond, tautomers, prodrugs or pharmaceutically acceptable salts of the compounds or solvates thereof.

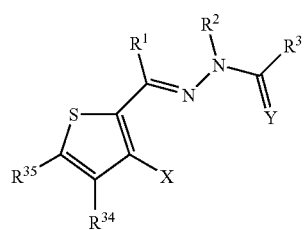

(V)

13) Compounds represented by the formula (VI), which are compounds represented by the formula (I) wherein $L^1$ is represented by the formula (II) wherein D=E, as a whole, means an oxygen atom, B is $CR^{35}$, and A is $CR^{34}$, and $L^2$ is a single bond, tautomers, prodrugs or pharmaceutically acceptable salts of the compounds or solvates thereof.

15) The compounds according to 12), 13) or 14), wherein $R^2$ is a hydrogen atom, tautomers, prodrugs or pharmaceutically acceptable salts of the compounds or solvates thereof.

16) The compounds according to 15), wherein Y is an oxygen atom, tautomers, prodrugs or pharmaceutically acceptable salts of the compounds or solvates thereof.

17) The compounds according to 16), wherein X is OH, tautomers, prodrugs or pharmaceutically acceptable salts of the compounds or solvates thereof.

18) The compounds according to 17), wherein $R^1$ is a hydrogen atom or a $C_{1-3}$ alykl group (the $C_{1-3}$ alykl group may be substituted with one or more halogen atoms), tautomers, prodrugs or pharmaceutically acceptable salts of the compounds or solvates thereof.

19) The compounds according to 18), wherein $R^{35}$ is a hydrogen atom or a $C_{1-3}$ alykl group (the $C_{1-3}$ alykl group may be substituted with one or more halogen atoms), tautomers, prodrugs or pharmaceutically acceptable salts of the compounds or solvates thereof.

20) The compounds according to 19), wherein $R^{34}$ is a phenyl group optionally substituted with one or more of the following substituents, tautomers, prodrugs or pharmaceutically acceptable salts of the compounds or solvates thereof.
Substituents: t-butyl groups, methyl groups, methoxy groups, trifluoromethyl groups, trifluoromethoxy groups, chlorine atoms, bromine atoms and fluorine atoms.

21) The compounds according to 20), wherein $R^3$ is a $C_{2-14}$ aryl group substituted with one or more substituents selected from the following substituent set A and with one or more substituents selected from the following substituent set B, tautomers, prodrugs or pharmaceutically acceptable salts of the compounds or solvates thereof.
Substituent Set A:
Hydrogen atoms, nitro groups, halogen atoms, carboxyl groups, carbamoyl groups, sulfamoyl groups, sulfo groups, formyl groups, $C_{1-10}$ alkoxycarbonyl groups, $C_{1-10}$ alkylaminosulfonyl groups and $C_{1-10}$ alkylaminocarbonyl groups.
Substituent Set B:
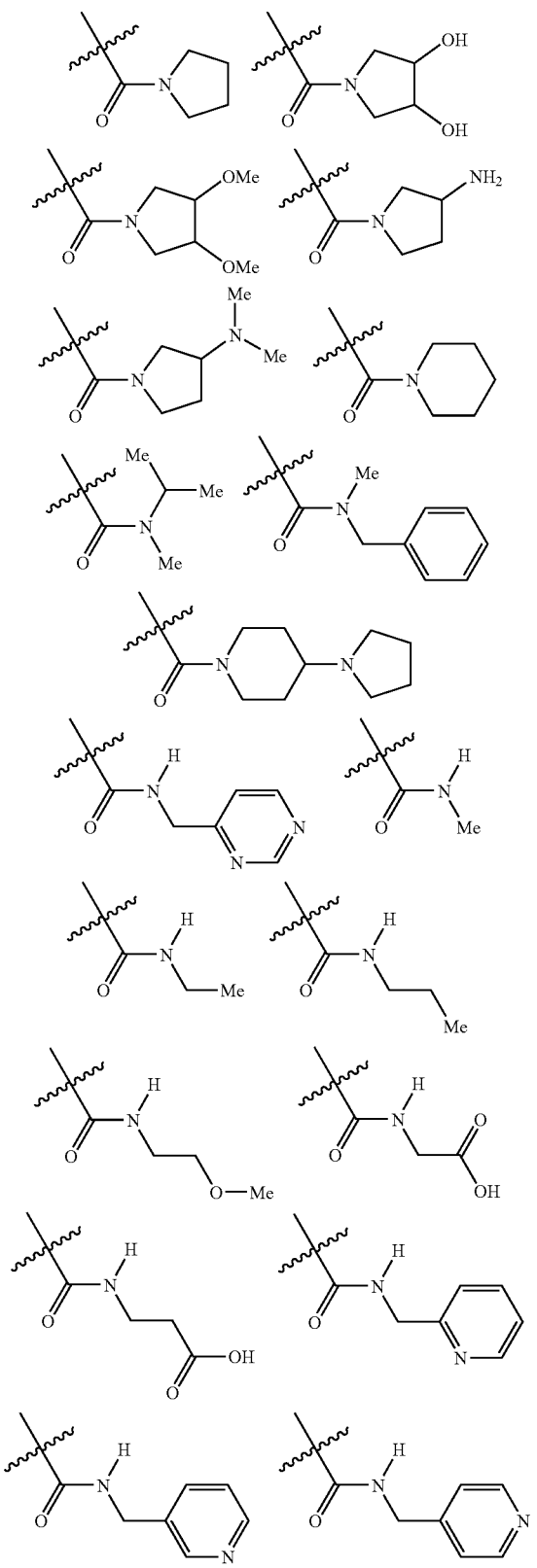
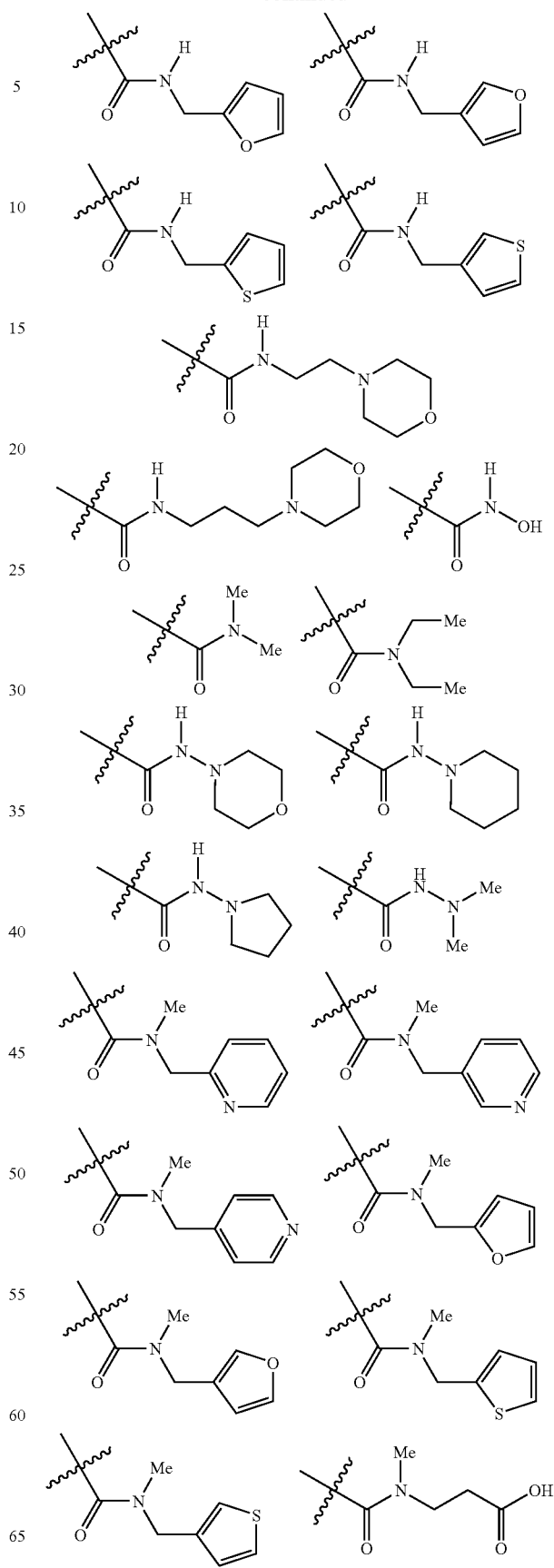

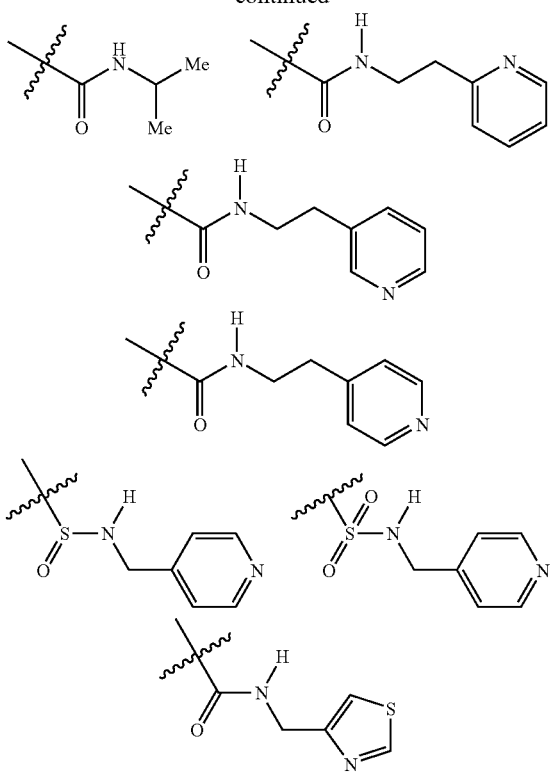

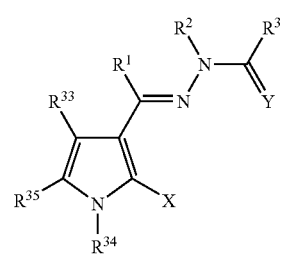

22) The compounds according to 21), wherein the $C_{2-14}$ aryl group as $R^3$ is a phenyl group, a thienyl group, a furyl group or a pyridyl group, tautomers, prodrugs or pharmaceutically acceptable salts of the compounds or solvates thereof.

23) The compounds according to 21), wherein the $C_{2-14}$ aryl group as $R^3$ is a thienyl group, tautomers, prodrugs or pharmaceutically acceptable salts of the compounds or solvates thereof.

24) Compounds represented by the formula (VIII), which are compounds represented by the formula (I) wherein $L^1$ is represented by the formula (II) wherein A=B, as a whole, means $NR^{34}$, D is $CR^{35}$, and E is $CR^{33}$, and $L^2$ is a single bond, tautomers, prodrugs or pharmaceutically acceptable salts of the compounds or solvates thereof.

(VIII)

25) Compounds represented by the formula (IX), which are compounds represented by the formula (I) wherein $L^1$ is represented by the formula (II) wherein D=E, as a whole, means $NR^{33}$, B is $CR^{35}$, and A is $CR^{33}$, and $L^2$ is a single bond, tautomers, prodrugs or pharmaceutically acceptable salts of the compounds or solvates thereof.

(IX)

26) The compounds according to 24) or 25), wherein $R^2$ is a hydrogen atom, tautomers, prodrugs or pharmaceutically acceptable salts of the compounds or solvates thereof.

27) The compounds according to 26), wherein Y is an oxygen atom, tautomers, prodrugs or pharmaceutically acceptable salts of the compounds or solvates thereof.

28) The compounds according to 27), wherein X is OH, tautomers, prodrugs or pharmaceutically acceptable salts of the compounds or solvates thereof.

29) The compounds according to 28), wherein $R^1$ is a hydrogen atom or a $C_{1-3}$ alykl group (the $C_{1-3}$ alykl group may be substituted with one or more halogen atoms), tautomers, prodrugs or pharmaceutically acceptable salts of the compounds or solvates thereof.

30) The compounds according to 29), wherein each of $R^{33}$ and $R^{35}$ is independently a hydrogen atom or a $C_{1-3}$ alykl group (the $C_{1-3}$ alykl group may be substituted with one or more halogen atoms), tautomers, prodrugs or pharmaceutically acceptable salts of the compounds or solvates thereof.

31) The compounds according to 30), wherein $R^{34}$ is a phenyl group optionally substituted with one or more of the following substituents, tautomers, prodrugs or pharmaceutically acceptable salts of the compounds or solvates thereof.

Substituents: t-butyl groups, methyl groups, methoxy groups, trifluoromethyl groups, trifluoromethoxy groups, chlorine atoms, bromine atoms and fluorine atoms.

32) The compound according to 31), wherein $R^3$ is a $C_{2-14}$ aryl group substituted with one or more substituents selected from the following substituent set A and with one or more substituents selected from the following substituent set B, tautomers, prodrugs or pharmaceutically acceptable salts of the compounds or solvates thereof.

Substituent Set A:

Hydrogen atoms, nitro groups, halogen atoms, carboxyl groups, carbamoyl groups, sulfamoyl groups, sulfo groups, formyl groups, $C_{1-10}$ alkoxycarbonyl groups, $C_{1-10}$ alkylaminosulfonyl groups and $C_{1-10}$ alkylaminocarbonyl groups.

Substituent Set B:

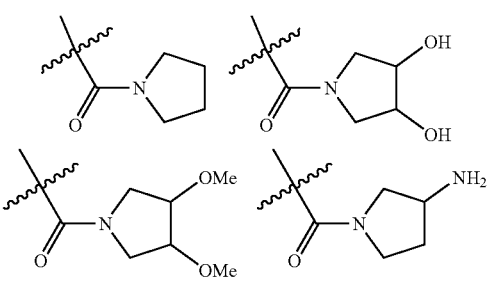

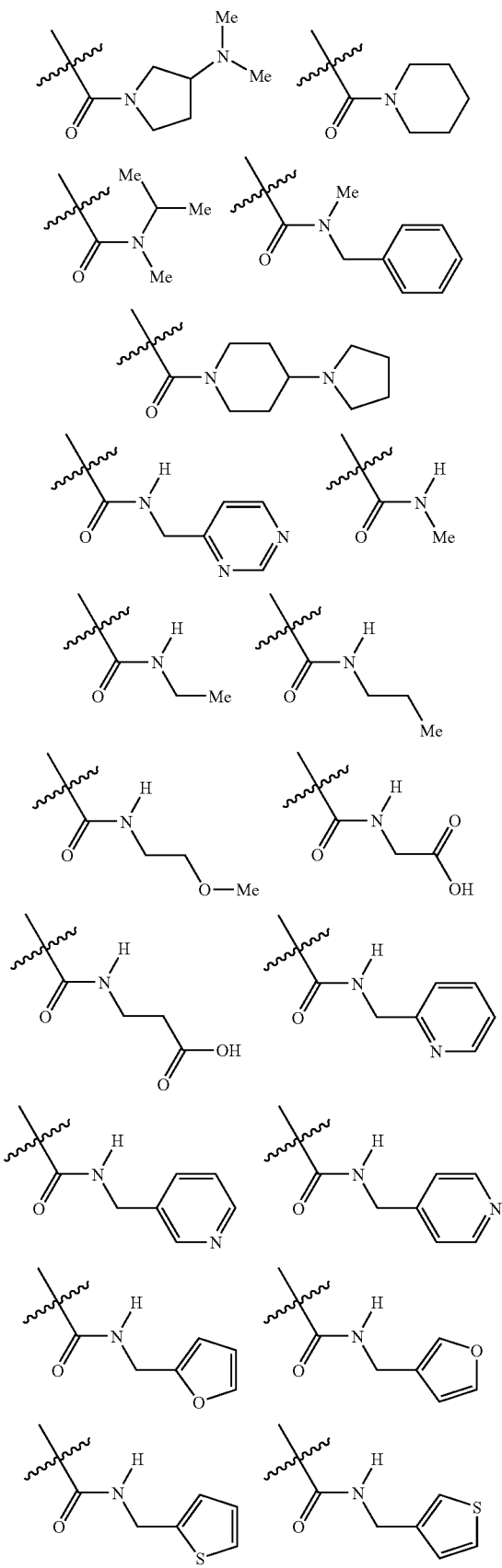
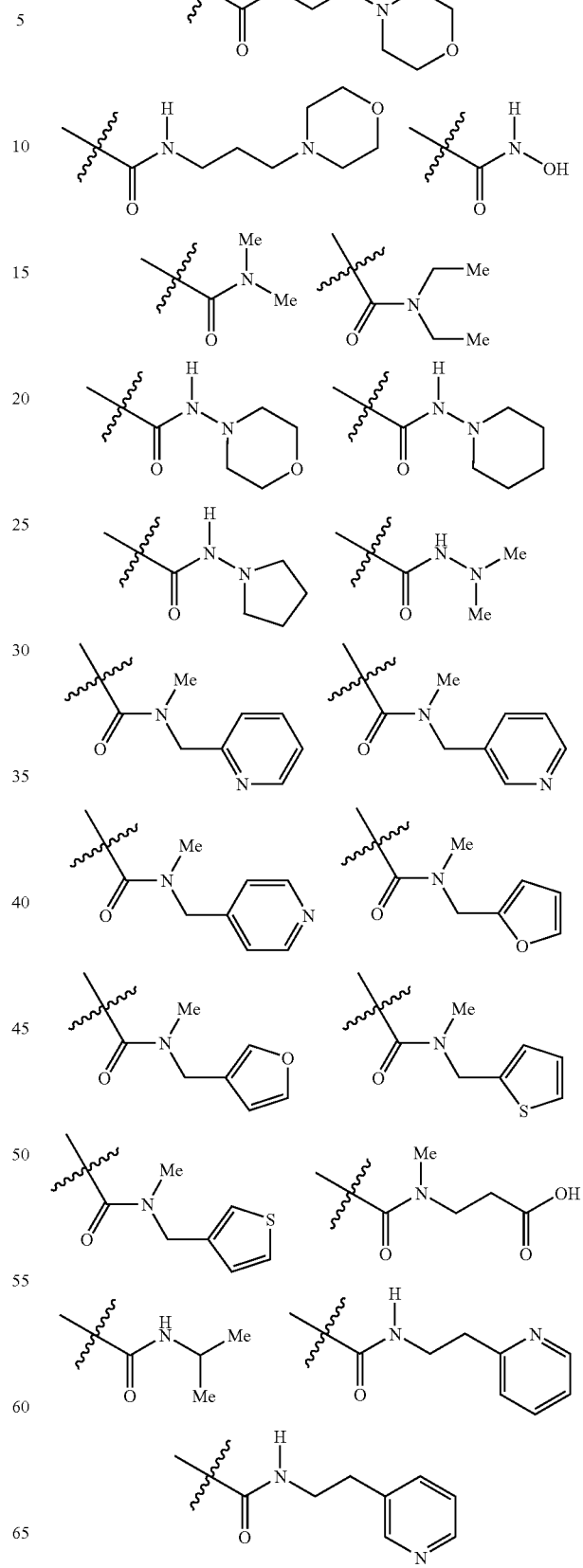

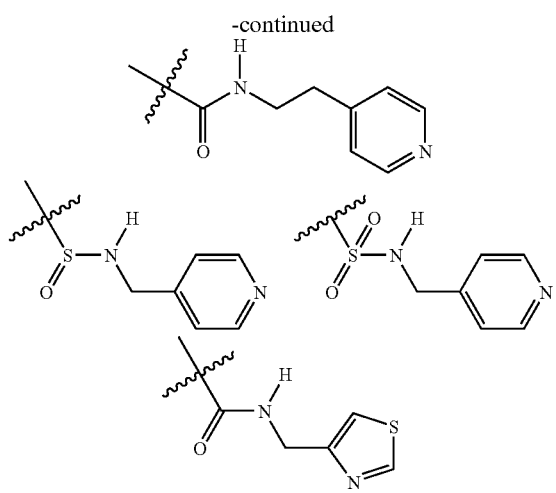

33) The compounds according to 32), wherein the $C_{2-14}$ aryl group as $R^3$ is a phenyl group, a thienyl group, a furyl group or a pyridyl group, tautomers, prodrugs or pharmaceutically acceptable salts of the compounds or solvates thereof.

34) The compounds according to 32), wherein the $C_{2-14}$ aryl group as $R^3$ is a thienyl group, tautomers, prodrugs or pharmaceutically acceptable salts of the compounds or solvates thereof.

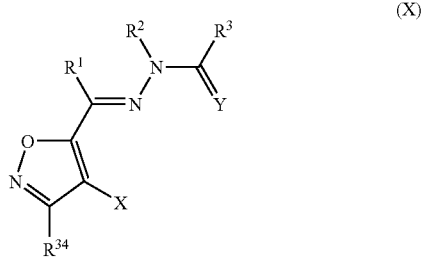

(X)

35) Compounds represented by the formula (X), which are compounds represented by the formula (I) wherein $L^1$ is represented by the formula (II) wherein B is a nitrogen atom, D=E, as a whole, means an oxygen atom, and A is $CR^{34}$, and $L^2$ is a single bond, tautomers, prodrugs or pharmaceutically acceptable salts of the compounds or solvates thereof.

36) Compounds represented by the formula (XI), which are compounds represented by the formula (I) wherein $L^1$ is represented by the formula (II) wherein B is a nitrogen atom, D=E, as a whole, means a sulfur atom, and A is $CR^{34}$, and $L^2$ is a single bond, tautomers, prodrugs or pharmaceutically acceptable salts of the compounds or solvates thereof.

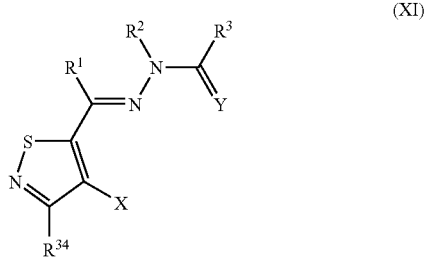

(XI)

37) Compounds represented by the formula (XII), which are compounds represented by the formula (I) wherein $L^1$ is represented by the formula (II) wherein A=B, as a whole, means $NR^{34}$, and each of D and E is a nitrogen atom, and $L^2$ is a single bond, tautomers, prodrugs or pharmaceutically acceptable salts of the compounds or solvates thereof.

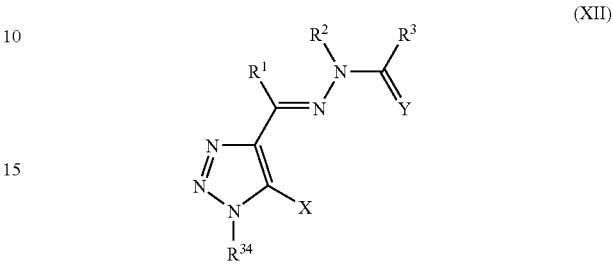

(XII)

38) The compounds according to 35), 36) or 37), wherein $R^2$ is a hydrogen atom, tautomers, prodrugs or pharmaceutically acceptable salts of the compounds or solvates thereof.

39) The compounds according to 38), wherein Y is an oxygen atom, tautomers, prodrugs or pharmaceutically acceptable salts of the compounds or solvates thereof.

40) The compounds according to 39), wherein X is OH, tautomers, prodrugs or pharmaceutically acceptable salts of the compounds or solvates thereof.

41) The compounds according to 40), wherein $R^1$ is a hydrogen atom or a $C_{1-3}$ alykl group (the $C_{1-3}$ alykl group may be substituted with one or more halogen atoms), tautomers, prodrugs or pharmaceutically acceptable salts of the compounds or solvates thereof.

42) The compounds according to 41), wherein $R^{34}$ is a phenyl group optionally substituted with one or more of the following substituents, tautomers, prodrugs or pharmaceutically acceptable salts of the compounds or solvates thereof.

Substituents: t-butyl groups, methyl groups, methoxy groups, trifluoromethyl groups, trifluoromethoxy groups, chlorine atoms, bromine atoms and fluorine atoms.

43) The compound according to 42), wherein $R^3$ is a $C_{2-14}$ aryl group substituted with one or more substituents selected from the following substituent set A and with one or more substituents selected from the following substituent set B, tautomers, prodrugs or pharmaceutically acceptable salts of the compounds or solvates thereof.

Substituent Set A:

Hydrogen atoms, nitro groups, halogen atoms, carboxyl groups, carbamoyl groups, sulfamoyl groups, sulfo groups, formyl groups, $C_{1-10}$ alkoxycarbonyl groups, $C_{1-10}$ alkylaminosulfonyl groups and $C_{1-10}$ alkylaminocarbonyl groups.

Substituent Set B:

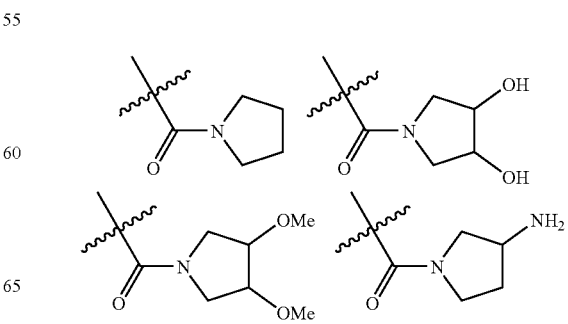

67
-continued
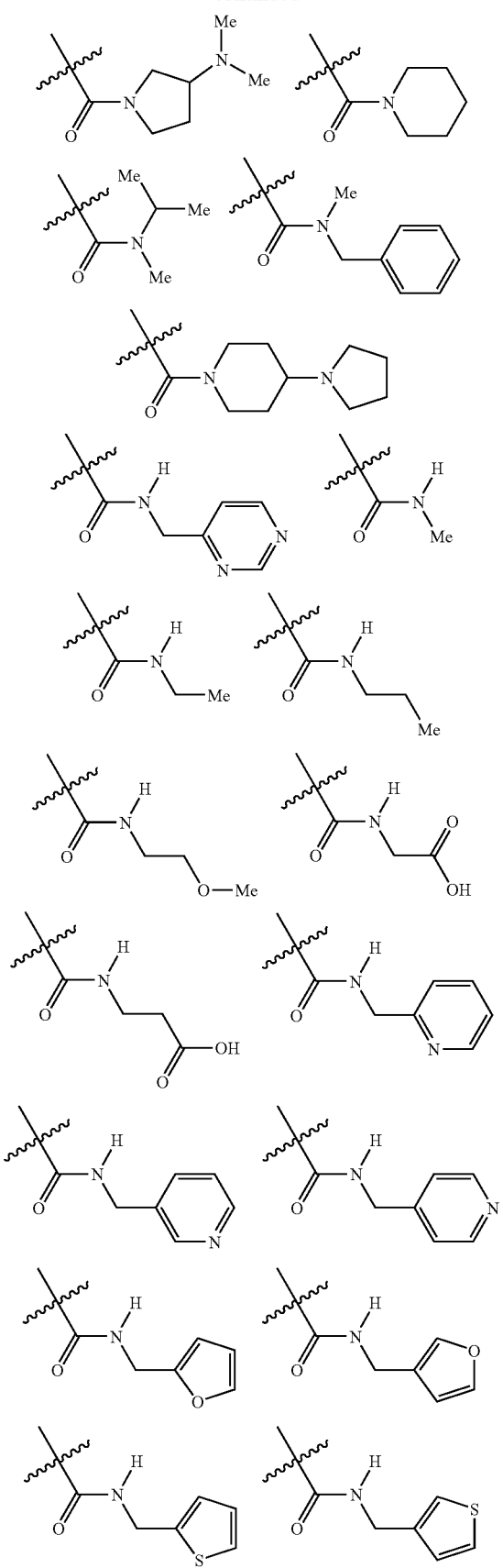
68
-continued
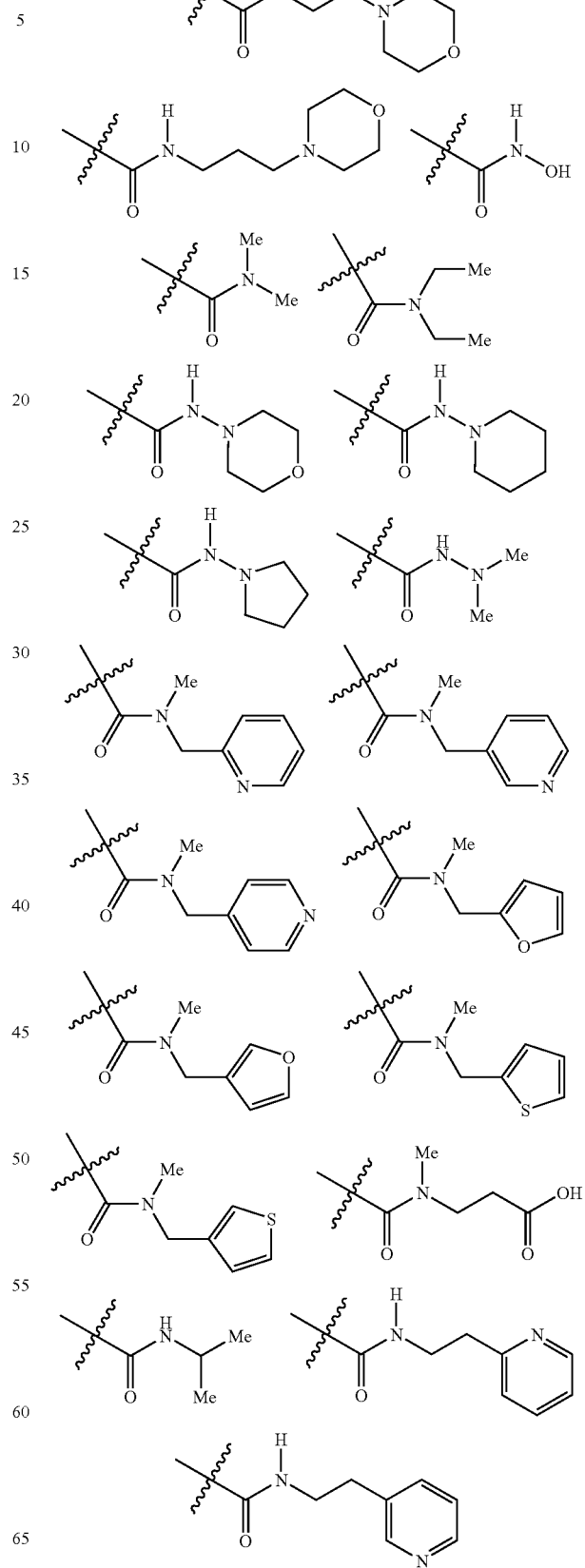

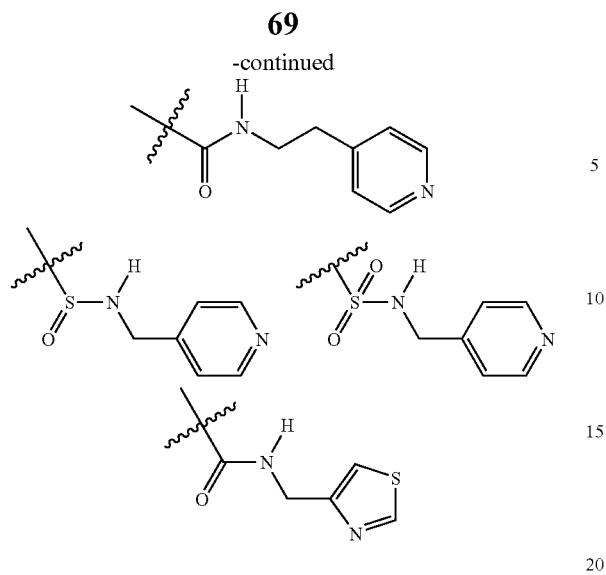

44) The compounds according to 44), wherein the $C_{2-14}$ aryl group is a phenyl group, a thienyl group, a furyl group or a pyridyl group, tautomers, prodrugs or pharmaceutically acceptable salts of the compounds or solvates thereof.

45) The compounds according to 44), wherein the $C_{2-14}$ aryl group is a thienyl group, tautomers, prodrugs or pharmaceutically acceptable salts of the compounds or solvates thereof.

46) Compounds represented by the formula (III), wherein $R^2$ is a hydrogen atom, $R^{33}$ is a methyl group, X is OH, Y is an oxygen atom, and $R^{34}$, $R^1$ and $R^3$ are any of the following combinations shown in Table 1, tautomers, prodrugs or pharmaceutically acceptable salts of the compounds or solvates thereof. The symbols in Table 1 denote the following substituents.

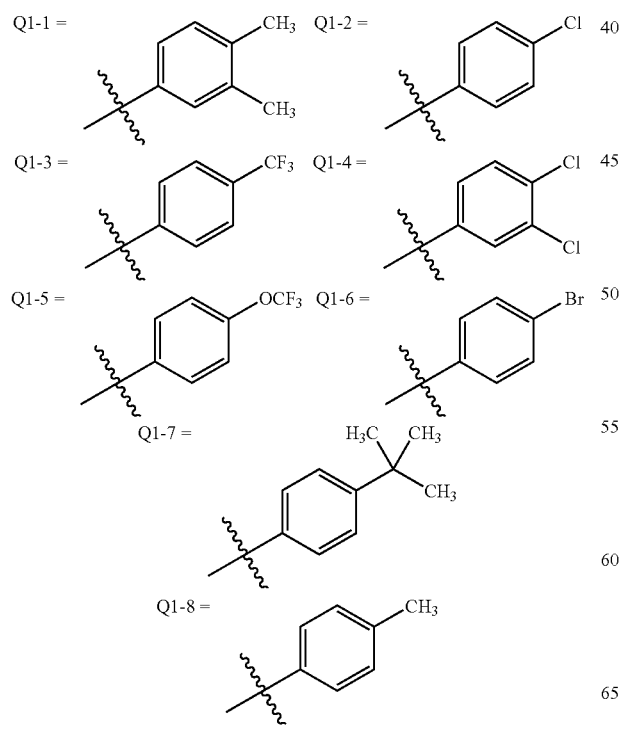

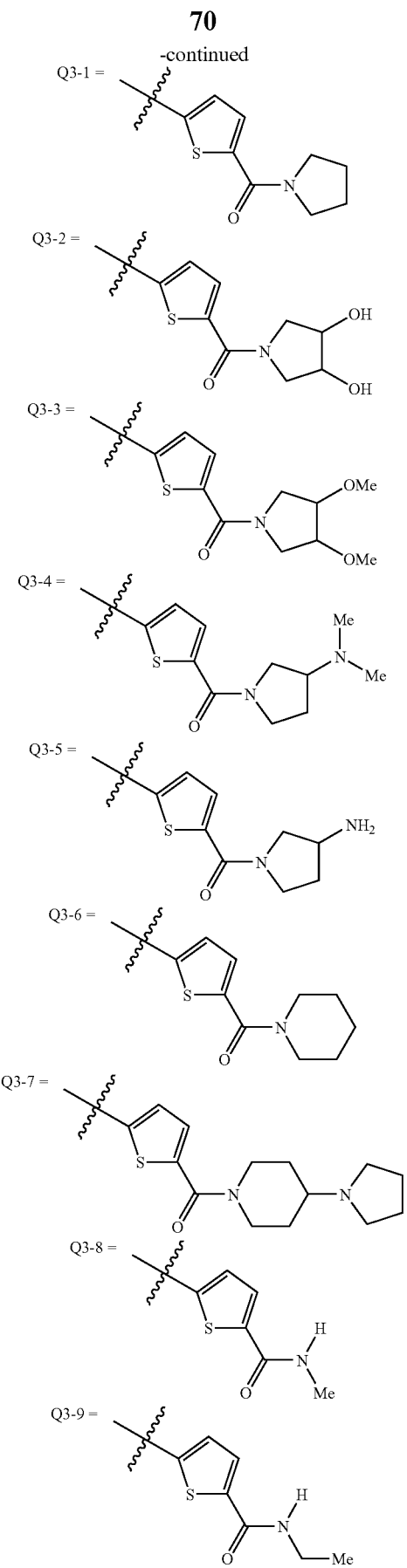

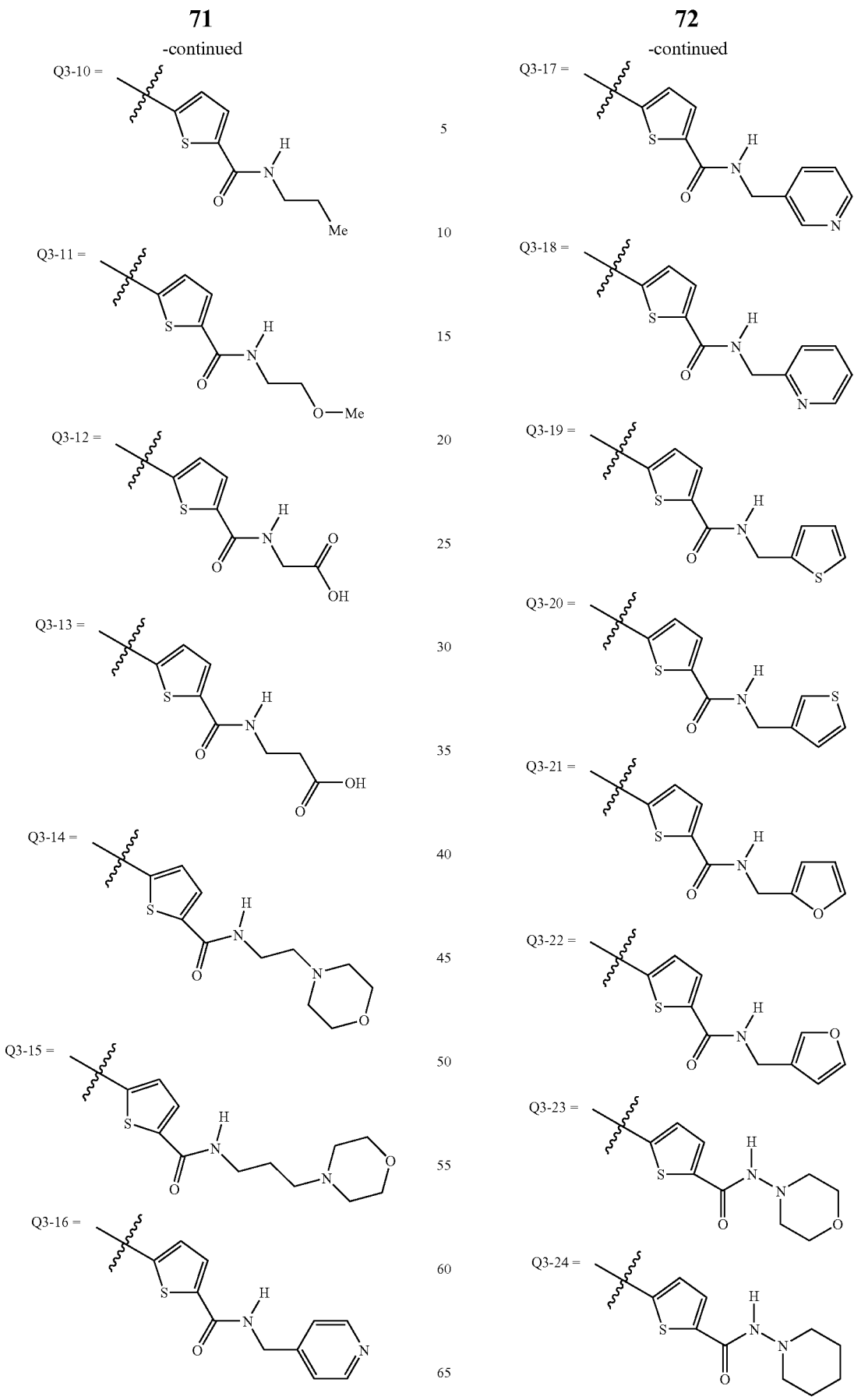

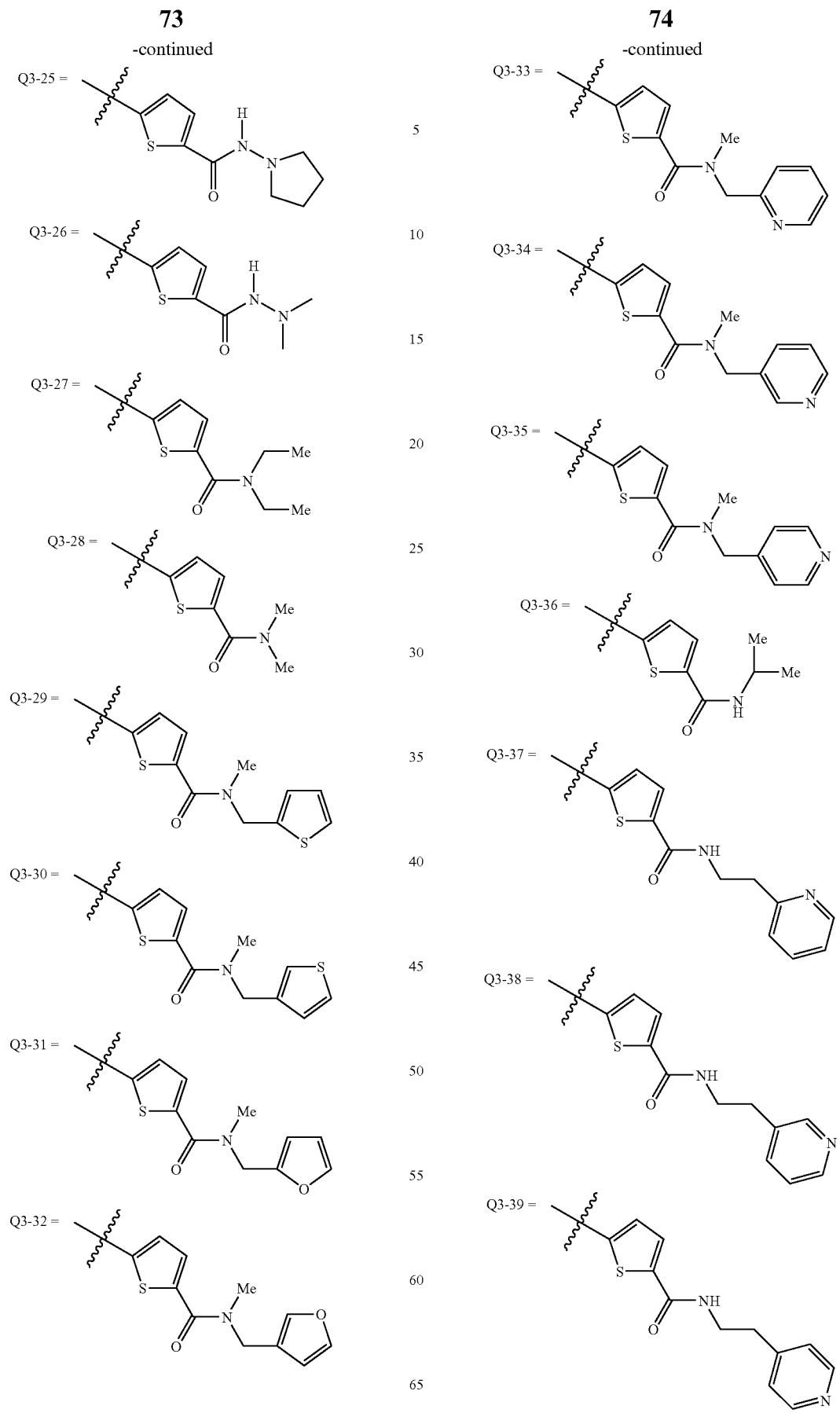

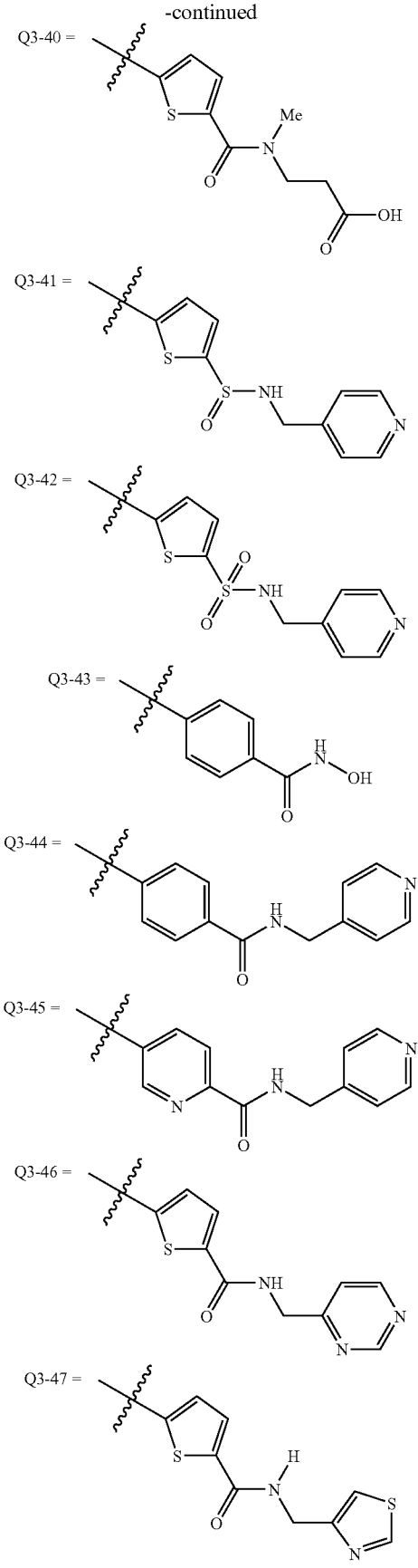

TABLE 1

| R³⁴ | R¹ | R³ | R³⁴ | R¹ | R³ |
|---|---|---|---|---|---|
| Q1-1 | Me | Q3-1 | Q1-2 | Me | Q3-1 |
| Q1-1 | Me | Q3-2 | Q1-2 | Me | Q3-2 |
| Q1-1 | Me | Q3-3 | Q1-2 | Me | Q3-3 |
| Q1-1 | Me | Q3-4 | Q1-2 | Me | Q3-4 |
| Q1-1 | Me | Q3-5 | Q1-2 | Me | Q3-5 |
| Q1-1 | Me | Q3-6 | Q1-2 | Me | Q3-6 |
| Q1-1 | Me | Q3-7 | Q1-2 | Me | Q3-7 |
| Q1-1 | Me | Q3-8 | Q1-2 | Me | Q3-8 |
| Q1-1 | Me | Q3-9 | Q1-2 | Me | Q3-9 |
| Q1-1 | Me | Q3-10 | Q1-2 | Me | Q3-10 |
| Q1-1 | Me | Q3-11 | Q1-2 | Me | Q3-11 |
| Q1-1 | Me | Q3-12 | Q1-2 | Me | Q3-12 |
| Q1-1 | Me | Q3-13 | Q1-2 | Me | Q3-13 |
| Q1-1 | Me | Q3-14 | Q1-2 | Me | Q3-14 |
| Q1-1 | Me | Q3-15 | Q1-2 | Me | Q3-15 |
| Q1-1 | Me | Q3-16 | Q1-2 | Me | Q3-16 |
| Q1-1 | Me | Q3-17 | Q1-2 | Me | Q3-17 |
| Q1-1 | Me | Q3-18 | Q1-2 | Me | Q3-18 |
| Q1-1 | Me | Q3-19 | Q1-2 | Me | Q3-19 |
| Q1-1 | Me | Q3-20 | Q1-2 | Me | Q3-20 |
| Q1-1 | Me | Q3-21 | Q1-2 | Me | Q3-21 |
| Q1-1 | Me | Q3-22 | Q1-2 | Me | Q3-22 |
| Q1-1 | Me | Q3-23 | Q1-2 | Me | Q3-23 |
| Q1-1 | Me | Q3-24 | Q1-2 | Me | Q3-24 |
| Q1-1 | Me | Q3-25 | Q1-2 | Me | Q3-25 |
| Q1-1 | Me | Q3-26 | Q1-2 | Me | Q3-26 |
| Q1-1 | Me | Q3-27 | Q1-2 | Me | Q3-27 |
| Q1-1 | Me | Q3-28 | Q1-2 | Me | Q3-28 |
| Q1-1 | Me | Q3-29 | Q1-2 | Me | Q3-29 |
| Q1-1 | Me | Q3-30 | Q1-2 | Me | Q3-30 |
| Q1-1 | Me | Q3-31 | Q1-2 | Me | Q3-31 |
| Q1-1 | Me | Q3-32 | Q1-2 | Me | Q3-32 |
| Q1-1 | Me | Q3-33 | Q1-2 | Me | Q3-33 |
| Q1-1 | Me | Q3-34 | Q1-2 | Me | Q3-34 |
| Q1-1 | Me | Q3-35 | Q1-2 | Me | Q3-35 |
| Q1-1 | Me | Q3-36 | Q1-2 | Me | Q3-36 |
| Q1-1 | Me | Q3-37 | Q1-2 | Me | Q3-37 |
| Q1-1 | Me | Q3-38 | Q1-2 | Me | Q3-38 |
| Q1-1 | Me | Q3-39 | Q1-2 | Me | Q3-39 |
| Q1-1 | Me | Q3-40 | Q1-2 | Me | Q3-40 |
| Q1-1 | Me | Q3-41 | Q1-2 | Me | Q3-41 |
| Q1-1 | Me | Q3-42 | Q1-2 | Me | Q3-42 |
| Q1-1 | Me | Q3-43 | Q1-2 | Me | Q3-43 |
| Q1-1 | Me | Q3-44 | Q1-2 | Me | Q3-44 |
| Q1-1 | Me | Q3-45 | Q1-2 | Me | Q3-45 |
| Q1-1 | Me | Q3-46 | Q1-2 | Me | Q3-46 |
| Q1-1 | Me | Q3-47 | Q1-2 | Me | Q3-47 |
| Q1-3 | Me | Q3-1 | Q1-4 | Me | Q3-1 |
| Q1-3 | Me | Q3-2 | Q1-4 | Me | Q3-2 |
| Q1-3 | Me | Q3-3 | Q1-4 | Me | Q3-3 |
| Q1-3 | Me | Q3-4 | Q1-4 | Me | Q3-4 |
| Q1-3 | Me | Q3-5 | Q1-4 | Me | Q3-5 |
| Q1-3 | Me | Q3-6 | Q1-4 | Me | Q3-6 |
| Q1-3 | Me | Q3-7 | Q1-4 | Me | Q3-7 |
| Q1-3 | Me | Q3-8 | Q1-4 | Me | Q3-8 |
| Q1-3 | Me | Q3-9 | Q1-4 | Me | Q3-9 |
| Q1-3 | Me | Q3-10 | Q1-4 | Me | Q3-10 |
| Q1-3 | Me | Q3-11 | Q1-4 | Me | Q3-11 |
| Q1-3 | Me | Q3-12 | Q1-4 | Me | Q3-12 |
| Q1-3 | Me | Q3-13 | Q1-4 | Me | Q3-13 |
| Q1-3 | Me | Q3-14 | Q1-4 | Me | Q3-14 |
| Q1-3 | Me | Q3-15 | Q1-4 | Me | Q3-15 |
| Q1-3 | Me | Q3-16 | Q1-4 | Me | Q3-16 |
| Q1-3 | Me | Q3-17 | Q1-4 | Me | Q3-17 |
| Q1-3 | Me | Q3-18 | Q1-4 | Me | Q3-18 |
| Q1-3 | Me | Q3-19 | Q1-4 | Me | Q3-19 |
| Q1-3 | Me | Q3-20 | Q1-4 | Me | Q3-20 |
| Q1-3 | Me | Q3-21 | Q1-4 | Me | Q3-21 |
| Q1-3 | Me | Q3-22 | Q1-4 | Me | Q3-22 |
| Q1-3 | Me | Q3-23 | Q1-4 | Me | Q3-23 |
| Q1-3 | Me | Q3-24 | Q1-4 | Me | Q3-24 |
| Q1-3 | Me | Q3-25 | Q1-4 | Me | Q3-25 |
| Q1-3 | Me | Q3-26 | Q1-4 | Me | Q3-26 |
| Q1-3 | Me | Q3-27 | Q1-4 | Me | Q3-27 |
| Q1-3 | Me | Q3-28 | Q1-4 | Me | Q3-28 |
| Q1-3 | Me | Q3-29 | Q1-4 | Me | Q3-29 |
| Q1-3 | Me | Q3-30 | Q1-4 | Me | Q3-30 |
| Q1-3 | Me | Q3-31 | Q1-4 | Me | Q3-31 |

TABLE 1-continued

| $R^{34}$ | $R^1$ | $R^3$ | $R^{34}$ | $R^1$ | $R^3$ |
|---|---|---|---|---|---|
| Q1-3 | Me | Q3-32 | Q1-4 | Me | Q3-32 |
| Q1-3 | Me | Q3-33 | Q1-4 | Me | Q3-33 |
| Q1-3 | Me | Q3-34 | Q1-4 | Me | Q3-34 |
| Q1-3 | Me | Q3-35 | Q1-4 | Me | Q3-35 |
| Q1-3 | Me | Q3-36 | Q1-4 | Me | Q3-36 |
| Q1-3 | Me | Q3-37 | Q1-4 | Me | Q3-37 |
| Q1-3 | Me | Q3-38 | Q1-4 | Me | Q3-38 |
| Q1-3 | Me | Q3-39 | Q1-4 | Me | Q3-39 |
| Q1-3 | Me | Q3-40 | Q1-4 | Me | Q3-40 |
| Q1-3 | Me | Q3-41 | Q1-4 | Me | Q3-41 |
| Q1-3 | Me | Q3-42 | Q1-4 | Me | Q3-42 |
| Q1-3 | Me | Q3-43 | Q1-4 | Me | Q3-43 |
| Q1-3 | Me | Q3-44 | Q1-4 | Me | Q3-44 |
| Q1-3 | Me | Q3-45 | Q1-4 | Me | Q3-45 |
| Q1-3 | Me | Q3-46 | Q1-4 | Me | Q3-46 |
| Q1-3 | Me | Q3-47 | Q1-4 | Me | Q3-47 |
| Q1-5 | Me | Q3-1 | Q1-6 | Me | Q3-1 |
| Q1-5 | Me | Q3-2 | Q1-6 | Me | Q3-2 |
| Q1-5 | Me | Q3-3 | Q1-6 | Me | Q3-3 |
| Q1-5 | Me | Q3-4 | Q1-6 | Me | Q3-4 |
| Q1-5 | Me | Q3-5 | Q1-6 | Me | Q3-5 |
| Q1-5 | Me | Q3-6 | Q1-6 | Me | Q3-6 |
| Q1-5 | Me | Q3-7 | Q1-6 | Me | Q3-7 |
| Q1-5 | Me | Q3-8 | Q1-6 | Me | Q3-8 |
| Q1-5 | Me | Q3-9 | Q1-6 | Me | Q3-9 |
| Q1-5 | Me | Q3-10 | Q1-6 | Me | Q3-10 |
| Q1-5 | Me | Q3-11 | Q1-6 | Me | Q3-11 |
| Q1-5 | Me | Q3-12 | Q1-6 | Me | Q3-12 |
| Q1-5 | Me | Q3-13 | Q1-6 | Me | Q3-13 |
| Q1-5 | Me | Q3-14 | Q1-6 | Me | Q3-14 |
| Q1-5 | Me | Q3-15 | Q1-6 | Me | Q3-15 |
| Q1-5 | Me | Q3-16 | Q1-6 | Me | Q3-16 |
| Q1-5 | Me | Q3-17 | Q1-6 | Me | Q3-17 |
| Q1-5 | Me | Q3-18 | Q1-6 | Me | Q3-18 |
| Q1-5 | Me | Q3-19 | Q1-6 | Me | Q3-19 |
| Q1-5 | Me | Q3-20 | Q1-6 | Me | Q3-20 |
| Q1-5 | Me | Q3-21 | Q1-6 | Me | Q3-21 |
| Q1-5 | Me | Q3-22 | Q1-6 | Me | Q3-22 |
| Q1-5 | Me | Q3-23 | Q1-6 | Me | Q3-23 |
| Q1-5 | Me | Q3-24 | Q1-6 | Me | Q3-24 |
| Q1-5 | Me | Q3-25 | Q1-6 | Me | Q3-25 |
| Q1-5 | Me | Q3-26 | Q1-6 | Me | Q3-26 |
| Q1-5 | Me | Q3-27 | Q1-6 | Me | Q3-27 |
| Q1-5 | Me | Q3-28 | Q1-6 | Me | Q3-28 |
| Q1-5 | Me | Q3-29 | Q1-6 | Me | Q3-29 |
| Q1-5 | Me | Q3-30 | Q1-6 | Me | Q3-30 |
| Q1-5 | Me | Q3-31 | Q1-6 | Me | Q3-31 |
| Q1-5 | Me | Q3-32 | Q1-6 | Me | Q3-32 |
| Q1-5 | Me | Q3-33 | Q1-6 | Me | Q3-33 |
| Q1-5 | Me | Q3-34 | Q1-6 | Me | Q3-34 |
| Q1-5 | Me | Q3-35 | Q1-6 | Me | Q3-35 |
| Q1-5 | Me | Q3-36 | Q1-6 | Me | Q3-36 |
| Q1-5 | Me | Q3-37 | Q1-6 | Me | Q3-37 |
| Q1-5 | Me | Q3-38 | Q1-6 | Me | Q3-38 |
| Q1-5 | Me | Q3-39 | Q1-6 | Me | Q3-39 |
| Q1-5 | Me | Q3-40 | Q1-6 | Me | Q3-40 |
| Q1-5 | Me | Q3-41 | Q1-6 | Me | Q3-41 |
| Q1-5 | Me | Q3-42 | Q1-6 | Me | Q3-42 |
| Q1-5 | Me | Q3-43 | Q1-6 | Me | Q3-43 |
| Q1-5 | Me | Q3-44 | Q1-6 | Me | Q3-44 |
| Q1-5 | Me | Q3-45 | Q1-6 | Me | Q3-45 |
| Q1-5 | Me | Q3-46 | Q1-6 | Me | Q3-46 |
| Q1-5 | Me | Q3-47 | Q1-6 | Me | Q3-47 |
| Q1-7 | Me | Q3-1 | Q1-8 | Me | Q3-1 |
| Q1-7 | Me | Q3-2 | Q1-8 | Me | Q3-2 |
| Q1-7 | Me | Q3-3 | Q1-8 | Me | Q3-3 |
| Q1-7 | Me | Q3-4 | Q1-8 | Me | Q3-4 |
| Q1-7 | Me | Q3-5 | Q1-8 | Me | Q3-5 |
| Q1-7 | Me | Q3-6 | Q1-8 | Me | Q3-6 |
| Q1-7 | Me | Q3-7 | Q1-8 | Me | Q3-7 |
| Q1-7 | Me | Q3-8 | Q1-8 | Me | Q3-8 |
| Q1-7 | Me | Q3-9 | Q1-8 | Me | Q3-9 |
| Q1-7 | Me | Q3-10 | Q1-8 | Me | Q3-10 |
| Q1-7 | Me | Q3-11 | Q1-8 | Me | Q3-11 |
| Q1-7 | Me | Q3-12 | Q1-8 | Me | Q3-12 |
| Q1-7 | Me | Q3-13 | Q1-8 | Me | Q3-13 |
| Q1-7 | Me | Q3-14 | Q1-8 | Me | Q3-14 |
| Q1-7 | Me | Q3-15 | Q1-8 | Me | Q3-15 |
| Q1-7 | Me | Q3-16 | Q1-8 | Me | Q3-16 |
| Q1-7 | Me | Q3-17 | Q1-8 | Me | Q3-17 |
| Q1-7 | Me | Q3-18 | Q1-8 | Me | Q3-18 |
| Q1-7 | Me | Q3-19 | Q1-8 | Me | Q3-19 |
| Q1-7 | Me | Q3-20 | Q1-8 | Me | Q3-20 |
| Q1-7 | Me | Q3-21 | Q1-8 | Me | Q3-21 |
| Q1-7 | Me | Q3-22 | Q1-8 | Me | Q3-22 |
| Q1-7 | Me | Q3-23 | Q1-8 | Me | Q3-23 |
| Q1-7 | Me | Q3-24 | Q1-8 | Me | Q3-24 |
| Q1-7 | Me | Q3-25 | Q1-8 | Me | Q3-25 |
| Q1-7 | Me | Q3-26 | Q1-8 | Me | Q3-26 |
| Q1-7 | Me | Q3-27 | Q1-8 | Me | Q3-27 |
| Q1-7 | Me | Q3-28 | Q1-8 | Me | Q3-28 |
| Q1-7 | Me | Q3-29 | Q1-8 | Me | Q3-29 |
| Q1-7 | Me | Q3-30 | Q1-8 | Me | Q3-30 |
| Q1-7 | Me | Q3-31 | Q1-8 | Me | Q3-31 |
| Q1-7 | Me | Q3-32 | Q1-8 | Me | Q3-32 |
| Q1-7 | Me | Q3-33 | Q1-8 | Me | Q3-33 |
| Q1-7 | Me | Q3-34 | Q1-8 | Me | Q3-34 |
| Q1-7 | Me | Q3-35 | Q1-8 | Me | Q3-35 |
| Q1-7 | Me | Q3-36 | Q1-8 | Me | Q3-36 |
| Q1-7 | Me | Q3-37 | Q1-8 | Me | Q3-37 |
| Q1-7 | Me | Q3-38 | Q1-8 | Me | Q3-38 |
| Q1-7 | Me | Q3-39 | Q1-8 | Me | Q3-39 |
| Q1-7 | Me | Q3-40 | Q1-8 | Me | Q3-40 |
| Q1-7 | Me | Q3-41 | Q1-8 | Me | Q3-41 |
| Q1-7 | Me | Q3-42 | Q1-8 | Me | Q3-42 |
| Q1-7 | Me | Q3-43 | Q1-8 | Me | Q3-43 |
| Q1-7 | Me | Q3-44 | Q1-8 | Me | Q3-44 |
| Q1-7 | Me | Q3-45 | Q1-8 | Me | Q3-45 |
| Q1-7 | Me | Q3-46 | Q1-8 | Me | Q3-46 |
| Q1-7 | Me | Q3-47 | Q1-8 | Me | Q3-47 |

47) Compounds represented by the formula (IV), wherein $R^2$ is a hydrogen atom, $R^{33}$ is a methyl group, X is OH, Y is an oxygen atom, and $R^{34}$, $R^1$ and $R^3$ are any of the following combinations shown in Table 2, tautomers, prodrugs or pharmaceutically acceptable salts of the compounds or solvates thereof. The symbols in Table 2 denote the same substituents as in Table 1.

TABLE 2

| $R^{34}$ | $R^1$ | $R^3$ | $R^{34}$ | $R^1$ | $R^3$ |
|---|---|---|---|---|---|
| Q1-1 | Me | Q3-1 | Q1-2 | Me | Q3-1 |
| Q1-1 | Me | Q3-2 | Q1-2 | Me | Q3-2 |
| Q1-1 | Me | Q3-3 | Q1-2 | Me | Q3-3 |
| Q1-1 | Me | Q3-4 | Q1-2 | Me | Q3-4 |
| Q1-1 | Me | Q3-5 | Q1-2 | Me | Q3-5 |
| Q1-1 | Me | Q3-6 | Q1-2 | Me | Q3-6 |
| Q1-1 | Me | Q3-7 | Q1-2 | Me | Q3-7 |
| Q1-1 | Me | Q3-8 | Q1-2 | Me | Q3-8 |
| Q1-1 | Me | Q3-9 | Q1-2 | Me | Q3-9 |
| Q1-1 | Me | Q3-10 | Q1-2 | Me | Q3-10 |
| Q1-1 | Me | Q3-11 | Q1-2 | Me | Q3-11 |
| Q1-1 | Me | Q3-12 | Q1-2 | Me | Q3-12 |
| Q1-1 | Me | Q3-13 | Q1-2 | Me | Q3-13 |
| Q1-1 | Me | Q3-14 | Q1-2 | Me | Q3-14 |
| Q1-1 | Me | Q3-15 | Q1-2 | Me | Q3-15 |
| Q1-1 | Me | Q3-16 | Q1-2 | Me | Q3-16 |
| Q1-1 | Me | Q3-17 | Q1-2 | Me | Q3-17 |
| Q1-1 | Me | Q3-18 | Q1-2 | Me | Q3-18 |
| Q1-1 | Me | Q3-19 | Q1-2 | Me | Q3-19 |
| Q1-1 | Me | Q3-20 | Q1-2 | Me | Q3-20 |
| Q1-1 | Me | Q3-21 | Q1-2 | Me | Q3-21 |
| Q1-1 | Me | Q3-22 | Q1-2 | Me | Q3-22 |
| Q1-1 | Me | Q3-23 | Q1-2 | Me | Q3-23 |
| Q1-1 | Me | Q3-24 | Q1-2 | Me | Q3-24 |
| Q1-1 | Me | Q3-25 | Q1-2 | Me | Q3-25 |
| Q1-1 | Me | Q3-26 | Q1-2 | Me | Q3-26 |
| Q1-1 | Me | Q3-27 | Q1-2 | Me | Q3-27 |
| Q1-1 | Me | Q3-28 | Q1-2 | Me | Q3-28 |
| Q1-1 | Me | Q3-29 | Q1-2 | Me | Q3-29 |
| Q1-1 | Me | Q3-30 | Q1-2 | Me | Q3-30 |

TABLE 2-continued

| R³⁴ | R¹ | R³ | R³⁴ | R¹ | R³ |
|---|---|---|---|---|---|
| Q1-1 | Me | Q3-31 | Q1-2 | Me | Q3-31 |
| Q1-1 | Me | Q3-32 | Q1-2 | Me | Q3-32 |
| Q1-1 | Me | Q3-33 | Q1-2 | Me | Q3-33 |
| Q1-1 | Me | Q3-34 | Q1-2 | Me | Q3-34 |
| Q1-1 | Me | Q3-35 | Q1-2 | Me | Q3-35 |
| Q1-1 | Me | Q3-36 | Q1-2 | Me | Q3-36 |
| Q1-1 | Me | Q3-37 | Q1-2 | Me | Q3-37 |
| Q1-1 | Me | Q3-38 | Q1-2 | Me | Q3-38 |
| Q1-1 | Me | Q3-39 | Q1-2 | Me | Q3-39 |
| Q1-1 | Me | Q3-40 | Q1-2 | Me | Q3-40 |
| Q1-1 | Me | Q3-41 | Q1-2 | Me | Q3-41 |
| Q1-1 | Me | Q3-42 | Q1-2 | Me | Q3-42 |
| Q1-1 | Me | Q3-43 | Q1-2 | Me | Q3-43 |
| Q1-1 | Me | Q3-44 | Q1-2 | Me | Q3-44 |
| Q1-1 | Me | Q3-45 | Q1-2 | Me | Q3-45 |
| Q1-1 | Me | Q3-46 | Q1-2 | Me | Q3-46 |
| Q1-1 | Me | Q3-47 | Q1-2 | Me | Q3-47 |
| Q1-3 | Me | Q3-1 | Q1-4 | Me | Q3-1 |
| Q1-3 | Me | Q3-2 | Q1-4 | Me | Q3-2 |
| Q1-3 | Me | Q3-3 | Q1-4 | Me | Q3-3 |
| Q1-3 | Me | Q3-4 | Q1-4 | Me | Q3-4 |
| Q1-3 | Me | Q3-5 | Q1-4 | Me | Q3-5 |
| Q1-3 | Me | Q3-6 | Q1-4 | Me | Q3-6 |
| Q1-3 | Me | Q3-7 | Q1-4 | Me | Q3-7 |
| Q1-3 | Me | Q3-8 | Q1-4 | Me | Q3-8 |
| Q1-3 | Me | Q3-9 | Q1-4 | Me | Q3-9 |
| Q1-3 | Me | Q3-10 | Q1-4 | Me | Q3-10 |
| Q1-3 | Me | Q3-11 | Q1-4 | Me | Q3-11 |
| Q1-3 | Me | Q3-12 | Q1-4 | Me | Q3-12 |
| Q1-3 | Me | Q3-13 | Q1-4 | Me | Q3-13 |
| Q1-3 | Me | Q3-14 | Q1-4 | Me | Q3-14 |
| Q1-3 | Me | Q3-15 | Q1-4 | Me | Q3-15 |
| Q1-3 | Me | Q3-16 | Q1-4 | Me | Q3-16 |
| Q1-3 | Me | Q3-17 | Q1-4 | Me | Q3-17 |
| Q1-3 | Me | Q3-18 | Q1-4 | Me | Q3-18 |
| Q1-3 | Me | Q3-19 | Q1-4 | Me | Q3-19 |
| Q1-3 | Me | Q3-20 | Q1-4 | Me | Q3-20 |
| Q1-3 | Me | Q3-21 | Q1-4 | Me | Q3-21 |
| Q1-3 | Me | Q3-22 | Q1-4 | Me | Q3-22 |
| Q1-3 | Me | Q3-23 | Q1-4 | Me | Q3-23 |
| Q1-3 | Me | Q3-24 | Q1-4 | Me | Q3-24 |
| Q1-3 | Me | Q3-25 | Q1-4 | Me | Q3-25 |
| Q1-3 | Me | Q3-26 | Q1-4 | Me | Q3-26 |
| Q1-3 | Me | Q3-27 | Q1-4 | Me | Q3-27 |
| Q1-3 | Me | Q3-28 | Q1-4 | Me | Q3-28 |
| Q1-3 | Me | Q3-29 | Q1-4 | Me | Q3-29 |
| Q1-3 | Me | Q3-30 | Q1-4 | Me | Q3-30 |
| Q1-3 | Me | Q3-31 | Q1-4 | Me | Q3-31 |
| Q1-3 | Me | Q3-32 | Q1-4 | Me | Q3-32 |
| Q1-3 | Me | Q3-33 | Q1-4 | Me | Q3-33 |
| Q1-3 | Me | Q3-34 | Q1-4 | Me | Q3-34 |
| Q1-3 | Me | Q3-35 | Q1-4 | Me | Q3-35 |
| Q1-3 | Me | Q3-36 | Q1-4 | Me | Q3-36 |
| Q1-3 | Me | Q3-37 | Q1-4 | Me | Q3-37 |
| Q1-3 | Me | Q3-38 | Q1-4 | Me | Q3-38 |
| Q1-3 | Me | Q3-39 | Q1-4 | Me | Q3-39 |
| Q1-3 | Me | Q3-40 | Q1-4 | Me | Q3-40 |
| Q1-3 | Me | Q3-41 | Q1-4 | Me | Q3-41 |
| Q1-3 | Me | Q3-42 | Q1-4 | Me | Q3-42 |
| Q1-3 | Me | Q3-43 | Q1-4 | Me | Q3-43 |
| Q1-3 | Me | Q3-44 | Q1-4 | Me | Q3-44 |
| Q1-3 | Me | Q3-45 | Q1-4 | Me | Q3-45 |
| Q1-3 | Me | Q3-46 | Q1-4 | Me | Q3-46 |
| Q1-3 | Me | Q3-47 | Q1-4 | Me | Q3-47 |
| Q1-5 | Me | Q3-1 | Q1-6 | Me | Q3-1 |
| Q1-5 | Me | Q3-2 | Q1-6 | Me | Q3-2 |
| Q1-5 | Me | Q3-3 | Q1-6 | Me | Q3-3 |
| Q1-5 | Me | Q3-4 | Q1-6 | Me | Q3-4 |
| Q1-5 | Me | Q3-5 | Q1-6 | Me | Q3-5 |
| Q1-5 | Me | Q3-6 | Q1-6 | Me | Q3-6 |
| Q1-5 | Me | Q3-7 | Q1-6 | Me | Q3-7 |
| Q1-5 | Me | Q3-8 | Q1-6 | Me | Q3-8 |
| Q1-5 | Me | Q3-9 | Q1-6 | Me | Q3-9 |
| Q1-5 | Me | Q3-10 | Q1-6 | Me | Q3-10 |
| Q1-5 | Me | Q3-11 | Q1-6 | Me | Q3-11 |
| Q1-5 | Me | Q3-12 | Q1-6 | Me | Q3-12 |
| Q1-5 | Me | Q3-13 | Q1-6 | Me | Q3-13 |
| Q1-5 | Me | Q3-14 | Q1-6 | Me | Q3-14 |
| Q1-5 | Me | Q3-15 | Q1-6 | Me | Q3-15 |
| Q1-5 | Me | Q3-16 | Q1-6 | Me | Q3-16 |
| Q1-5 | Me | Q3-17 | Q1-6 | Me | Q3-17 |
| Q1-5 | Me | Q3-18 | Q1-6 | Me | Q3-18 |
| Q1-5 | Me | Q3-19 | Q1-6 | Me | Q3-19 |
| Q1-5 | Me | Q3-20 | Q1-6 | Me | Q3-20 |
| Q1-5 | Me | Q3-21 | Q1-6 | Me | Q3-21 |
| Q1-5 | Me | Q3-22 | Q1-6 | Me | Q3-22 |
| Q1-5 | Me | Q3-23 | Q1-6 | Me | Q3-23 |
| Q1-5 | Me | Q3-24 | Q1-6 | Me | Q3-24 |
| Q1-5 | Me | Q3-25 | Q1-6 | Me | Q3-25 |
| Q1-5 | Me | Q3-26 | Q1-6 | Me | Q3-26 |
| Q1-5 | Me | Q3-27 | Q1-6 | Me | Q3-27 |
| Q1-5 | Me | Q3-28 | Q1-6 | Me | Q3-28 |
| Q1-5 | Me | Q3-29 | Q1-6 | Me | Q3-29 |
| Q1-5 | Me | Q3-30 | Q1-6 | Me | Q3-30 |
| Q1-5 | Me | Q3-31 | Q1-6 | Me | Q3-31 |
| Q1-5 | Me | Q3-32 | Q1-6 | Me | Q3-32 |
| Q1-5 | Me | Q3-33 | Q1-6 | Me | Q3-33 |
| Q1-5 | Me | Q3-34 | Q1-6 | Me | Q3-34 |
| Q1-5 | Me | Q3-35 | Q1-6 | Me | Q3-35 |
| Q1-5 | Me | Q3-36 | Q1-6 | Me | Q3-36 |
| Q1-5 | Me | Q3-37 | Q1-6 | Me | Q3-37 |
| Q1-5 | Me | Q3-38 | Q1-6 | Me | Q3-38 |
| Q1-5 | Me | Q3-39 | Q1-6 | Me | Q3-39 |
| Q1-5 | Me | Q3-40 | Q1-6 | Me | Q3-40 |
| Q1-5 | Me | Q3-41 | Q1-6 | Me | Q3-41 |
| Q1-5 | Me | Q3-42 | Q1-6 | Me | Q3-42 |
| Q1-5 | Me | Q3-43 | Q1-6 | Me | Q3-43 |
| Q1-5 | Me | Q3-44 | Q1-6 | Me | Q3-44 |
| Q1-5 | Me | Q3-45 | Q1-6 | Me | Q3-45 |
| Q1-5 | Me | Q3-46 | Q1-6 | Me | Q3-46 |
| Q1-5 | Me | Q3-47 | Q1-6 | Me | Q3-47 |
| Q1-7 | Me | Q3-1 | Q1-8 | Me | Q3-1 |
| Q1-7 | Me | Q3-2 | Q1-8 | Me | Q3-2 |
| Q1-7 | Me | Q3-3 | Q1-8 | Me | Q3-3 |
| Q1-7 | Me | Q3-4 | Q1-8 | Me | Q3-4 |
| Q1-7 | Me | Q3-5 | Q1-8 | Me | Q3-5 |
| Q1-7 | Me | Q3-6 | Q1-8 | Me | Q3-6 |
| Q1-7 | Me | Q3-7 | Q1-8 | Me | Q3-7 |
| Q1-7 | Me | Q3-8 | Q1-8 | Me | Q3-8 |
| Q1-7 | Me | Q3-9 | Q1-8 | Me | Q3-9 |
| Q1-7 | Me | Q3-10 | Q1-8 | Me | Q3-10 |
| Q1-7 | Me | Q3-11 | Q1-8 | Me | Q3-11 |
| Q1-7 | Me | Q3-12 | Q1-8 | Me | Q3-12 |
| Q1-7 | Me | Q3-13 | Q1-8 | Me | Q3-13 |
| Q1-7 | Me | Q3-14 | Q1-8 | Me | Q3-14 |
| Q1-7 | Me | Q3-15 | Q1-8 | Me | Q3-15 |
| Q1-7 | Me | Q3-16 | Q1-8 | Me | Q3-16 |
| Q1-7 | Me | Q3-17 | Q1-8 | Me | Q3-17 |
| Q1-7 | Me | Q3-18 | Q1-8 | Me | Q3-18 |
| Q1-7 | Me | Q3-19 | Q1-8 | Me | Q3-19 |
| Q1-7 | Me | Q3-20 | Q1-8 | Me | Q3-20 |
| Q1-7 | Me | Q3-21 | Q1-8 | Me | Q3-21 |
| Q1-7 | Me | Q3-22 | Q1-8 | Me | Q3-22 |
| Q1-7 | Me | Q3-23 | Q1-8 | Me | Q3-23 |
| Q1-7 | Me | Q3-24 | Q1-8 | Me | Q3-24 |
| Q1-7 | Me | Q3-25 | Q1-8 | Me | Q3-25 |
| Q1-7 | Me | Q3-26 | Q1-8 | Me | Q3-26 |
| Q1-7 | Me | Q3-27 | Q1-8 | Me | Q3-27 |
| Q1-7 | Me | Q3-28 | Q1-8 | Me | Q3-28 |
| Q1-7 | Me | Q3-29 | Q1-8 | Me | Q3-29 |
| Q1-7 | Me | Q3-30 | Q1-8 | Me | Q3-30 |
| Q1-7 | Me | Q3-31 | Q1-8 | Me | Q3-31 |
| Q1-7 | Me | Q3-32 | Q1-8 | Me | Q3-32 |
| Q1-7 | Me | Q3-33 | Q1-8 | Me | Q3-33 |
| Q1-7 | Me | Q3-34 | Q1-8 | Me | Q3-34 |
| Q1-7 | Me | Q3-35 | Q1-8 | Me | Q3-35 |
| Q1-7 | Me | Q3-36 | Q1-8 | Me | Q3-36 |
| Q1-7 | Me | Q3-37 | Q1-8 | Me | Q3-37 |
| Q1-7 | Me | Q3-38 | Q1-8 | Me | Q3-38 |
| Q1-7 | Me | Q3-39 | Q1-8 | Me | Q3-39 |
| Q1-7 | Me | Q3-40 | Q1-8 | Me | Q3-40 |
| Q1-7 | Me | Q3-41 | Q1-8 | Me | Q3-41 |
| Q1-7 | Me | Q3-42 | Q1-8 | Me | Q3-42 |
| Q1-7 | Me | Q3-43 | Q1-8 | Me | Q3-43 |
| Q1-7 | Me | Q3-44 | Q1-8 | Me | Q3-44 |
| Q1-7 | Me | Q3-45 | Q1-8 | Me | Q3-45 |

TABLE 2-continued

| R³⁴ | R¹ | R³ | R³⁴ | R¹ | R³ |
|---|---|---|---|---|---|
| Q1-7 | Me | Q3-46 | Q1-8 | Me | Q3-46 |
| Q1-7 | Me | Q3-47 | Q1-8 | Me | Q3-47 |

48) The compounds according to 46) or 47), wherein $R^1$ is converted to a hydrogen atom, tautomers, prodrugs or pharmaceutically acceptable salts of the compounds or solvates thereof.

49) The compounds according to 46) or 47), wherein $R^1$ is converted to a trifluoromethyl group, tautomers, prodrugs or pharmaceutically acceptable salts of the compounds or solvates thereof.

50) The compounds according to 46) or 47), wherein $R^1$ is converted to an ethyl group, tautomers, prodrugs or pharmaceutically acceptable salts of the compounds or solvates thereof.

51) The compounds according to 46) or 47), wherein $R^1$ is converted to a n-propyl group, tautomers, prodrugs or pharmaceutically acceptable salts of the compounds or solvates thereof.

52) The compounds according to 46) or 47), wherein $R^1$ is converted to an i-propyl group, tautomers, prodrugs or pharmaceutically acceptable salts of the compounds or solvates thereof.

53) The compounds according to any of 46) to 52), wherein $R^{33}$ is converted to a hydrogen atom, tautomers, prodrugs or pharmaceutically acceptable salts of the compounds or solvates thereof.

54) The compounds according to any of 46) to 52), wherein $R^{33}$ is converted to a trifluoromethyl group, tautomers, prodrugs or pharmaceutically acceptable salts of the compounds or solvates thereof.

55) The compounds according to any of 46) to 52), wherein $R^{33}$ is converted to an ethyl group, tautomers, prodrugs or pharmaceutically acceptable salts of the compounds or solvates thereof.

56) The compounds according to any of 46) to 52), wherein $R^{33}$ is converted to a n-propyl group, tautomers, prodrugs or pharmaceutically acceptable salts of the compounds or solvates thereof.

57) The compounds according to any of 46) to 52), wherein $R^{33}$ is converted to an i-propyl group, tautomers, prodrugs or pharmaceutically acceptable salts of the compounds or solvates thereof.

58) Compounds represented by the formula (V), wherein $R^2$ is a hydrogen atom, $R^{35}$ is a methyl group, X is OH, Y is an oxygen atom, and $R^{34}$, $R^1$ and $R^3$ are any of the following combinations shown in Table 3, tautomers, prodrugs or pharmaceutically acceptable salts of the compounds or solvates thereof. The symbols in Table 3 denote the same substituents as in Table 1.

TABLE 3

| R³⁴ | R¹ | R³ | R³⁴ | R¹ | R³ |
|---|---|---|---|---|---|
| Q1-1 | Me | Q3-1 | Q1-2 | Me | Q3-1 |
| Q1-1 | Me | Q3-2 | Q1-2 | Me | Q3-2 |
| Q1-1 | Me | Q3-3 | Q1-2 | Me | Q3-3 |
| Q1-1 | Me | Q3-4 | Q1-2 | Me | Q3-4 |
| Q1-1 | Me | Q3-5 | Q1-2 | Me | Q3-5 |
| Q1-1 | Me | Q3-6 | Q1-2 | Me | Q3-6 |
| Q1-1 | Me | Q3-7 | Q1-2 | Me | Q3-7 |
| Q1-1 | Me | Q3-8 | Q1-2 | Me | Q3-8 |
| Q1-1 | Me | Q3-9 | Q1-2 | Me | Q3-9 |
| Q1-1 | Me | Q3-10 | Q1-2 | Me | Q3-10 |
| Q1-1 | Me | Q3-11 | Q1-2 | Me | Q3-11 |
| Q1-1 | Me | Q3-12 | Q1-2 | Me | Q3-12 |
| Q1-1 | Me | Q3-13 | Q1-2 | Me | Q3-13 |
| Q1-1 | Me | Q3-14 | Q1-2 | Me | Q3-14 |
| Q1-1 | Me | Q3-15 | Q1-2 | Me | Q3-15 |
| Q1-1 | Me | Q3-16 | Q1-2 | Me | Q3-16 |
| Q1-1 | Me | Q3-17 | Q1-2 | Me | Q3-17 |
| Q1-1 | Me | Q3-18 | Q1-2 | Me | Q3-18 |
| Q1-1 | Me | Q3-19 | Q1-2 | Me | Q3-19 |
| Q1-1 | Me | Q3-20 | Q1-2 | Me | Q3-20 |
| Q1-1 | Me | Q3-21 | Q1-2 | Me | Q3-21 |
| Q1-1 | Me | Q3-22 | Q1-2 | Me | Q3-22 |
| Q1-1 | Me | Q3-23 | Q1-2 | Me | Q3-23 |
| Q1-1 | Me | Q3-24 | Q1-2 | Me | Q3-24 |
| Q1-1 | Me | Q3-25 | Q1-2 | Me | Q3-25 |
| Q1-1 | Me | Q3-26 | Q1-2 | Me | Q3-26 |
| Q1-1 | Me | Q3-27 | Q1-2 | Me | Q3-27 |
| Q1-1 | Me | Q3-28 | Q1-2 | Me | Q3-28 |
| Q1-1 | Me | Q3-29 | Q1-2 | Me | Q3-29 |
| Q1-1 | Me | Q3-30 | Q1-2 | Me | Q3-30 |
| Q1-1 | Me | Q3-31 | Q1-2 | Me | Q3-31 |
| Q1-1 | Me | Q3-32 | Q1-2 | Me | Q3-32 |
| Q1-1 | Me | Q3-33 | Q1-2 | Me | Q3-33 |
| Q1-1 | Me | Q3-34 | Q1-2 | Me | Q3-34 |
| Q1-1 | Me | Q3-35 | Q1-2 | Me | Q3-35 |
| Q1-1 | Me | Q3-36 | Q1-2 | Me | Q3-36 |
| Q1-1 | Me | Q3-37 | Q1-2 | Me | Q3-37 |
| Q1-1 | Me | Q3-38 | Q1-2 | Me | Q3-38 |
| Q1-1 | Me | Q3-39 | Q1-2 | Me | Q3-39 |
| Q1-1 | Me | Q3-40 | Q1-2 | Me | Q3-40 |
| Q1-1 | Me | Q3-41 | Q1-2 | Me | Q3-41 |
| Q1-1 | Me | Q3-42 | Q1-2 | Me | Q3-42 |
| Q1-1 | Me | Q3-43 | Q1-2 | Me | Q3-43 |
| Q1-1 | Me | Q3-44 | Q1-2 | Me | Q3-44 |
| Q1-1 | Me | Q3-45 | Q1-2 | Me | Q3-45 |
| Q1-1 | Me | Q3-46 | Q1-2 | Me | Q3-46 |
| Q1-1 | Me | Q3-47 | Q1-2 | Me | Q3-47 |
| Q1-3 | Me | Q3-1 | Q1-4 | Me | Q3-1 |
| Q1-3 | Me | Q3-2 | Q1-4 | Me | Q3-2 |
| Q1-3 | Me | Q3-3 | Q1-4 | Me | Q3-3 |
| Q1-3 | Me | Q3-4 | Q1-4 | Me | Q3-4 |
| Q1-3 | Me | Q3-5 | Q1-4 | Me | Q3-5 |
| Q1-3 | Me | Q3-6 | Q1-4 | Me | Q3-6 |
| Q1-3 | Me | Q3-7 | Q1-4 | Me | Q3-7 |
| Q1-3 | Me | Q3-8 | Q1-4 | Me | Q3-8 |
| Q1-3 | Me | Q3-9 | Q1-4 | Me | Q3-9 |
| Q1-3 | Me | Q3-10 | Q1-4 | Me | Q3-10 |
| Q1-3 | Me | Q3-11 | Q1-4 | Me | Q3-11 |
| Q1-3 | Me | Q3-12 | Q1-4 | Me | Q3-12 |
| Q1-3 | Me | Q3-13 | Q1-4 | Me | Q3-13 |
| Q1-3 | Me | Q3-14 | Q1-4 | Me | Q3-14 |
| Q1-3 | Me | Q3-15 | Q1-4 | Me | Q3-15 |
| Q1-3 | Me | Q3-16 | Q1-4 | Me | Q3-16 |
| Q1-3 | Me | Q3-17 | Q1-4 | Me | Q3-17 |
| Q1-3 | Me | Q3-18 | Q1-4 | Me | Q3-18 |
| Q1-3 | Me | Q3-19 | Q1-4 | Me | Q3-19 |
| Q1-3 | Me | Q3-20 | Q1-4 | Me | Q3-20 |
| Q1-3 | Me | Q3-21 | Q1-4 | Me | Q3-21 |
| Q1-3 | Me | Q3-22 | Q1-4 | Me | Q3-22 |
| Q1-3 | Me | Q3-23 | Q1-4 | Me | Q3-23 |
| Q1-3 | Me | Q3-24 | Q1-4 | Me | Q3-24 |
| Q1-3 | Me | Q3-25 | Q1-4 | Me | Q3-25 |
| Q1-3 | Me | Q3-26 | Q1-4 | Me | Q3-26 |
| Q1-3 | Me | Q3-27 | Q1-4 | Me | Q3-27 |
| Q1-3 | Me | Q3-28 | Q1-4 | Me | Q3-28 |
| Q1-3 | Me | Q3-29 | Q1-4 | Me | Q3-29 |
| Q1-3 | Me | Q3-30 | Q1-4 | Me | Q3-30 |
| Q1-3 | Me | Q3-31 | Q1-4 | Me | Q3-31 |
| Q1-3 | Me | Q3-32 | Q1-4 | Me | Q3-32 |
| Q1-3 | Me | Q3-33 | Q1-4 | Me | Q3-33 |
| Q1-3 | Me | Q3-34 | Q1-4 | Me | Q3-34 |
| Q1-3 | Me | Q3-35 | Q1-4 | Me | Q3-35 |
| Q1-3 | Me | Q3-36 | Q1-4 | Me | Q3-36 |
| Q1-3 | Me | Q3-37 | Q1-4 | Me | Q3-37 |
| Q1-3 | Me | Q3-38 | Q1-4 | Me | Q3-38 |
| Q1-3 | Me | Q3-39 | Q1-4 | Me | Q3-39 |
| Q1-3 | Me | Q3-40 | Q1-4 | Me | Q3-40 |
| Q1-3 | Me | Q3-41 | Q1-4 | Me | Q3-41 |

TABLE 3-continued

| R³⁴ | R¹ | R³ | R³⁴ | R¹ | R³ |
|---|---|---|---|---|---|
| Q1-3 | Me | Q3-42 | Q1-4 | Me | Q3-42 |
| Q1-3 | Me | Q3-43 | Q1-4 | Me | Q3-43 |
| Q1-3 | Me | Q3-44 | Q1-4 | Me | Q3-44 |
| Q1-3 | Me | Q3-45 | Q1-4 | Me | Q3-45 |
| Q1-3 | Me | Q3-46 | Q1-4 | Me | Q3-46 |
| Q1-3 | Me | Q3-47 | Q1-4 | Me | Q3-47 |
| Q1-5 | Me | Q3-1 | Q1-6 | Me | Q3-1 |
| Q1-5 | Me | Q3-2 | Q1-6 | Me | Q3-2 |
| Q1-5 | Me | Q3-3 | Q1-6 | Me | Q3-3 |
| Q1-5 | Me | Q3-4 | Q1-6 | Me | Q3-4 |
| Q1-5 | Me | Q3-5 | Q1-6 | Me | Q3-5 |
| Q1-5 | Me | Q3-6 | Q1-6 | Me | Q3-6 |
| Q1-5 | Me | Q3-7 | Q1-6 | Me | Q3-7 |
| Q1-5 | Me | Q3-8 | Q1-6 | Me | Q3-8 |
| Q1-5 | Me | Q3-9 | Q1-6 | Me | Q3-9 |
| Q1-5 | Me | Q3-10 | Q1-6 | Me | Q3-10 |
| Q1-5 | Me | Q3-11 | Q1-6 | Me | Q3-11 |
| Q1-5 | Me | Q3-12 | Q1-6 | Me | Q3-12 |
| Q1-5 | Me | Q3-13 | Q1-6 | Me | Q3-13 |
| Q1-5 | Me | Q3-14 | Q1-6 | Me | Q3-14 |
| Q1-5 | Me | Q3-15 | Q1-6 | Me | Q3-15 |
| Q1-5 | Me | Q3-16 | Q1-6 | Me | Q3-16 |
| Q1-5 | Me | Q3-17 | Q1-6 | Me | Q3-17 |
| Q1-5 | Me | Q3-18 | Q1-6 | Me | Q3-18 |
| Q1-5 | Me | Q3-19 | Q1-6 | Me | Q3-19 |
| Q1-5 | Me | Q3-20 | Q1-6 | Me | Q3-20 |
| Q1-5 | Me | Q3-21 | Q1-6 | Me | Q3-21 |
| Q1-5 | Me | Q3-22 | Q1-6 | Me | Q3-22 |
| Q1-5 | Me | Q3-23 | Q1-6 | Me | Q3-23 |
| Q1-5 | Me | Q3-24 | Q1-6 | Me | Q3-24 |
| Q1-5 | Me | Q3-25 | Q1-6 | Me | Q3-25 |
| Q1-5 | Me | Q3-26 | Q1-6 | Me | Q3-26 |
| Q1-5 | Me | Q3-27 | Q1-6 | Me | Q3-27 |
| Q1-5 | Me | Q3-28 | Q1-6 | Me | Q3-28 |
| Q1-5 | Me | Q3-29 | Q1-6 | Me | Q3-29 |
| Q1-5 | Me | Q3-30 | Q1-6 | Me | Q3-30 |
| Q1-5 | Me | Q3-31 | Q1-6 | Me | Q3-31 |
| Q1-5 | Me | Q3-32 | Q1-6 | Me | Q3-32 |
| Q1-5 | Me | Q3-33 | Q1-6 | Me | Q3-33 |
| Q1-5 | Me | Q3-34 | Q1-6 | Me | Q3-34 |
| Q1-5 | Me | Q3-35 | Q1-6 | Me | Q3-35 |
| Q1-5 | Me | Q3-36 | Q1-6 | Me | Q3-36 |
| Q1-5 | Me | Q3-37 | Q1-6 | Me | Q3-37 |
| Q1-5 | Me | Q3-38 | Q1-6 | Me | Q3-38 |
| Q1-5 | Me | Q3-39 | Q1-6 | Me | Q3-39 |
| Q1-5 | Me | Q3-40 | Q1-6 | Me | Q3-40 |
| Q1-5 | Me | Q3-41 | Q1-6 | Me | Q3-41 |
| Q1-5 | Me | Q3-42 | Q1-6 | Me | Q3-42 |
| Q1-5 | Me | Q3-43 | Q1-6 | Me | Q3-43 |
| Q1-5 | Me | Q3-44 | Q1-6 | Me | Q3-44 |
| Q1-5 | Me | Q3-45 | Q1-6 | Me | Q3-45 |
| Q1-5 | Me | Q3-46 | Q1-6 | Me | Q3-46 |
| Q1-5 | Me | Q3-47 | Q1-6 | Me | Q3-47 |
| Q1-7 | Me | Q3-1 | Q1-8 | Me | Q3-1 |
| Q1-7 | Me | Q3-2 | Q1-8 | Me | Q3-2 |
| Q1-7 | Me | Q3-3 | Q1-8 | Me | Q3-3 |
| Q1-7 | Me | Q3-4 | Q1-8 | Me | Q3-4 |
| Q1-7 | Me | Q3-5 | Q1-8 | Me | Q3-5 |
| Q1-7 | Me | Q3-6 | Q1-8 | Me | Q3-6 |
| Q1-7 | Me | Q3-7 | Q1-8 | Me | Q3-7 |
| Q1-7 | Me | Q3-8 | Q1-8 | Me | Q3-8 |
| Q1-7 | Me | Q3-9 | Q1-8 | Me | Q3-9 |
| Q1-7 | Me | Q3-10 | Q1-8 | Me | Q3-10 |
| Q1-7 | Me | Q3-11 | Q1-8 | Me | Q3-11 |
| Q1-7 | Me | Q3-12 | Q1-8 | Me | Q3-12 |
| Q1-7 | Me | Q3-13 | Q1-8 | Me | Q3-13 |
| Q1-7 | Me | Q3-14 | Q1-8 | Me | Q3-14 |
| Q1-7 | Me | Q3-15 | Q1-8 | Me | Q3-15 |
| Q1-7 | Me | Q3-16 | Q1-8 | Me | Q3-16 |
| Q1-7 | Me | Q3-17 | Q1-8 | Me | Q3-17 |
| Q1-7 | Me | Q3-18 | Q1-8 | Me | Q3-18 |
| Q1-7 | Me | Q3-19 | Q1-8 | Me | Q3-19 |
| Q1-7 | Me | Q3-20 | Q1-8 | Me | Q3-20 |
| Q1-7 | Me | Q3-21 | Q1-8 | Me | Q3-21 |
| Q1-7 | Me | Q3-22 | Q1-8 | Me | Q3-22 |
| Q1-7 | Me | Q3-23 | Q1-8 | Me | Q3-23 |
| Q1-7 | Me | Q3-24 | Q1-8 | Me | Q3-24 |
| Q1-7 | Me | Q3-25 | Q1-8 | Me | Q3-25 |
| Q1-7 | Me | Q3-26 | Q1-8 | Me | Q3-26 |
| Q1-7 | Me | Q3-27 | Q1-8 | Me | Q3-27 |
| Q1-7 | Me | Q3-28 | Q1-8 | Me | Q3-28 |
| Q1-7 | Me | Q3-29 | Q1-8 | Me | Q3-29 |
| Q1-7 | Me | Q3-30 | Q1-8 | Me | Q3-30 |
| Q1-7 | Me | Q3-31 | Q1-8 | Me | Q3-31 |
| Q1-7 | Me | Q3-32 | Q1-8 | Me | Q3-32 |
| Q1-7 | Me | Q3-33 | Q1-8 | Me | Q3-33 |
| Q1-7 | Me | Q3-34 | Q1-8 | Me | Q3-34 |
| Q1-7 | Me | Q3-35 | Q1-8 | Me | Q3-35 |
| Q1-7 | Me | Q3-36 | Q1-8 | Me | Q3-36 |
| Q1-7 | Me | Q3-37 | Q1-8 | Me | Q3-37 |
| Q1-7 | Me | Q3-38 | Q1-8 | Me | Q3-38 |
| Q1-7 | Me | Q3-39 | Q1-8 | Me | Q3-39 |
| Q1-7 | Me | Q3-40 | Q1-B | Me | Q3-40 |
| Q1-7 | Me | Q3-41 | Q1-8 | Me | Q3-41 |
| Q1-7 | Me | Q3-42 | Q1-8 | Me | Q3-42 |
| Q1-7 | Me | Q3-43 | Q1-8 | Me | Q3-43 |
| Q1-7 | Me | Q3-44 | Q1-8 | Me | Q3-44 |
| Q1-7 | Me | Q3-45 | Q1-8 | Me | Q3-45 |
| Q1-7 | Me | Q3-46 | Q1-8 | Me | Q3-46 |
| Q1-7 | Me | Q3-47 | Q1-8 | Me | Q3-47 |

59) Compounds represented by the formula (VI), wherein $R^2$ is a hydrogen atom, $R^{35}$ is a methyl group, X is OH, Y is an oxygen atom, and $R^{34}$, $R^1$ and $R^3$ are any of the following combinations shown in Table 4, tautomers, prodrugs or pharmaceutically acceptable salts of the compounds or solvates thereof. The symbols in Table 4 denote the same substituents as in Table 1.

TABLE 4

| R³⁴ | R¹ | R³ | R³⁴ | R¹ | R³ |
|---|---|---|---|---|---|
| Q1-1 | Me | Q3-1 | Q1-2 | Me | Q3-1 |
| Q1-1 | Me | Q3-2 | Q1-2 | Me | Q3-2 |
| Q1-1 | Me | Q3-3 | Q1-2 | Me | Q3-3 |
| Q1-1 | Me | Q3-4 | Q1-2 | Me | Q3-4 |
| Q1-1 | Me | Q3-5 | Q1-2 | Me | Q3-5 |
| Q1-1 | Me | Q3-6 | Q1-2 | Me | Q3-6 |
| Q1-1 | Me | Q3-7 | Q1-2 | Me | Q3-7 |
| Q1-1 | Me | Q3-8 | Q1-2 | Me | Q3-8 |
| Q1-1 | Me | Q3-9 | Q1-2 | Me | Q3-9 |
| Q1-1 | Me | Q3-10 | Q1-2 | Me | Q3-10 |
| Q1-1 | Me | Q3-11 | Q1-2 | Me | Q3-11 |
| Q1-1 | Me | Q3-12 | Q1-2 | Me | Q3-12 |
| Q1-1 | Me | Q3-13 | Q1-2 | Me | Q3-13 |
| Q1-1 | Me | Q3-14 | Q1-2 | Me | Q3-14 |
| Q1-1 | Me | Q3-15 | Q1-2 | Me | Q3-15 |
| Q1-1 | Me | Q3-16 | Q1-2 | Me | Q3-16 |
| Q1-1 | Me | Q3-17 | Q1-2 | Me | Q3-17 |
| Q1-1 | Me | Q3-18 | Q1-2 | Me | Q3-18 |
| Q1-1 | Me | Q3-19 | Q1-2 | Me | Q3-19 |
| Q1-1 | Me | Q3-20 | Q1-2 | Me | Q3-20 |
| Q1-1 | Me | Q3-21 | Q1-2 | Me | Q3-21 |
| Q1-1 | Me | Q3-22 | Q1-2 | Me | Q3-22 |
| Q1-1 | Me | Q3-23 | Q1-2 | Me | Q3-23 |
| Q1-1 | Me | Q3-24 | Q1-2 | Me | Q3-24 |
| Q1-1 | Me | Q3-25 | Q1-2 | Me | Q3-25 |
| Q1-1 | Me | Q3-26 | Q1-2 | Me | Q3-26 |
| Q1-1 | Me | Q3-27 | Q1-2 | Me | Q3-27 |
| Q1-1 | Me | Q3-28 | Q1-2 | Me | Q3-28 |
| Q1-1 | Me | Q3-29 | Q1-2 | Me | Q3-29 |
| Q1-1 | Me | Q3-30 | Q1-2 | Me | Q3-30 |
| Q1-1 | Me | Q3-31 | Q1-2 | Me | Q3-31 |
| Q1-1 | Me | Q3-32 | Q1-2 | Me | Q3-32 |
| Q1-1 | Me | Q3-33 | Q1-2 | Me | Q3-33 |
| Q1-1 | Me | Q3-34 | Q1-2 | Me | Q3-34 |
| Q1-1 | Me | Q3-35 | Q1-2 | Me | Q3-35 |
| Q1-1 | Me | Q3-36 | Q1-2 | Me | Q3-36 |
| Q1-1 | Me | Q3-37 | Q1-2 | Me | Q3-37 |
| Q1-1 | Me | Q3-38 | Q1-2 | Me | Q3-38 |
| Q1-1 | Me | Q3-39 | Q1-2 | Me | Q3-39 |
| Q1-1 | Me | Q3-40 | Q1-2 | Me | Q3-40 |

TABLE 4-continued

| R³⁴ | R¹ | R³ | R³⁴ | R¹ | R³ |
|---|---|---|---|---|---|
| Q1-1 | Me | Q3-41 | Q1-2 | Me | Q3-41 |
| Q1-1 | Me | Q3-42 | Q1-2 | Me | Q3-42 |
| Q1-1 | Me | Q3-43 | Q1-2 | Me | Q3-43 |
| Q1-1 | Me | Q3-44 | Q1-2 | Me | Q3-44 |
| Q1-1 | Me | Q3-45 | Q1-2 | Me | Q3-45 |
| Q1-1 | Me | Q3-46 | Q1-2 | Me | Q3-46 |
| Q1-1 | Me | Q3-47 | Q1-2 | Me | Q3-47 |
| Q1-3 | Me | Q3-1 | Q1-4 | Me | Q3-1 |
| Q1-3 | Me | Q3-2 | Q1-4 | Me | Q3-2 |
| Q1-3 | Me | Q3-3 | Q1-4 | Me | Q3-3 |
| Q1-3 | Me | Q3-4 | Q1-4 | Me | Q3-4 |
| Q1-3 | Me | Q3-5 | Q1-4 | Me | Q3-5 |
| Q1-3 | Me | Q3-6 | Q1-4 | Me | Q3-6 |
| Q1-3 | Me | Q3-7 | Q1-4 | Me | Q3-7 |
| Q1-3 | Me | Q3-8 | Q1-4 | Me | Q3-8 |
| Q1-3 | Me | Q3-9 | Q1-4 | Me | Q3-9 |
| Q1-3 | Me | Q3-10 | Q1-4 | Me | Q3-10 |
| Q1-3 | Me | Q3-11 | Q1-4 | Me | Q3-11 |
| Q1-3 | Me | Q3-12 | Q1-4 | Me | Q3-12 |
| Q1-3 | Me | Q3-13 | Q1-4 | Me | Q3-13 |
| Q1-3 | Me | Q3-14 | Q1-4 | Me | Q3-14 |
| Q1-3 | Me | Q3-15 | Q1-4 | Me | Q3-15 |
| Q1-3 | Me | Q3-16 | Q1-4 | Me | Q3-16 |
| Q1-3 | Me | Q3-17 | Q1-4 | Me | Q3-17 |
| Q1-3 | Me | Q3-18 | Q1-4 | Me | Q3-18 |
| Q1-3 | Me | Q3-19 | Q1-4 | Me | Q3-19 |
| Q1-3 | Me | Q3-20 | Q1-4 | Me | Q3-20 |
| Q1-3 | Me | Q3-21 | Q1-4 | Me | Q3-21 |
| Q1-3 | Me | Q3-22 | Q1-4 | Me | Q3-22 |
| Q1-3 | Me | Q3-23 | Q1-4 | Me | Q3-23 |
| Q1-3 | Me | Q3-24 | Q1-4 | Me | Q3-24 |
| Q1-3 | Me | Q3-25 | Q1-4 | Me | Q3-25 |
| Q1-3 | Me | Q3-26 | Q1-4 | Me | Q3-26 |
| Q1-3 | Me | Q3-27 | Q1-4 | Me | Q3-27 |
| Q1-3 | Me | Q3-28 | Q1-4 | Me | Q3-28 |
| Q1-3 | Me | Q3-29 | Q1-4 | Me | Q3-29 |
| Q1-3 | Me | Q3-30 | Q1-4 | Me | Q3-30 |
| Q1-3 | Me | Q3-31 | Q1-4 | Me | Q3-31 |
| Q1-3 | Me | Q3-32 | Q1-4 | Me | Q3-32 |
| Q1-3 | Me | Q3-33 | Q1-4 | Me | Q3-33 |
| Q1-3 | Me | Q3-34 | Q1-4 | Me | Q3-34 |
| Q1-3 | Me | Q3-35 | Q1-4 | Me | Q3-35 |
| Q1-3 | Me | Q3-36 | Q1-4 | Me | Q3-36 |
| Q1-3 | Me | Q3-37 | Q1-4 | Me | Q3-37 |
| Q1-3 | Me | Q3-38 | Q1-4 | Me | Q3-38 |
| Q1-3 | Me | Q3-39 | Q1-4 | Me | Q3-39 |
| Q1-3 | Me | Q3-40 | Q1-4 | Me | Q3-40 |
| Q1-3 | Me | Q3-41 | Q1-4 | Me | Q3-41 |
| Q1-3 | Me | Q3-42 | Q1-4 | Me | Q3-42 |
| Q1-3 | Me | Q3-43 | Q1-4 | Me | Q3-43 |
| Q1-3 | Me | Q3-44 | Q1-4 | Me | Q3-44 |
| Q1-3 | Me | Q3-45 | Q1-4 | Me | Q3-45 |
| Q1-3 | Me | Q3-46 | Q1-4 | Me | Q3-46 |
| Q1-3 | Me | Q3-47 | Q1-4 | Me | Q3-47 |
| Q1-5 | Me | Q3-1 | Q1-6 | Me | Q3-1 |
| Q1-5 | Me | Q3-2 | Q1-6 | Me | Q3-2 |
| Q1-5 | Me | Q3-3 | Q1-6 | Me | Q3-3 |
| Q1-5 | Me | Q3-4 | Q1-6 | Me | Q3-4 |
| Q1-5 | Me | Q3-5 | Q1-6 | Me | Q3-5 |
| Q1-5 | Me | Q3-6 | Q1-6 | Me | Q3-6 |
| Q1-5 | Me | Q3-7 | Q1-6 | Me | Q3-7 |
| Q1-5 | Me | Q3-8 | Q1-6 | Me | Q3-8 |
| Q1-5 | Me | Q3-9 | Q1-6 | Me | Q3-9 |
| Q1-5 | Me | Q3-10 | Q1-6 | Me | Q3-10 |
| Q1-5 | Me | Q3-11 | Q1-6 | Me | Q3-11 |
| Q1-5 | Me | Q3-12 | Q1-6 | Me | Q3-12 |
| Q1-5 | Me | Q3-13 | Q1-6 | Me | Q3-13 |
| Q1-5 | Me | Q3-14 | Q1-6 | Me | Q3-14 |
| Q1-5 | Me | Q3-15 | Q1-6 | Me | Q3-15 |
| Q1-5 | Me | Q3-16 | Q1-6 | Me | Q3-16 |
| Q1-5 | Me | Q3-17 | Q1-6 | Me | Q3-17 |
| Q1-5 | Me | Q3-18 | Q1-6 | Me | Q3-18 |
| Q1-5 | Me | Q3-19 | Q1-6 | Me | Q3-19 |
| Q1-5 | Me | Q3-20 | Q1-6 | Me | Q3-20 |
| Q1-5 | Me | Q3-21 | Q1-6 | Me | Q3-21 |
| Q1-5 | Me | Q3-22 | Q1-6 | Me | Q3-22 |
| Q1-5 | Me | Q3-23 | Q1-6 | Me | Q3-23 |
| Q1-5 | Me | Q3-24 | Q1-6 | Me | Q3-24 |
| Q1-5 | Me | Q3-25 | Q1-6 | Me | Q3-25 |
| Q1-5 | Me | Q3-26 | Q1-6 | Me | Q3-26 |
| Q1-5 | Me | Q3-27 | Q1-6 | Me | Q3-27 |
| Q1-5 | Me | Q3-28 | Q1-6 | Me | Q3-28 |
| Q1-5 | Me | Q3-29 | Q1-6 | Me | Q3-29 |
| Q1-5 | Me | Q3-30 | Q1-6 | Me | Q3-30 |
| Q1-5 | Me | Q3-31 | Q1-6 | Me | Q3-31 |
| Q1-5 | Me | Q3-32 | Q1-6 | Me | Q3-32 |
| Q1-5 | Me | Q3-33 | Q1-6 | Me | Q3-33 |
| Q1-5 | Me | Q3-34 | Q1-6 | Me | Q3-34 |
| Q1-5 | Me | Q3-35 | Q1-6 | Me | Q3-35 |
| Q1-5 | Me | Q3-36 | Q1-6 | Me | Q3-36 |
| Q1-5 | Me | Q3-37 | Q1-6 | Me | Q3-37 |
| Q1-5 | Me | Q3-38 | Q1-6 | Me | Q3-38 |
| Q1-5 | Me | Q3-39 | Q1-6 | Me | Q3-39 |
| Q1-5 | Me | Q3-40 | Q1-6 | Me | Q3-40 |
| Q1-5 | Me | Q3-41 | Q1-6 | Me | Q3-41 |
| Q1-5 | Me | Q3-42 | Q1-6 | Me | Q3-42 |
| Q1-5 | Me | Q3-43 | Q1-6 | Me | Q3-43 |
| Q1-5 | Me | Q3-44 | Q1-6 | Me | Q3-44 |
| Q1-5 | Me | Q3-45 | Q1-6 | Me | Q3-45 |
| Q1-5 | Me | Q3-46 | Q1-6 | Me | Q3-46 |
| Q1-5 | Me | Q3-47 | Q1-6 | Me | Q3-47 |
| Q1-7 | Me | Q3-1 | Q1-8 | Me | Q3-1 |
| Q1-7 | Me | Q3-2 | Q1-8 | Me | Q3-2 |
| Q1-7 | Me | Q3-3 | Q1-8 | Me | Q3-3 |
| Q1-7 | Me | Q3-4 | Q1-8 | Me | Q3-4 |
| Q1-7 | Me | Q3-5 | Q1-8 | Me | Q3-5 |
| Q1-7 | Me | Q3-6 | Q1-8 | Me | Q3-6 |
| Q1-7 | Me | Q3-7 | Q1-8 | Me | Q3-7 |
| Q1-7 | Me | Q3-8 | Q1-8 | Me | Q3-8 |
| Q1-7 | Me | Q3-9 | Q1-8 | Me | Q3-9 |
| Q1-7 | Me | Q3-10 | Q1-8 | Me | Q3-10 |
| Q1-7 | Me | Q3-11 | Q1-8 | Me | Q3-11 |
| Q1-7 | Me | Q3-12 | Q1-8 | Me | Q3-12 |
| Q1-7 | Me | Q3-13 | Q1-8 | Me | Q3-13 |
| Q1-7 | Me | Q3-14 | Q1-8 | Me | Q3-14 |
| Q1-7 | Me | Q3-15 | Q1-8 | Me | Q3-15 |
| Q1-7 | Me | Q3-16 | Q1-8 | Me | Q3-16 |
| Q1-7 | Me | Q3-17 | Q1-8 | Me | Q3-17 |
| Q1-7 | Me | Q3-18 | Q1-8 | Me | Q3-18 |
| Q1-7 | Me | Q3-19 | Q1-8 | Me | Q3-19 |
| Q1-7 | Me | Q3-20 | Q1-8 | Me | Q3-20 |
| Q1-7 | Me | Q3-21 | Q1-8 | Me | Q3-21 |
| Q1-7 | Me | Q3-22 | Q1-8 | Me | Q3-22 |
| Q1-7 | Me | Q3-23 | Q1-8 | Me | Q3-23 |
| Q1-7 | Me | Q3-24 | Q1-8 | Me | Q3-24 |
| Q1-7 | Me | Q3-25 | Q1-8 | Me | Q3-25 |
| Q1-7 | Me | Q3-26 | Q1-8 | Me | Q3-26 |
| Q1-7 | Me | Q3-27 | Q1-8 | Me | Q3-27 |
| Q1-7 | Me | Q3-28 | Q1-8 | Me | Q3-28 |
| Q1-7 | Me | Q3-29 | Q1-8 | Me | Q3-29 |
| Q1-7 | Me | Q3-30 | Q1-8 | Me | Q3-30 |
| Q1-7 | Me | Q3-31 | Q1-8 | Me | Q3-31 |
| Q1-7 | Me | Q3-32 | Q1-8 | Me | Q3-32 |
| Q1-7 | Me | Q3-33 | Q1-8 | Me | Q3-33 |
| Q1-7 | Me | Q3-34 | Q1-8 | Me | Q3-34 |
| Q1-7 | Me | Q3-35 | Q1-8 | Me | Q3-35 |
| Q1-7 | Me | Q3-36 | Q1-8 | Me | Q3-36 |
| Q1-7 | Me | Q3-37 | Q1-8 | Me | Q3-37 |
| Q1-7 | Me | Q3-38 | Q1-8 | Me | Q3-38 |
| Q1-7 | Me | Q3-39 | Q1-8 | Me | Q3-39 |
| Q1-7 | Me | Q3-40 | Q1-8 | Me | Q3-40 |
| Q1-7 | Me | Q3-41 | Q1-8 | Me | Q3-41 |
| Q1-7 | Me | Q3-42 | Q1-8 | Me | Q3-42 |
| Q1-7 | Me | Q3-43 | Q1-8 | Me | Q3-43 |
| Q1-7 | Me | Q3-44 | Q1-8 | Me | Q3-44 |
| Q1-7 | Me | Q3-45 | Q1-8 | Me | Q3-45 |
| Q1-7 | Me | Q3-46 | Q1-8 | Me | Q3-46 |
| Q1-7 | Me | Q3-47 | Q1-8 | Me | Q3-47 |

60) Compounds represented by the formula (VII), wherein $R^2$ is a hydrogen atom, $R^{35}$ is a methyl group, X is OH, Y is an oxygen atom, and $R^{34}$, $R^1$ and $R^3$ are any of the following combinations shown in Table 5, tautomers, prodrugs or pharmaceutically acceptable salts of the compounds or solvates thereof. The symbols in Table 5 denote the same substituents as in Table 1.

TABLE 5

| $R^{34}$ | $R^1$ | $R^3$ |
|---|---|---|
| Q1-1 | Me | Q3-1 |
| Q1-1 | Me | Q3-2 |
| Q1-1 | Me | Q3-3 |
| Q1-1 | Me | Q3-4 |
| Q1-1 | Me | Q3-5 |
| Q1-1 | Me | Q3-6 |
| Q1-1 | Me | Q3-7 |
| Q1-1 | Me | Q3-8 |
| Q1-1 | Me | Q3-9 |
| Q1-1 | Me | Q3-10 |
| Q1-1 | Me | Q3-11 |
| Q1-1 | Me | Q3-12 |
| Q1-1 | Me | Q3-13 |
| Q1-1 | Me | Q3-14 |
| Q1-1 | Me | Q3-15 |
| Q1-1 | Me | Q3-16 |
| Q1-1 | Me | Q3-17 |
| Q1-1 | Me | Q3-18 |
| Q1-1 | Me | Q3-19 |
| Q1-1 | Me | Q3-20 |
| Q1-1 | Me | Q3-21 |
| Q1-1 | Me | Q3-22 |
| Q1-1 | Me | Q3-23 |
| Q1-1 | Me | Q3-24 |
| Q1-1 | Me | Q3-25 |
| Q1-1 | Me | Q3-26 |
| Q1-1 | Me | Q3-27 |
| Q1-1 | Me | Q3-28 |
| Q1-1 | Me | Q3-29 |
| Q1-1 | Me | Q3-30 |
| Q1-1 | Me | Q3-31 |
| Q1-1 | Me | Q3-32 |
| Q1-1 | Me | Q3-33 |
| Q1-1 | Me | Q3-34 |
| Q1-1 | Me | Q3-35 |
| Q1-1 | Me | Q3-36 |
| Q1-1 | Me | Q3-37 |
| Q1-1 | Me | Q3-38 |
| Q1-1 | Me | Q3-39 |
| Q1-1 | Me | Q3-40 |
| Q1-1 | Me | Q3-41 |
| Q1-1 | Me | Q3-42 |
| Q1-1 | Me | Q3-43 |
| Q1-1 | Me | Q3-44 |
| Q1-1 | Me | Q3-45 |
| Q1-1 | Me | Q3-46 |
| Q1-1 | Me | Q3-47 |
| Q1-2 | Me | Q3-1 |
| Q1-2 | Me | Q3-2 |
| Q1-2 | Me | Q3-3 |
| Q1-2 | Me | Q3-4 |
| Q1-2 | Me | Q3-5 |
| Q1-2 | Me | Q3-6 |
| Q1-2 | Me | Q3-7 |
| Q1-2 | Me | Q3-8 |
| Q1-2 | Me | Q3-9 |
| Q1-2 | Me | Q3-10 |
| Q1-2 | Me | Q3-11 |
| Q1-2 | Me | Q3-12 |
| Q1-2 | Me | Q3-13 |
| Q1-2 | Me | Q3-14 |
| Q1-2 | Me | Q3-15 |
| Q1-2 | Me | Q3-16 |
| Q1-2 | Me | Q3-17 |
| Q1-2 | Me | Q3-18 |
| Q1-2 | Me | Q3-19 |
| Q1-2 | Me | Q3-20 |
| Q1-2 | Me | Q3-21 |
| Q1-2 | Me | Q3-22 |
| Q1-2 | Me | Q3-23 |
| Q1-2 | Me | Q3-24 |
| Q1-2 | Me | Q3-25 |
| Q1-2 | Me | Q3-26 |
| Q1-2 | Me | Q3-27 |
| Q1-2 | Me | Q3-28 |
| Q1-2 | Me | Q3-29 |
| Q1-2 | Me | Q3-30 |
| Q1-2 | Me | Q3-31 |
| Q1-2 | Me | Q3-32 |
| Q1-2 | Me | Q3-33 |
| Q1-2 | Me | Q3-34 |
| Q1-2 | Me | Q3-35 |
| Q1-2 | Me | Q3-36 |
| Q1-2 | Me | Q3-37 |
| Q1-2 | Me | Q3-38 |
| Q1-2 | Me | Q3-39 |
| Q1-2 | Me | Q3-40 |
| Q1-2 | Me | Q3-41 |
| Q1-2 | Me | Q3-42 |
| Q1-2 | Me | Q3-43 |
| Q1-2 | Me | Q3-44 |
| Q1-2 | Me | Q3-45 |
| Q1-2 | Me | Q3-46 |
| Q1-2 | Me | Q3-47 |
| Q1-3 | Me | Q3-1 |
| Q1-3 | Me | Q3-2 |
| Q1-3 | Me | Q3-3 |
| Q1-3 | Me | Q3-4 |
| Q1-3 | Me | Q3-5 |
| Q1-3 | Me | Q3-6 |
| Q1-3 | Me | Q3-7 |
| Q1-3 | Me | Q3-8 |
| Q1-3 | Me | Q3-9 |
| Q1-3 | Me | Q3-10 |
| Q1-3 | Me | Q3-11 |
| Q1-3 | Me | Q3-12 |
| Q1-3 | Me | Q3-13 |
| Q1-3 | Me | Q3-14 |
| Q1-3 | Me | Q3-15 |
| Q1-3 | Me | Q3-16 |
| Q1-3 | Me | Q3-17 |
| Q1-3 | Me | Q3-18 |
| Q1-3 | Me | Q3-19 |
| Q1-3 | Me | Q3-20 |
| Q1-3 | Me | Q3-21 |
| Q1-3 | Me | Q3-22 |
| Q1-3 | Me | Q3-23 |
| Q1-3 | Me | Q3-24 |
| Q1-3 | Me | Q3-25 |
| Q1-3 | Me | Q3-26 |
| Q1-3 | Me | Q3-27 |
| Q1-3 | Me | Q3-28 |
| Q1-3 | Me | Q3-29 |
| Q1-3 | Me | Q3-30 |
| Q1-3 | Me | Q3-31 |
| Q1-3 | Me | Q3-32 |
| Q1-3 | Me | Q3-33 |
| Q1-3 | Me | Q3-34 |
| Q1-3 | Me | Q3-35 |
| Q1-3 | Me | Q3-36 |
| Q1-3 | Me | Q3-37 |
| Q1-3 | Me | Q3-38 |
| Q1-3 | Me | Q3-39 |
| Q1-3 | Me | Q3-40 |
| Q1-3 | Me | Q3-41 |
| Q1-3 | Me | Q3-42 |
| Q1-3 | Me | Q3-43 |
| Q1-3 | Me | Q3-44 |
| Q1-3 | Me | Q3-45 |
| Q1-3 | Me | Q3-46 |
| Q1-3 | Me | Q3-47 |
| Q1-4 | Me | Q3-1 |
| Q1-4 | Me | Q3-2 |
| Q1-4 | Me | Q3-3 |
| Q1-4 | Me | Q3-4 |
| Q1-4 | Me | Q3-5 |
| Q1-4 | Me | Q3-6 |
| Q1-4 | Me | Q3-7 |
| Q1-4 | Me | Q3-8 |
| Q1-4 | Me | Q3-9 |
| Q1-4 | Me | Q3-10 |

TABLE 5-continued

| $R^{34}$ | $R^1$ | $R^3$ |
|---|---|---|
| Q1-4 | Me | Q3-11 |
| Q1-4 | Me | Q3-12 |
| Q1-4 | Me | Q3-13 |
| Q1-4 | Me | Q3-14 |
| Q1-4 | Me | Q3-15 |
| Q1-4 | Me | Q3-16 |
| Q1-4 | Me | Q3-17 |
| Q1-4 | Me | Q3-18 |
| Q1-4 | Me | Q3-19 |
| Q1-4 | Me | Q3-20 |
| Q1-4 | Me | Q3-21 |
| Q1-4 | Me | Q3-22 |
| Q1-4 | Me | Q3-23 |
| Q1-4 | Me | Q3-24 |
| Q1-4 | Me | Q3-25 |
| Q1-4 | Me | Q3-26 |
| Q1-4 | Me | Q3-27 |
| Q1-4 | Me | Q3-28 |
| Q1-4 | Me | Q3-29 |
| Q1-4 | Me | Q3-30 |
| Q1-4 | Me | Q3-31 |
| Q1-4 | Me | Q3-32 |
| Q1-4 | Me | Q3-33 |
| Q1-4 | Me | Q3-34 |
| Q1-4 | Me | Q3-35 |
| Q1-4 | Me | Q3-36 |
| Q1-4 | Me | Q3-37 |
| Q1-4 | Me | Q3-38 |
| Q1-4 | Me | Q3-39 |
| Q1-4 | Me | Q3-40 |
| Q1-4 | Me | Q3-41 |
| Q1-4 | Me | Q3-42 |
| Q1-4 | Me | Q3-43 |
| Q1-4 | Me | Q3-44 |
| Q1-4 | Me | Q3-45 |
| Q1-4 | Me | Q3-46 |
| Q1-4 | Me | Q3-47 |
| Q1-5 | Me | Q3-1 |
| Q1-5 | Me | Q3-2 |
| Q1-5 | Me | Q3-3 |
| Q1-5 | Me | Q3-4 |
| Q1-5 | Me | Q3-5 |
| Q1-5 | Me | Q3-6 |
| Q1-5 | Me | Q3-7 |
| Q1-5 | Me | Q3-8 |
| Q1-5 | Me | Q3-9 |
| Q1-5 | Me | Q3-10 |
| Q1-5 | Me | Q3-11 |
| Q1-5 | Me | Q3-12 |
| Q1-5 | Me | Q3-13 |
| Q1-5 | Me | Q3-14 |
| Q1-5 | Me | Q3-15 |
| Q1-5 | Me | Q3-16 |
| Q1-5 | Me | Q3-17 |
| Q1-5 | Me | Q3-18 |
| Q1-5 | Me | Q3-19 |
| Q1-5 | Me | Q3-20 |
| Q1-5 | Me | Q3-21 |
| Q1-5 | Me | Q3-22 |
| Q1-5 | Me | Q3-23 |
| Q1-5 | Me | Q3-24 |
| Q1-5 | Me | Q3-25 |
| Q1-5 | Me | Q3-26 |
| Q1-5 | Me | Q3-27 |
| Q1-5 | Me | Q3-28 |
| Q1-5 | Me | Q3-29 |
| Q1-5 | Me | Q3-30 |
| Q1-5 | Me | Q3-31 |
| Q1-5 | Me | Q3-32 |
| Q1-5 | Me | Q3-33 |
| Q1-5 | Me | Q3-34 |
| Q1-5 | Me | Q3-35 |
| Q1-5 | Me | Q3-36 |
| Q1-5 | Me | Q3-37 |
| Q1-5 | Me | Q3-38 |
| Q1-5 | Me | Q3-39 |
| Q1-5 | Me | Q3-40 |
| Q1-5 | Me | Q3-41 |
| Q1-5 | Me | Q3-42 |
| Q1-5 | Me | Q3-43 |
| Q1-5 | Me | Q3-44 |
| Q1-5 | Me | Q3-45 |
| Q1-5 | Me | Q3-46 |
| Q1-5 | Me | Q3-47 |
| Q1-6 | Me | Q3-1 |
| Q1-6 | Me | Q3-2 |
| Q1-6 | Me | Q3-3 |
| Q1-6 | Me | Q3-4 |
| Q1-6 | Me | Q3-5 |
| Q1-6 | Me | Q3-6 |
| Q1-6 | Me | Q3-7 |
| Q1-6 | Me | Q3-8 |
| Q1-6 | Me | Q3-9 |
| Q1-6 | Me | Q3-10 |
| Q1-6 | Me | Q3-11 |
| Q1-6 | Me | Q3-12 |
| Q1-6 | Me | Q3-13 |
| Q1-6 | Me | Q3-14 |
| Q1-6 | Me | Q3-15 |
| Q1-6 | Me | Q3-16 |
| Q1-6 | Me | Q3-17 |
| Q1-6 | Me | Q3-18 |
| Q1-6 | Me | Q3-19 |
| Q1-6 | Me | Q3-20 |
| Q1-6 | Me | Q3-21 |
| Q1-6 | Me | Q3-22 |
| Q1-6 | Me | Q3-23 |
| Q1-6 | Me | Q3-24 |
| Q1-6 | Me | Q3-25 |
| Q1-6 | Me | Q3-26 |
| Q1-6 | Me | Q3-27 |
| Q1-6 | Me | Q3-28 |
| Q1-6 | Me | Q3-29 |
| Q1-6 | Me | Q3-30 |
| Q1-6 | Me | Q3-31 |
| Q1-6 | Me | Q3-32 |
| Q1-6 | Me | Q3-33 |
| Q1-6 | Me | Q3-34 |
| Q1-6 | Me | Q3-35 |
| Q1-6 | Me | Q3-36 |
| Q1-6 | Me | Q3-37 |
| Q1-6 | Me | Q3-38 |
| Q1-6 | Me | Q3-39 |
| Q1-6 | Me | Q3-40 |
| Q1-6 | Me | Q3-41 |
| Q1-6 | Me | Q3-42 |
| Q1-6 | Me | Q3-43 |
| Q1-6 | Me | Q3-44 |
| Q1-6 | Me | Q3-45 |
| Q1-6 | Me | Q3-46 |
| Q1-6 | Me | Q3-47 |
| Q1-7 | Me | Q3-1 |
| Q1-7 | Me | Q3-2 |
| Q1-7 | Me | Q3-3 |
| Q1-7 | Me | Q3-4 |
| Q1-7 | Me | Q3-5 |
| Q1-7 | Me | Q3-6 |
| Q1-7 | Me | Q3-7 |
| Q1-7 | Me | Q3-8 |
| Q1-7 | Me | Q3-9 |
| Q1-7 | Me | Q3-10 |
| Q1-7 | Me | Q3-11 |
| Q1-7 | Me | Q3-12 |
| Q1-7 | Me | Q3-13 |
| Q1-7 | Me | Q3-14 |
| Q1-7 | Me | Q3-15 |
| Q1-7 | Me | Q3-16 |
| Q1-7 | Me | Q3-17 |
| Q1-7 | Me | Q3-18 |
| Q1-7 | Me | Q3-19 |
| Q1-7 | Me | Q3-20 |
| Q1-7 | Me | Q3-21 |
| Q1-7 | Me | Q3-22 |
| Q1-7 | Me | Q3-23 |
| Q1-7 | Me | Q3-24 |
| Q1-7 | Me | Q3-25 |

TABLE 5-continued

| R³⁴ | R¹ | R³ |
|---|---|---|
| Q1-7 | Me | Q3-26 |
| Q1-7 | Me | Q3-27 |
| Q1-7 | Me | Q3-28 |
| Q1-7 | Me | Q3-29 |
| Q1-7 | Me | Q3-30 |
| Q1-7 | Me | Q3-31 |
| Q1-7 | Me | Q3-32 |
| Q1-7 | Me | Q3-33 |
| Q1-7 | Me | Q3-34 |
| Q1-7 | Me | Q3-35 |
| Q1-7 | Me | Q3-36 |
| Q1-7 | Me | Q3-37 |
| Q1-7 | Me | Q3-38 |
| Q1-7 | Me | Q3-39 |
| Q1-7 | Me | Q3-40 |
| Q1-7 | Me | Q3-41 |
| Q1-7 | Me | Q3-42 |
| Q1-7 | Me | Q3-43 |
| Q1-7 | Me | Q3-44 |
| Q1-7 | Me | Q3-45 |
| Q1-7 | Me | Q3-46 |
| Q1-7 | Me | Q3-47 |
| Q1-8 | Me | Q3-1 |
| Q1-8 | Me | Q3-2 |
| Q1-8 | Me | Q3-3 |
| Q1-8 | Me | Q3-4 |
| Q1-8 | Me | Q3-5 |
| Q1-8 | Me | Q3-6 |
| Q1-8 | Me | Q3-7 |
| Q1-8 | Me | Q3-8 |
| Q1-8 | Me | Q3-9 |
| Q1-8 | Me | Q3-10 |
| Q1-8 | Me | Q3-11 |
| Q1-8 | Me | Q3-12 |
| Q1-8 | Me | Q3-13 |
| Q1-8 | Me | Q3-14 |
| Q1-8 | Me | Q3-15 |
| Q1-8 | Me | Q3-16 |
| Q1-8 | Me | Q3-17 |
| Q1-8 | Me | Q3-18 |
| Q1-8 | Me | Q3-19 |
| Q1-8 | Me | Q3-20 |
| Q1-8 | Me | Q3-21 |
| Q1-8 | Me | Q3-22 |
| Q1-8 | Me | Q3-23 |
| Q1-8 | Me | Q3-24 |
| Q1-8 | Me | Q3-25 |
| Q1-8 | Me | Q3-26 |
| Q1-8 | Me | Q3-27 |
| Q1-8 | Me | Q3-28 |
| Q1-8 | Me | Q3-29 |
| Q1-8 | Me | Q3-30 |
| Q1-8 | Me | Q3-31 |
| Q1-8 | Me | Q3-32 |
| Q1-8 | Me | Q3-33 |
| Q1-8 | Me | Q3-34 |
| Q1-8 | Me | Q3-35 |
| Q1-8 | Me | Q3-36 |
| Q1-8 | Me | Q3-37 |
| Q1-8 | Me | Q3-38 |
| Q1-8 | Me | Q3-39 |
| Q1-8 | Me | Q3-40 |
| Q1-8 | Me | Q3-41 |
| Q1-8 | Me | Q3-42 |
| Q1-8 | Me | Q3-43 |
| Q1-8 | Me | Q3-44 |
| Q1-8 | Me | Q3-45 |
| Q1-8 | Me | Q3-46 |
| Q1-8 | Me | Q3-47 |

61) The compounds according to 58), 59) or 60), wherein $R^{35}$ is converted to a hydrogen atom, tautomers, prodrugs or pharmaceutically acceptable salts of the compounds or solvates thereof.

62) The compounds according to 58), 59) or 60), wherein $R^{35}$ is converted to a trifluoromethyl group, tautomers, prodrugs or pharmaceutically acceptable salts of the compounds or solvates thereof.

63) The compounds according to 58), 59) or 60), wherein $R^{35}$ is converted to an ethyl group, tautomers, prodrugs or pharmaceutically acceptable salts of the compounds or solvates thereof.

64) The compounds according to 58), 59) or 60), is wherein $R^{35}$ is converted to a n-propyl group, tautomers, prodrugs or pharmaceutically acceptable salts of the compounds or solvates thereof.

65) The compounds according to 58), 59) or 60), wherein $R^{35}$ is converted to an i-propyl group, tautomers, prodrugs or pharmaceutically acceptable salts of the compounds or solvates thereof.

66) The compounds according to any of 58) to 65), wherein $R^1$ is converted to a hydrogen atom, tautomers, prodrugs or pharmaceutically acceptable salts of the compounds or solvates thereof.

67) The compounds according to any of 58) to 65), wherein $R^1$ is converted to a trifluoromethyl group, tautomers, prodrugs or pharmaceutically acceptable salts of the compounds or solvates thereof.

68) The compounds according to any of 58) to 65), wherein $R^1$ is converted to an ethyl group, tautomers, prodrugs or pharmaceutically acceptable salts of the compounds or solvates thereof.

69) The compounds according to any of 58) to 65), wherein $R^1$ is converted to a n-propyl group, tautomers, prodrugs or pharmaceutically acceptable salts of the compounds or solvates thereof.

70) The compounds according to any of 58) to 65), wherein $R^1$ is converted to an i-propyl group, tautomers, prodrugs or pharmaceutically acceptable salts of the compounds or solvates thereof.

71) Compounds represented by the formula (VIII), wherein $R^2$ is a hydrogen atom, $R^{33}$ is a hydrogen atom, $R^{35}$ is a hydrogen atom, X is OH, Y is an oxygen atom, and $R^{34}$, $R^1$ and $R^3$ are any of the following combinations shown in Table 6, tautomers, prodrugs or pharmaceutically acceptable salts of the compounds or solvates thereof. The symbols in Table 6 denote the same substituents as in Table 1.

TABLE 6

| R³⁴ | R¹ | R³ |
|---|---|---|
| Q1-1 | Me | Q3-1 |
| Q1-1 | Me | Q3-2 |
| Q1-1 | Me | Q3-3 |
| Q1-1 | Me | Q3-4 |
| Q1-1 | Me | Q3-5 |
| Q1-1 | Me | Q3-6 |
| Q1-1 | Me | Q3-7 |
| Q1-1 | Me | Q3-8 |
| Q1-1 | Me | Q3-9 |
| Q1-1 | Me | Q3-10 |
| Q1-1 | Me | Q3-11 |
| Q1-1 | Me | Q3-12 |
| Q1-1 | Me | Q3-13 |
| Q1-1 | Me | Q3-14 |
| Q1-1 | Me | Q3-15 |
| Q1-1 | Me | Q3-16 |
| Q1-1 | Me | Q3-17 |
| Q1-1 | Me | Q3-18 |
| Q1-1 | Me | Q3-19 |
| Q1-1 | Me | Q3-20 |
| Q1-1 | Me | Q3-21 |
| Q1-1 | Me | Q3-22 |
| Q1-1 | Me | Q3-23 |

TABLE 6-continued

| R³⁴ | R¹ | R³ |
|---|---|---|
| Q1-1 | Me | Q3-24 |
| Q1-1 | Me | Q3-25 |
| Q1-1 | Me | Q3-26 |
| Q1-1 | Me | Q3-27 |
| Q1-1 | Me | Q3-28 |
| Q1-1 | Me | Q3-29 |
| Q1-1 | Me | Q3-30 |
| Q1-1 | Me | Q3-31 |
| Q1-1 | Me | Q3-32 |
| Q1-1 | Me | Q3-33 |
| Q1-1 | Me | Q3-34 |
| Q1-1 | Me | Q3-35 |
| Q1-1 | Me | Q3-36 |
| Q1-1 | Me | Q3-37 |
| Q1-1 | Me | Q3-38 |
| Q1-1 | Me | Q3-39 |
| Q1-1 | Me | Q3-40 |
| Q1-1 | Me | Q3-41 |
| Q1-1 | Me | Q3-42 |
| Q1-1 | Me | Q3-43 |
| Q1-1 | Me | Q3-44 |
| Q1-1 | Me | Q3-45 |
| Q1-1 | Me | Q3-46 |
| Q1-1 | Me | Q3-47 |
| Q1-2 | Me | Q3-1 |
| Q1-2 | Me | Q3-2 |
| Q1-2 | Me | Q3-3 |
| Q1-2 | Me | Q3-4 |
| Q1-2 | Me | Q3-5 |
| Q1-2 | Me | Q3-6 |
| Q1-2 | Me | Q3-7 |
| Q1-2 | Me | Q3-8 |
| Q1-2 | Me | Q3-9 |
| Q1-2 | Me | Q3-10 |
| Q1-2 | Me | Q3-11 |
| Q1-2 | Me | Q3-12 |
| Q1-2 | Me | Q3-13 |
| Q1-2 | Me | Q3-14 |
| Q1-2 | Me | Q3-15 |
| Q1-2 | Me | Q3-16 |
| Q1-2 | Me | Q3-17 |
| Q1-2 | Me | Q3-18 |
| Q1-2 | Me | Q3-19 |
| Q1-2 | Me | Q3-20 |
| Q1-2 | Me | Q3-21 |
| Q1-2 | Me | Q3-22 |
| Q1-2 | Me | Q3-23 |
| Q1-2 | Me | Q3-24 |
| Q1-2 | Me | Q3-25 |
| Q1-2 | Me | Q3-26 |
| Q1-2 | Me | Q3-27 |
| Q1-2 | Me | Q3-28 |
| Q1-2 | Me | Q3-29 |
| Q1-2 | Me | Q3-30 |
| Q1-2 | Me | Q3-31 |
| Q1-2 | Me | Q3-32 |
| Q1-2 | Me | Q3-33 |
| Q1-2 | Me | Q3-34 |
| Q1-2 | Me | Q3-35 |
| Q1-2 | Me | Q3-36 |
| Q1-2 | Me | Q3-37 |
| Q1-2 | Me | Q3-38 |
| Q1-2 | Me | Q3-39 |
| Q1-2 | Me | Q3-40 |
| Q1-2 | Me | Q3-41 |
| Q1-2 | Me | Q3-42 |
| Q1-2 | Me | Q3-43 |
| Q1-2 | Me | Q3-44 |
| Q1-2 | Me | Q3-45 |
| Q1-2 | Me | Q3-46 |
| Q1-2 | Me | Q3-47 |
| Q1-3 | Me | Q3-1 |
| Q1-3 | Me | Q3-2 |
| Q1-3 | Me | Q3-3 |
| Q1-3 | Me | Q3-4 |
| Q1-3 | Me | Q3-5 |
| Q1-3 | Me | Q3-6 |
| Q1-3 | Me | Q3-7 |
| Q1-3 | Me | Q3-8 |
| Q1-3 | Me | Q3-9 |
| Q1-3 | Me | Q3-10 |
| Q1-3 | Me | Q3-11 |
| Q1-3 | Me | Q3-12 |
| Q1-3 | Me | Q3-13 |
| Q1-3 | Me | Q3-14 |
| Q1-3 | Me | Q3-15 |
| Q1-3 | Me | Q3-16 |
| Q1-3 | Me | Q3-17 |
| Q1-3 | Me | Q3-18 |
| Q1-3 | Me | Q3-19 |
| Q1-3 | Me | Q3-20 |
| Q1-3 | Me | Q3-21 |
| Q1-3 | Me | Q3-22 |
| Q1-3 | Me | Q3-23 |
| Q1-3 | Me | Q3-24 |
| Q1-3 | Me | Q3-25 |
| Q1-3 | Me | Q3-26 |
| Q1-3 | Me | Q3-27 |
| Q1-3 | Me | Q3-28 |
| Q1-3 | Me | Q3-29 |
| Q1-3 | Me | Q3-30 |
| Q1-3 | Me | Q3-31 |
| Q1-3 | Me | Q3-32 |
| Q1-3 | Me | Q3-33 |
| Q1-3 | Me | Q3-34 |
| Q1-3 | Me | Q3-35 |
| Q1-3 | Me | Q3-36 |
| Q1-3 | Me | Q3-37 |
| Q1-3 | Me | Q3-38 |
| Q1-3 | Me | Q3-39 |
| Q1-3 | Me | Q3-40 |
| Q1-3 | Me | Q3-41 |
| Q1-3 | Me | Q3-42 |
| Q1-3 | Me | Q3-43 |
| Q1-3 | Me | Q3-44 |
| Q1-3 | Me | Q3-45 |
| Q1-3 | Me | Q3-46 |
| Q1-3 | Me | Q3-47 |
| Q1-4 | Me | Q3-1 |
| Q1-4 | Me | Q3-2 |
| Q1-4 | Me | Q3-3 |
| Q1-4 | Me | Q3-4 |
| Q1-4 | Me | Q3-5 |
| Q1-4 | Me | Q3-6 |
| Q1-4 | Me | Q3-7 |
| Q1-4 | Me | Q3-8 |
| Q1-4 | Me | Q3-9 |
| Q1-4 | Me | Q3-10 |
| Q1-4 | Me | Q3-11 |
| Q1-4 | Me | Q3-12 |
| Q1-4 | Me | Q3-13 |
| Q1-4 | Me | Q3-14 |
| Q1-4 | Me | Q3-15 |
| Q1-4 | Me | Q3-16 |
| Q1-4 | Me | Q3-17 |
| Q1-4 | Me | Q3-18 |
| Q1-4 | Me | Q3-19 |
| Q1-4 | Me | Q3-20 |
| Q1-4 | Me | Q3-21 |
| Q1-4 | Me | Q3-22 |
| Q1-4 | Me | Q3-23 |
| Q1-4 | Me | Q3-24 |
| Q1-4 | Me | Q3-25 |
| Q1-4 | Me | Q3-26 |
| Q1-4 | Me | Q3-27 |
| Q1-4 | Me | Q3-28 |
| Q1-4 | Me | Q3-29 |
| Q1-4 | Me | Q3-30 |
| Q1-4 | Me | Q3-31 |
| Q1-4 | Me | Q3-32 |
| Q1-4 | Me | Q3-33 |
| Q1-4 | Me | Q3-34 |
| Q1-4 | Me | Q3-35 |
| Q1-4 | Me | Q3-36 |
| Q1-4 | Me | Q3-37 |
| Q1-4 | Me | Q3-38 |

TABLE 6-continued

| R³⁴ | R¹ | R³ |
|---|---|---|
| Q1-4 | Me | Q3-39 |
| Q1-4 | Me | Q3-40 |
| Q1-4 | Me | Q3-41 |
| Q1-4 | Me | Q3-42 |
| Q1-4 | Me | Q3-43 |
| Q1-4 | Me | Q3-44 |
| Q1-4 | Me | Q3-45 |
| Q1-4 | Me | Q3-46 |
| Q1-4 | Me | Q3-47 |
| Q1-5 | Me | Q3-1 |
| Q1-5 | Me | Q3-2 |
| Q1-5 | Me | Q3-3 |
| Q1-5 | Me | Q3-4 |
| Q1-5 | Me | Q3-5 |
| Q1-5 | Me | Q3-6 |
| Q1-5 | Me | Q3-7 |
| Q1-5 | Me | Q3-8 |
| Q1-5 | Me | Q3-9 |
| Q1-5 | Me | Q3-10 |
| Q1-5 | Me | Q3-11 |
| Q1-5 | Me | Q3-12 |
| Q1-5 | Me | Q3-13 |
| Q1-5 | Me | Q3-14 |
| Q1-5 | Me | Q3-15 |
| Q1-5 | Me | Q3-16 |
| Q1-5 | Me | Q3-17 |
| Q1-5 | Me | Q3-18 |
| Q1-5 | Me | Q3-19 |
| Q1-5 | Me | Q3-20 |
| Q1-5 | Me | Q3-21 |
| Q1-5 | Me | Q3-22 |
| Q1-5 | Me | Q3-23 |
| Q1-5 | Me | Q3-24 |
| Q1-5 | Me | Q3-25 |
| Q1-5 | Me | Q3-26 |
| Q1-5 | Me | Q3-27 |
| Q1-5 | Me | Q3-28 |
| Q1-5 | Me | Q3-29 |
| Q1-5 | Me | Q3-30 |
| Q1-5 | Me | Q3-31 |
| Q1-5 | Me | Q3-32 |
| Q1-5 | Me | Q3-33 |
| Q1-5 | Me | Q3-34 |
| Q1-5 | Me | Q3-35 |
| Q1-5 | Me | Q3-36 |
| Q1-5 | Me | Q3-37 |
| Q1-5 | Me | Q3-38 |
| Q1-5 | Me | Q3-39 |
| Q1-5 | Me | Q3-40 |
| Q1-5 | Me | Q3-41 |
| Q1-5 | Me | Q3-42 |
| Q1-5 | Me | Q3-43 |
| Q1-5 | Me | Q3-44 |
| Q1-5 | Me | Q3-45 |
| Q1-5 | Me | Q3-46 |
| Q1-5 | Me | Q3-47 |
| Q1-6 | Me | Q3-1 |
| Q1-6 | Me | Q3-2 |
| Q1-6 | Me | Q3-3 |
| Q1-6 | Me | Q3-4 |
| Q1-6 | Me | Q3-5 |
| Q1-6 | Me | Q3-6 |
| Q1-6 | Me | Q3-7 |
| Q1-6 | Me | Q3-8 |
| Q1-6 | Me | Q3-9 |
| Q1-6 | Me | Q3-10 |
| Q1-6 | Me | Q3-11 |
| Q1-6 | Me | Q3-12 |
| Q1-6 | Me | Q3-13 |
| Q1-6 | Me | Q3-14 |
| Q1-6 | Me | Q3-15 |
| Q1-6 | Me | Q3-16 |
| Q1-6 | Me | Q3-17 |
| Q1-6 | Me | Q3-18 |
| Q1-6 | Me | Q3-19 |
| Q1-6 | Me | Q3-20 |
| Q1-6 | Me | Q3-21 |
| Q1-6 | Me | Q3-22 |
| Q1-6 | Me | Q3-23 |
| Q1-6 | Me | Q3-24 |
| Q1-6 | Me | Q3-25 |
| Q1-6 | Me | Q3-26 |
| Q1-6 | Me | Q3-27 |
| Q1-6 | Me | Q3-28 |
| Q1-6 | Me | Q3-29 |
| Q1-6 | Me | Q3-30 |
| Q1-6 | Me | Q3-31 |
| Q1-6 | Me | Q3-32 |
| Q1-6 | Me | Q3-33 |
| Q1-6 | Me | Q3-34 |
| Q1-6 | Me | Q3-35 |
| Q1-6 | Me | Q3-36 |
| Q1-6 | Me | Q3-37 |
| Q1-6 | Me | Q3-38 |
| Q1-6 | Me | Q3-39 |
| Q1-6 | Me | Q3-40 |
| Q1-6 | Me | Q3-41 |
| Q1-6 | Me | Q3-42 |
| Q1-6 | Me | Q3-43 |
| Q1-6 | Me | Q3-44 |
| Q1-6 | Me | Q3-45 |
| Q1-6 | Me | Q3-46 |
| Q1-6 | Me | Q3-47 |
| Q1-7 | Me | Q3-1 |
| Q1-7 | Me | Q3-2 |
| Q1-7 | Me | Q3-3 |
| Q1-7 | Me | Q3-4 |
| Q1-7 | Me | Q3-5 |
| Q1-7 | Me | Q3-6 |
| Q1-7 | Me | Q3-7 |
| Q1-7 | Me | Q3-8 |
| Q1-7 | Me | Q3-9 |
| Q1-7 | Me | Q3-10 |
| Q1-7 | Me | Q3-11 |
| Q1-7 | Me | Q3-12 |
| Q1-7 | Me | Q3-13 |
| Q1-7 | Me | Q3-14 |
| Q1-7 | Me | Q3-15 |
| Q1-7 | Me | Q3-16 |
| Q1-7 | Me | Q3-17 |
| Q1-7 | Me | Q3-18 |
| Q1-7 | Me | Q3-19 |
| Q1-7 | Me | Q3-20 |
| Q1-7 | Me | Q3-21 |
| Q1-7 | Me | Q3-22 |
| Q1-7 | Me | Q3-23 |
| Q1-7 | Me | Q3-24 |
| Q1-7 | Me | Q3-25 |
| Q1-7 | Me | Q3-26 |
| Q1-7 | Me | Q3-27 |
| Q1-7 | Me | Q3-28 |
| Q1-7 | Me | Q3-29 |
| Q1-7 | Me | Q3-30 |
| Q1-7 | Me | Q3-31 |
| Q1-7 | Me | Q3-32 |
| Q1-7 | Me | Q3-33 |
| Q1-7 | Me | Q3-34 |
| Q1-7 | Me | Q3-35 |
| Q1-7 | Me | Q3-36 |
| Q1-7 | Me | Q3-37 |
| Q1-7 | Me | Q3-38 |
| Q1-7 | Me | Q3-39 |
| Q1-7 | Me | Q3-40 |
| Q1-7 | Me | Q3-41 |
| Q1-7 | Me | Q3-42 |
| Q1-7 | Me | Q3-43 |
| Q1-7 | Me | Q3-44 |
| Q1-7 | Me | Q3-45 |
| Q1-7 | Me | Q3-46 |
| Q1-7 | Me | Q3-47 |
| Q1-8 | Me | Q3-1 |
| Q1-8 | Me | Q3-2 |
| Q1-8 | Me | Q3-3 |
| Q1-8 | Me | Q3-4 |
| Q1-8 | Me | Q3-5 |
| Q1-8 | Me | Q3-6 |

TABLE 6-continued

| $R^{34}$ | $R^1$ | $R^3$ |
|---|---|---|
| Q1-8 | Me | Q3-7 |
| Q1-8 | Me | Q3-8 |
| Q1-8 | Me | Q3-9 |
| Q1-8 | Me | Q3-10 |
| Q1-8 | Me | Q3-11 |
| Q1-8 | Me | Q3-12 |
| Q1-8 | Me | Q3-13 |
| Q1-8 | Me | Q3-14 |
| Q1-8 | Me | Q3-15 |
| Q1-8 | Me | Q3-16 |
| Q1-8 | Me | Q3-17 |
| Q1-8 | Me | Q3-18 |
| Q1-8 | Me | Q3-19 |
| Q1-8 | Me | Q3-20 |
| Q1-8 | Me | Q3-21 |
| Q1-8 | Me | Q3-22 |
| Q1-8 | Me | Q3-23 |
| Q1-8 | Me | Q3-24 |
| Q1-8 | Me | Q3-25 |
| Q1-8 | Me | Q3-26 |
| Q1-8 | Me | Q3-27 |
| Q1-8 | Me | Q3-28 |
| Q1-8 | Me | Q3-29 |
| Q1-8 | Me | Q3-30 |
| Q1-8 | Me | Q3-31 |
| Q1-8 | Me | Q3-32 |
| Q1-8 | Me | Q3-33 |
| Q1-8 | Me | Q3-34 |
| Q1-8 | Me | Q3-35 |
| Q1-8 | Me | Q3-36 |
| Q1-8 | Me | Q3-37 |
| Q1-8 | Me | Q3-38 |
| Q1-8 | Me | Q3-39 |
| Q1-8 | Me | Q3-40 |
| Q1-8 | Me | Q3-41 |
| Q1-8 | Me | Q3-42 |
| Q1-8 | Me | Q3-43 |
| Q1-8 | Me | Q3-44 |
| Q1-8 | Me | Q3-45 |
| Q1-8 | Me | Q3-46 |
| Q1-8 | Me | Q3-47 |

72) Compounds represented by the formula (IX), wherein $R^2$ is a hydrogen atom, $R^{33}$ is a hydrogen atom, $R^{35}$ is a hydrogen atom, X is OH, Y is an oxygen atom, and $R^{34}$, $R^1$ and $R^3$ are any of the following combinations shown in Table 7, tautomers, prodrugs or pharmaceutically acceptable salts of the compounds or solvates thereof. The symbols in Table 7 denote the same substituents as in Table 1.

TABLE 7

| $R^{34}$ | $R^1$ | $R^3$ |
|---|---|---|
| Q1-1 | Me | Q3-1 |
| Q1-1 | Me | Q3-2 |
| Q1-1 | Me | Q3-3 |
| Q1-1 | Me | Q3-4 |
| Q1-1 | Me | Q3-5 |
| Q1-1 | Me | Q3-6 |
| Q1-1 | Me | Q3-7 |
| Q1-1 | Me | Q3-8 |
| Q1-1 | Me | Q3-9 |
| Q1-1 | Me | Q3-10 |
| Q1-1 | Me | Q3-11 |
| Q1-1 | Me | Q3-12 |
| Q1-1 | Me | Q3-13 |
| Q1-1 | Me | Q3-14 |
| Q1-1 | Me | Q3-15 |
| Q1-1 | Me | Q3-16 |
| Q1-1 | Me | Q3-17 |
| Q1-1 | Me | Q3-18 |
| Q1-1 | Me | Q3-19 |
| Q1-1 | Me | Q3-20 |
| Q1-1 | Me | Q3-21 |
| Q1-1 | Me | Q3-22 |
| Q1-1 | Me | Q3-23 |
| Q1-1 | Me | Q3-24 |
| Q1-1 | Me | Q3-25 |
| Q1-1 | Me | Q3-26 |
| Q1-1 | Me | Q3-27 |
| Q1-1 | Me | Q3-28 |
| Q1-1 | Me | Q3-29 |
| Q1-1 | Me | Q3-30 |
| Q1-1 | Me | Q3-31 |
| Q1-1 | Me | Q3-32 |
| Q1-1 | Me | Q3-33 |
| Q1-1 | Me | Q3-34 |
| Q1-1 | Me | Q3-35 |
| Q1-1 | Me | Q3-36 |
| Q1-1 | Me | Q3-37 |
| Q1-1 | Me | Q3-38 |
| Q1-1 | Me | Q3-39 |
| Q1-1 | Me | Q3-40 |
| Q1-1 | Me | Q3-41 |
| Q1-1 | Me | Q3-42 |
| Q1-1 | Me | Q3-43 |
| Q1-1 | Me | Q3-44 |
| Q1-1 | Me | Q3-45 |
| Q1-1 | Me | Q3-46 |
| Q1-1 | Me | Q3-47 |
| Q1-2 | Me | Q3-1 |
| Q1-2 | Me | Q3-2 |
| Q1-2 | Me | Q3-3 |
| Q1-2 | Me | Q3-4 |
| Q1-2 | Me | Q3-5 |
| Q1-2 | Me | Q3-6 |
| Q1-2 | Me | Q3-7 |
| Q1-2 | Me | Q3-8 |
| Q1-2 | Me | Q3-9 |
| Q1-2 | Me | Q3-10 |
| Q1-2 | Me | Q3-11 |
| Q1-2 | Me | Q3-12 |
| Q1-2 | Me | Q3-13 |
| Q1-2 | Me | Q3-14 |
| Q1-2 | Me | Q3-15 |
| Q1-2 | Me | Q3-16 |
| Q1-2 | Me | Q3-17 |
| Q1-2 | Me | Q3-18 |
| Q1-2 | Me | Q3-19 |
| Q1-2 | Me | Q3-20 |
| Q1-2 | Me | Q3-21 |
| Q1-2 | Me | Q3-22 |
| Q1-2 | Me | Q3-23 |
| Q1-2 | Me | Q3-24 |
| Q1-2 | Me | Q3-25 |
| Q1-2 | Me | Q3-26 |
| Q1-2 | Me | Q3-27 |
| Q1-2 | Me | Q3-28 |
| Q1-2 | Me | Q3-29 |
| Q1-2 | Me | Q3-30 |
| Q1-2 | Me | Q3-31 |
| Q1-2 | Me | Q3-32 |
| Q1-2 | Me | Q3-33 |
| Q1-2 | Me | Q3-34 |
| Q1-2 | Me | Q3-35 |
| Q1-2 | Me | Q3-36 |
| Q1-2 | Me | Q3-37 |
| Q1-2 | Me | Q3-38 |
| Q1-2 | Me | Q3-39 |
| Q1-2 | Me | Q3-40 |
| Q1-2 | Me | Q3-41 |
| Q1-2 | Me | Q3-42 |
| Q1-2 | Me | Q3-43 |
| Q1-2 | Me | Q3-44 |
| Q1-2 | Me | Q3-45 |
| Q1-2 | Me | Q3-46 |
| Q1-2 | Me | Q3-47 |
| Q1-3 | Me | Q3-1 |
| Q1-3 | Me | Q3-2 |
| Q1-3 | Me | Q3-3 |
| Q1-3 | Me | Q3-4 |
| Q1-3 | Me | Q3-5 |

TABLE 7-continued

| $R^{34}$ | $R^1$ | $R^3$ |
|---|---|---|
| Q1-3 | Me | Q3-6 |
| Q1-3 | Me | Q3-7 |
| Q1-3 | Me | Q3-8 |
| Q1-3 | Me | Q3-9 |
| Q1-3 | Me | Q3-10 |
| Q1-3 | Me | Q3-11 |
| Q1-3 | Me | Q3-12 |
| Q1-3 | Me | Q3-13 |
| Q1-3 | Me | Q3-14 |
| Q1-3 | Me | Q3-15 |
| Q1-3 | Me | Q3-16 |
| Q1-3 | Me | Q3-17 |
| Q1-3 | Me | Q3-18 |
| Q1-3 | Me | Q3-19 |
| Q1-3 | Me | Q3-20 |
| Q1-3 | Me | Q3-21 |
| Q1-3 | Me | Q3-22 |
| Q1-3 | Me | Q3-23 |
| Q1-3 | Me | Q3-24 |
| Q1-3 | Me | Q3-25 |
| Q1-3 | Me | Q3-26 |
| Q1-3 | Me | Q3-27 |
| Q1-3 | Me | Q3-28 |
| Q1-3 | Me | Q3-29 |
| Q1-3 | Me | Q3-30 |
| Q1-3 | Me | Q3-31 |
| Q1-3 | Me | Q3-32 |
| Q1-3 | Me | Q3-33 |
| Q1-3 | Me | Q3-34 |
| Q1-3 | Me | Q3-35 |
| Q1-3 | Me | Q3-36 |
| Q1-3 | Me | Q3-37 |
| Q1-3 | Me | Q3-38 |
| Q1-3 | Me | Q3-39 |
| Q1-3 | Me | Q3-40 |
| Q1-3 | Me | Q3-41 |
| Q1-3 | Me | Q3-42 |
| Q1-3 | Me | Q3-43 |
| Q1-3 | Me | Q3-44 |
| Q1-3 | Me | Q3-45 |
| Q1-3 | Me | Q3-46 |
| Q1-3 | Me | Q3-47 |
| Q1-4 | Me | Q3-1 |
| Q1-4 | Me | Q3-2 |
| Q1-4 | Me | Q3-3 |
| Q1-4 | Me | Q3-4 |
| Q1-4 | Me | Q3-5 |
| Q1-4 | Me | Q3-6 |
| Q1-4 | Me | Q3-7 |
| Q1-4 | Me | Q3-8 |
| Q1-4 | Me | Q3-9 |
| Q1-4 | Me | Q3-10 |
| Q1-4 | Me | Q3-11 |
| Q1-4 | Me | Q3-12 |
| Q1-4 | Me | Q3-13 |
| Q1-4 | Me | Q3-14 |
| Q1-4 | Me | Q3-15 |
| Q1-4 | Me | Q3-16 |
| Q1-4 | Me | Q3-17 |
| Q1-4 | Me | Q3-18 |
| Q1-4 | Me | Q3-19 |
| Q1-4 | Me | Q3-20 |
| Q1-4 | Me | Q3-21 |
| Q1-4 | Me | Q3-22 |
| Q1-4 | Me | Q3-23 |
| Q1-4 | Me | Q3-24 |
| Q1-4 | Me | Q3-25 |
| Q1-4 | Me | Q3-26 |
| Q1-4 | Me | Q3-27 |
| Q1-4 | Me | Q3-28 |
| Q1-4 | Me | Q3-29 |
| Q1-4 | Me | Q3-30 |
| Q1-4 | Me | Q3-31 |
| Q1-4 | Me | Q3-32 |
| Q1-4 | Me | Q3-33 |
| Q1-4 | Me | Q3-34 |
| Q1-4 | Me | Q3-35 |
| Q1-4 | Me | Q3-36 |
| Q1-4 | Me | Q3-37 |
| Q1-4 | Me | Q3-38 |
| Q1-4 | Me | Q3-39 |
| Q1-4 | Me | Q3-40 |
| Q1-4 | Me | Q3-41 |
| Q1-4 | Me | Q3-42 |
| Q1-4 | Me | Q3-43 |
| Q1-4 | Me | Q3-44 |
| Q1-4 | Me | Q3-45 |
| Q1-4 | Me | Q3-46 |
| Q1-4 | Me | Q3-47 |
| Q1-5 | Me | Q3-1 |
| Q1-5 | Me | Q3-2 |
| Q1-5 | Me | Q3-3 |
| Q1-5 | Me | Q3-4 |
| Q1-5 | Me | Q3-5 |
| Q1-5 | Me | Q3-6 |
| Q1-5 | Me | Q3-7 |
| Q1-5 | Me | Q3-8 |
| Q1-5 | Me | Q3-9 |
| Q1-5 | Me | Q3-10 |
| Q1-5 | Me | Q3-11 |
| Q1-5 | Me | Q3-12 |
| Q1-5 | Me | Q3-13 |
| Q1-5 | Me | Q3-14 |
| Q1-5 | Me | Q3-15 |
| Q1-5 | Me | Q3-16 |
| Q1-5 | Me | Q3-17 |
| Q1-5 | Me | Q3-18 |
| Q1-5 | Me | Q3-19 |
| Q1-5 | Me | Q3-20 |
| Q1-5 | Me | Q3-21 |
| Q1-5 | Me | Q3-22 |
| Q1-5 | Me | Q3-23 |
| Q1-5 | Me | Q3-24 |
| Q1-5 | Me | Q3-25 |
| Q1-5 | Me | Q3-26 |
| Q1-5 | Me | Q3-27 |
| Q1-5 | Me | Q3-28 |
| Q1-5 | Me | Q3-29 |
| Q1-5 | Me | Q3-30 |
| Q1-5 | Me | Q3-31 |
| Q1-5 | Me | Q3-32 |
| Q1-5 | Me | Q3-33 |
| Q1-5 | Me | Q3-34 |
| Q1-5 | Me | Q3-35 |
| Q1-5 | Me | Q3-36 |
| Q1-5 | Me | Q3-37 |
| Q1-5 | Me | Q3-38 |
| Q1-5 | Me | Q3-39 |
| Q1-5 | Me | Q3-40 |
| Q1-5 | Me | Q3-41 |
| Q1-5 | Me | Q3-42 |
| Q1-5 | Me | Q3-43 |
| Q1-5 | Me | Q3-44 |
| Q1-5 | Me | Q3-45 |
| Q1-5 | Me | Q3-46 |
| Q1-5 | Me | Q3-47 |
| Q1-6 | Me | Q3-1 |
| Q1-6 | Me | Q3-2 |
| Q1-6 | Me | Q3-3 |
| Q1-6 | Me | Q3-4 |
| Q1-6 | Me | Q3-5 |
| Q1-6 | Me | Q3-6 |
| Q1-6 | Me | Q3-7 |
| Q1-6 | Me | Q3-8 |
| Q1-6 | Me | Q3-9 |
| Q1-6 | Me | Q3-10 |
| Q1-6 | Me | Q3-11 |
| Q1-6 | Me | Q3-12 |
| Q1-6 | Me | Q3-13 |
| Q1-6 | Me | Q3-14 |
| Q1-6 | Me | Q3-15 |
| Q1-6 | Me | Q3-16 |
| Q1-6 | Me | Q3-17 |
| Q1-6 | Me | Q3-18 |
| Q1-6 | Me | Q3-19 |
| Q1-6 | Me | Q3-20 |

TABLE 7-continued

| $R^{34}$ | $R^1$ | $R^3$ |
|---|---|---|
| Q1-6 | Me | Q3-21 |
| Q1-6 | Me | Q3-22 |
| Q1-6 | Me | Q3-23 |
| Q1-6 | Me | Q3-24 |
| Q1-6 | Me | Q3-25 |
| Q1-6 | Me | Q3-26 |
| Q1-6 | Me | Q3-27 |
| Q1-6 | Me | Q3-28 |
| Q1-6 | Me | Q3-29 |
| Q1-6 | Me | Q3-30 |
| Q1-6 | Me | Q3-31 |
| Q1-6 | Me | Q3-32 |
| Q1-6 | Me | Q3-33 |
| Q1-6 | Me | Q3-34 |
| Q1-6 | Me | Q3-35 |
| Q1-6 | Me | Q3-36 |
| Q1-6 | Me | Q3-37 |
| Q1-6 | Me | Q3-38 |
| Q1-6 | Me | Q3-39 |
| Q1-6 | Me | Q3-40 |
| Q1-6 | Me | Q3-41 |
| Q1-6 | Me | Q3-42 |
| Q1-6 | Me | Q3-43 |
| Q1-6 | Me | Q3-44 |
| Q1-6 | Me | Q3-45 |
| Q1-6 | Me | Q3-46 |
| Q1-6 | Me | Q3-47 |
| Q1-7 | Me | Q3-1 |
| Q1-7 | Me | Q3-2 |
| Q1-7 | Me | Q3-3 |
| Q1-7 | Me | Q3-4 |
| Q1-7 | Me | Q3-5 |
| Q1-7 | Me | Q3-6 |
| Q1-7 | Me | Q3-7 |
| Q1-7 | Me | Q3-8 |
| Q1-7 | Me | Q3-9 |
| Q1-7 | Me | Q3-10 |
| Q1-7 | Me | Q3-11 |
| Q1-7 | Me | Q3-12 |
| Q1-7 | Me | Q3-13 |
| Q1-7 | Me | Q3-14 |
| Q1-7 | Me | Q3-15 |
| Q1-7 | Me | Q3-16 |
| Q1-7 | Me | Q3-17 |
| Q1-7 | Me | Q3-18 |
| Q1-7 | Me | Q3-19 |
| Q1-7 | Me | Q3-20 |
| Q1-7 | Me | Q3-21 |
| Q1-7 | Me | Q3-22 |
| Q1-7 | Me | Q3-23 |
| Q1-7 | Me | Q3-24 |
| Q1-7 | Me | Q3-25 |
| Q1-7 | Me | Q3-26 |
| Q1-7 | Me | Q3-27 |
| Q1-7 | Me | Q3-28 |
| Q1-7 | Me | Q3-29 |
| Q1-7 | Me | Q3-30 |
| Q1-7 | Me | Q3-31 |
| Q1-7 | Me | Q3-32 |
| Q1-7 | Me | Q3-33 |
| Q1-7 | Me | Q3-34 |
| Q1-7 | Me | Q3-35 |
| Q1-7 | Me | Q3-36 |
| Q1-7 | Me | Q3-37 |
| Q1-7 | Me | Q3-38 |
| Q1-7 | Me | Q3-39 |
| Q1-7 | Me | Q3-40 |
| Q1-7 | Me | Q3-41 |
| Q1-7 | Me | Q3-42 |
| Q1-7 | Me | Q3-43 |
| Q1-7 | Me | Q3-44 |
| Q1-7 | Me | Q3-45 |
| Q1-7 | Me | Q3-46 |
| Q1-7 | Me | Q3-47 |
| Q1-8 | Me | Q3-1 |
| Q1-8 | Me | Q3-2 |
| Q1-8 | Me | Q3-3 |
| Q1-8 | Me | Q3-4 |
| Q1-8 | Me | Q3-5 |
| Q1-8 | Me | Q3-6 |
| Q1-8 | Me | Q3-7 |
| Q1-8 | Me | Q3-8 |
| Q1-8 | Me | Q3-9 |
| Q1-8 | Me | Q3-10 |
| Q1-8 | Me | Q3-11 |
| Q1-8 | Me | Q3-12 |
| Q1-8 | Me | Q3-13 |
| Q1-8 | Me | Q3-14 |
| Q1-8 | Me | Q3-15 |
| Q1-8 | Me | Q3-16 |
| Q1-8 | Me | Q3-17 |
| Q1-8 | Me | Q3-18 |
| Q1-8 | Me | Q3-19 |
| Q1-8 | Me | Q3-20 |
| Q1-8 | Me | Q3-21 |
| Q1-8 | Me | Q3-22 |
| Q1-8 | Me | Q3-23 |
| Q1-8 | Me | Q3-24 |
| Q1-8 | Me | Q3-25 |
| Q1-8 | Me | Q3-26 |
| Q1-8 | Me | Q3-27 |
| Q1-8 | Me | Q3-28 |
| Q1-8 | Me | Q3-29 |
| Q1-8 | Me | Q3-30 |
| Q1-8 | Me | Q3-31 |
| Q1-8 | Me | Q3-32 |
| Q1-8 | Me | Q3-33 |
| Q1-8 | Me | Q3-34 |
| Q1-8 | Me | Q3-35 |
| Q1-8 | Me | Q3-36 |
| Q1-8 | Me | Q3-37 |
| Q1-8 | Me | Q3-38 |
| Q1-8 | Me | Q3-39 |
| Q1-8 | Me | Q3-40 |
| Q1-8 | Me | Q3-41 |
| Q1-8 | Me | Q3-42 |
| Q1-8 | Me | Q3-43 |
| Q1-8 | Me | Q3-44 |
| Q1-8 | Me | Q3-45 |
| Q1-8 | Me | Q3-46 |
| Q1-8 | Me | Q3-47 |

73) The compounds according to 70) or 71), wherein $R^{35}$ is converted to a methyl group, tautomers, prodrugs or pharmaceutically acceptable salts of the compounds or solvates thereof.

74) The compounds according to 70) or 71), wherein $R^{33}$ is converted to a methyl group, tautomers, prodrugs or pharmaceutically acceptable salts of the compounds or solvates thereof.

75) The compounds according to 70) or 71), wherein each of $R^{33}$ and $R^{35}$ is converted to a methyl group, tautomers, prodrugs or pharmaceutically acceptable salts of the compounds or solvates thereof.

76) The compounds according to 70) or 71), wherein $R^{33}$ is converted to a trifluoromethyl group, tautomers, prodrugs or pharmaceutically acceptable salts of the compounds or solvates thereof.

77) The compounds according to 70) or 71), wherein $R^{35}$ is converted to a trifluoromethyl group, tautomers, prodrugs or pharmaceutically acceptable salts of the compounds or solvates thereof.

78) The compounds according to 70) or 71), wherein each of $R^{33}$ and $R^{35}$ is converted to a trifluoromethyl group, tautomers, prodrugs or pharmaceutically acceptable salts of the compounds or solvates thereof.

79) The compounds according to 70) or 71), wherein $R^{33}$ is converted to a methyl group, and $R^{35}$ is converted to a trifluoromethyl group, tautomers, prodrugs or pharmaceutically acceptable salts of the compounds or solvates thereof.

80) The compounds according to 70) or 71), wherein $R^{33}$ is converted to a trifluoromethyl group, and $R^{35}$ is converted to a methyl group, tautomers, prodrugs or pharmaceutically acceptable salts of the compounds or solvates thereof.

81) The compounds according to any of 73) to 80), wherein $R^{33}$ is converted to an ethyl group, tautomers, prodrugs or pharmaceutically acceptable salts of the compounds or solvates thereof.

82) The compounds according to any of 73) to 80), wherein $R^{33}$ is converted to a n-propyl group, tautomers, prodrugs or pharmaceutically acceptable salts of the compounds or solvates thereof.

83) The compounds according to any of 73) to 80), wherein $R^{33}$ is converted to an i-propyl group, tautomers, prodrugs or pharmaceutically acceptable salts of the compounds or solvates thereof.

84) The compounds according to any of 73) to 83), wherein $R^{35}$ is converted to an ethyl group, tautomers, prodrugs or pharmaceutically acceptable salts of the compounds or solvates thereof.

85) The compounds according to any of 73) to 83), wherein $R^{35}$ is converted to a n-propyl group, tautomers, prodrugs or pharmaceutically acceptable salts of the compounds or solvates thereof.

86) The compounds according to any of 73) to 83), wherein $R^{35}$ is converted to an i-propyl group, tautomers, prodrugs or pharmaceutically acceptable salts of the compounds or solvates thereof.

87) The compounds according to any of 73) to 86), wherein $R^1$ is converted to a hydrogen atom, tautomers, prodrugs or pharmaceutically acceptable salts of the compounds or solvates thereof.

88) The compounds according to any of 73) to 86), wherein $R^1$ is converted to a trifluoromethyl group, tautomers, prodrugs or pharmaceutically acceptable salts of the compounds or solvates thereof.

89) The compounds according to any of 73) to 86), wherein $R^1$ is converted to an ethyl group, tautomers, prodrugs or pharmaceutically acceptable salts of the compounds or solvates thereof.

90) The compounds according to any of 73) to 86), wherein $R^1$ is converted to a n-propyl group, tautomers, prodrugs or pharmaceutically acceptable salts of the compounds or solvates thereof.

91) The compounds according to any of 73) to 86), wherein $R^1$ is converted to an i-propyl group, tautomers, prodrugs or pharmaceutically acceptable salts of the compounds or solvates thereof.

92) Compounds represented by the formula (X), wherein $R^2$ is a hydrogen atom, X is OH, Y is an oxygen atom, and $R^{34}$, $R^1$ and $R^3$ are any of the following combinations shown in Table 8, tautomers, prodrugs or pharmaceutically acceptable salts of the compounds or solvates thereof. The symbols in Table 8 denote the same substituents as in Table 1.

TABLE 8

| $R^{34}$ | $R^1$ | $R^3$ |
|---|---|---|
| Q1-1 | Me | Q3-1 |
| Q1-1 | Me | Q3-2 |
| Q1-1 | Me | Q3-3 |
| Q1-1 | Me | Q3-4 |
| Q1-1 | Me | Q3-5 |
| Q1-1 | Me | Q3-6 |
| Q1-1 | Me | Q3-7 |
| Q1-1 | Me | Q3-8 |
| Q1-1 | Me | Q3-9 |
| Q1-1 | Me | Q3-10 |
| Q1-1 | Me | Q3-11 |
| Q1-1 | Me | Q3-12 |
| Q1-1 | Me | Q3-13 |
| Q1-1 | Me | Q3-14 |
| Q1-1 | Me | Q3-15 |
| Q1-1 | Me | Q3-16 |
| Q1-1 | Me | Q3-17 |
| Q1-1 | Me | Q3-18 |
| Q1-1 | Me | Q3-19 |
| Q1-1 | Me | Q3-20 |
| Q1-1 | Me | Q3-21 |
| Q1-1 | Me | Q3-22 |
| Q1-1 | Me | Q3-23 |
| Q1-1 | Me | Q3-24 |
| Q1-1 | Me | Q3-25 |
| Q1-1 | Me | Q3-26 |
| Q1-1 | Me | Q3-27 |
| Q1-1 | Me | Q3-28 |
| Q1-1 | Me | Q3-29 |
| Q1-1 | Me | Q3-30 |
| Q1-1 | Me | Q3-31 |
| Q1-1 | Me | Q3-32 |
| Q1-1 | Me | Q3-33 |
| Q1-1 | Me | Q3-34 |
| Q1-1 | Me | Q3-35 |
| Q1-1 | Me | Q3-36 |
| Q1-1 | Me | Q3-37 |
| Q1-1 | Me | Q3-38 |
| Q1-1 | Me | Q3-39 |
| Q1-1 | Me | Q3-40 |
| Q1-1 | Me | Q3-41 |
| Q1-1 | Me | Q3-42 |
| Q1-1 | Me | Q3-43 |
| Q1-1 | Me | Q3-44 |
| Q1-1 | Me | Q3-45 |
| Q1-1 | Me | Q3-46 |
| Q1-1 | Me | Q3-47 |
| Q1-2 | Me | Q3-1 |
| Q1-2 | Me | Q3-2 |
| Q1-2 | Me | Q3-3 |
| Q1-2 | Me | Q3-4 |
| Q1-2 | Me | Q3-5 |
| Q1-2 | Me | Q3-6 |
| Q1-2 | Me | Q3-7 |
| Q1-2 | Me | Q3-8 |
| Q1-2 | Me | Q3-9 |
| Q1-2 | Me | Q3-10 |
| Q1-2 | Me | Q3-11 |
| Q1-2 | Me | Q3-12 |
| Q1-2 | Me | Q3-13 |
| Q1-2 | Me | Q3-14 |
| Q1-2 | Me | Q3-15 |
| Q1-2 | Me | Q3-16 |
| Q1-2 | Me | Q3-17 |
| Q1-2 | Me | Q3-18 |
| Q1-2 | Me | Q3-19 |
| Q1-2 | Me | Q3-20 |
| Q1-2 | Me | Q3-21 |
| Q1-2 | Me | Q3-22 |
| Q1-2 | Me | Q3-23 |
| Q1-2 | Me | Q3-24 |
| Q1-2 | Me | Q3-25 |
| Q1-2 | Me | Q3-26 |
| Q1-2 | Me | Q3-27 |
| Q1-2 | Me | Q3-28 |
| Q1-2 | Me | Q3-29 |
| Q1-2 | Me | Q3-30 |
| Q1-2 | Me | Q3-31 |
| Q1-2 | Me | Q3-32 |
| Q1-2 | Me | Q3-33 |
| Q1-2 | Me | Q3-34 |
| Q1-2 | Me | Q3-35 |
| Q1-2 | Me | Q3-36 |
| Q1-2 | Me | Q3-37 |
| Q1-2 | Me | Q3-38 |
| Q1-2 | Me | Q3-39 |
| Q1-2 | Me | Q3-40 |

TABLE 8-continued

| $R^{34}$ | $R^1$ | $R^3$ |
|---|---|---|
| Q1-2 | Me | Q3-41 |
| Q1-2 | Me | Q3-42 |
| Q1-2 | Me | Q3-43 |
| Q1-2 | Me | Q3-44 |
| Q1-2 | Me | Q3-45 |
| Q1-2 | Me | Q3-46 |
| Q1-2 | Me | Q3-47 |
| Q1-3 | Me | Q3-1 |
| Q1-3 | Me | Q3-2 |
| Q1-3 | Me | Q3-3 |
| Q1-3 | Me | Q3-4 |
| Q1-3 | Me | Q3-5 |
| Q1-3 | Me | Q3-6 |
| Q1-3 | Me | Q3-7 |
| Q1-3 | Me | Q3-8 |
| Q1-3 | Me | Q3-9 |
| Q1-3 | Me | Q3-10 |
| Q1-3 | Me | Q3-11 |
| Q1-3 | Me | Q3-12 |
| Q1-3 | Me | Q3-13 |
| Q1-3 | Me | Q3-14 |
| Q1-3 | Me | Q3-15 |
| Q1-3 | Me | Q3-16 |
| Q1-3 | Me | Q3-17 |
| Q1-3 | Me | Q3-18 |
| Q1-3 | Me | Q3-19 |
| Q1-3 | Me | Q3-20 |
| Q1-3 | Me | Q3-21 |
| Q1-3 | Me | Q3-22 |
| Q1-3 | Me | Q3-23 |
| Q1-3 | Me | Q3-24 |
| Q1-3 | Me | Q3-25 |
| Q1-3 | Me | Q3-26 |
| Q1-3 | Me | Q3-27 |
| Q1-3 | Me | Q3-28 |
| Q1-3 | Me | Q3-29 |
| Q1-3 | Me | Q3-30 |
| Q1-3 | Me | Q3-31 |
| Q1-3 | Me | Q3-32 |
| Q1-3 | Me | Q3-33 |
| Q1-3 | Me | Q3-34 |
| Q1-3 | Me | Q3-35 |
| Q1-3 | Me | Q3-36 |
| Q1-3 | Me | Q3-37 |
| Q1-3 | Me | Q3-38 |
| Q1-3 | Me | Q3-39 |
| Q1-3 | Me | Q3-40 |
| Q1-3 | Me | Q3-41 |
| Q1-3 | Me | Q3-42 |
| Q1-3 | Me | Q3-43 |
| Q1-3 | Me | Q3-44 |
| Q1-3 | Me | Q3-45 |
| Q1-3 | Me | Q3-46 |
| Q1-3 | Me | Q3-47 |
| Q1-4 | Me | Q3-1 |
| Q1-4 | Me | Q3-2 |
| Q1-4 | Me | Q3-3 |
| Q1-4 | Me | Q3-4 |
| Q1-4 | Me | Q3-5 |
| Q1-4 | Me | Q3-6 |
| Q1-4 | Me | Q3-7 |
| Q1-4 | Me | Q3-8 |
| Q1-4 | Me | Q3-9 |
| Q1-4 | Me | Q3-10 |
| Q1-4 | Me | Q3-11 |
| Q1-4 | Me | Q3-12 |
| Q1-4 | Me | Q3-13 |
| Q1-4 | Me | Q3-14 |
| Q1-4 | Me | Q3-15 |
| Q1-4 | Me | Q3-16 |
| Q1-4 | Me | Q3-17 |
| Q1-4 | Me | Q3-18 |
| Q1-4 | Me | Q3-19 |
| Q1-4 | Me | Q3-20 |
| Q1-4 | Me | Q3-21 |
| Q1-4 | Me | Q3-22 |
| Q1-4 | Me | Q3-23 |
| Q1-4 | Me | Q3-24 |
| Q1-4 | Me | Q3-25 |
| Q1-4 | Me | Q3-26 |
| Q1-4 | Me | Q3-27 |
| Q1-4 | Me | Q3-28 |
| Q1-4 | Me | Q3-29 |
| Q1-4 | Me | Q3-30 |
| Q1-4 | Me | Q3-31 |
| Q1-4 | Me | Q3-32 |
| Q1-4 | Me | Q3-33 |
| Q1-4 | Me | Q3-34 |
| Q1-4 | Me | Q3-35 |
| Q1-4 | Me | Q3-36 |
| Q1-4 | Me | Q3-37 |
| Q1-4 | Me | Q3-38 |
| Q1-4 | Me | Q3-39 |
| Q1-4 | Me | Q3-40 |
| Q1-4 | Me | Q3-41 |
| Q1-4 | Me | Q3-42 |
| Q1-4 | Me | Q3-43 |
| Q1-4 | Me | Q3-44 |
| Q1-4 | Me | Q3-45 |
| Q1-4 | Me | Q3-46 |
| Q1-4 | Me | Q3-47 |
| Q1-5 | Me | Q3-1 |
| Q1-5 | Me | Q3-2 |
| Q1-5 | Me | Q3-3 |
| Q1-5 | Me | Q3-4 |
| Q1-5 | Me | Q3-5 |
| Q1-5 | Me | Q3-6 |
| Q1-5 | Me | Q3-7 |
| Q1-5 | Me | Q3-8 |
| Q1-5 | Me | Q3-9 |
| Q1-5 | Me | Q3-10 |
| Q1-5 | Me | Q3-11 |
| Q1-5 | Me | Q3-12 |
| Q1-5 | Me | Q3-13 |
| Q1-5 | Me | Q3-14 |
| Q1-5 | Me | Q3-15 |
| Q1-5 | Me | Q3-16 |
| Q1-5 | Me | Q3-17 |
| Q1-5 | Me | Q3-18 |
| Q1-5 | Me | Q3-19 |
| Q1-5 | Me | Q3-20 |
| Q1-5 | Me | Q3-21 |
| Q1-5 | Me | Q3-22 |
| Q1-5 | Me | Q3-23 |
| Q1-5 | Me | Q3-24 |
| Q1-5 | Me | Q3-25 |
| Q1-5 | Me | Q3-26 |
| Q1-5 | Me | Q3-27 |
| Q1-5 | Me | Q3-28 |
| Q1-5 | Me | Q3-29 |
| Q1-5 | Me | Q3-30 |
| Q1-5 | Me | Q3-31 |
| Q1-5 | Me | Q3-32 |
| Q1-5 | Me | Q3-33 |
| Q1-5 | Me | Q3-34 |
| Q1-5 | Me | Q3-35 |
| Q1-5 | Me | Q3-36 |
| Q1-5 | Me | Q3-37 |
| Q1-5 | Me | Q3-38 |
| Q1-5 | Me | Q3-39 |
| Q1-5 | Me | Q3-40 |
| Q1-5 | Me | Q3-41 |
| Q1-5 | Me | Q3-42 |
| Q1-5 | Me | Q3-43 |
| Q1-5 | Me | Q3-44 |
| Q1-5 | Me | Q3-45 |
| Q1-5 | Me | Q3-46 |
| Q1-5 | Me | Q3-47 |
| Q1-6 | Me | Q3-1 |
| Q1-6 | Me | Q3-2 |
| Q1-6 | Me | Q3-3 |
| Q1-6 | Me | Q3-4 |
| Q1-6 | Me | Q3-5 |
| Q1-6 | Me | Q3-6 |
| Q1-6 | Me | Q3-7 |
| Q1-6 | Me | Q3-8 |

TABLE 8-continued

| R³⁴ | R¹ | R³ |
|---|---|---|
| Q1-6 | Me | Q3-9 |
| Q1-6 | Me | Q3-10 |
| Q1-6 | Me | Q3-11 |
| Q1-6 | Me | Q3-12 |
| Q1-6 | Me | Q3-13 |
| Q1-6 | Me | Q3-14 |
| Q1-6 | Me | Q3-15 |
| Q1-6 | Me | Q3-16 |
| Q1-6 | Me | Q3-17 |
| Q1-6 | Me | Q3-18 |
| Q1-6 | Me | Q3-19 |
| Q1-6 | Me | Q3-20 |
| Q1-6 | Me | Q3-21 |
| Q1-6 | Me | Q3-22 |
| Q1-6 | Me | Q3-23 |
| Q1-6 | Me | Q3-24 |
| Q1-6 | Me | Q3-25 |
| Q1-6 | Me | Q3-26 |
| Q1-6 | Me | Q3-27 |
| Q1-6 | Me | Q3-28 |
| Q1-6 | Me | Q3-29 |
| Q1-6 | Me | Q3-30 |
| Q1-6 | Me | Q3-31 |
| Q1-6 | Me | Q3-32 |
| Q1-6 | Me | Q3-33 |
| Q1-6 | Me | Q3-34 |
| Q1-6 | Me | Q3-35 |
| Q1-6 | Me | Q3-36 |
| Q1-6 | Me | Q3-37 |
| Q1-6 | Me | Q3-38 |
| Q1-6 | Me | Q3-39 |
| Q1-6 | Me | Q3-40 |
| Q1-6 | Me | Q3-41 |
| Q1-6 | Me | Q3-42 |
| Q1-6 | Me | Q3-43 |
| Q1-6 | Me | Q3-44 |
| Q1-6 | Me | Q3-45 |
| Q1-6 | Me | Q3-46 |
| Q1-6 | Me | Q3-47 |
| Q1-7 | Me | Q3-1 |
| Q1-7 | Me | Q3-2 |
| Q1-7 | Me | Q3-3 |
| Q1-7 | Me | Q3-4 |
| Q1-7 | Me | Q3-5 |
| Q1-7 | Me | Q3-6 |
| Q1-7 | Me | Q3-7 |
| Q1-7 | Me | Q3-8 |
| Q1-7 | Me | Q3-9 |
| Q1-7 | Me | Q3-10 |
| Q1-7 | Me | Q3-11 |
| Q1-7 | Me | Q3-12 |
| Q1-7 | Me | Q3-13 |
| Q1-7 | Me | Q3-14 |
| Q1-7 | Me | Q3-15 |
| Q1-7 | Me | Q3-16 |
| Q1-7 | Me | Q3-17 |
| Q1-7 | Me | Q3-18 |
| Q1-7 | Me | Q3-19 |
| Q1-7 | Me | Q3-20 |
| Q1-7 | Me | Q3-21 |
| Q1-7 | Me | Q3-22 |
| Q1-7 | Me | Q3-23 |
| Q1-7 | Me | Q3-24 |
| Q1-7 | Me | Q3-25 |
| Q1-7 | Me | Q3-26 |
| Q1-7 | Me | Q3-27 |
| Q1-7 | Me | Q3-28 |
| Q1-7 | Me | Q3-29 |
| Q1-7 | Me | Q3-30 |
| Q1-7 | Me | Q3-31 |
| Q1-7 | Me | Q3-32 |
| Q1-7 | Me | Q3-33 |
| Q1-7 | Me | Q3-34 |
| Q1-7 | Me | Q3-35 |
| Q1-7 | Me | Q3-36 |
| Q1-7 | Me | Q3-37 |
| Q1-7 | Me | Q3-38 |
| Q1-7 | Me | Q3-39 |
| Q1-7 | Me | Q3-40 |
| Q1-7 | Me | Q3-41 |
| Q1-7 | Me | Q3-42 |
| Q1-7 | Me | Q3-43 |
| Q1-7 | Me | Q3-44 |
| Q1-7 | Me | Q3-45 |
| Q1-7 | Me | Q3-46 |
| Q1-7 | Me | Q3-47 |
| Q1-8 | Me | Q3-1 |
| Q1-8 | Me | Q3-2 |
| Q1-8 | Me | Q3-3 |
| Q1-8 | Me | Q3-4 |
| Q1-8 | Me | Q3-5 |
| Q1-8 | Me | Q3-6 |
| Q1-8 | Me | Q3-7 |
| Q1-8 | Me | Q3-8 |
| Q1-8 | Me | Q3-9 |
| Q1-8 | Me | Q3-10 |
| Q1-8 | Me | Q3-11 |
| Q1-8 | Me | Q3-12 |
| Q1-8 | Me | Q3-13 |
| Q1-8 | Me | Q3-14 |
| Q1-8 | Me | Q3-15 |
| Q1-8 | Me | Q3-16 |
| Q1-8 | Me | Q3-17 |
| Q1-8 | Me | Q3-18 |
| Q1-8 | Me | Q3-19 |
| Q1-8 | Me | Q3-20 |
| Q1-8 | Me | Q3-21 |
| Q1-8 | Me | Q3-22 |
| Q1-8 | Me | Q3-23 |
| Q1-8 | Me | Q3-24 |
| Q1-8 | Me | Q3-25 |
| Q1-8 | Me | Q3-26 |
| Q1-8 | Me | Q3-27 |
| Q1-8 | Me | Q3-28 |
| Q1-8 | Me | Q3-29 |
| Q1-8 | Me | Q3-30 |
| Q1-8 | Me | Q3-31 |
| Q1-8 | Me | Q3-32 |
| Q1-8 | Me | Q3-33 |
| Q1-8 | Me | Q3-34 |
| Q1-8 | Me | Q3-35 |
| Q1-8 | Me | Q3-36 |
| Q1-8 | Me | Q3-37 |
| Q1-8 | Me | Q3-38 |
| Q1-8 | Me | Q3-39 |
| Q1-8 | Me | Q3-40 |
| Q1-8 | Me | Q3-41 |
| Q1-8 | Me | Q3-42 |
| Q1-8 | Me | Q3-43 |
| Q1-8 | Me | Q3-44 |
| Q1-8 | Me | Q3-45 |
| Q1-8 | Me | Q3-46 |
| Q1-8 | Me | Q3-47 |

93) Compounds represented by the formula (XI), wherein $R^2$ is a hydrogen atom, X is OH, Y is an oxygen atom, and $R^{34}$, $R^1$ and $R^3$ are any of the following combinations shown in Table 9, tautomers, prodrugs or pharmaceutically acceptable salts of the compounds or solvates thereof. The symbols in Table 9 denote the same substituents as in Table 1.

TABLE 9

| R³⁴ | R¹ | R³ | R³⁴ | R¹ | R³ |
|---|---|---|---|---|---|
| Q1-1 | Me | Q3-1 | Q1-2 | Me | Q3-1 |
| Q1-1 | Me | Q3-2 | Q1-2 | Me | Q3-2 |
| Q1-1 | Me | Q3-3 | Q1-2 | Me | Q3-3 |
| Q1-1 | Me | Q3-4 | Q1-2 | Me | Q3-4 |
| Q1-1 | Me | Q3-5 | Q1-2 | Me | Q3-5 |
| Q1-1 | Me | Q3-6 | Q1-2 | Me | Q3-6 |
| Q1-1 | Me | Q3-7 | Q1-2 | Me | Q3-7 |
| Q1-1 | Me | Q3-8 | Q1-2 | Me | Q3-8 |

TABLE 9-continued

| R³⁴ | R¹ | R³ | R³⁴ | R¹ | R³ |
|---|---|---|---|---|---|
| Q1-1 | Me | Q3-9 | Q1-2 | Me | Q3-9 |
| Q1-1 | Me | Q3-10 | Q1-2 | Me | Q3-10 |
| Q1-1 | Me | Q3-11 | Q1-2 | Me | Q3-11 |
| Q1-1 | Me | Q3-12 | Q1-2 | Me | Q3-12 |
| Q1-1 | Me | Q3-13 | Q1-2 | Me | Q3-13 |
| Q1-1 | Me | Q3-14 | Q1-2 | Me | Q3-14 |
| Q1-1 | Me | Q3-15 | Q1-2 | Me | Q3-15 |
| Q1-1 | Me | Q3-16 | Q1-2 | Me | Q3-16 |
| Q1-1 | Me | Q3-17 | Q1-2 | Me | Q3-17 |
| Q1-1 | Me | Q3-18 | Q1-2 | Me | Q3-18 |
| Q1-1 | Me | Q3-19 | Q1-2 | Me | Q3-19 |
| Q1-1 | Me | Q3-20 | Q1-2 | Me | Q3-20 |
| Q1-1 | Me | Q3-21 | Q1-2 | Me | Q3-21 |
| Q1-1 | Me | Q3-22 | Q1-2 | Me | Q3-22 |
| Q1-1 | Me | Q3-23 | Q1-2 | Me | Q3-23 |
| Q1-1 | Me | Q3-24 | Q1-2 | Me | Q3-24 |
| Q1-1 | Me | Q3-25 | Q1-2 | Me | Q3-25 |
| Q1-1 | Me | Q3-26 | Q1-2 | Me | Q3-26 |
| Q1-1 | Me | Q3-27 | Q1-2 | Me | Q3-27 |
| Q1-1 | Me | Q3-28 | Q1-2 | Me | Q3-28 |
| Q1-1 | Me | Q3-29 | Q1-2 | Me | Q3-29 |
| Q1-1 | Me | Q3-30 | Q1-2 | Me | Q3-30 |
| Q1-1 | Me | Q3-31 | Q1-2 | Me | Q3-31 |
| Q1-1 | Me | Q3-32 | Q1-2 | Me | Q3-32 |
| Q1-1 | Me | Q3-33 | Q1-2 | Me | Q3-33 |
| Q1-1 | Me | Q3-34 | Q1-2 | Me | Q3-34 |
| Q1-1 | Me | Q3-35 | Q1-2 | Me | Q3-35 |
| Q1-1 | Me | Q3-36 | Q1-2 | Me | Q3-36 |
| Q1-1 | Me | Q3-37 | Q1-2 | Me | Q3-37 |
| Q1-1 | Me | Q3-38 | Q1-2 | Me | Q3-38 |
| Q1-1 | Me | Q3-39 | Q1-2 | Me | Q3-39 |
| Q1-1 | Me | Q3-40 | Q1-2 | Me | Q3-40 |
| Q1-1 | Me | Q3-41 | Q1-2 | Me | Q3-41 |
| Q1-1 | Me | Q3-42 | Q1-2 | Me | Q3-42 |
| Q1-1 | Me | Q3-43 | Q1-2 | Me | Q3-43 |
| Q1-1 | Me | Q3-44 | Q1-2 | Me | Q3-44 |
| Q1-1 | Me | Q3-45 | Q1-2 | Me | Q3-45 |
| Q1-1 | Me | Q3-46 | Q1-2 | Me | Q3-46 |
| Q1-1 | Me | Q3-47 | Q1-2 | Me | Q3-47 |
| Q1-3 | Me | Q3-1 | Q1-4 | Me | Q3-1 |
| Q1-3 | Me | Q3-2 | Q1-4 | Me | Q3-2 |
| Q1-3 | Me | Q3-3 | Q1-4 | Me | Q3-3 |
| Q1-3 | Me | Q3-4 | Q1-4 | Me | Q3-4 |
| Q1-3 | Me | Q3-5 | Q1-4 | Me | Q3-5 |
| Q1-3 | Me | Q3-6 | Q1-4 | Me | Q3-6 |
| Q1-3 | Me | Q3-7 | Q1-4 | Me | Q3-7 |
| Q1-3 | Me | Q3-8 | Q1-4 | Me | Q3-8 |
| Q1-3 | Me | Q3-9 | Q1-4 | Me | Q3-9 |
| Q1-3 | Me | Q3-10 | Q1-4 | Me | Q3-10 |
| Q1-3 | Me | Q3-11 | Q1-4 | Me | Q3-11 |
| Q1-3 | Me | Q3-12 | Q1-4 | Me | Q3-12 |
| Q1-3 | Me | Q3-13 | Q1-4 | Me | Q3-13 |
| Q1-3 | Me | Q3-14 | Q1-4 | Me | Q3-14 |
| Q1-3 | Me | Q3-15 | Q1-4 | Me | Q3-15 |
| Q1-3 | Me | Q3-16 | Q1-4 | Me | Q3-16 |
| Q1-3 | Me | Q3-17 | Q1-4 | Me | Q3-17 |
| Q1-3 | Me | Q3-18 | Q1-4 | Me | Q3-18 |
| Q1-3 | Me | Q3-19 | Q1-4 | Me | Q3-19 |
| Q1-3 | Me | Q3-20 | Q1-4 | Me | Q3-20 |
| Q1-3 | Me | Q3-21 | Q1-4 | Me | Q3-21 |
| Q1-3 | Me | Q3-22 | Q1-4 | Me | Q3-22 |
| Q1-3 | Me | Q3-23 | Q1-4 | Me | Q3-23 |
| Q1-3 | Me | Q3-24 | Q1-4 | Me | Q3-24 |
| Q1-3 | Me | Q3-25 | Q1-4 | Me | Q3-25 |
| Q1-3 | Me | Q3-26 | Q1-4 | Me | Q3-26 |
| Q1-3 | Me | Q3-27 | Q1-4 | Me | Q3-27 |
| Q1-3 | Me | Q3-28 | Q1-4 | Me | Q3-28 |
| Q1-3 | Me | Q3-29 | Q1-4 | Me | Q3-29 |
| Q1-3 | Me | Q3-30 | Q1-4 | Me | Q3-30 |
| Q1-3 | Me | Q3-31 | Q1-4 | Me | Q3-31 |
| Q1-3 | Me | Q3-32 | Q1-4 | Me | Q3-32 |
| Q1-3 | Me | Q3-33 | Q1-4 | Me | Q3-33 |
| Q1-3 | Me | Q3-34 | Q1-4 | Me | Q3-34 |
| Q1-3 | Me | Q3-35 | Q1-4 | Me | Q3-35 |
| Q1-3 | Me | Q3-36 | Q1-4 | Me | Q3-36 |
| Q1-3 | Me | Q3-37 | Q1-4 | Me | Q3-37 |
| Q1-3 | Me | Q3-38 | Q1-4 | Me | Q3-38 |
| Q1-3 | Me | Q3-39 | Q1-4 | Me | Q3-39 |
| Q1-3 | Me | Q3-40 | Q1-4 | Me | Q3-40 |
| Q1-3 | Me | Q3-41 | Q1-4 | Me | Q3-41 |
| Q1-3 | Me | Q3-42 | Q1-4 | Me | Q3-42 |
| Q1-3 | Me | Q3-43 | Q1-4 | Me | Q3-43 |
| Q1-3 | Me | Q3-44 | Q1-4 | Me | Q3-44 |
| Q1-3 | Me | Q3-45 | Q1-4 | Me | Q3-45 |
| Q1-3 | Me | Q3-46 | Q1-4 | Me | Q3-46 |
| Q1-3 | Me | Q3-47 | Q1-4 | Me | Q3-47 |
| Q1-5 | Me | Q3-1 | Q1-6 | Me | Q3-1 |
| Q1-5 | Me | Q3-2 | Q1-6 | Me | Q3-2 |
| Q1-5 | Me | Q3-3 | Q1-6 | Me | Q3-3 |
| Q1-5 | Me | Q3-4 | Q1-6 | Me | Q3-4 |
| Q1-5 | Me | Q3-5 | Q1-6 | Me | Q3-5 |
| Q1-5 | Me | Q3-6 | Q1-6 | Me | Q3-6 |
| Q1-5 | Me | Q3-7 | Q1-6 | Me | Q3-7 |
| Q1-5 | Me | Q3-8 | Q1-6 | Me | Q3-8 |
| Q1-5 | Me | Q3-9 | Q1-6 | Me | Q3-9 |
| Q1-5 | Me | Q3-10 | Q1-6 | Me | Q3-10 |
| Q1-5 | Me | Q3-11 | Q1-6 | Me | Q3-11 |
| Q1-5 | Me | Q3-12 | Q1-6 | Me | Q3-12 |
| Q1-5 | Me | Q3-13 | Q1-6 | Me | Q3-13 |
| Q1-5 | Me | Q3-14 | Q1-6 | Me | Q3-14 |
| Q1-5 | Me | Q3-15 | Q1-6 | Me | Q3-15 |
| Q1-5 | Me | Q3-16 | Q1-6 | Me | Q3-16 |
| Q1-5 | Me | Q3-17 | Q1-6 | Me | Q3-17 |
| Q1-5 | Me | Q3-18 | Q1-6 | Me | Q3-18 |
| Q1-5 | Me | Q3-19 | Q1-6 | Me | Q3-19 |
| Q1-5 | Me | Q3-20 | Q1-6 | Me | Q3-20 |
| Q1-5 | Me | Q3-21 | Q1-6 | Me | Q3-21 |
| Q1-5 | Me | Q3-22 | Q1-6 | Me | Q3-22 |
| Q1-5 | Me | Q3-23 | Q1-6 | Me | Q3-23 |
| Q1-5 | Me | Q3-24 | Q1-6 | Me | Q3-24 |
| Q1-5 | Me | Q3-25 | Q1-6 | Me | Q3-25 |
| Q1-5 | Me | Q3-26 | Q1-6 | Me | Q3-26 |
| Q1-5 | Me | Q3-27 | Q1-6 | Me | Q3-27 |
| Q1-5 | Me | Q3-28 | Q1-6 | Me | Q3-28 |
| Q1-5 | Me | Q3-29 | Q1-6 | Me | Q3-29 |
| Q1-5 | Me | Q3-30 | Q1-6 | Me | Q3-30 |
| Q1-5 | Me | Q3-31 | Q1-6 | Me | Q3-31 |
| Q1-5 | Me | Q3-32 | Q1-6 | Me | Q3-32 |
| Q1-5 | Me | Q3-33 | Q1-6 | Me | Q3-33 |
| Q1-5 | Me | Q3-34 | Q1-6 | Me | Q3-34 |
| Q1-5 | Me | Q3-35 | Q1-6 | Me | Q3-35 |
| Q1-5 | Me | Q3-36 | Q1-6 | Me | Q3-36 |
| Q1-5 | Me | Q3-37 | Q1-6 | Me | Q3-37 |
| Q1-5 | Me | Q3-38 | Q1-6 | Me | Q3-38 |
| Q1-5 | Me | Q3-39 | Q1-6 | Me | Q3-39 |
| Q1-5 | Me | Q3-40 | Q1-6 | Me | Q3-40 |
| Q1-5 | Me | Q3-41 | Q1-6 | Me | Q3-41 |
| Q1-5 | Me | Q3-42 | Q1-6 | Me | Q3-42 |
| Q1-5 | Me | Q3-43 | Q1-6 | Me | Q3-43 |
| Q1-5 | Me | Q3-44 | Q1-6 | Me | Q3-44 |
| Q1-5 | Me | Q3-45 | Q1-6 | Me | Q3-45 |
| Q1-5 | Me | Q3-46 | Q1-6 | Me | Q3-46 |
| Q1-5 | Me | Q3-47 | Q1-6 | Me | Q3-47 |
| Q1-7 | Me | Q3-1 | Q1-8 | Me | Q3-1 |
| Q1-7 | Me | Q3-2 | Q1-8 | Me | Q3-2 |
| Q1-7 | Me | Q3-3 | Q1-8 | Me | Q3-3 |
| Q1-7 | Me | Q3-4 | Q1-8 | Me | Q3-4 |
| Q1-7 | Me | Q3-5 | Q1-8 | Me | Q3-5 |
| Q1-7 | Me | Q3-6 | Q1-8 | Me | Q3-6 |
| Q1-7 | Me | Q3-7 | Q1-8 | Me | Q3-7 |
| Q1-7 | Me | Q3-8 | Q1-8 | Me | Q3-8 |
| Q1-7 | Me | Q3-9 | Q1-8 | Me | Q3-9 |
| Q1-7 | Me | Q3-10 | Q1-8 | Me | Q3-10 |
| Q1-7 | Me | Q3-11 | Q1-8 | Me | Q3-11 |
| Q1-7 | Me | Q3-12 | Q1-8 | Me | Q3-12 |
| Q1-7 | Me | Q3-13 | Q1-8 | Me | Q3-13 |
| Q1-7 | Me | Q3-14 | Q1-8 | Me | Q3-14 |
| Q1-7 | Me | Q3-15 | Q1-8 | Me | Q3-15 |
| Q1-7 | Me | Q3-16 | Q1-8 | Me | Q3-16 |
| Q1-7 | Me | Q3-17 | Q1-8 | Me | Q3-17 |
| Q1-7 | Me | Q3-18 | Q1-8 | Me | Q3-18 |
| Q1-7 | Me | Q3-19 | Q1-8 | Me | Q3-19 |
| Q1-7 | Me | Q3-20 | Q1-8 | Me | Q3-20 |
| Q1-7 | Me | Q3-21 | Q1-8 | Me | Q3-21 |
| Q1-7 | Me | Q3-22 | Q1-8 | Me | Q3-22 |
| Q1-7 | Me | Q3-23 | Q1-8 | Me | Q3-23 |

TABLE 9-continued

| R³⁴ | R¹ | R³ | R³⁴ | R¹ | R³ |
|---|---|---|---|---|---|
| Q1-7 | Me | Q3-24 | Q1-8 | Me | Q3-24 |
| Q1-7 | Me | Q3-25 | Q1-8 | Me | Q3-25 |
| Q1-7 | Me | Q3-26 | Q1-8 | Me | Q3-26 |
| Q1-7 | Me | Q3-27 | Q1-8 | Me | Q3-27 |
| Q1-7 | Me | Q3-28 | Q1-8 | Me | Q3-28 |
| Q1-7 | Me | Q3-29 | Q1-8 | Me | Q3-29 |
| Q1-7 | Me | Q3-30 | Q1-8 | Me | Q3-30 |
| Q1-7 | Me | Q3-31 | Q1-8 | Me | Q3-31 |
| Q1-7 | Me | Q3-32 | Q1-8 | Me | Q3-32 |
| Q1-7 | Me | Q3-33 | Q1-8 | Me | Q3-33 |
| Q1-7 | Me | Q3-34 | Q1-8 | Me | Q3-34 |
| Q1-7 | Me | Q3-35 | Q1-8 | Me | Q3-35 |
| Q1-7 | Me | Q3-36 | Q1-8 | Me | Q3-36 |
| Q1-7 | Me | Q3-37 | Q1-8 | Me | Q3-37 |
| Q1-7 | Me | Q3-38 | Q1-8 | Me | Q3-38 |
| Q1-7 | Me | Q3-39 | Q1-8 | Me | Q3-39 |
| Q1-7 | Me | Q3-40 | Q1-8 | Me | Q3-40 |
| Q1-7 | Me | Q3-41 | Q1-8 | Me | Q3-41 |
| Q1-7 | Me | Q3-42 | Q1-8 | Me | Q3-42 |
| Q1-7 | Me | Q3-43 | Q1-8 | Me | Q3-43 |
| Q1-7 | Me | Q3-44 | Q1-8 | Me | Q3-44 |
| Q1-7 | Me | Q3-45 | Q1-8 | Me | Q3-45 |
| Q1-7 | Me | Q3-46 | Q1-8 | Me | Q3-46 |
| Q1-7 | Me | Q3-47 | Q1-8 | Me | Q3-47 |

94) Compounds represented by the formula (XII), wherein $R^2$ is a hydrogen atom, X is OH, Y is an oxygen atom, and $R^{34}$, $R^1$ and $R^3$ are any of the following combinations shown in Table 10, tautomers, prodrugs or pharmaceutically acceptable salts of the compounds or solvates thereof. The symbols in Table 10 denote the same substituents as in Table 1.

TABLE 10

| R³⁴ | R¹ | R³ | R³⁴ | R¹ | R³ |
|---|---|---|---|---|---|
| Q1-1 | Me | Q3-1 | Q1-2 | Me | Q3-1 |
| Q1-1 | Me | Q3-2 | Q1-2 | Me | Q3-2 |
| Q1-1 | Me | Q3-3 | Q1-2 | Me | Q3-3 |
| Q1-1 | Me | Q3-4 | Q1-2 | Me | Q3-4 |
| Q1-1 | Me | Q3-5 | Q1-2 | Me | Q3-5 |
| Q1-1 | Me | Q3-6 | Q1-2 | Me | Q3-6 |
| Q1-1 | Me | Q3-7 | Q1-2 | Me | Q3-7 |
| Q1-1 | Me | Q3-8 | Q1-2 | Me | Q3-8 |
| Q1-1 | Me | Q3-9 | Q1-2 | Me | Q3-9 |
| Q1-1 | Me | Q3-10 | Q1-2 | Me | Q3-10 |
| Q1-1 | Me | Q3-11 | Q1-2 | Me | Q3-11 |
| Q1-1 | Me | Q3-12 | Q1-2 | Me | Q3-12 |
| Q1-1 | Me | Q3-13 | Q1-2 | Me | Q3-13 |
| Q1-1 | Me | Q3-14 | Q1-2 | Me | Q3-14 |
| Q1-1 | Me | Q3-15 | Q1-2 | Me | Q3-15 |
| Q1-1 | Me | Q3-16 | Q1-2 | Me | Q3-16 |
| Q1-1 | Me | Q3-17 | Q1-2 | Me | Q3-17 |
| Q1-1 | Me | Q3-18 | Q1-2 | Me | Q3-18 |
| Q1-1 | Me | Q3-19 | Q1-2 | Me | Q3-19 |
| Q1-1 | Me | Q3-20 | Q1-2 | Me | Q3-20 |
| Q1-1 | Me | Q3-21 | Q1-2 | Me | Q3-21 |
| Q1-1 | Me | Q3-22 | Q1-2 | Me | Q3-22 |
| Q1-1 | Me | Q3-23 | Q1-2 | Me | Q3-23 |
| Q1-1 | Me | Q3-24 | Q1-2 | Me | Q3-24 |
| Q1-1 | Me | Q3-25 | Q1-2 | Me | Q3-25 |
| Q1-1 | Me | Q3-26 | Q1-2 | Me | Q3-26 |
| Q1-1 | Me | Q3-27 | Q1-2 | Me | Q3-27 |
| Q1-1 | Me | Q3-28 | Q1-2 | Me | Q3-28 |
| Q1-1 | Me | Q3-29 | Q1-2 | Me | Q3-29 |
| Q1-1 | Me | Q3-30 | Q1-2 | Me | Q3-30 |
| Q1-1 | Me | Q3-31 | Q1-2 | Me | Q3-31 |
| Q1-1 | Me | Q3-32 | Q1-2 | Me | Q3-32 |
| Q1-1 | Me | Q3-33 | Q1-2 | Me | Q3-33 |
| Q1-1 | Me | Q3-34 | Q1-2 | Me | Q3-34 |
| Q1-1 | Me | Q3-35 | Q1-2 | Me | Q3-35 |
| Q1-1 | Me | Q3-36 | Q1-2 | Me | Q3-36 |
| Q1-1 | Me | Q3-37 | Q1-2 | Me | Q3-37 |
| Q1-1 | Me | Q3-38 | Q1-2 | Me | Q3-38 |
| Q1-1 | Me | Q3-39 | Q1-2 | Me | Q3-39 |
| Q1-1 | Me | Q3-40 | Q1-2 | Me | Q3-40 |
| Q1-1 | Me | Q3-41 | Q1-2 | Me | Q3-41 |
| Q1-1 | Me | Q3-42 | Q1-2 | Me | Q3-42 |
| Q1-1 | Me | Q3-43 | Q1-2 | Me | Q3-43 |
| Q1-1 | Me | Q3-44 | Q1-2 | Me | Q3-44 |
| Q1-1 | Me | Q3-45 | Q1-2 | Me | Q3-45 |
| Q1-1 | Me | Q3-46 | Q1-2 | Me | Q3-46 |
| Q1-1 | Me | Q3-47 | Q1-2 | Me | Q3-47 |
| Q1-3 | Me | Q3-1 | Q1-4 | Me | Q3-1 |
| Q1-3 | Me | Q3-2 | Q1-4 | Me | Q3-2 |
| Q1-3 | Me | Q3-3 | Q1-4 | Me | Q3-3 |
| Q1-3 | Me | Q3-4 | Q1-4 | Me | Q3-4 |
| Q1-3 | Me | Q3-5 | Q1-4 | Me | Q3-5 |
| Q1-3 | Me | Q3-6 | Q1-4 | Me | Q3-6 |
| Q1-3 | Me | Q3-7 | Q1-4 | Me | Q3-7 |
| Q1-3 | Me | Q3-8 | Q1-4 | Me | Q3-8 |
| Q1-3 | Me | Q3-9 | Q1-4 | Me | Q3-9 |
| Q1-3 | Me | Q3-10 | Q1-4 | Me | Q3-10 |
| Q1-3 | Me | Q3-11 | Q1-4 | Me | Q3-11 |
| Q1-3 | Me | Q3-12 | Q1-4 | Me | Q3-12 |
| Q1-3 | Me | Q3-13 | Q1-4 | Me | Q3-13 |
| Q1-3 | Me | Q3-14 | Q1-4 | Me | Q3-14 |
| Q1-3 | Me | Q3-15 | Q1-4 | Me | Q3-15 |
| Q1-3 | Me | Q3-16 | Q1-4 | Me | Q3-16 |
| Q1-3 | Me | Q3-17 | Q1-4 | Me | Q3-17 |
| Q1-3 | Me | Q3-18 | Q1-4 | Me | Q3-18 |
| Q1-3 | Me | Q3-19 | Q1-4 | Me | Q3-19 |
| Q1-3 | Me | Q3-20 | Q1-4 | Me | Q3-20 |
| Q1-3 | Me | Q3-21 | Q1-4 | Me | Q3-21 |
| Q1-3 | Me | Q3-22 | Q1-4 | Me | Q3-22 |
| Q1-3 | Me | Q3-23 | Q1-4 | Me | Q3-23 |
| Q1-3 | Me | Q3-24 | Q1-4 | Me | Q3-24 |
| Q1-3 | Me | Q3-25 | Q1-4 | Me | Q3-25 |
| Q1-3 | Me | Q3-26 | Q1-4 | Me | Q3-26 |
| Q1-3 | Me | Q3-27 | Q1-4 | Me | Q3-27 |
| Q1-3 | Me | Q3-28 | Q1-4 | Me | Q3-28 |
| Q1-3 | Me | Q3-29 | Q1-4 | Me | Q3-29 |
| Q1-3 | Me | Q3-30 | Q1-4 | Me | Q3-30 |
| Q1-3 | Me | Q3-31 | Q1-4 | Me | Q3-31 |
| Q1-3 | Me | Q3-32 | Q1-4 | Me | Q3-32 |
| Q1-3 | Me | Q3-33 | Q1-4 | Me | Q3-33 |
| Q1-3 | Me | Q3-34 | Q1-4 | Me | Q3-34 |
| Q1-3 | Me | Q3-35 | Q1-4 | Me | Q3-35 |
| Q1-3 | Me | Q3-36 | Q1-4 | Me | Q3-36 |
| Q1-3 | Me | Q3-37 | Q1-4 | Me | Q3-37 |
| Q1-3 | Me | Q3-38 | Q1-4 | Me | Q3-38 |
| Q1-3 | Me | Q3-39 | Q1-4 | Me | Q3-39 |
| Q1-3 | Me | Q3-40 | Q1-4 | Me | Q3-40 |
| Q1-3 | Me | Q3-41 | Q1-4 | Me | Q3-41 |
| Q1-3 | Me | Q3-42 | Q1-4 | Me | Q3-42 |
| Q1-3 | Me | Q3-43 | Q1-4 | Me | Q3-43 |
| Q1-3 | Me | Q3-44 | Q1-4 | Me | Q3-44 |
| Q1-3 | Me | Q3-45 | Q1-4 | Me | Q3-45 |
| Q1-3 | Me | Q3-46 | Q1-4 | Me | Q3-46 |
| Q1-3 | Me | Q3-47 | Q1-4 | Me | Q3-47 |
| Q1-5 | Me | Q3-1 | Q1-6 | Me | Q3-1 |
| Q1-5 | Me | Q3-2 | Q1-6 | Me | Q3-2 |
| Q1-5 | Me | Q3-3 | Q1-6 | Me | Q3-3 |
| Q1-5 | Me | Q3-4 | Q1-6 | Me | Q3-4 |
| Q1-5 | Me | Q3-5 | Q1-6 | Me | Q3-5 |
| Q1-5 | Me | Q3-6 | Q1-6 | Me | Q3-6 |
| Q1-5 | Me | Q3-7 | Q1-6 | Me | Q3-7 |
| Q1-5 | Me | Q3-8 | Q1-6 | Me | Q3-8 |
| Q1-5 | Me | Q3-9 | Q1-6 | Me | Q3-9 |
| Q1-5 | Me | Q3-10 | Q1-6 | Me | Q3-10 |
| Q1-5 | Me | Q3-11 | Q1-6 | Me | Q3-11 |
| Q1-5 | Me | Q3-12 | Q1-6 | Me | Q3-12 |
| Q1-5 | Me | Q3-13 | Q1-6 | Me | Q3-13 |
| Q1-5 | Me | Q3-14 | Q1-6 | Me | Q3-14 |
| Q1-5 | Me | Q3-15 | Q1-6 | Me | Q3-15 |
| Q1-5 | Me | Q3-16 | Q1-6 | Me | Q3-16 |
| Q1-5 | Me | Q3-17 | Q1-6 | Me | Q3-17 |
| Q1-5 | Me | Q3-18 | Q1-6 | Me | Q3-18 |
| Q1-5 | Me | Q3-19 | Q1-6 | Me | Q3-19 |
| Q1-5 | Me | Q3-20 | Q1-6 | Me | Q3-20 |
| Q1-5 | Me | Q3-21 | Q1-6 | Me | Q3-21 |
| Q1-5 | Me | Q3-22 | Q1-6 | Me | Q3-22 |
| Q1-5 | Me | Q3-23 | Q1-6 | Me | Q3-23 |

TABLE 10-continued

| $R^{34}$ | $R^1$ | $R^3$ | $R^{34}$ | $R^1$ | $R^3$ |
|---|---|---|---|---|---|
| Q1-5 | Me | Q3-24 | Q1-6 | Me | Q3-24 |
| Q1-5 | Me | Q3-25 | Q1-6 | Me | Q3-25 |
| Q1-5 | Me | Q3-26 | Q1-6 | Me | Q3-26 |
| Q1-5 | Me | Q3-27 | Q1-6 | Me | Q3-27 |
| Q1-5 | Me | Q3-28 | Q1-6 | Me | Q3-28 |
| Q1-5 | Me | Q3-29 | Q1-6 | Me | Q3-29 |
| Q1-5 | Me | Q3-30 | Q1-6 | Me | Q3-30 |
| Q1-5 | Me | Q3-31 | Q1-6 | Me | Q3-31 |
| Q1-5 | Me | Q3-32 | Q1-6 | Me | Q3-32 |
| Q1-5 | Me | Q3-33 | Q1-6 | Me | Q3-33 |
| Q1-5 | Me | Q3-34 | Q1-6 | Me | Q3-34 |
| Q1-5 | Me | Q3-35 | Q1-6 | Me | Q3-35 |
| Q1-5 | Me | Q3-36 | Q1-6 | Me | Q3-36 |
| Q1-5 | Me | Q3-37 | Q1-6 | Me | Q3-37 |
| Q1-5 | Me | Q3-38 | Q1-6 | Me | Q3-38 |
| Q1-5 | Me | Q3-39 | Q1-6 | Me | Q3-39 |
| Q1-5 | Me | Q3-40 | Q1-6 | Me | Q3-40 |
| Q1-5 | Me | Q3-41 | Q1-6 | Me | Q3-41 |
| Q1-5 | Me | Q3-42 | Q1-6 | Me | Q3-42 |
| Q1-5 | Me | Q3-43 | Q1-6 | Me | Q3-43 |
| Q1-5 | Me | Q3-44 | Q1-6 | Me | Q3-44 |
| Q1-5 | Me | Q3-45 | Q1-6 | Me | Q3-45 |
| Q1-5 | Me | Q3-46 | Q1-6 | Me | Q3-46 |
| Q1-5 | Me | Q3-47 | Q1-6 | Me | Q3-47 |
| Q1-7 | Me | Q3-1 | Q1-8 | Me | Q3-1 |
| Q1-7 | Me | Q3-2 | Q1-8 | Me | Q3-2 |
| Q1-7 | Me | Q3-3 | Q1-8 | Me | Q3-3 |
| Q1-7 | Me | Q3-4 | Q1-8 | Me | Q3-4 |
| Q1-7 | Me | Q3-5 | Q1-8 | Me | Q3-5 |
| Q1-7 | Me | Q3-6 | Q1-8 | Me | Q3-6 |
| Q1-7 | Me | Q3-7 | Q1-8 | Me | Q3-7 |
| Q1-7 | Me | Q3-8 | Q1-8 | Me | Q3-8 |
| Q1-7 | Me | Q3-9 | Q1-8 | Me | Q3-9 |
| Q1-7 | Me | Q3-10 | Q1-8 | Me | Q3-10 |
| Q1-7 | Me | Q3-11 | Q1-8 | Me | Q3-11 |
| Q1-7 | Me | Q3-12 | Q1-8 | Me | Q3-12 |
| Q1-7 | Me | Q3-13 | Q1-8 | Me | Q3-13 |
| Q1-7 | Me | Q3-14 | Q1-8 | Me | Q3-14 |
| Q1-7 | Me | Q3-15 | Q1-8 | Me | Q3-15 |
| Q1-7 | Me | Q3-16 | Q1-8 | Me | Q3-16 |
| Q1-7 | Me | Q3-17 | Q1-8 | Me | Q3-17 |
| Q1-7 | Me | Q3-18 | Q1-8 | Me | Q3-18 |
| Q1-7 | Me | Q3-19 | Q1-8 | Me | Q3-19 |
| Q1-7 | Me | Q3-20 | Q1-8 | Me | Q3-20 |
| Q1-7 | Me | Q3-21 | Q1-8 | Me | Q3-21 |
| Q1-7 | Me | Q3-22 | Q1-8 | Me | Q3-22 |
| Q1-7 | Me | Q3-23 | Q1-8 | Me | Q3-23 |
| Q1-7 | Me | Q3-24 | Q1-8 | Me | Q3-24 |
| Q1-7 | Me | Q3-25 | Q1-8 | Me | Q3-25 |
| Q1-7 | Me | Q3-26 | Q1-8 | Me | Q3-26 |
| Q1-7 | Me | Q3-27 | Q1-8 | Me | Q3-27 |
| Q1-7 | Me | Q3-28 | Q1-8 | Me | Q3-28 |
| Q1-7 | Me | Q3-29 | Q1-8 | Me | Q3-29 |
| Q1-7 | Me | Q3-30 | Q1-8 | Me | Q3-30 |
| Q1-7 | Me | Q3-31 | Q1-8 | Me | Q3-31 |
| Q1-7 | Me | Q3-32 | Q1-8 | Me | Q3-32 |
| Q1-7 | Me | Q3-33 | Q1-8 | Me | Q3-33 |
| Q1-7 | Me | Q3-34 | Q1-8 | Me | Q3-34 |
| Q1-7 | Me | Q3-35 | Q1-8 | Me | Q3-35 |
| Q1-7 | Me | Q3-36 | Q1-8 | Me | Q3-36 |
| Q1-7 | Me | Q3-37 | Q1-8 | Me | Q3-37 |
| Q1-7 | Me | Q3-38 | Q1-8 | Me | Q3-38 |
| Q1-7 | Me | Q3-39 | Q1-8 | Me | Q3-39 |
| Q1-7 | Me | Q3-40 | Q1-8 | Me | Q3-40 |
| Q1-7 | Me | Q3-41 | Q1-8 | Me | Q3-41 |
| Q1-7 | Me | Q3-42 | Q1-8 | Me | Q3-42 |
| Q1-7 | Me | Q3-43 | Q1-8 | Me | Q3-43 |
| Q1-7 | Me | Q3-44 | Q1-8 | Me | Q3-44 |
| Q1-7 | Me | Q3-45 | Q1-8 | Me | Q3-45 |
| Q1-7 | Me | Q3-46 | Q1-8 | Me | Q3-46 |
| Q1-7 | Me | Q3-47 | Q1-8 | Me | Q3-47 |

95) The compounds according to 92), 93) or 94), wherein $R^1$ is converted to a hydrogen atom, tautomers, prodrugs or pharmaceutically acceptable salts of the compounds or solvates thereof.

96) The compounds according to 92), 93) or 94), wherein $R^1$ is converted to a trifluoromethyl group, tautomers, prodrugs or pharmaceutically acceptable salts of the compounds or solvates thereof.

97) The compounds according to 92), 93) or 94), wherein $R^1$ is converted to an ethyl group, tautomers, prodrugs or pharmaceutically acceptable salts of the compounds or solvates thereof.

98) The compounds according to 92), 93) or 94), wherein $R^1$ is converted to a n-propyl group, tautomers, prodrugs or pharmaceutically acceptable salts of the compounds or solvates thereof.

99) The compounds according to 92), 93) or 94), wherein $R^1$ is converted to an i-propyl group, tautomers, prodrugs or pharmaceutically acceptable salts of the compounds or solvates thereof.

100) The thrombopoietin receptor activators represented by the compounds according to any of 1) to 99).

101) Preventive, therapeutic and improving agents for diseases against which activation of the thrombopoietin receptor is effective, which contain the thrombopoietin receptor activators according to 100) or represented by the formula (I), tautomers, prodrugs or pharmaceutically acceptable salts of the activators or solvates thereof, as an active ingredient.

102) Platelet increasing agents containing the thrombopoietin receptor activators according to 100) or represented by the formula (I), tautomers, prodrugs or pharmaceutically acceptable salts of the activators or solvates thereof, as an active ingredient.

103) Medicaments containing the compounds according to any of 1) to 93) or represented by the formula (I), tautomers, prodrugs or pharmaceutically acceptable salts of the compounds or solvates thereof, as an active ingredient.

In the present invention, the compounds of the present invention represented by the formula (I) may be present in the form of tautomers or geometrical isomers which undergo endocyclic or exocyclic isomerization, mixtures of tautomers or geometric isomers or mixtures of thereof. When the compounds of the present invention have an asymmetric center, whether or not resulting from an isomerization, the compounds of the present invention may be in the form of resolved optical isomers or in the form of mixtures containing them in certain ratios.

For example, pyrazole compounds represented by the formula (III) wherein $R^2$=H may be present in the form of pyrazolones resulting from tautomerization as shown below, mixtures therefore, or mixtures of isomers thereof. When the compounds of the present invention have optically active forms, diastereomers or geometrical isomers, the present invention covers mixtures of thereof and resolved forms thereof.

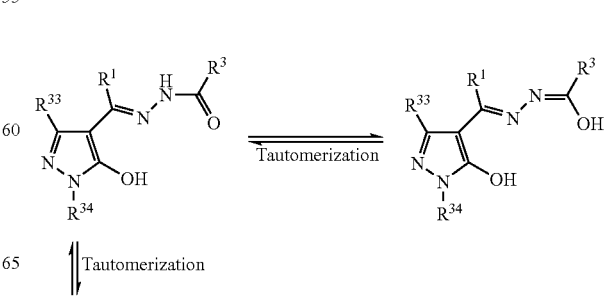

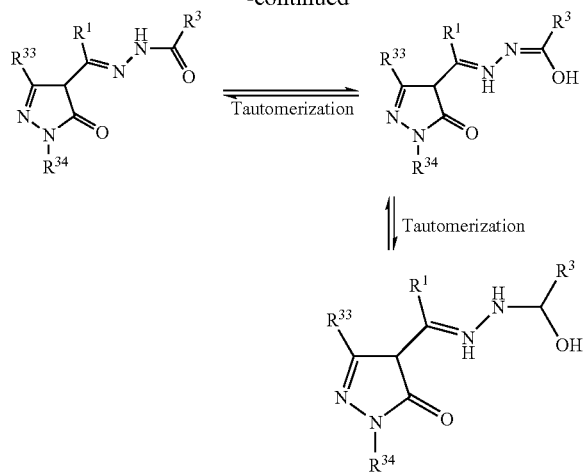

The compounds of the present invention represented by the formula (1) or pharmaceutically acceptable salts thereof may be in the form of arbitrary crystals or arbitrary hydrates, depending on the production conditions. The present invention covers these crystals, hydrates and mixtures. They may be in the form of solvates with organic solvents such as acetone, ethanol and tetrahydrofuran, and the present invention covers any of these forms.

The compounds of the present invention represented by the formula (1) may be converted to pharmaceutically acceptable salts or may be liberated from the resulting salts, if necessary. The pharmaceutically acceptable salts of the present invention may be, for example, salts with alkali metals (such as lithium, sodium and potassium), alkaline earth metals (such as magnesium and calcium), ammonium, organic bases and amino acids. They may be salts with inorganic acids (such as hydrochloric acid, hydrobromic acid, phosphoric acid and sulfuric acid) and organic acids (such as acetic acid, citric acid, maleic acid, fumaric acid, benzenesulfonic acid and p-toluenesulfonic acid).

The compounds which serve as prodrugs are derivatives of the present invention having chemically or metabolically degradable groups which give pharmacologically active compounds of the present invention upon solvolysis or under physiological conditions in vivo. Methods for selecting or producing appropriate prodrugs are disclosed, for example, in Design of Prodrug (Elsevier, Amsterdam 1985). In the present invention, when the compound has a hydroxyl group, acyloxy derivatives obtained by reacting the compound with appropriate acyl halides or appropriate acid anhydrides may, for example, be mentioned as prodrugs. Acyloxys particularly preferred as prodrugs include —OCOC$_2$H$_5$, —OCO(t-Bu), —OCOC$_{15}$H$_{31}$, —OCO(m-CO$_2$Na-Ph) —OCOCH$_2$CH$_2$CO$_2$Na, —OCOCH(NH$_2$)CH$_3$, —OCOCH$_2$N(CH$_3$)$_2$ and the like. When the compound of the present invention has an amino group, amide derivatives obtained by reacting the compound having an amino group with appropriate acid halides or appropriate mixed acid anhydrides may, for example, be mentioned as prodrugs. Amides particularly preferred as prodrugs include —NHCO(CH$_2$)$_{20}$OCH$_3$, —NHCOCH(NH$_2$)CH$_3$ and the like.

The preventive, therapeutic and improving agents for diseases against which activation of the thrombopoietin receptor is effective or platelet increasing agents which contain the thrombopoietin receptor activators of the present invention, tautomers, prodrugs or pharmaceutically acceptable salts of the activators or solvates thereof as an active ingredient may usually be administered as oral medicines such as tablets, capsules, powder, granules, pills and syrup, as rectal medicines, percutaneous medicines or injections. The agents of the present invention may be administered as a single therapeutic agent or as a mixture with other therapeutic agents. Though they may be administered as they are, they are usually administered in the form of pharmaceutical compositions. These pharmaceutical preparations can be obtained by adding pharmacologically and pharmaceutically acceptable additives by conventional methods. Namely, for oral medicines, ordinary excipients, lubricants, binders, disintegrants, humectants, plasticizers and coating agents may be used. Oral liquid preparations may be in the form of aqueous or oily suspensions, solutions, emulsions, syrups or elixirs or may be supplied as dry syrups to be mixed with water or other appropriate solvents before use. Such liquid preparations may contain ordinary additives such as suspending agents, perfumes, diluents and emulsifiers. In the case of rectal administration, they may be administered as suppositories. Suppositories may use an appropriate substance such as cacao butter, laurin tallow, Macrogol, glycerogelatin, Witepsol, sodium stearate and mixtures thereof as the base and may, if necessary, contain an emulsifier, a suspending agent, a preservative and the like. For injections, pharmaceutical ingredients such as distilled water for injection, physiological saline, 5% glucose solution, propylene glycol and other solvents or solubilizing agents, a pH regulator, an isotonizing agent and a stabilizer may be used to form aqueous dosage forms or dosage forms which need dissolution before use.

The dose of the agents of the present invention for administration to human is usually about from 0.1 to 1000 mg/human/day in the case of oral drugs or rectal administration and about from 0.05 mg to 500 mg/human/day in the case of injections into an adult, though it depends on the age and conditions of the patient. The above-mentioned ranges are mere examples, and the dose should be determined from the conditions of the patient.

The present invention is used when the use of compounds which have thrombopoietin receptor affinity and act as thrombopoietin receptor agonists are expected to improve pathological conditions. For example, hematological disorders accompanied by abnormal platelet count may be mentioned. Specifically, it is effective for therapy or prevention of human and mammalian diseases caused by abnormal megakaryopoiesis, especially those accompanied by thrombocytopenia. Examples of such diseases include thrombocytopenia accompanying chemotherapy or radiotherapy of cancer, thrombocytopenia accompanying antiviral therapy for diseases such as hepatitis C, thrombocytopenia caused by bone marrow transplantation, surgery and serious infections, or gastrointestinal bleeding, but such diseases are not restricted to those mentioned. Typical thrombocytopenias such as aplastic anemia, idiopathic thrombocytopenic purpura, myelodysplastic syndrome, hepatic disease, HIV infection and thrombopoietin deficiency are also targets of the agents of the present invention. The present invention may be used as a peripheral stem cell mobilizer, a megakaryoblastic or megakaryocytic leukemia cell differentiation inducer and a platelet increasing agent for platelet donors. In addition, potential applications include therapeutic angiogenesis based on differentiation and proliferation of vascular endothelial cells and endothelial progenitor cells, prevention and therapy of arteriosclerosis, myocardial infarction, unstable angina, peripheral artery occlusive disease, but there is no restriction.

The compounds represented by the formula (I) such as pyrazole compounds represented by the formula (III) are prepared by the process represented by the formula (1) illustrated below.

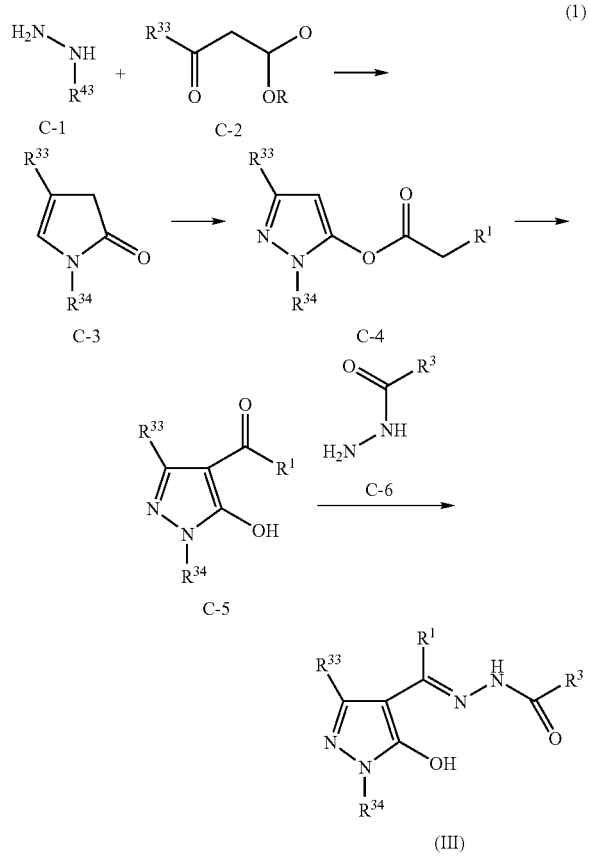

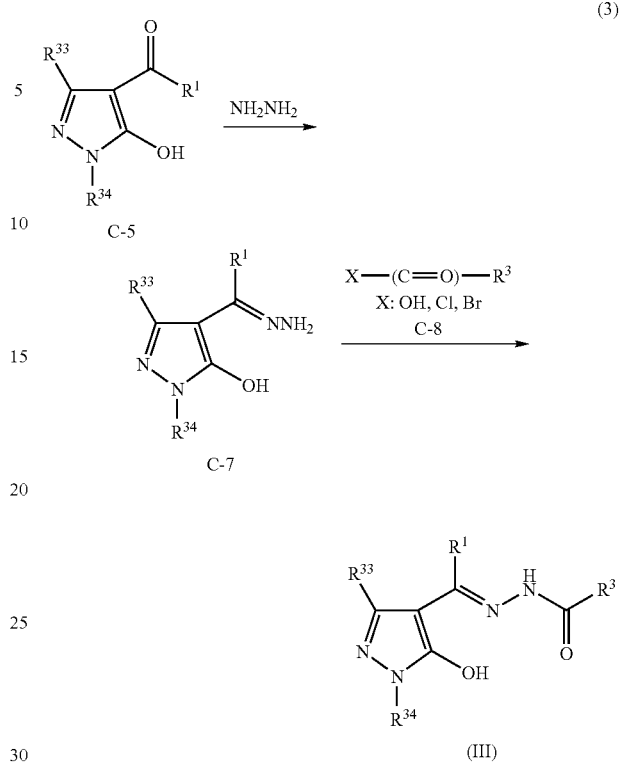

A pyrazolone (C-3) is synthesized by known processes (Syn. Comm., 20(20), 3213 (1990), Chem. Ber., 59, 320 (1926), Monatsh. Chem., 89, 30 (1958)), for example, by reacting a β-ketoester (C-2) with a hydrazine ($R^{34}NHNH_2$ (C-1) or a salt thereof) in acetic acid under reflux, and then converted to a 4-acyl-5-hydroxypyrazole (C-5) by acylation (C-4) with an acyl halide ($R^1COOCl$) or acid anhydride (($R^1CO)_2O$) followed by Fries rearrangement in the presence of potassium carbonate in dioxane with heating. A 4-formyl-5-hydroxypyrazole (C-5) ($R^1$=H) is obtainable by reacting a pyrazolone (C-3) with $POCl_3$-DMF. These pyrazoles are heated with a hydrazide ($R^3CONHNH_2$ (C-6) or a salt thereof) in a solvent with stirring, if necessary in the presence of a catalyst, to give the desired product. The hydrazide (C-6) can be synthesized by known methods for which the following are referred to.
1) Synthetic Commun., 28 (7) 1223-1231 (1998)
2) J. Chem. Soc., 1225 (1948)
3) J. Chem. Soc., 2831 (1952)
4) WO03/7328
5) Journal of the Chemical Society of Japan, 88(5), 73 (1967)
6) Journal of Heterocyclic Chemistry, 28(17), 17 (1991)

The compounds represented by the formula (I) such as pyrazole compounds represented by the formula (III) are also prepared by the process represented by the formula (3) illustrated below.

A compound (C-7) is obtainable by heating a compound (C-5) and hydrazine or a synthon thereof in a solvent with stirring, if necessary in the presence of a catalyst.

The compound (C-7) is stirred with a compound (C-8) in a solvent, if necessary in the presence of a catalyst, a dehydrating condensation agent or a base, if necessary with heating to give the desired product or a precursor thereof. The precursor is converted to the desired product by hydrolysis, deprotection, reduction, oxidation or the like, depending on the precursor. The compounds of the present invention can usually be purified by column chromatography, thin layer chromatography, high performance liquid chromatography (HPLC), high performance liquid chromatography-mass spectrometry (LC-MS) and, if necessary, are obtainable with high purity by recrystallization or washing with a solvent.

Other starting materials for synthesis of the compounds represented by the formula (I) are known to be obtainable by the following methods.

1) The starting material for synthesis of the compounds represented by the formula (V)

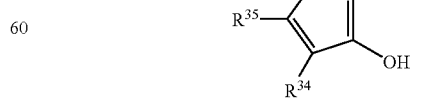

is obtainable from the following (C-9) synthesized in accordance with Journal of Heterocyclic Chemistry, 27(2), 315 (1990), by the method disclosed in WO04/108683.

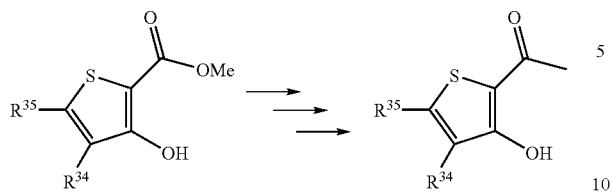

2) The starting material for synthesis of the compounds represented by the formula (VII)

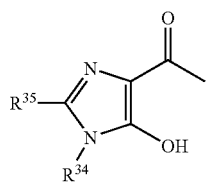

is obtainable from the following (C-10) synthesized in accordance with Zhurnal Obshchei Khimii, 47(5), 1201 (1977), by the method disclosed in WO04/108683.

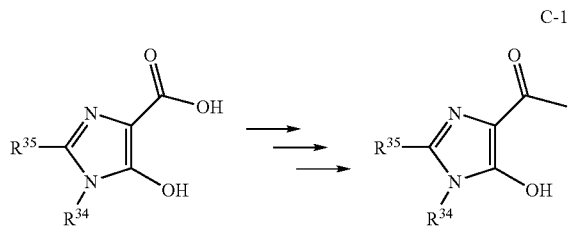

3) The starting material for synthesis of the compounds represented by the formula (X)

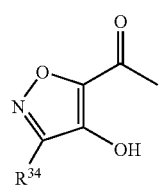

is obtainable from the following (C-11) synthesized in accordance with Journal of Organic Chemistry, 54(3), 706 (1989), by the method disclosed in WO04/108683.

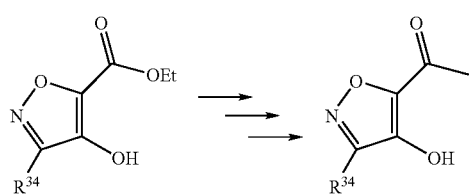

4) The starting material for synthesis of the compounds represented by the formula (XI)

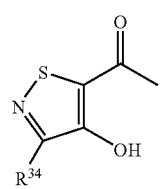

is obtainable from the following (C-12) synthesized in accordance with Eur. Pat. Appl., 48615 (1982), by the method disclosed in WO04/108683.

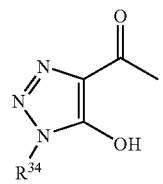

5) The starting material for synthesis of the compounds represented by the formula (XII)

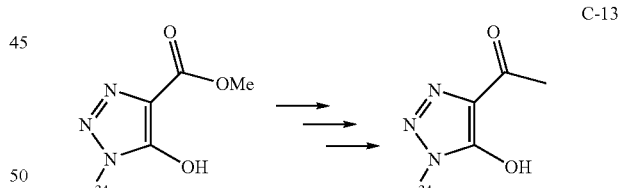

is obtainable from the following (C-13) synthesized in accordance with Act Chemica Scandinavica, 22(8), 2476 (1968), by the method disclosed in WO04/108683.

The starting material for synthesis of the compounds represented by the formula (V), the starting material for synthesis of the compounds represented by the formula (VII), the starting material for synthesis of the compounds represented by the formula (X), the starting material for synthesis of the compounds represented by the formula (XI) and the starting material for synthesis of the compounds represented by the formula (XII) are used similarly to C-5 in the formula (1) to give the compounds of the present invention represented by the formula (I).

EXAMPLES

Now, the present invention will be described in further detail with reference to Reference Synthetic Examples, Synthetic Examples, Assay Examples and Formulation Examples. However, it should be understood that the present invention is by no means restricted by these specific Examples.

LC/MS was measured under the following conditions.
LC/MS Condition 1
Column: Waters SunFire C18 (3.5 μm, 4.6×30 mm)
Eluent: acetonitrile/0.1% aqueous formic acid (10/90→30/70)
LC/MS Condition 2
Column: Waters SunFire C18 (3.5 μm, 4.6×30 mm)
Eluent: acetonitrile/0.1% aqueous formic acid (10/90→60/40)
LC/MS Conditions 3
Column: Waters SunFire C18 (3.5 μm, 4.6×30 mm)
Eluent: acetonitrile/0.1% aqueous formic acid (10/90→85/15)
LC/MS Conditions 4
Column: Waters Xterra MSC18 (5 μm, 4.6×50 mm)
Eluent: acetonitrile/0.1% aqueous formic acid (10/90→30/70)
LC/MS Conditions 5
Column: Waters Xterra MSC18 (5 μm, 4.6×50 mm)
Eluent: acetonitrile/0.1% aqueous formic acid (10/90→60/40)
LC/MS Conditions 6
Column: Waters Xterra MSC18 (5 μm, 4.6×50 mm)
Eluent: acetonitrile/0.1% aqueous formic acid (10/90→85/15)
LC/MS Conditions 7
Column: Waters Xterra MSC18 (5 μm, 4.6×50 mm)
Eluent: acetonitrile/0.1% aqueous formic acid (20/80→100/0)
LC/MS Conditions 8
Column: Waters Xterra MSC18 (3.5 μm, 2.1×20 mm)
Eluent: acetonitrile/0.2% aqueous formic acid (20/80→90/10)

Reference Synthetic Example 1

Synthesis of 5-hydrazinocarbonyl-thiophene-2-carboxylic acid 2-propylamide

Methyl 5-(2-propylcarbamyl)-thiophene-2-carboxylate (1.22 g, 5.37 mmol) in ethanol (40 ml) was refluxed with heating with hydrazine monohydrate (2.7 g) at 85° C. for 16 hours. After cooling, the solvent was evaporated, and the resulting solid was recrystallized from chloroform to give 549.2 mg of the desired product (yield 45%).

Morphology: colorless solid
LC/MS: condition 2 Retention time 1.07 (min)
LC/MS (ESI⁺) m/z; 228 [M+1]⁺
LC/MS (ESI⁻) m/z; 226 [M−1]⁻

Reference Synthetic Examples 2 to 17

Synthesis was carried out in the same manner as in Reference Synthetic Example 1, and the yields and morphology of the resulting compounds, the LC/MS conditions used for their analysis and the observed peaks and retention times are shown in Table 11.

TABLE 11

| Reference Synthetic Example No. | Yield (%) | Morphology | LC/MS conditions | Observed peak ESI⁺ | Observed peak ESI⁻ | Retention time (min) |
|---|---|---|---|---|---|---|
| 2 | 81 | White solid | 1 | 277 | 275 | 0.23 |
| 3 | 89 | White solid | | | | |
| 4 | 89 | White solid | 8 | 242 | | 0.63 |
| 5 | | White solid | 8 | 240 | | 0.50 |
| 6 | 92 | Pale yellow solid | 3 | 229 | 227 | 0.37 |
| 7 | 73 | White solid | 8 | 228 | 226 | 0.52 |
| 8 | 72 | Pale yellow solid | 3 | 323 | 321 | 0.28 |
| 9 | 82 | White solid | 1 | 283 | 281 | 0.22 |
| 10 | 81 | White solid | 1 | 277 | 275 | 0.28 |
| 11 | 92 | White solid | 1 | 277 | 275 | 0.23 |
| 12 | 68 | Pale yellow solid | | | | |
| 13 | 77 | Pale yellow amorphous | 1 | 300 | 298 | 0.48 |
| 14 | 100 | Pale yellow solid | | | | |
| 15 | 98 | Pale yellow solid | 2 | 258 | 256 | 0.32 |
| 16 | 83 | White solid | 3 | 200 | 198 | 0.37 |
| 17 | 84 | White solid | 1 | 244 | 242 | 0.34 |

The structures of the compounds obtained in the Reference Synthetic Examples are shown below.

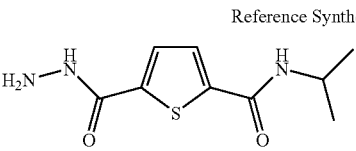

Reference Synthetic Example 1

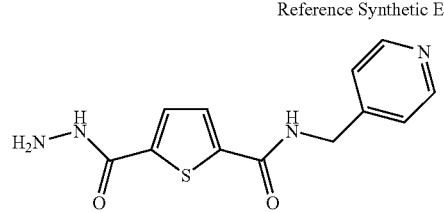

Reference Synthetic Example 2

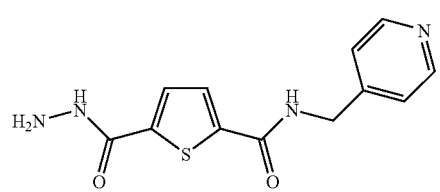

Reference Synthetic Example 3

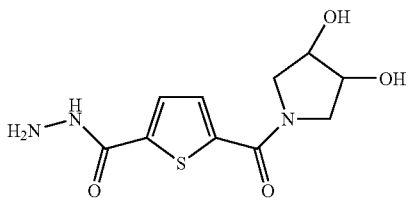

Reference Synthetic Example 4

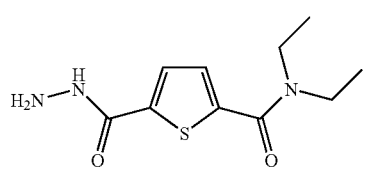

Reference Synthetic Example 5

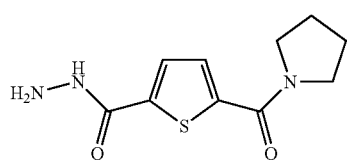

Reference Synthetic Example 6

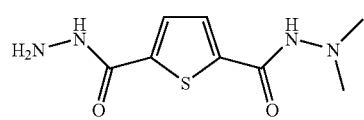

Reference Synthetic Example 7

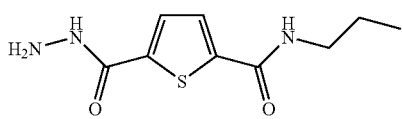

Reference Synthetic Example 8

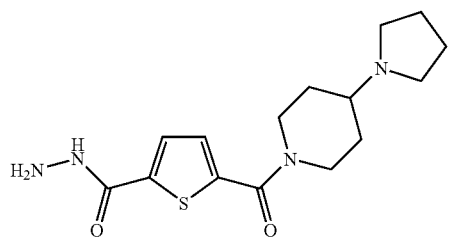

Reference Synthetic Example 9

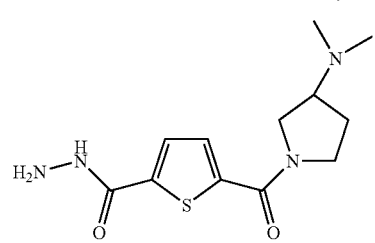

Reference Synthetic Example 10

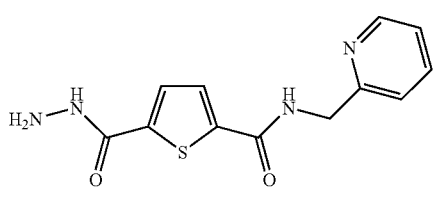

Reference Synthetic Example 11

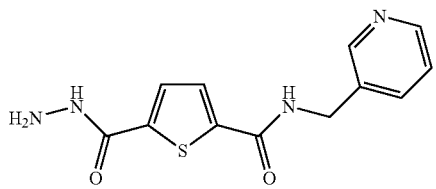

Reference Synthetic Example 12

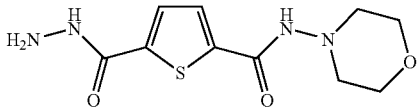

Reference Synthetic Example 13

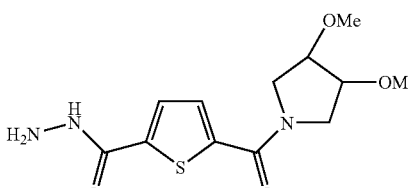

Reference Synthetic Example 14

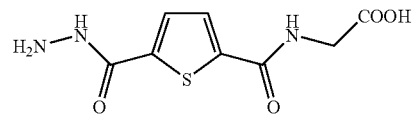

Reference Synthetic Example 15

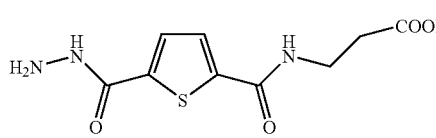

Refernce Synthetic Example 16

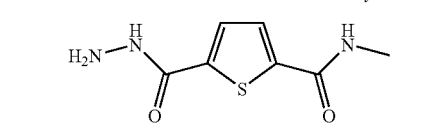

Reference Synthetic Example 17

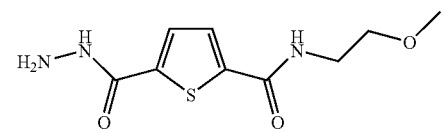

Synthetic Example 1

5-(N'-{1-[1-(3,4-Dimethylphenyl)-3-methyl-5-oxo-1, 5-dihydropyrazol-4-ylidene]-ethyl}hydrazinocarbonyl)-thiophene-2-carboxylic acid isopropylamide 1-(5-Hydroxy-3-methyl-1-(3,4-dimethylphenyl)-1H-pyrazol-4-yl)-ethanone (30 mg, 0.123 mmol, synthesized in accordance with patent document 25), 5-hydrazinocarbonyl-thiophene-2-carboxylic acid 2-propylamide prepared in Reference Synthetic Example 1 and p-toluenesulfonic acid monohydrate (2 mg) in isopropanol (1 mL) were heated at 90° C. overnight under reflux. After cooling, chloroform-ether was added, and the resulting crystals were collected by filtration, washed with chloroform-ether and dried to give 24 mg of the desired product (yield 43%).
Morphology: white solid
LC/MS: condition 2 Retention time 4.17 (min)
LC/MS (ESI$^+$) m/z; 454 [M+1]$^+$
LC/MS (ESI$^-$) m/z; 452 [M−1]$^-$ Synthetic Examples 2 to 10

Synthesis was carried out in the same manner as in Synthetic Example 1, and the yields and morphology of the resulting compounds, the LC/MS conditions used for their analysis, the observed peaks, the retention times and Reference Synthetic Examples in which the hydrazides used were synthesized are shown in Table 12.

In Synthetic Examples 2 to 10, the desired products were prepared by mixing 1 equivalent of 1-(5-hydroxy-3-methyl-1-(3,4-dimethylphenyl)-1H-pyrazol-4-yl)-ethanone with 1 equivalent of the hydrazides prepared in the indicated Reference Synthetic Examples in dimethyl sulfoxide, in isopropanol-p-toluenesulfonic acid or in dimethylformamide-hydrochloric acid, if necessary with heating and subsequent cooling, and if necessary, concentrating the reaction mixture, adding a poor solvent such as ethanol, methanol, water, chloroform, ether or hexane and collecting the resulting crystals by filtration.

TABLE 12

| Synthetic Example No. | Yield (%) | Morphology | LC/MS conditions | Observed peak ESI+ | Observed peak ESI− | Retention time (min) | Reference Synthetic Example No. |
|---|---|---|---|---|---|---|---|
| 2 | 58 | Yellow solid | 8 | 503 | 501 | 2.97 | 2 |
| 3 | 25 | Pale yellow solid | 8 | 498 | 496 | 3.53 | 3 |
| 4 | 86 | Pale yellow solid | 2 | 466 | 464 | 3.54 | 5 |
| 5 | 77 | Yello solid | 8 | 455 | 453 | 3.78 | 6 |
| 6 | 39 | Brown solid | 8 | 549 | 547 | 2.50 | 8 |
| 7 | 49 | White solid | 8 | 503 | 501 | 3.32 | 10 |
| 8 | 5 | Brown solid | 8 | 503 | 501 | 2.93 | 11 |
| 9 | 50 | Pale yellow solid | 8 | 484 | 482 | 3.73 | 15 |
| 10 | 34 | Yellow solid | 2 | 426 | 424 | 3.25 | 16 |

Synthetic Examples 11 to 27

Synthesis was carried out in the same manner as in Synthetic Example 1, and the yields and morphology of the resulting compounds, the LC/MS conditions used for their analysis, the observed peaks, the retention times and Reference Synthetic Examples in which the hydrazides used were synthesized are shown in Table 13.

In Synthetic Examples 11 to 27, the desired products were prepared by mixing 1 equivalent of 1-(5-hydroxy-3-methyl-1-(4-t-butylphenyl)-1H-pyrazol-4-yl)-ethanone (prepared in accordance with patent document 25) with 1 equivalent of the hydrazides prepared in the indicated Reference Synthetic Examples in dimethyl sulfoxide, in isopropanol-p-toluenesulfonic acid or in dimethylformamide-hydrochloric acid, if necessary with heating and subsequent cooling, and if necessary, concentrating the reaction mixture, adding a poor solvent such as ethanol, methanol, water, chloroform, ether or hexane and collecting the resulting crystals by filtration.

TABLE 13

| Synthetic Example No. | Yield (%) | Morphology | LC/MS conditions | Observed peak ESI+ | Observed peak ESI− | Retention time (min) | Reference Synthetic Example No. |
|---|---|---|---|---|---|---|---|
| 11 | 44 | Yellow solid | 3 | 482 | 480 | 3.29 | 1 |
| 12 | 74 | Brown solid | 3 | 531 | 529 | 2.25 | 2 |
| 13 | 35 | Yellow solid | 3 | 526 | 524 | 2.75 | 3 |
| 14 | 76 | White solid | 3 | 496 | 494 | 3.35 | 4 |
| 15 | 71 | Pale yellow solid | 3 | 494 | 492 | 3.25 | 5 |
| 16 | 70 | Pale yellow solid | 3 | 483 | 481 | 3.02 | 6 |
| 17 | 98 | Brown solid | 3 | 577 | 575 | 2.13 | 8 |
| 18 | 74 | Yellow solid | 3 | 537 | 535 | 2.10 | 9 |
| 19 | 89 | Pale yellow solid | 3 | 531 | 529 | 2.70 | 10 |
| 20 | 70 | Yellow solid | 3 | 531 | 529 | 2.38 | 11 |
| 21 | 68 | Yellow solid | 3 | 525 | 523 | 2.98 | 12 |
| 22 | 57 | Yellow solid | 3 | 554 | 552 | 3.07 | 13 |
| 23 | 71 | Ivory solid | 3 | 498 | 496 | 2.98 | 14 |
| 24 | 49 | Pale brown solid | 3 | 512 | 510 | 2.92 | 15 |
| 25 | 62 | Yellow solid | 3 | 454 | 452 | 3.04 | 16 |
| 26 | 33 | Yellow solid | 3 | 498 | 496 | 3.09 | 17 |
| 27 | 41 | Yellow solid | 3 | 482 | 480 | 3.29 | 7 |

Synthetic Examples 28 to 36

Synthesis was carried out in the same manner as in Synthetic Example 1, and the yields and morphology of the resulting compounds, the LC/MS conditions used for their analysis, the observed peaks, the retention times and Reference Synthetic Examples in which the hydrazides used were synthesized are shown in Table 14.

In Synthetic Examples 28 to 36, the desired products were prepared by mixing 1 equivalent of 1-(5-hydroxy-3-methyl-1-(4-trifluoromethylphenyl)-1H-pyrazol-4-yl)-ethanone (prepared in accordance with patent document 25) with 1 equivalent of the hydrazides prepared in the indicated Reference Synthetic Examples in dimethyl sulfoxide, in isopropanol-p-toluenesulfonic acid or in dimethylformamide-hydrochloric acid, if necessary with heating and subsequent cooling, and if necessary, concentrating the reaction mixture, adding a poor solvent such as ethanol, methanol, water, chloroform, ether or hexane and collecting the resulting crystals by filtration.

TABLE 14

| Synthetic Example No. | Yield (%) | Morphology | LC/MS conditions | Observed peak ESI+ | Observed peak ESI− | Retention time (min) | Reference Synthetic Example No. |
|---|---|---|---|---|---|---|---|
| 28 | 33 | Pale yellow solid | 8 | 494 | 492 | 4.47 | 1 |
| 29 | 75 | Brown solid | 3 | 543 | 541 | 2.20 | 2 |
| 30 | 59 | Pale yellow solid | 3 | 538 | 536 | 2.68 | 3 |
| 31 | 54 | Pale yellow solid | 3 | 508 | 506 | 3.34 | 4 |
| 32 | 86 | Pale yellow solid | 3 | 506 | 504 | 3.20 | 5 |
| 33 | 54 | Pale yellow solid | 3 | 495 | 493 | 3.00 | 6 |
| 34 | 65 | Dark brown solid | 3 | 589 | 587 | 2.15 | 8 |
| 35 | 74 | Yellow solid | 3 | 549 | 547 | 2.12 | 9 |
| 36 | 70 | Yellow solid | 3 | 543 | 541 | 2.38 | 11 |

Synthetic Examples 37 to 44

Synthesis was carried out in the same manner as in Synthetic Example 1, and the yields and morphology of the resulting compounds, the LC/MS conditions used for their analysis, the observed peaks, the retention times and Reference Synthetic Examples in which the hydrazides used were synthesized are shown in Table 15.

In Synthetic Examples 37 to 44, the desired products were prepared by mixing 1 equivalent of 1-(5-hydroxy-3-methyl-1-(3,4-dichlorophenyl)-1H-pyrazol-4-yl)-ethanone (prepared in accordance with patent document 25) with 1 equivalent of the hydrazides prepared in the indicated Reference Synthetic Examples in dimethyl sulfoxide, in isopropanol-p-toluenesulfonic acid or in dimethylformamide-hydrochloric acid, if necessary with heating and subsequent cooling, and if necessary, concentrating the reaction mixture, adding a poor solvent such as ethanol, methanol, water, chloroform, ether or hexane and collecting the resulting crystals by filtration.

TABLE 15

| Synthetic Example No. | Yield (%) | Morphology | LC/MS conditions | Observed peak ESI+ | Observed peak ESI− | Retention time (min) | Reference Synthetic Example No. |
|---|---|---|---|---|---|---|---|
| 37 | 92 | Yellow solid | 8 | 494/496 | 492/494 | 0.23 | 1 |
| 38 | 86 | Brown solid | 3 | 543/545 | 541/543 | 2.29 | 2 |
| 39 | 46 | Pale yellow solid | 3 | 538/540 | 536/538 | 2.79 | 3 |
| 40 | 70 | Ivory solid | 8 | 495/497 | 493/495 | 0.23 | 6 |
| 41 | 70 | Ocher solid | 8 | 589/591 | 587/589 | 0.23 | 8 |
| 42 | 83 | Ivory solid | 8 | 543/545 | 541/543 | 0.23 | 10 |
| 43 | 64 | Orange solid | 8 | 543/545 | 541/543 | 0.23 | 11 |
| 44 | 85 | White solid | 8 | 566/568 | 564/566 | 0.23 | 13 |

The structures of the compounds obtained in the Synthetic Examples are shown below.
Synthetic Example 1
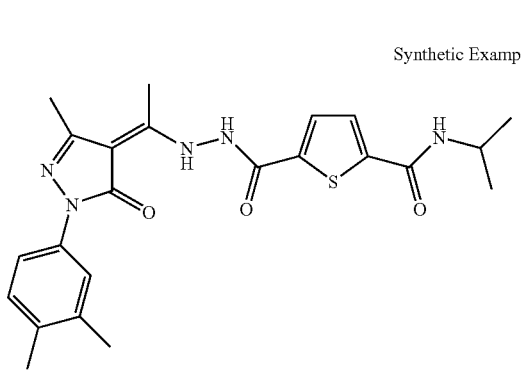
Synthetic Example 2
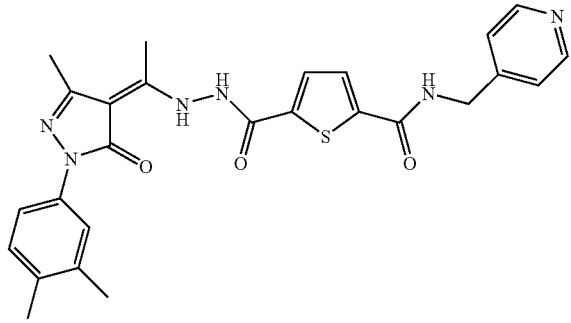
Synthetic Example 3
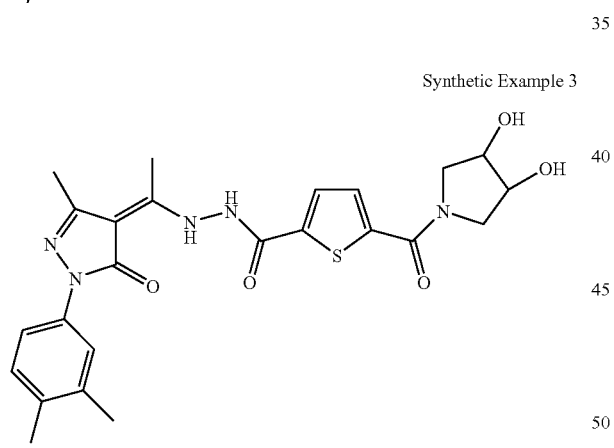
Synthetic Example 4
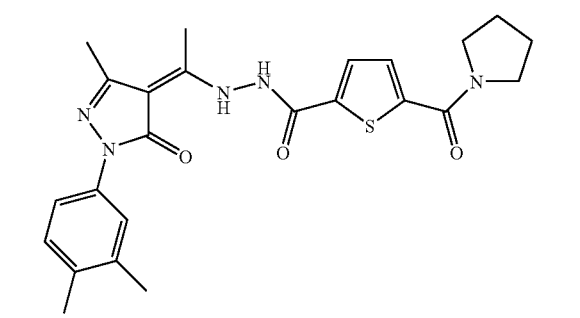
Synthetic Example 5
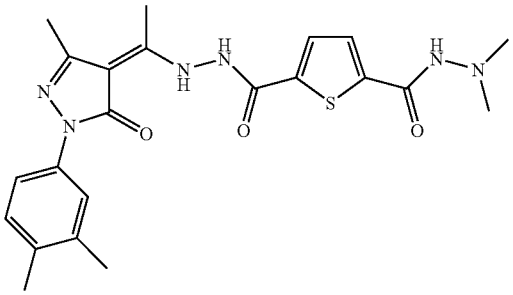
Synthetic Example 6
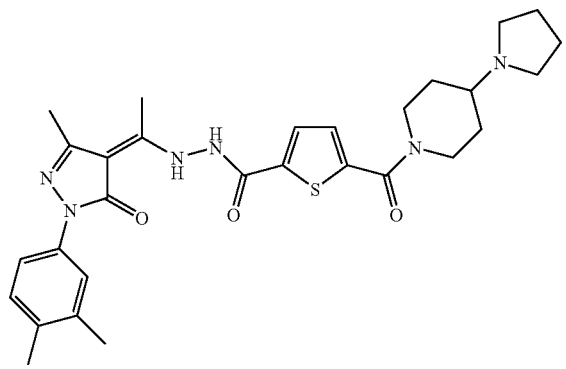
Synthetic Example 7
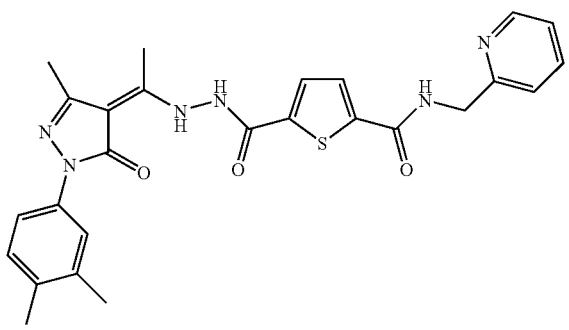
Synthetic Example 8
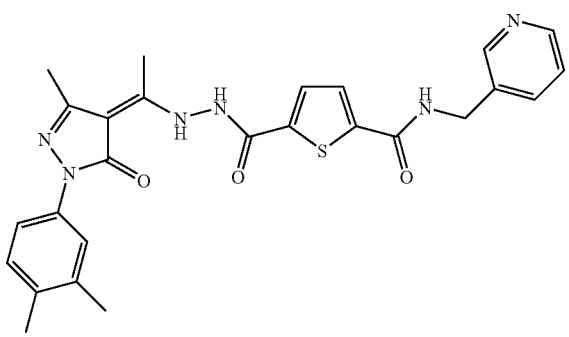

Synthetic Example 9
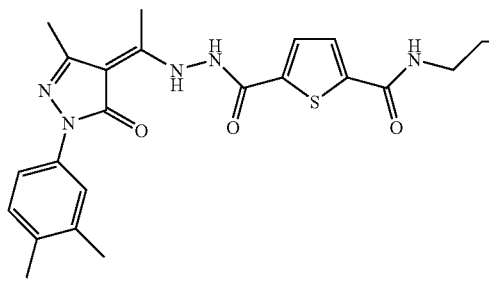
Synthetic Example 13
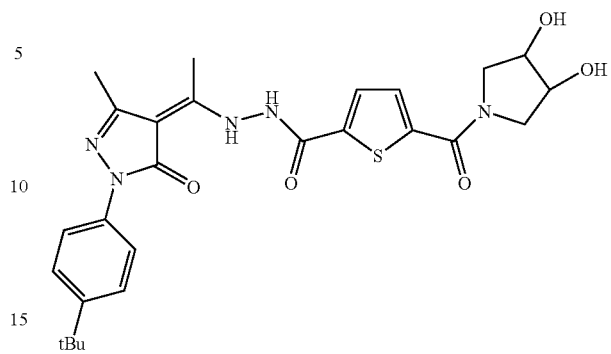
Synthetic Example 10
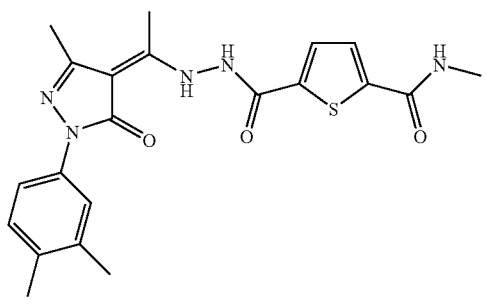
Synthetic Example 14
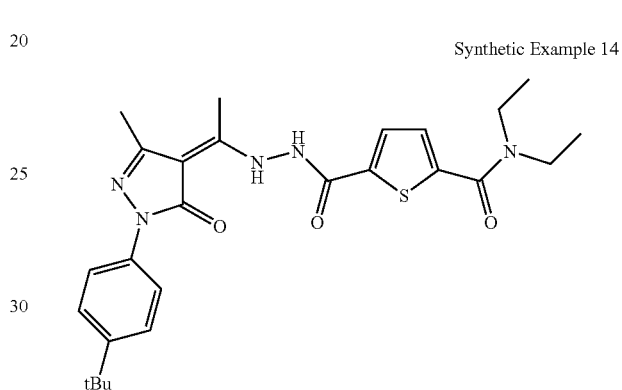
Synthetic Example 11
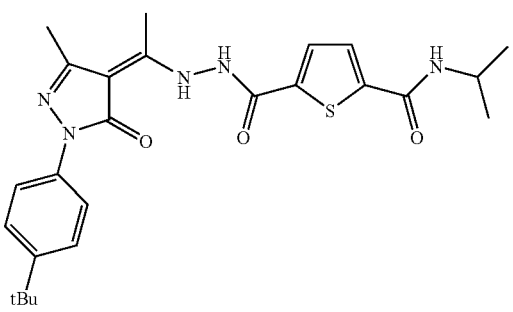
Synthetic Example 15
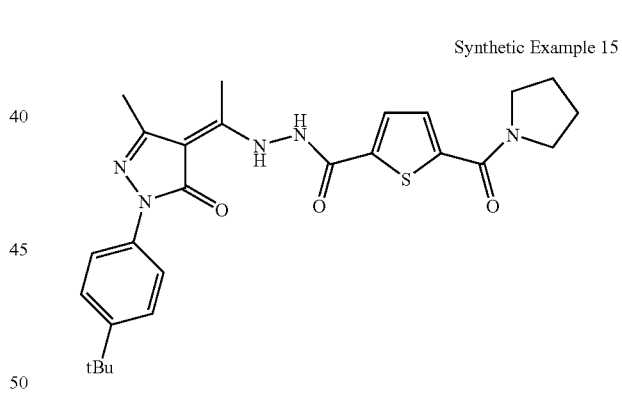
Synthetic Example 12
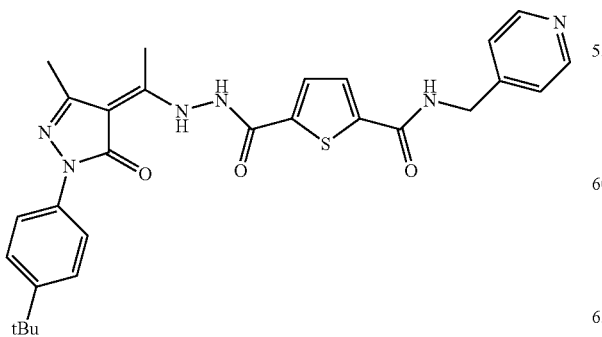
Synthetic Example 16
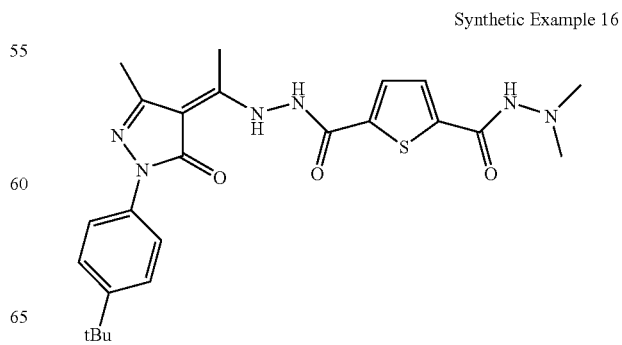

-continued
Synthetic Example 17
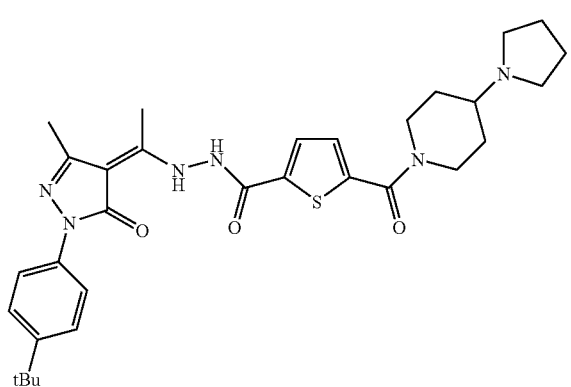
Synthetic Example 18
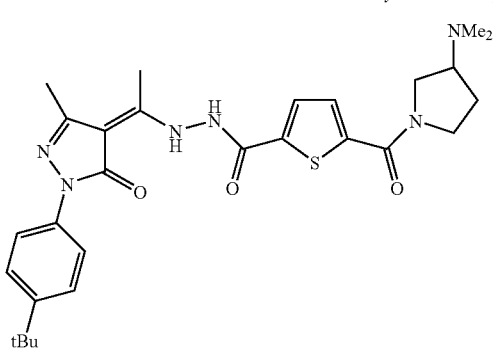
Synthetic Example 19
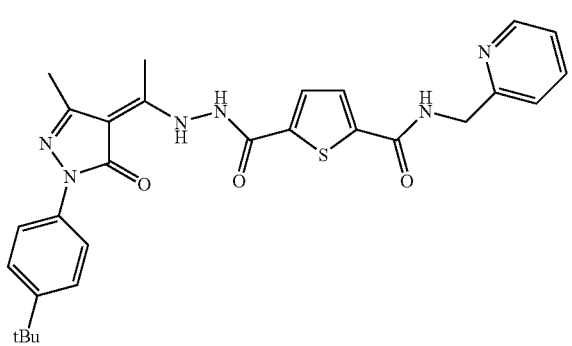
Synthetic Example 20
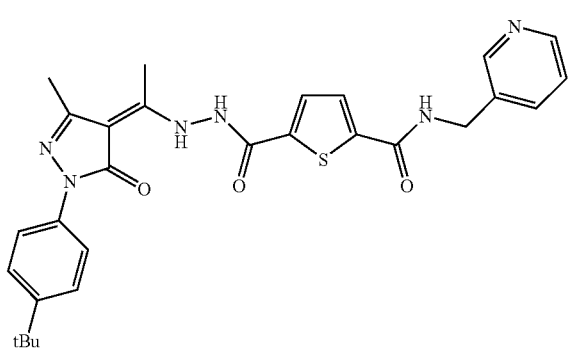
-continued
Synthetic Example 21
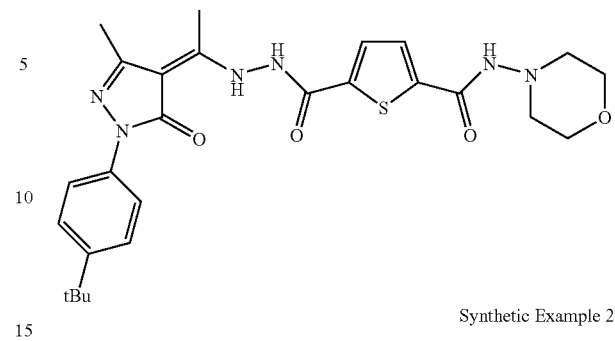
Synthetic Example 22
Synthetic Example 23
Synthetic Example 24
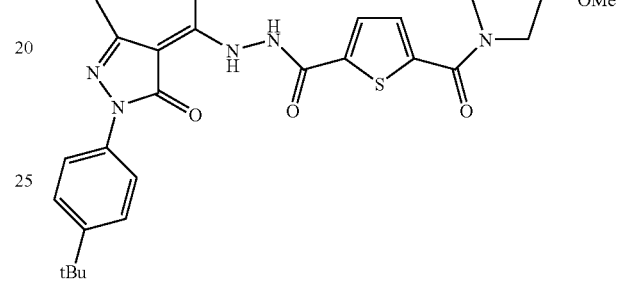
Synthetic Example 25
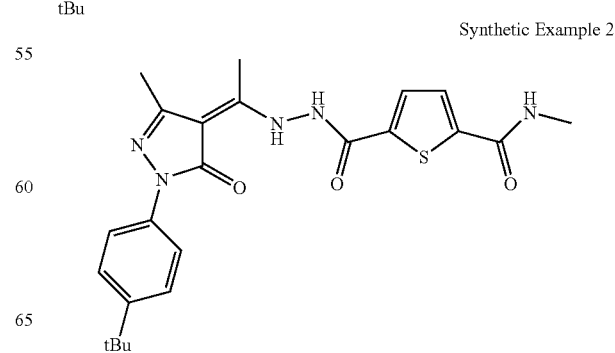

Synthetic Example 26
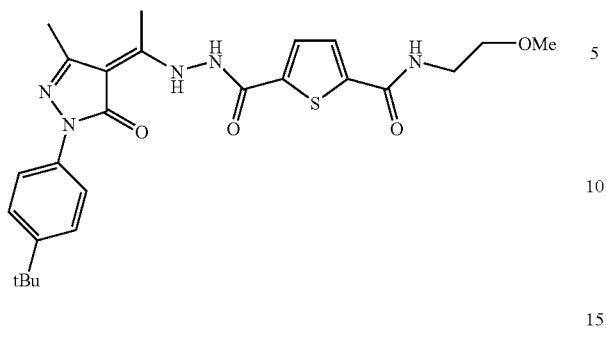
Synthetic Example 30
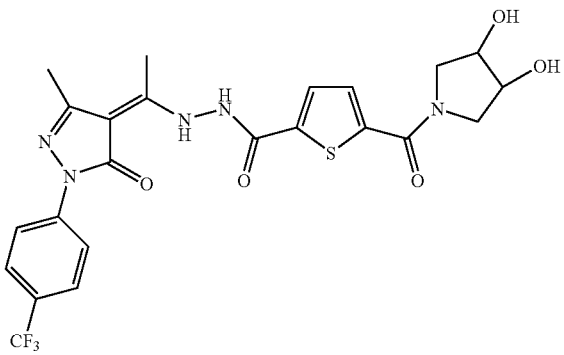
Synthetic Example 27
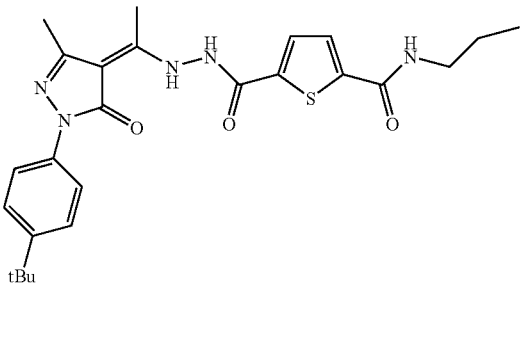
Synthetic Example 31
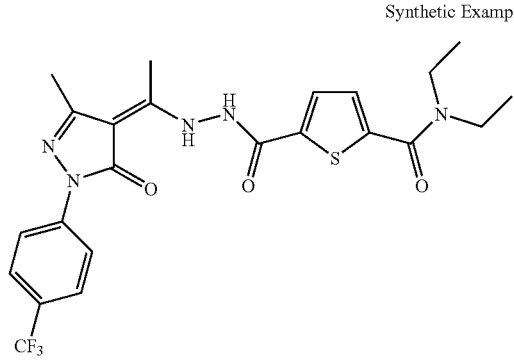
Synthetic Example 28
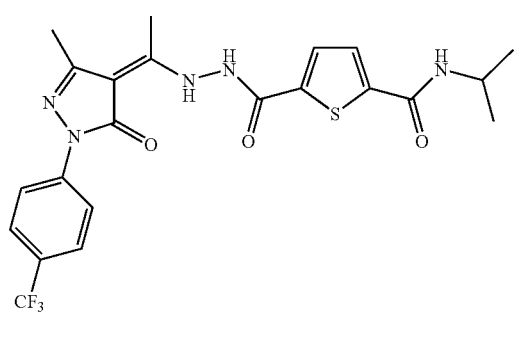
Synthetic Example 32
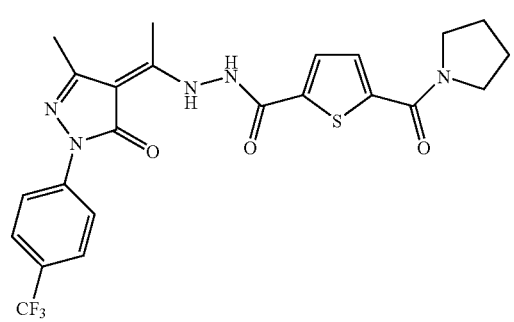
Synthetic Example 29
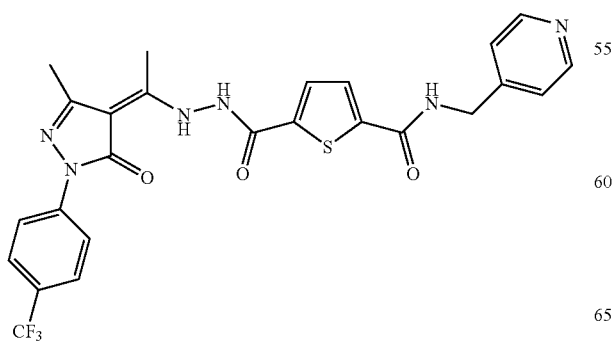
Synthetic Example 33
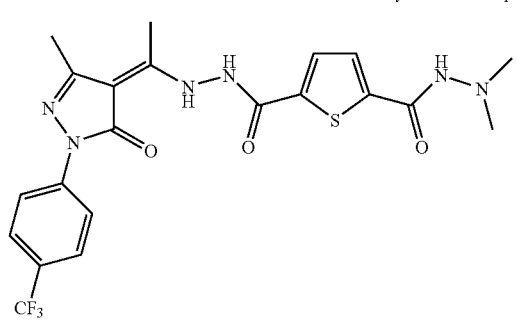

Synthetic Example 34
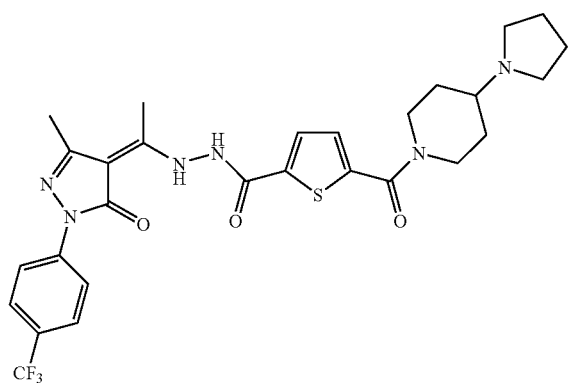
Synthetic Example 38
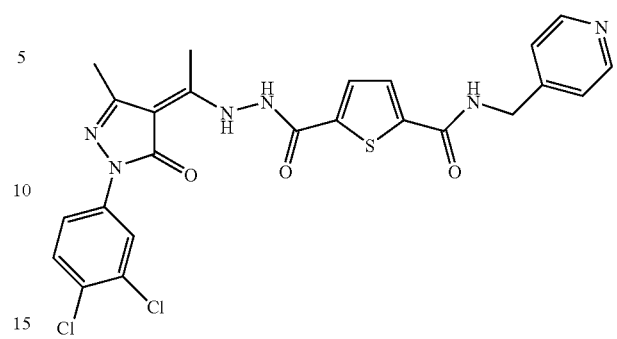
Synthetic Example 35
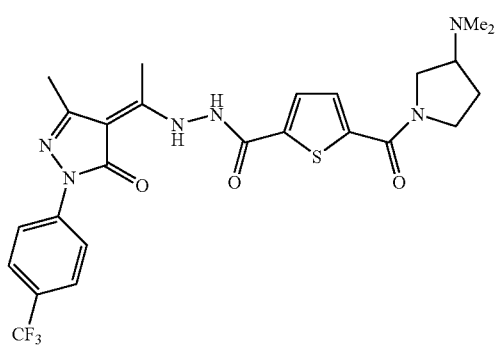
Synthetic Example 39
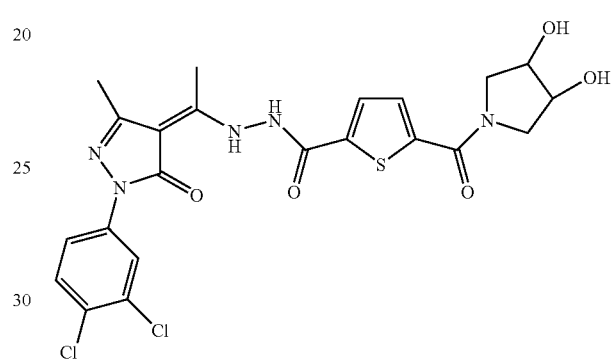
Synthetic Example 36
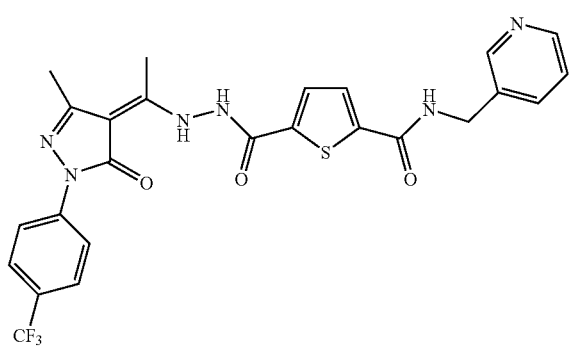
Synthetic Example 40
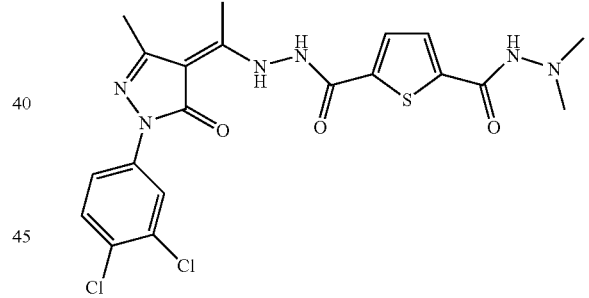
Synthetic Example 37
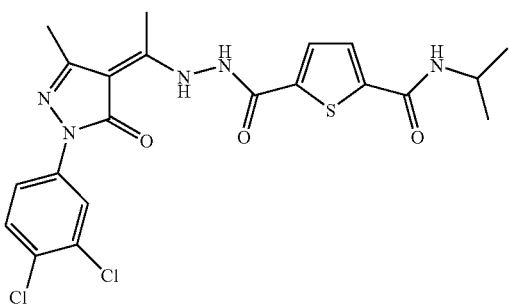
Synthetic Example 41
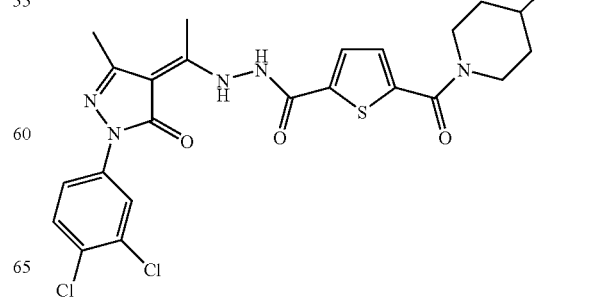

Synthetic Example 42

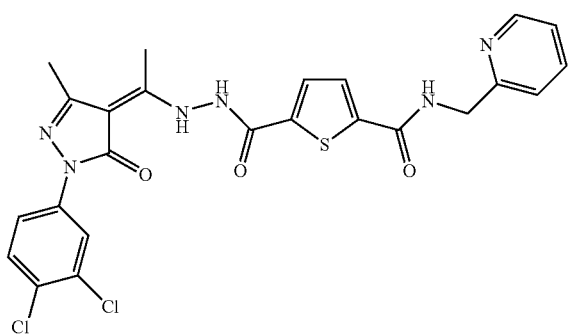

Synthetic Example 43

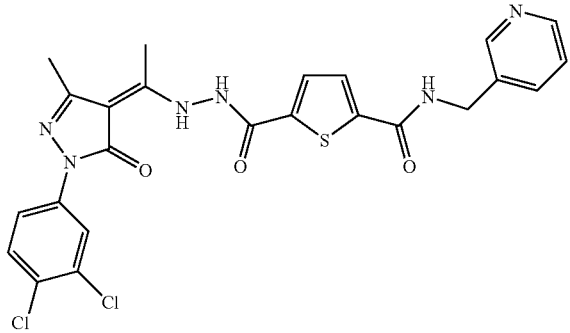

Synthetic Example 44

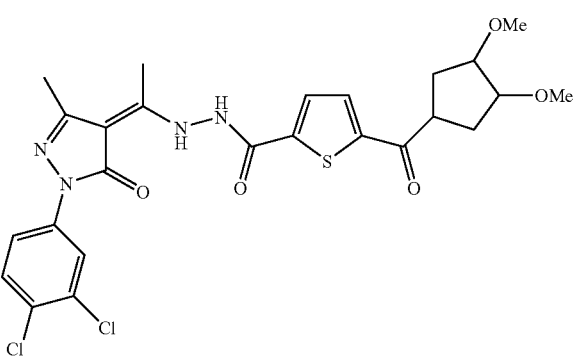

Assay Example 1

Stimulation of Proliferation of a Thrombopoietin-dependent Cell Line

The responses of thrombopoietin receptor to the compounds of the present invention prepared in the Synthetic Examples were assayed using a human leukemic cell line, UT7/EPO-mpl.

(1) Cells and Cell Culture

UT7/EPO-mpl is a stable transformed cell line obtained by introducing into human leukemic cell line UT7/EPO a vector that induces expression of human thrombopoietin receptor (c-mpl) under control of cytomegalovirus immediate-early promoter by the method of Takatoku et al. (J. Biol. Chem., 272:7259-7263 (1997)). Proliferation of this cell line is stimulated by TPO, while its mother cell line UT7/EPO exhibits no response to TPO. These two cell lines were subcultured in IMDM (GIBCO) containing 10% fetal bovine serum (Thermo Electron or BioWest) using a $CO_2$ incubator (5% $CO_2$, 37° C.).

(2) Cell Proliferation Assay

The subcultured cells described above were washed twice with PBS and suspended in IMDM containing 10% fetal bovine serum at a cell density of $6\times10^4$ cells/ml. The cell suspension was transferred to a 96-well tissue culture plate (CORNING) in 100-μl aliquots. Then either thrombopoietin (Pepro Tech EC) or the compounds of the Synthetic Examples dissolved in dimethyl sulfoxide were diluted 83-fold with IMDM containing 10% fetal bovine serum and added to the aforementioned cell suspension in 20-μl aliquots. The cell suspension was incubated in a $CO_2$ incubator (5% $CO_2$, 37° C.) for 4 days. Cell proliferation was assayed using WST-8 reagent (Kishida Chemical Co., Ltd.) according to instructions by the manufacturer. A 10-μl aliquot of 5 mM WST-8 reagent solution was added to each well of the tissue culture plate, and the plate was incubated at 37° C. for 4 hours. The formazan pigment generated was detected by measuring the absorbance at 450 nm with a 96-well microplate reader (Nihon Molecular Devices, Spectramax 190). Proliferation of thrombopoietin-responsive UT7/EPO-mpl cells was stimulated by the compounds of the Synthetic Examples in a concentration-dependent manner, while no effect of this compounds on proliferation was observed with UT7/EPO, the mother cell line. These results indicate that the compound of the Synthetic Examples of the present invention acts on the thrombopoietin receptor selectively as an activator.

The concentration of each compound that yields a growth rate corresponding to 50% of the growth of human leukemic cell line UT-7/EPO-mpl observed in the presence of 10 ng/mL TPO ($EC_{50}$) in the test on the compounds of the Synthetic Examples in Assay Example 1 are shown in Table 16.

TABLE 16

| Synthetic Example No. | $EC_{50}$ (ng/mL) |
|---|---|
| 1 | 2.3 |
| 2 | 0.82 |
| 3 | 2.8 |
| 4 | 3.5 |
| 5 | 2.8 |
| 6 | 3.2 |
| 7 | 1.8 |
| 8 | 0.34 |
| 9 | 4.3 |
| 10 | 2.2 |
| 11 | 0.56 |
| 12 | 0.28 |
| 13 | 0.53 |
| 14 | 5.8 |
| 15 | 2.6 |
| 16 | 1.9 |
| 17 | 2.3 |
| 18 | 2.7 |
| 19 | 1.4 |
| 20 | 0.28 |
| 21 | 0.63 |
| 22 | 3.2 |
| 23 | 3.1 |
| 24 | 3.0 |
| 25 | 0.30 |
| 26 | 0.61 |
| 27 | 0.77 |
| 28 | 0.43 |
| 29 | 0.86 |
| 30 | 2.7 |
| 31 | 4.2 |
| 32 | 3.3 |
| 33 | 2.2 |
| 34 | 2.5 |
| 35 | 3.8 |

TABLE 16-continued

| Synthetic Example No. | EC$_{50}$ (ng/mL) |
|---|---|
| 36 | 0.26 |
| 37 | 2.7 |
| 38 | 2.7 |
| 39 | 2.1 |
| 40 | 2.8 |
| 41 | 2.8 |
| 42 | 2.9 |
| 43 | 2.5 |
| 44 | 6.4 |

Formulation Example 1

A granule preparation containing the following ingredients is prepared.

| Ingredients | |
|---|---|
| Compound represented by the formula (I) | 10 mg |
| Lactose | 700 mg |
| Corn Starch | 274 mg |
| HPC-L | 16 mg |
| | 1000 mg |

A compound represented by the formula (I) and lactose are sifted through a 60-mesh sieve. Corn starch is sifted though a 120-mesh sieve. They are mixed in a V-type blender. The powder mixture is kneaded with a low-viscosity hydroxypropylcellulose (HPC-L) aqueous solution, granulated (extrusion granulation, die size 0.5-1 mm) and dried. The resulting dry granules are sifted through a shaking sieve (12/60 mesh) to obtain a granule preparation.

Formulation Example 2

A powder preparation for capsulation containing the following ingredients is prepared.

| Ingredients | |
|---|---|
| Compound represented by the formula (I) | 10 mg |
| Lactose | 79 mg |
| Corn Starch | 10 mg |
| Magnesium Stearate | 1 mg |
| | 100 mg |

A compound represented by the formula (I) and lactose are sifted through a 60-mesh sieve. Corn starch is sifted though a 120-mesh sieve. They are mixed with magnesium stearate in a V-type blender. The 10% powder is put in hard gelatin capsules No. 5, 100 mg each.

Formulation Example 3

A granule preparation for capsulation containing the following ingredients is prepared.

| Ingredients | |
|---|---|
| Compound represented by the formula (I) | 15 mg |
| Lactose | 90 mg |
| Corn Starch | 42 mg |
| HPC-L | 3 mg |
| | 150 mg |

A compound represented by the formula (I) and lactose are sifted through a 60-mesh sieve. Corn starch is sifted though a 120-mesh sieve. They are mixed in a V-type blender. The powder mixture is kneaded with a low-viscosity hydroxypropylcellulose (HPC-L) aqueous solution, granulated and dried. The resulting dry granules are sifted through a shaking sieve (12/60 mesh). The granules are put in hard capsules No. 4, 150 mg each.

Formulation Example 4

A tablet preparation containing the following ingredients is prepared.

| Ingredients | |
|---|---|
| Compound represented by the formula (I) | 10 mg |
| Lactose | 90 mg |
| Microcrystalline cellulose | 30 mg |
| Magnesium Stearate | 5 mg |
| CMC-Na | 15 mg |
| | 150 mg |

A compound represented by the formula (I), lactose, microcrystalline cellulose and CMC-Na (carboxymethylcellulose sodium salt) are sifted through a 60-mesh sieve and mixed. The powder mixture is mixed with magnesium stearate to give a bulk powder mixture. The powder mixture is compressed directly into 150 mg tablets.

Formulation Example 5

An intravenous preparation is prepared as follows.

| Ingredients | |
|---|---|
| Compound represented by the formula (I) | 100 mg |
| Saturated Fatty Acid Glyceride | 1000 ml |

Solutions having the above-mentioned composition are usually administered to a patient intravenously at a rate of 1 ml per 1 minute.

INDUSTRIAL APPLICABILITY

The compounds of the present invention which have affinity for thrombopoietin receptor and act as thrombopoietin receptor agonists are useful as preventive, therapeutic and improving agents for diseases against which activation of the thrombopoietin receptor is effective, especially as drugs for hematological disorders accompanied by abnormal platelet count and as drugs for diseases treated or prevented by stimulating differentiation and proliferation of vascular endothelial cells and endothelial progenitor cells, and are useful as medicines.

The entire disclosure of Japanese Patent Application No. 2005-322114 filed on Nov. 7, 2005 including specification, claims and summary is incorporated herein by reference in its entirety.

The invention claimed is:

1. A compound represented by formula (I):

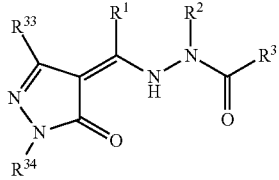

wherein each of $R^1$ and $R^2$ is independently a hydrogen atom, a $C_{1-6}$ alkyl group, a $C_{1-6}$ alkoxy group, a halogenated $C_{1-3}$ alkyl group, or a halogenated $C_{1-3}$ alkoxy group;

$R^3$ is

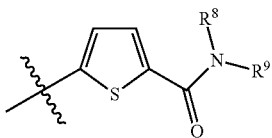

wherein each of $R^8$ and $R^9$ is independently a hydrogen atom or a $C_{1-6}$ alkyl group, wherein the $C_{1-6}$ alkyl group is optionally substituted with at least one substituent selected from the group consisting of a carboxyl group, a $C_{1-6}$ alkoxy group, and a $C_{2-14}$ aryl group, or $R^8$ and $R^9$ together are —$(CH_2)_{m1}$—E—$(CH_2)_{m2}$—, wherein E is $CR^{10}R^{11}$ wherein each of $R^{10}$ and $R^{11}$ is independently a hydrogen atom or a $C_{1-6}$ alkyl group, and each of m1 and m2 is independently an integer of from 0 to 5, provided that m1+m2 is 2, 3, 4, or 5, or $R^3$ is

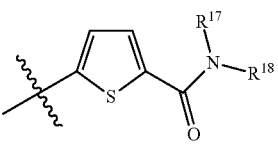

wherein $R^{17}$ is a hydrogen atom or a $C_{1-6}$ alkyl group, and $R^{18}$ is an amino group, a mono- or di-$C_{1-6}$ alkylamino group, or a $C_{2-9}$ heterocyclyl group, or $R^{17}$ and $R^{18}$ together are —$(CH_2)_{m3}$—G—$(CH_2)_{m4}$—, wherein G is $CR^{19}R^{20}$, wherein $R^{19}$ is a hydrogen atom, and $R^{20}$ is an amino group, a mono- or di-$C_{1-6}$ alkylamino group, or a $C_{2-9}$ heterocyclyl group, each of m3 and m4 is independently an integer of from 0 to 5, provided that m3+m4 is 2, 3, 4, or 5, or $NR^{17}R^{18}$, as a whole, is a nitrogen-containing $C_{2-9}$ cyclyl group which is substituted with two or three substituents selected from the group consisting of a hydroxyl group, an amino group, a protected amino group, and a $C_{1-6}$ alkoxy group;

$R^{33}$ is a hydrogen atom, a $C_{1-6}$ alkoxy group, a $C_{1-6}$ alkyl group, a halogenated $C_{1-3}$ alkyl group, or a halogenated $C_{1-3}$ alkoxy group; and $R^{34}$ is a phenyl group, which is optionally substituted with at least one substituent selected from the group consisting of a $C_{1-6}$ alkyl group, a halogenated $C_{1-6}$ alkyl group, a halogen atom, a $C_{1-6}$ alkoxy group, and a halogenated $C_{1-3}$ alkoxy group, or a tautomer or pharmaceutically acceptable salt of the compound.

2. The compound of claim 1, wherein $R^2$ is a hydrogen atom, or a tautomer or pharmaceutically acceptable salt of the compound.

3. The compound of claim 1, wherein $R^1$ is a $C_{1-6}$ alkyl group, or a tautomer or pharmaceutically acceptable salt of the compound.

4. The compound of claim 2, wherein $R^1$ is a $C_{1-6}$ alkyl group, or a tautomer or pharmaceutically acceptable salt of the compound.

5. The compound of claim 1, wherein $R^1$ is a methyl group, or a tautomer or pharmaceutically acceptable salt of the compound.

6. The compound of claim 1, wherein $R^{33}$ is a $C_{1-6}$ alkyl group, or a tautomer or pharmaceutically acceptable salt of the compound.

7. The compound of claim 2, wherein $R^{33}$ is a $C_{1-6}$ alkyl group, or a tautomer or pharmaceutically acceptable salt of the compound.

8. The compound of claim 3, wherein $R^{33}$ is a $C_{1-6}$ alkyl group, or a tautomer or pharmaceutically acceptable salt of the compound.

9. The compound of claim 1, wherein $R^{33}$ is a methyl group, or a tautomer or pharmaceutically acceptable salt of the compound.

10. The compound of claim 1, wherein $R^3$ is

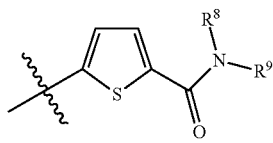

wherein each of $R^8$ and $R^9$ is independently a hydrogen atom or a $C_{1-6}$ alkyl group, wherein the $C_{1-6}$ alkyl group is optionally substituted with at least one substituent selected from the group consisting of a carboxyl group, a $C_{1-6}$ alkoxy group, and a $C_{2-14}$ aryl group, or a tautomer or pharmaceutically acceptable salt of the compound.

11. The compound of claim 1, wherein $R^3$ is

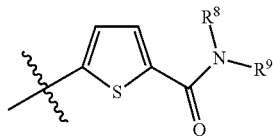

wherein $R^8$ is a hydrogen atom and $R^9$ is a $C_{1-6}$ alkyl group, wherein the $C_{1-6}$ alkyl group is substituted with at least one substituent selected from the group consisting of a carboxyl group, a $C_{1-6}$ alkoxy group, and a $C_{2-14}$ aryl group, or a tautomer or pharmaceutically acceptable salt of the compound.

12. The compound of claim 2, wherein R³ is

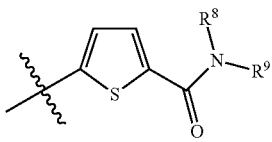

wherein R⁸ is a hydrogen atom and R⁹ is a $C_{1-6}$ alkyl group, wherein the $C_{1-6}$ alkyl group is substituted with at least one substituent selected from the group consisting of a carboxyl group, a $C_{1-6}$ alkoxy group, and a $C_{2-14}$ aryl group, or a tautomer or pharmaceutically acceptable salt of the compound.

13. The compound of claim 3, wherein R³ is

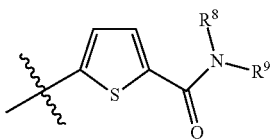

wherein R⁸ is a hydrogen atom and R⁹ is a $C_{1-6}$ alkyl group, wherein the $C_{1-6}$ alkyl group is substituted with at least one substituent selected from the group consisting of a carboxyl group, a $C_{1-6}$ alkoxy group, and a $C_{2-14}$ aryl group, or a tautomer or pharmaceutically acceptable salt of the compound.

14. The compound of claim 1, wherein R³ is

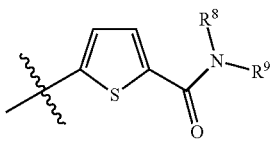

wherein R⁸ and R⁹ together are —$(CH_2)_{m1}$—E—$(CH_2)_{m2}$—, wherein E is $CR^{10}R^{11}$ wherein each of R¹⁰ and R¹¹ is independently a hydrogen atom or a $C_{1-6}$ alkyl group, and each of m1 and m2 is independently an integer of from 0 to 5, provided that m1+m2 is 2, 3, 4, or 5, or a tautomer or pharmaceutically acceptable salt of the compound.

15. The compound of claim 1, wherein R³ is

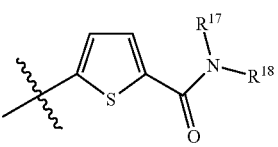

wherein R¹⁷ is a hydrogen atom or a $C_{1-6}$ alkyl group, and R¹⁸ is an amino group, a mono- or di-$C_{1-6}$ alkylamino group, or a $C_{2-9}$ heterocyclyl group, or a tautomer or pharmaceutically acceptable salt of the compound.

16. The compound of claim 2, wherein R³ is

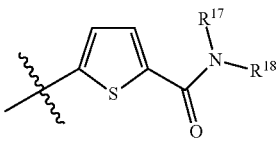

wherein R¹⁷ is a hydrogen atom or a $C_{1-6}$ alkyl group, and R¹⁸ is an amino group, a mono- or di-$C_{1-6}$ alkylamino group, or a $C_{2-9}$ heterocyclyl group, or a tautomer or pharmaceutically acceptable salt of the compound.

17. The compound of claim 3, wherein R³ is

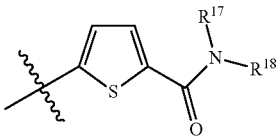

wherein R¹⁷ is a hydrogen atom or a $C_{1-6}$ alkyl group, and R¹⁸ is an amino group, a mono- or di-$C_{1-6}$ alkylamino group, or a $C_{2-9}$ heterocyclyl group, or a tautomer or pharmaceutically acceptable salt of the compound.

18. The compound of claim 1, wherein R³ is

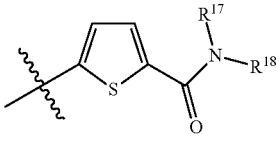

wherein R¹⁷ and R¹⁸ together are —$(CH_2)_{m3}$—G—$(CH_2)_{m4}$—, wherein G is $CR^{19}R^{20}$, wherein R¹⁹ is a hydrogen atom, and R²⁰ is an amino group, a mono- or di-$C_{1-6}$ alkylamino group, or a $C_{2-9}$ heterocyclyl group, each of m3 and m4 is independently an integer of from 0 to 5, provided that m3+m4 is 2, 3, 4, or 5, or a tautomer or pharmaceutically acceptable salt of the compound.

19. The compound of claim 2, wherein R³ is

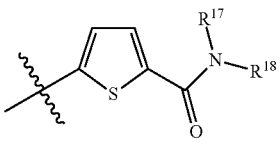

wherein R¹⁷ and R¹⁸ together are —$(CH_2)_{m3}$—G—$(CH_2)_{m4}$—, wherein G is $CR^{19}R^{20}$, wherein R¹⁹ is a hydrogen atom, and R²⁰ is an amino group, a mono- or di-$C_{1-6}$ alkylamino group, or a $C_{2-9}$ heterocyclyl group, each of m3 and m4 is independently an integer of from 0 to 5, provided that m3+m4 is 2, 3, 4, or 5, or a tautomer or pharmaceutically acceptable salt of the compound.

20. The compound of claim 3, wherein $R^3$ is

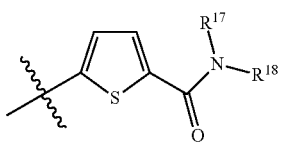

wherein $R^{17}$ and $R^{18}$ together are $-(CH_2)_{m3}-G-(CH_2)_{m4}-$, wherein G is $CR^{19}R^{20}$, wherein $R^{19}$ is a hydrogen atom, and $R^{20}$ is an amino group, a mono- or di-$C_{1-6}$ alkylamino group, or a $C_{2-9}$ heterocyclyl group, each of m3 and m4 is independently an integer of from 0 to 5, provided that m3+m4 is 2, 3, 4, or 5, or a tautomer or pharmaceutically acceptable salt of the compound.

21. The compound of claim 1, wherein $NR^{17}R^{18}$, as a whole, is a nitrogen-containing $C_{2-9}$ cyclyl group which is substituted with two or three substituents selected from the group consisting of a hydroxyl group, an amino group, a protected amino group, and a $C_{1-6}$ alkoxy group, or a tautomer or pharmaceutically acceptable salt of the compound.

22. The compound of claim 2, wherein $NR^{17}R^{18}$, as a whole, is a nitrogen-containing $C_{2-9}$ cyclyl group which is substituted with two or three substituents selected from the group consisting of a hydroxyl group, an amino group, a protected amino group, and a $C_{1-6}$ alkoxy group, or a tautomer or pharmaceutically acceptable salt of the compound.

23. The compound of claim 3, wherein $NR^{17}R^{18}$, as a whole, is a nitrogen-containing $C_{2-9}$ cyclyl group which is substituted with two or three substituents selected from the group consisting of a hydroxyl group, an amino group, a protected amino group, and a $C_{1-6}$ alkoxy group, or a tautomer or pharmaceutically acceptable salt of the compound.

24. The compound of claim 1, wherein $R^{34}$ is a phenyl group, which is substituted with at least one substituent selected from the group consisting of a $C_{1-6}$ alkyl group, a halogenated $C_{1-6}$ alkyl group, a halogen atom, a $C_{1-6}$ alkoxy group, and a halogenated $C_{1-3}$ alkoxy group, or a tautomer or pharmaceutically acceptable salt of the compound.

25. The compound of claim 2, wherein $R^{34}$ is a phenyl group, which is substituted with at least one substituent selected from the group consisting of a $C_{1-6}$ alkyl group, a halogenated $C_{1-6}$ alkyl group, a halogen atom, a $C_{1-6}$ alkoxy group, and a halogenated $C_{1-3}$ alkoxy group, or a tautomer or pharmaceutically acceptable salt of the compound.

26. The compound of claim 3, wherein $R^{34}$ is a phenyl group, which is substituted with at least one substituent selected from the group consisting of a $C_{1-6}$ alkyl group, a halogenated $C_{1-6}$ alkyl group, a halogen atom, a $C_{1-6}$ alkoxy group, and a halogenated $C_{1-3}$ alkoxy group, or a tautomer or pharmaceutically acceptable salt of the compound.

27. The compound of claim 11, wherein $R^{34}$ is a phenyl group, which is substituted with at least one substituent selected from the group consisting of a $C_{1-6}$ alkyl group, a halogenated $C_{1-6}$ alkyl group, a halogen atom, a $C_{1-6}$ alkoxy group, and a halogenated $C_{1-3}$ alkoxy group, or a tautomer or pharmaceutically acceptable salt of the compound.

28. The compound of claim 14, wherein $R^{34}$ is a phenyl group, which is substituted with at least one substituent selected from the group consisting of a $C_{1-6}$ alkyl group, a halogenated $C_{1-6}$ alkyl group, a halogen atom, a $C_{1-6}$ alkoxy group, and a halogenated $C_{1-3}$ alkoxy group, or a tautomer or pharmaceutically acceptable salt of the compound.

29. The compound of claim 15, wherein $R^{34}$ is a phenyl group, which is substituted with at least one substituent selected from the group consisting of a $C_{1-6}$ alkyl group, a halogenated $C_{1-6}$ alkyl group, a halogen atom, a $C_{1-6}$ alkoxy group, and a halogenated $C_{1-3}$ alkoxy group, or a tautomer or pharmaceutically acceptable salt of the compound.

30. The compound of claim 18, wherein $R^{34}$ is a phenyl group, which is substituted with at least one substituent selected from the group consisting of a $C_{1-6}$ alkyl group, a halogenated $C_{1-6}$ alkyl group, a halogen atom, a $C_{1-6}$ alkoxy group, and a halogenated $C_{1-3}$ alkoxy group, or a tautomer or pharmaceutically acceptable salt of the compound.

31. The compound of claim 21, wherein $R^{34}$ is a phenyl group, which is substituted with at least one substituent selected from the group consisting of a $C_{1-6}$ alkyl group, a halogenated $C_{1-6}$ alkyl group, a halogen atom, a $C_{1-6}$ alkoxy group, and a halogenated $C_{1-3}$ alkoxy group, or a tautomer or pharmaceutically acceptable salt of the compound.

32. The compound of claim 1, wherein $R^{34}$ is a phenyl group, which is substituted with at least two substituents selected from the group consisting of a $C_{1-6}$ alkyl group and a halogen atom, or a tautomer or pharmaceutically acceptable salt of the compound.

33. The compound of claim 1, wherein $R^{34}$ is a phenyl group, which is substituted with at least one substituent selected from the group consisting of a methyl group, a trifluoromethyl group, a halogen atom, and a tert-butyl group, or a tautomer or pharmaceutically acceptable salt of the compound.

34. The compound of claim 1, selected from the group consisting of:

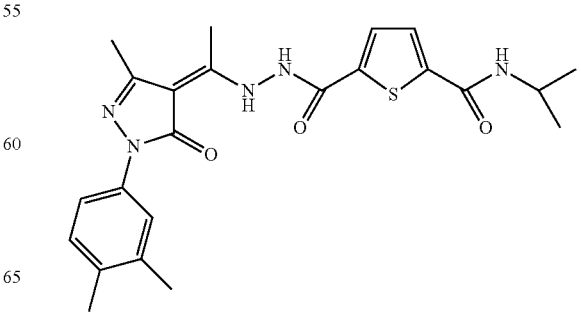

149
-continued
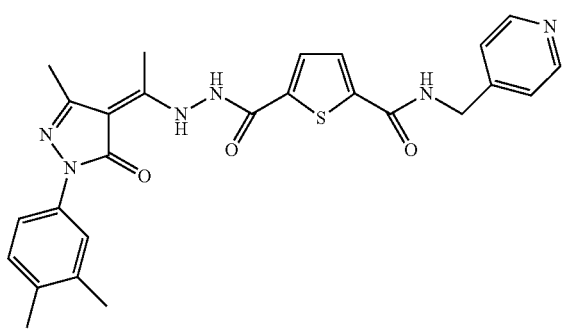
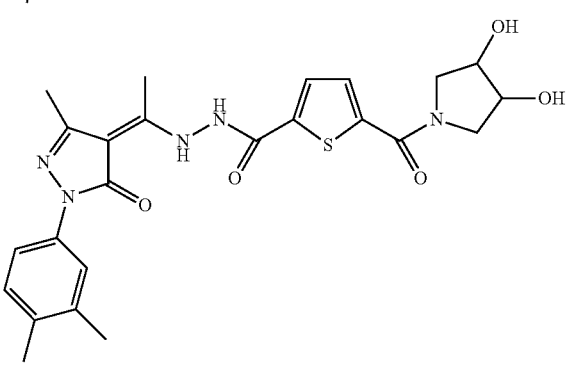
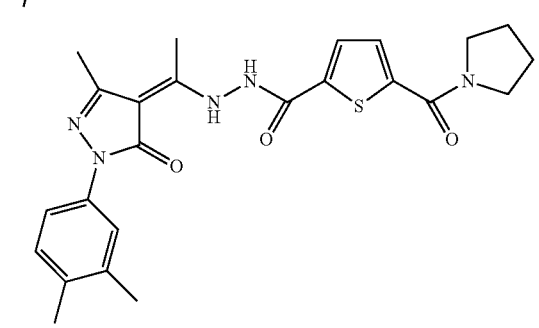
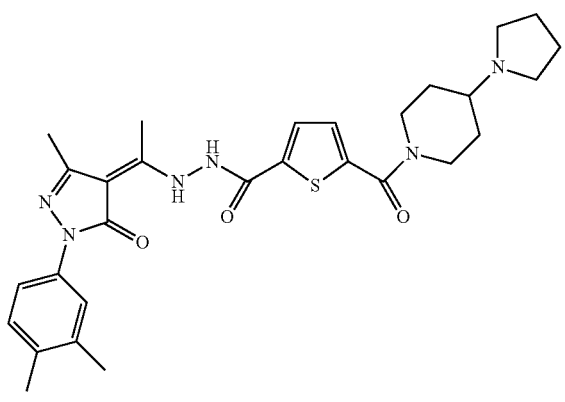
150
-continued
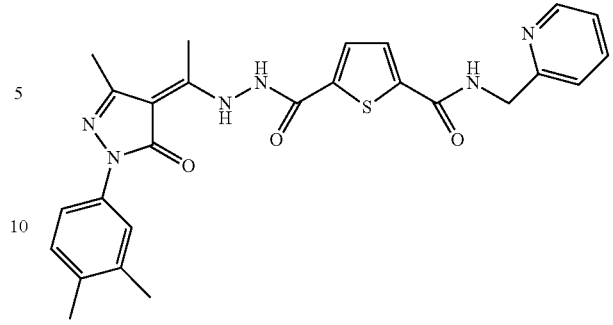
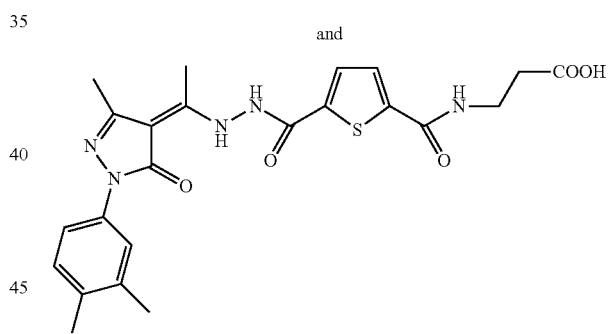
and
or a tautomer or pharmaceutically acceptable salt of the compound.
35. The compound of claim 1, selected from the group consisting of:
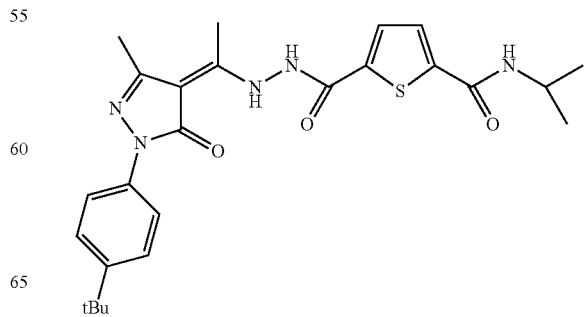

-continued
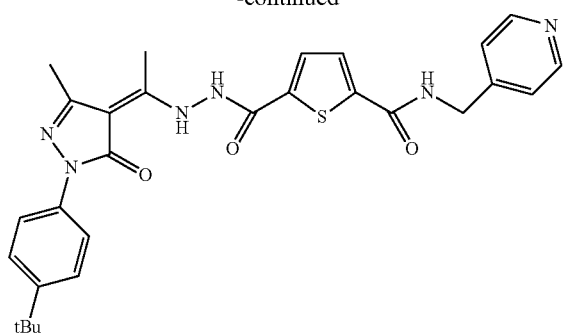
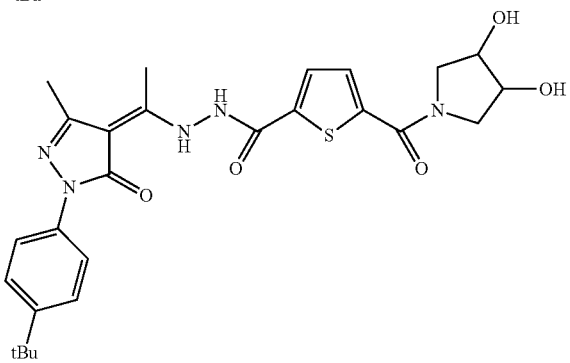
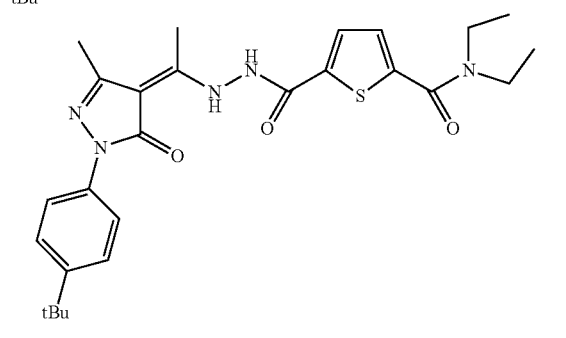
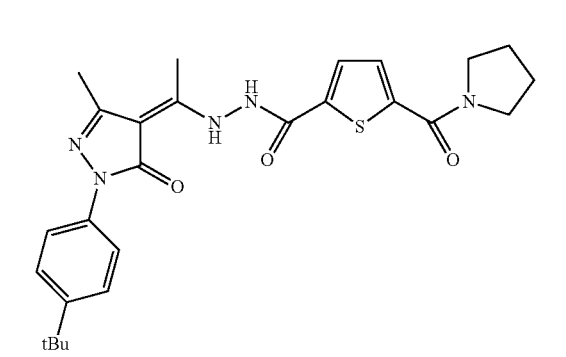
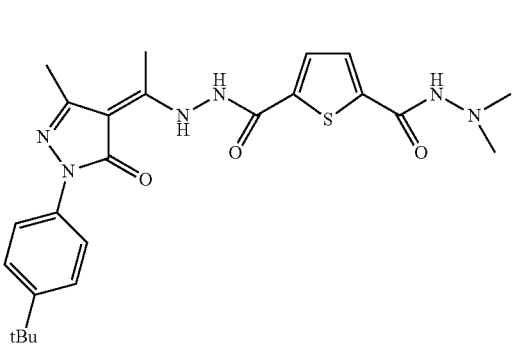
-continued
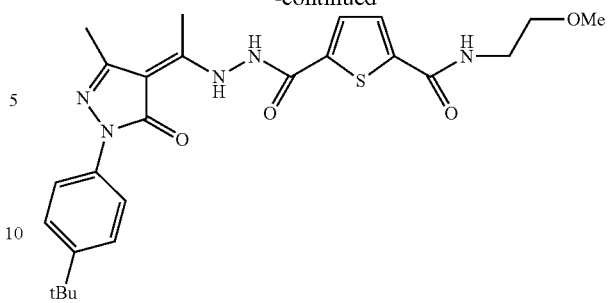
and
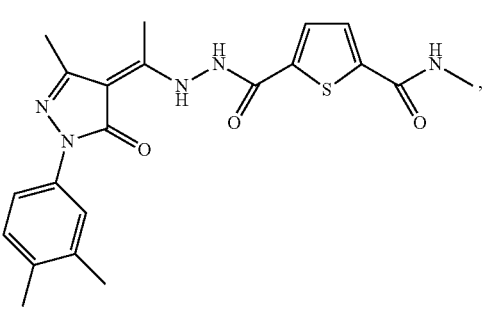
or a tautomer or pharmaceutically acceptable salt of the compound.
36. The compound of claim 1, selected from the group consisting of:
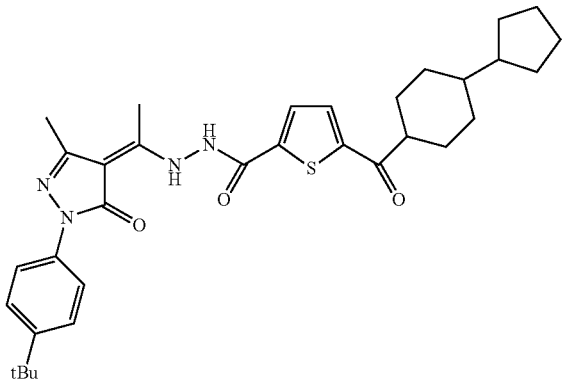

153
-continued
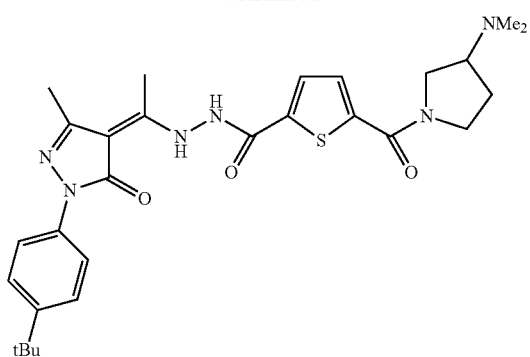
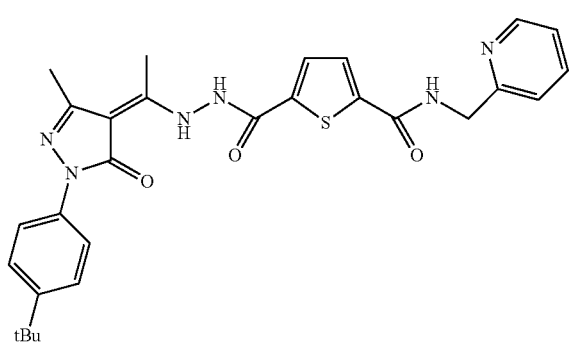
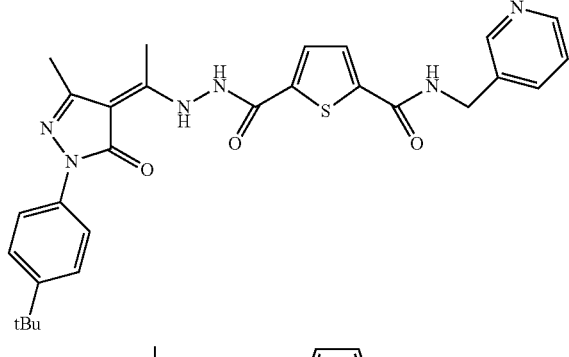
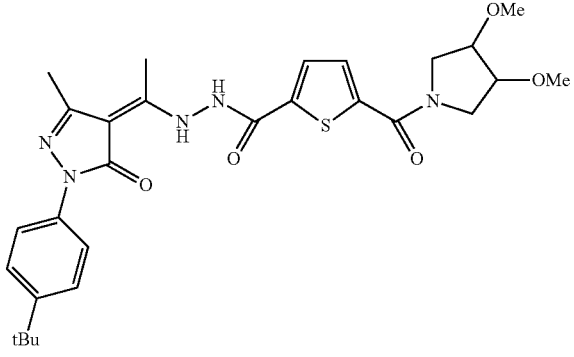
154
-continued
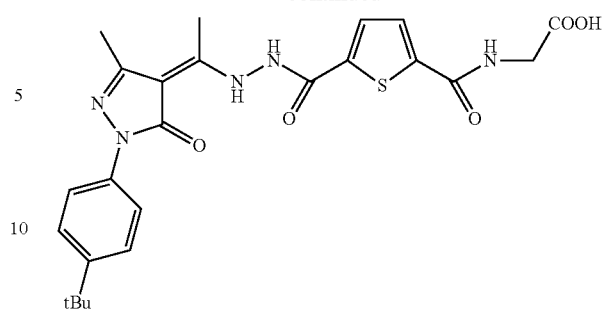
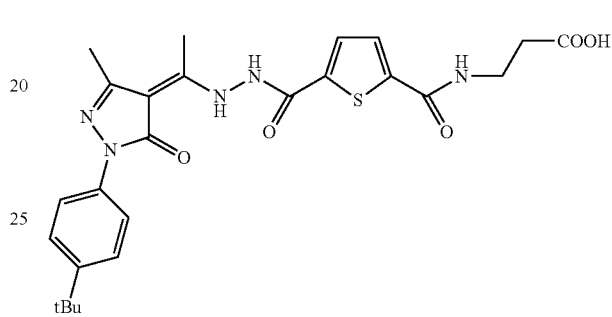
and
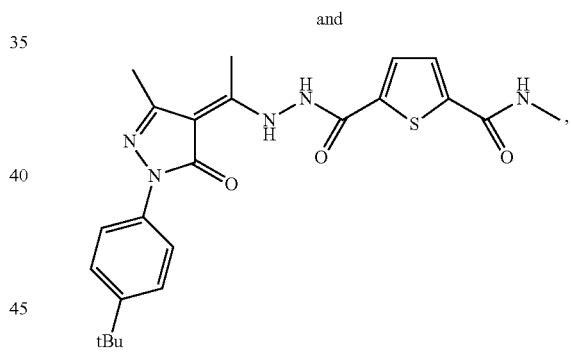
or a tautomer or pharmaceutically acceptable salt of the compound.
37. The compound of claim 1, selected from the group consisting of:
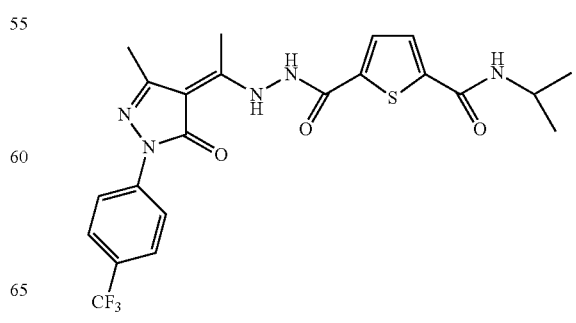

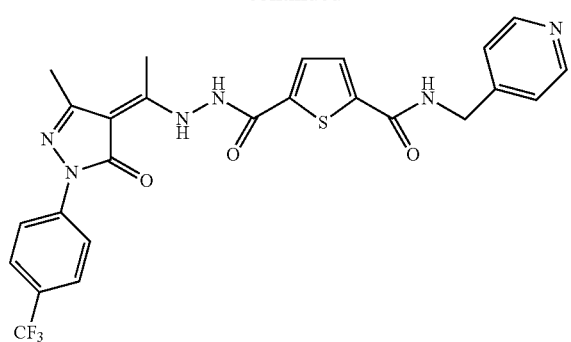
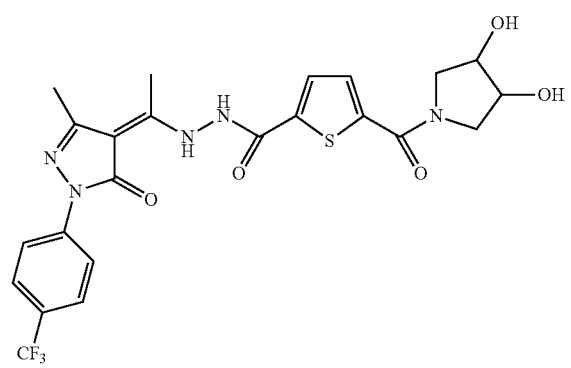
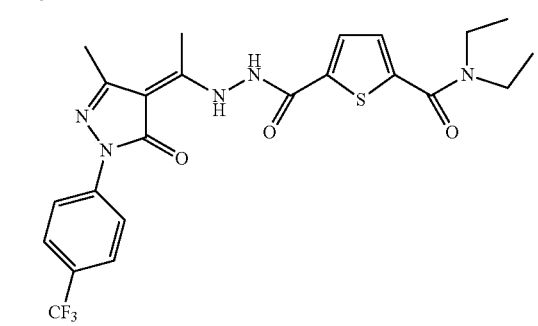
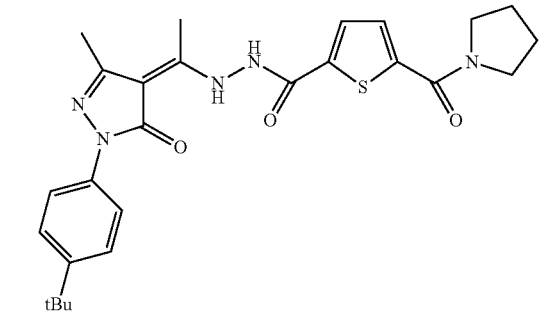
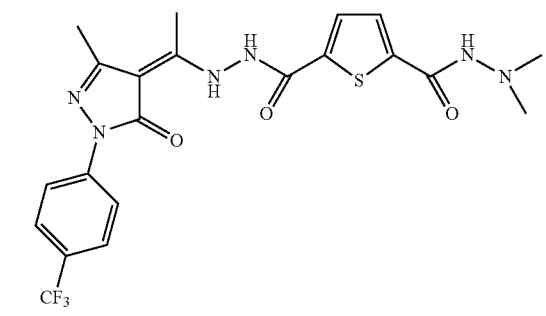
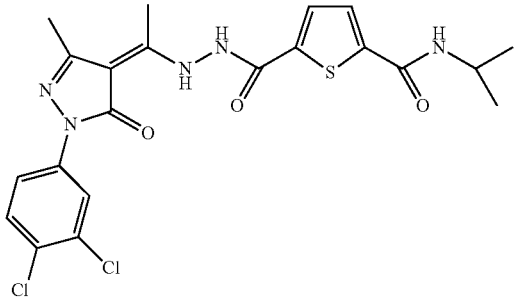
or a tautomer or pharmaceutically acceptable salt of the compound.
38. The compound of claim 1, selected from the group consisting of:

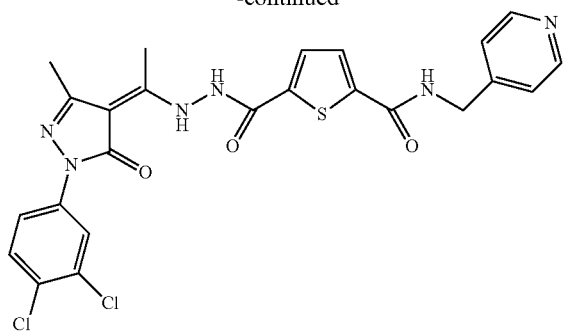
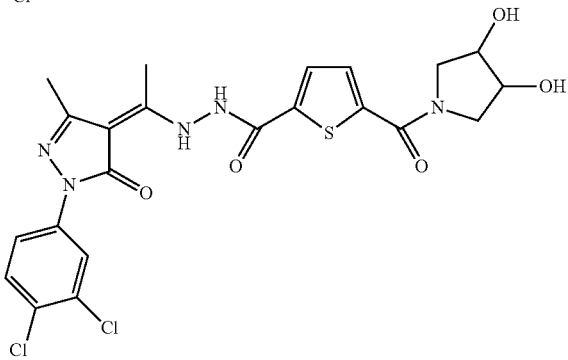
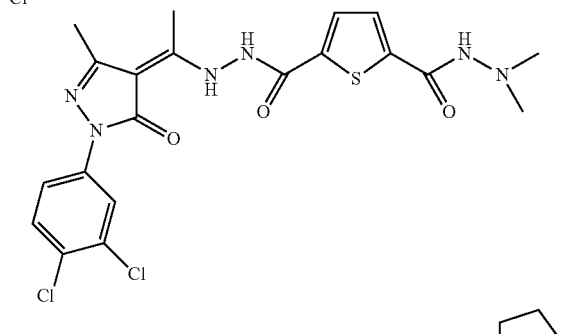
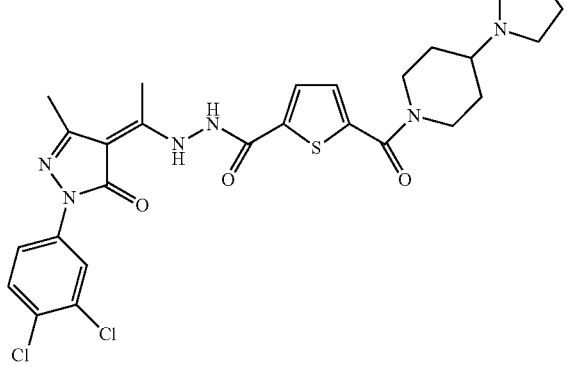
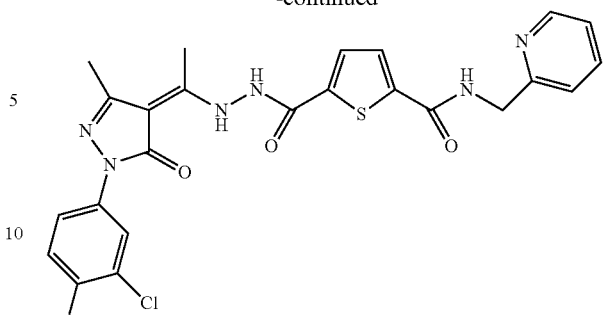
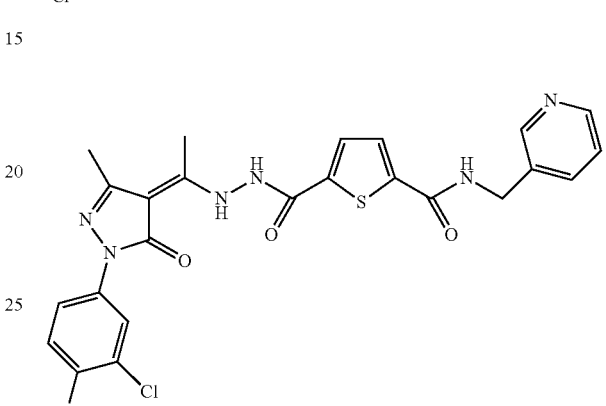
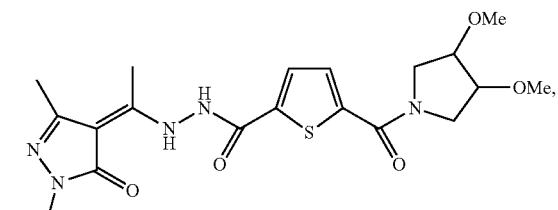
and
or a tautomer or pharmaceutically acceptable salt of the compound.
* * * * *

UNITED STATES PATENT AND TRADEMARK OFFICE
CERTIFICATE OF CORRECTION

| | | |
|---|---|---|
| PATENT NO. | : 8,026,368 B2 | |
| APPLICATION NO. | : 12/092834 | |
| DATED | : September 27, 2011 | |
| INVENTOR(S) | : Katsuaki Miyaji et al. | |

It is certified that error appears in the above-identified patent and that said Letters Patent is hereby corrected as shown below:

at column 44, line 20, the first structure in the row

"... ..." should read -- ... ... -- at column 45, line 34,
"...$C_{2-9}$ heterocyclyl group..." should read -- ...$C_{2-9}$ cyclyl group... -- at column 61, line 37,
"... according to 21), wherein..." should read -- ... according to 22), wherein... -- at column 69, line 22,
"...according to 44), wherein..." should read -- ...according to 43), wherein...-- at column 69, line 26,
"...according to 44), wherein..." should read -- ...according to 43), wherein...-- at column 103, line 29,
"...according to any of 73) to 86), wherein..." should read -- ...according to any of 70) to 86), wherein... -- at column 103, line 33,
"...according to any of 73) to 86), wherein..." should read -- ...according to any of 70) to 86), wherein... -- at column 103, line 37,
"...according to any of 73) to 86), wherein..." should read -- ...according to any of 70) to 86), wherein... --

Signed and Sealed this
Fifteenth Day of November, 2011

David J. Kappos
*Director of the United States Patent and Trademark Office*

CERTIFICATE OF CORRECTION (continued)
U.S. Pat. No. 8,026,368 B2 at column 103, line 41,
"...according to any of 73) to 86), wherein..." should read -- ...according to any of 70) to 86), wherein... -- at column 103, line 45,
"...according to any of 73) to 86), wherein..." should read -- ...according to any of 70) to 86), wherein... -- at column 114, line 34,
"...any of 1) to 93) or..." should read -- ...any of 1) to 99) or... -- at column 115, line 15,

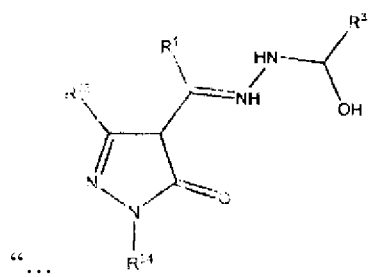 "..." should read -- 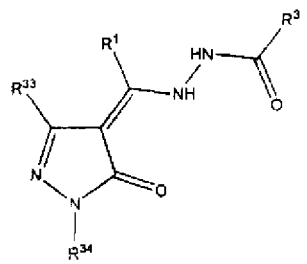 ... -- at column 117, line 10, first structure

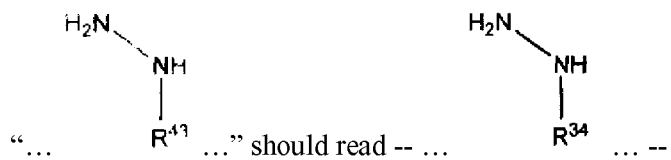 should read -- at column 117, line 10, second structure

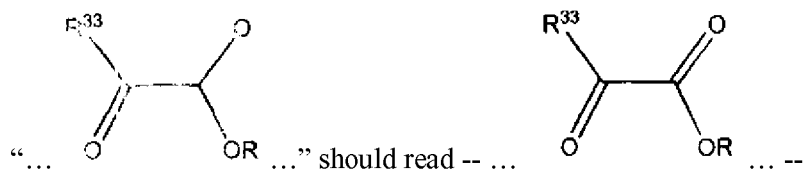 should read -- at column 117, line 15, second structure

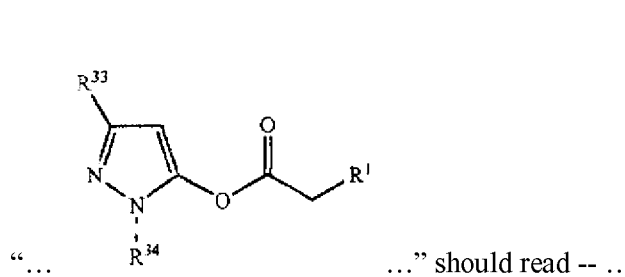 "..." should read -- 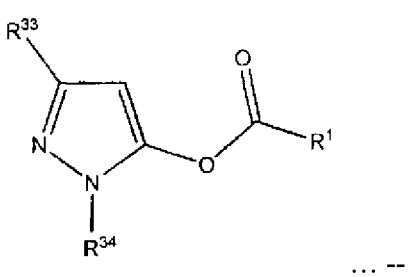 ... --

CERTIFICATE OF CORRECTION (continued)
U.S. Pat. No. 8,026,368 B2 at column 117, line 47,

"...an acid halide ($R^1COOCl$) or..." should read -- ...an acid halide ($R^1COCl$) or ... -- at column 119, lines 1-10,

"... 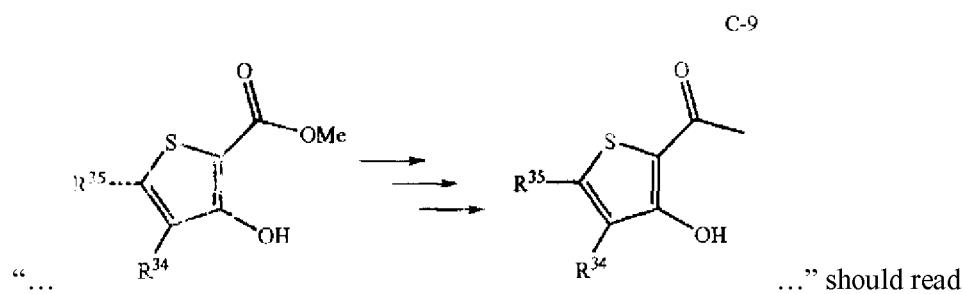 ..." should read

-- ... 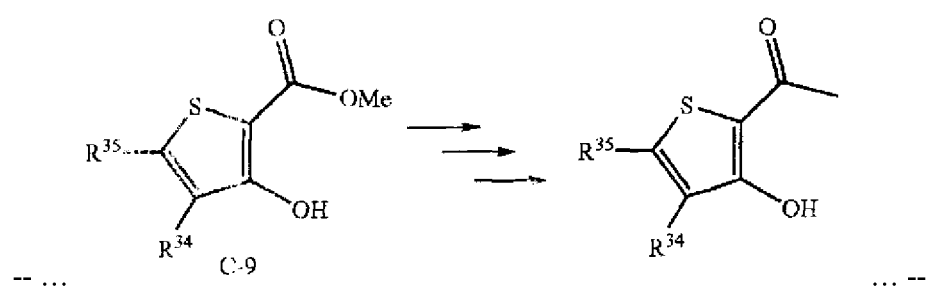 ... -- at column 119, lines 30-39,

"... 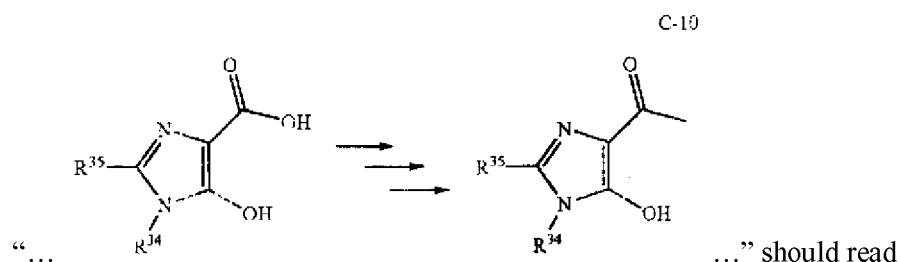 ..." should read

-- ... 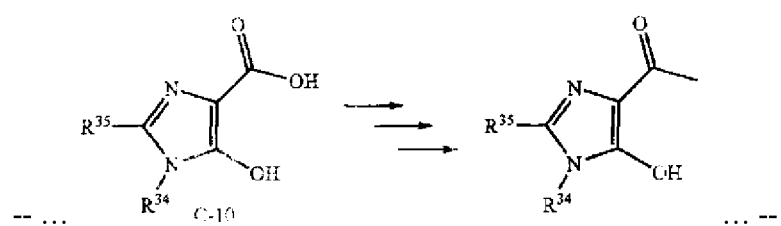 ... --

CERTIFICATE OF CORRECTION (continued)
U.S. Pat. No. 8,026,368 B2 at column 119, lines 57-65,

"... 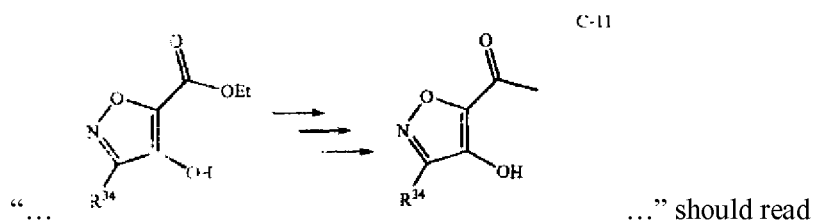 ..." should read

-- ... 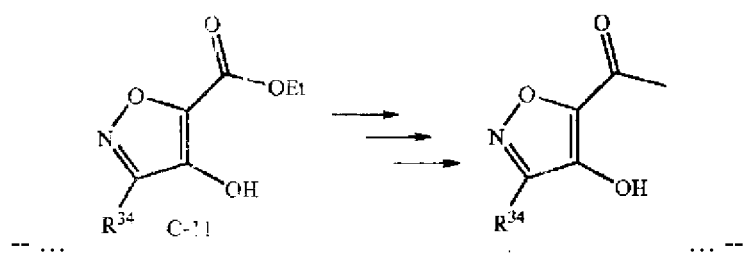 ... -- at column 120, line 17-25,

"... 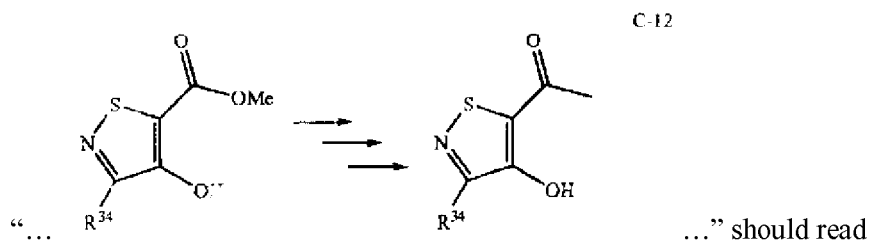 ..." should read

-- ... 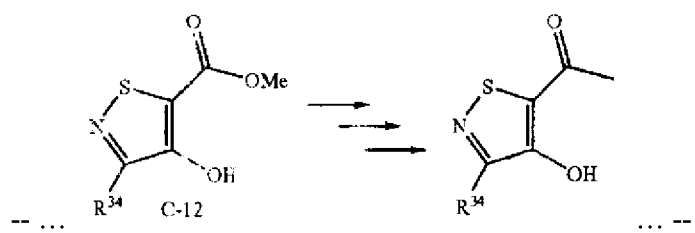 ... -- at column 120, line 44-52, (note the methyl ester should be an ethyl ester)
"... 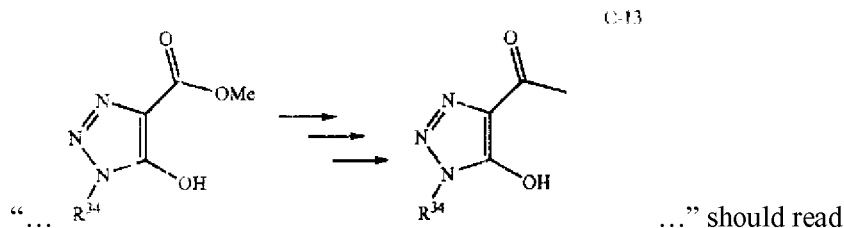 ..." should read
-- ... 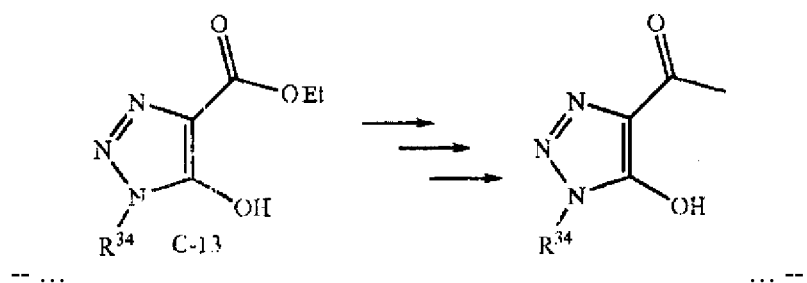 ... --
at column 122, line 9,
"...226 [M-l]⁻ ..." should read -- ...226 [M-l]⁺ ... --
at column 124, line 62,
"...452 [M-l]⁻ ..." should read -- ...452 [M-l]⁺ ... --
at column 143, line 9-16,
"... 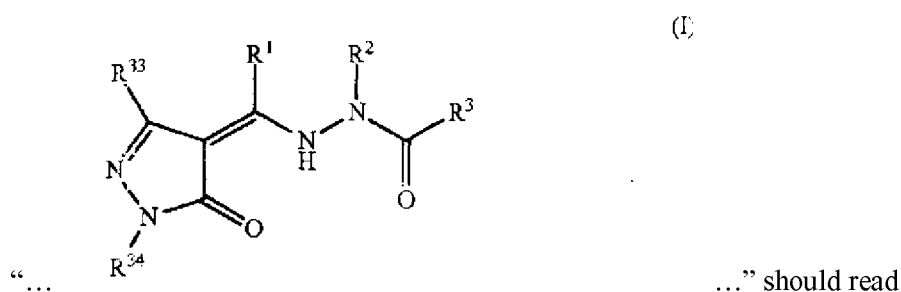 ..." should read
-- ... 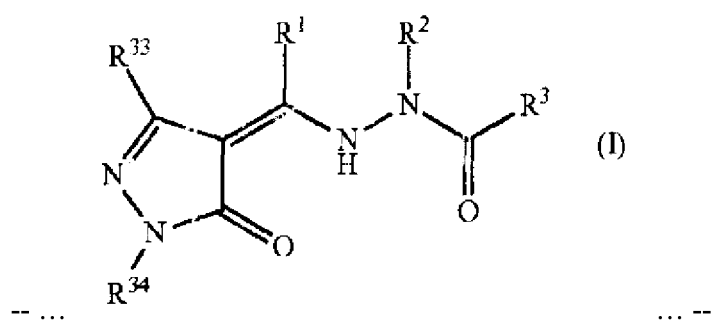 ... --

CERTIFICATE OF CORRECTION (continued)
U.S. Pat. No. 8,026,368 B2 at column 152, line 55-67,

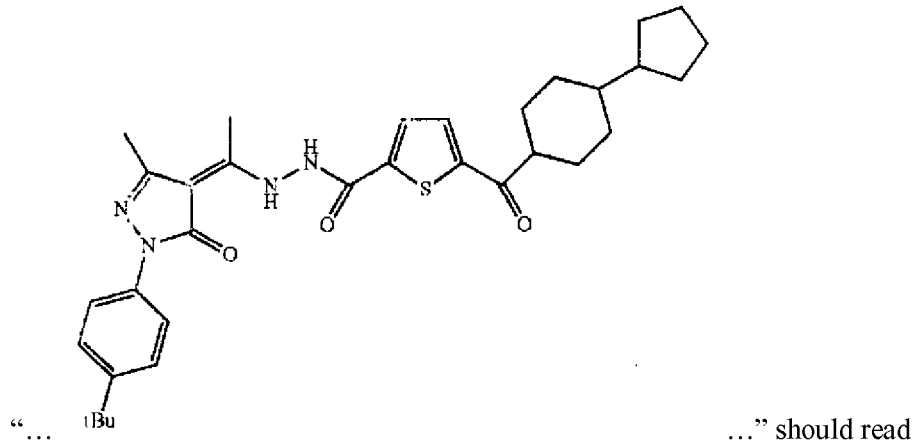

"..." should read

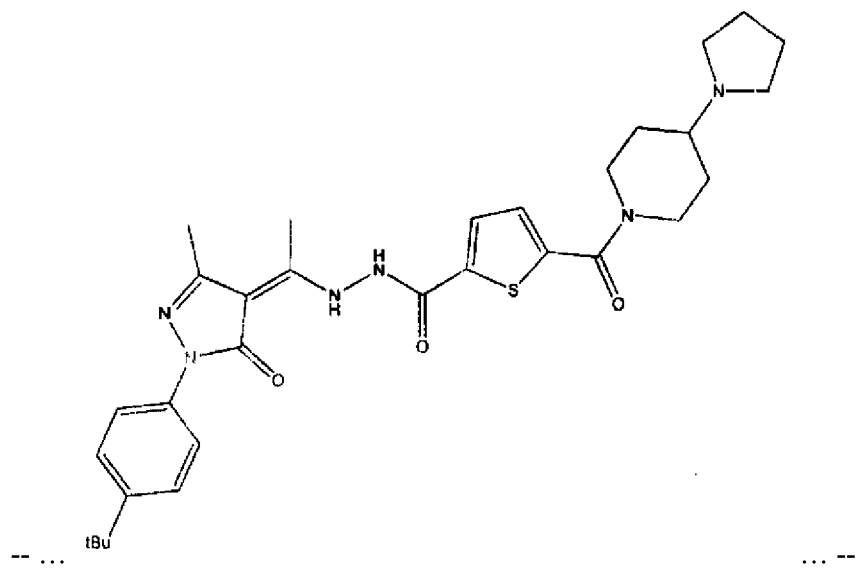

-- ... ... -- at column 155, line 42-54,

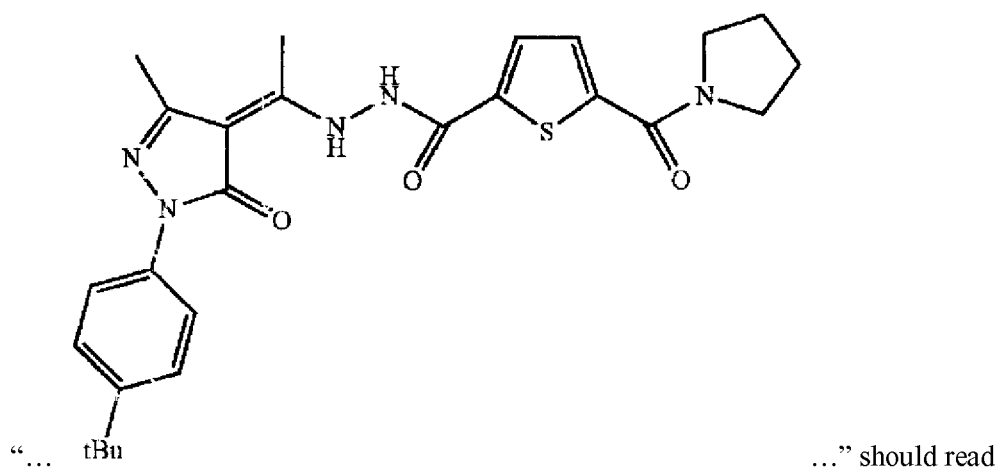

"..." should read

CERTIFICATE OF CORRECTION (continued)
U.S. Pat. No. 8,026,368 B2

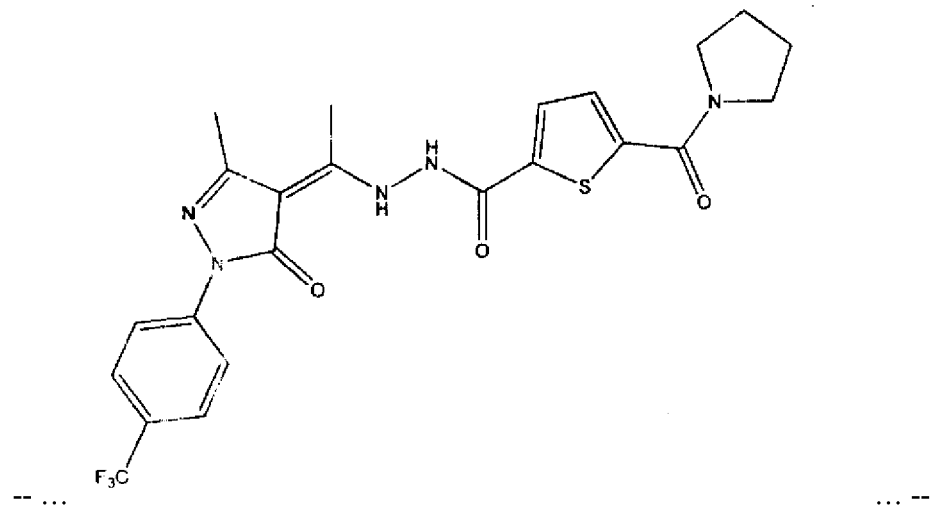

-- ...                                                              ... --